US007795388B2

(12) United States Patent
Paavola et al.

(10) Patent No.: US 7,795,388 B2
(45) Date of Patent: Sep. 14, 2010

(54) VERSATILE PLATFORM FOR NANOTECHNOLOGY BASED ON CIRCULAR PERMUTATIONS OF CHAPERONIN PROTEIN

(75) Inventors: Chad D. Paavola, Mountain View, CA (US); Jonathan D. Trent, Watsonville, CA (US); Suzanne L. Chan, Oakland, CA (US); Yi-Fen Li, Sunnyvale, CA (US); R. Andrew McMillan, San Francisco, CA (US); Hiromi Kagawa, Sunnyvale, CA (US)

(73) Assignee: The United States of America as represented by the Administrator of the National Aeronautics and Space Administration (NASA), Washington, DC (US)

( * ) Notice: Subject to any disclaimer, the term of this patent is extended or adjusted under 35 U.S.C. 154(b) by 362 days.

(21) Appl. No.: 11/194,991

(22) Filed: Aug. 1, 2005

(65) Prior Publication Data

US 2006/0084792 A1 Apr. 20, 2006

Related U.S. Application Data

(63) Continuation-in-part of application No. 10/494,853, filed as application No. PCT/US02/35889 on Nov. 8, 2002.

(60) Provisional application No. 60/340,538, filed on Nov. 8, 2001.

(51) Int. Cl.
*C07K 14/00* (2006.01)
*A61K 38/00* (2006.01)

(52) U.S. Cl. ........................................ 530/350; 514/2

(58) Field of Classification Search ....................... None
See application file for complete search history.

(56) References Cited

U.S. PATENT DOCUMENTS

| | | | | |
|---|---|---|---|---|
| 5,428,131 | A | 6/1995 | Trent et al. | |
| 6,338,952 | B1 | 1/2002 | Young | |
| 6,858,318 | B2 | 2/2005 | Kogiso et al. | |
| 2002/0130353 | A1 | 9/2002 | Lieber et al. | |
| 2003/0078373 | A1 | 4/2003 | Fersht et al. | |
| 2005/0130258 | A1* | 6/2005 | Trent et al. | 435/68.1 |

FOREIGN PATENT DOCUMENTS

| | | | |
|---|---|---|---|
| JP | 07-067641 | | 3/1995 |
| JP | 11-045990 | | 2/1999 |
| JP | 11-204774 | | 7/1999 |
| WO | WO00/77196 | A1 | 12/2000 |
| WO | WO 03/080796 | | 10/2003 |

OTHER PUBLICATIONS

Bosch et al., "Crystal structure of the beta-apical domain of the thermosome reveals structural plasticity in the protrusion region", Journal of Molecular Biology 301: 19-25 (Aug. 4, 2000).*
Archibald, et al., "Recurrent parology in the evolution of archaeal chaperonins" 1999 Current Biology 9: 1053-1056.
Beernink, et al., "Random circular permutation leading to chain disruption . . . " 2001 Protein Sci 10:528-537.
Brown, et al., "A Genetic Analysis of Crystal Growth" 2000 J. Mol. Biol. 299: 725-735.
Brown "Metal-recognition by repeating polypeptides" 1997 Nature Biotechnol. 15: 269-272.
Bruchez, et al., "Semiconductor Nanocrystals as Fluorescent Biological Labels" 1998 Science 281: 2013-16.
Charlebois, et al., "*Sulfolobus* genome: from genomics to biology" 1998 Curr Opin in Microbio 1: 584-588.
Douglas and Clark "Nanometer molecular lithography" 1986 Appl Phys Lett 48:676-678.
Ellis, et al., "Two-Dimensional Crystallization of the Chaperonin TF55 from the Hyperthermophilic Archaeon *Sulfolobus solfataricus*" 1998 J. Struc. Biol. 123, 30-36.
Fenton "GroEL-mediated protein folding" 1997 Protein Science 6: 743-760.
Furutani, et al., "Group II Chaperonin in a Thermophilic Methanogen, *Methanococcus thermolithotrophicus*" 1998 J. Biol. Chem. 273: 28399-28407.

(Continued)

*Primary Examiner*—Anand U Desai
(74) *Attorney, Agent, or Firm*—John F. Schipper; Robert M. Padilla

(57) ABSTRACT

The present invention provides chaperonin polypeptides which are modified to include N-terminal and C-terminal ends that are relocated from the central pore region to various different positions in the polypeptide which are located on the exterior of the folded modified chaperonin polypeptide. In the modified chaperonin polypeptide, the naturally-occurring N-terminal and C-terminal ends are joined together directly or with an intervening linker peptide sequence. The relocated N-terminal or C-terminal ends can be covalently joined to, or bound with another molecule such as a nucleic acid molecule, a lipid, a carbohydrate, a second polypeptide, or a nanoparticle. The modified chaperonin polypeptides can assemble into double-ringed chaperonin structures. Further, the chaperonin structures can organize into higher order structures such as nanofilaments or nanoarrays which can be used to produce nanodevices and nanocoatings.

10 Claims, 62 Drawing Sheets

OTHER PUBLICATIONS

Galagan, et al., "The Genome of *M. acetivorans* Reveals Extensive Metabolic and Physiological Diversity" 2002 Genome Research 12: 532-542.
Griesbeck, et al., "Reducing the Environmental Sensitivity of Yellow Fluorescent Protein" 2001 J. Biol. Chem. 276:29188-29194.
Guex, et al., "Protein modeling for all" 1999 TiBS 24: 364.
Hartl and Hayer-Hartl "Molecular Chaperones in the Cytosol: from Nascent Chain to Folded Protein" 2002 Science 295:1852-1858.
Hartl "Molecular chaperones in cellular protein folding" 1996 Nature 381:571-580.
Heinemann and Hahn "Circular Permutation of Polypeptide Chains: Implications for Protein Folding and Stability" 1995 Prog Biophys Mol Biol 64:121-143.
Horwich, et al., "Protein folding in the cell: functions of two families of molecular chaperone. hsp60 and TF55-TCP1" 1993 Phil. Trans R. Soc. Lond. B 339: 313-326.
Iwakura, et al., "Systemic circular permutation of an entire protein reveals essential folding elements" 2000 Nat Struct Biol 7:580-585.
Kagawa, et al., "The 60 kDa Heat Shock Proteins in the Hyperthermophilic Archaeon *Sulfolobus shibatae*" 1995 J Mol Biol 253:712-25.
Kagawa, et al., "The composition, structure and stability of a group II chaperonin are temperature regulated . . . " 2003 Molec Microbio 48:143-156.
Karlin, et al., "Characterizations of Highly Expressed Genes of Four Fast Growing Bacteria" 2001 J. Bacteriol. 183: 5025-5040.
Klumpp and Baumeister "The thermosome: archetype of group II chaperonins" 1998 FEBS Letters 430: 73-77.
Koeck, et al., "Two-dimensional crystals of reconstituted β-subunits of the chaperonin TF55 from *Sulfolobus shibatae*" 1998 Biochim Biophys Acta 1429: 40-44.
Kroger, et al., "Polycationic Peptides from Diatom Biosilica That Direct Silica Nanosphere Formation" 1999 Science 286:1129-1132.
Labas, et al., "Diversity and evolution of the green fluorescent protein family" 2002 Proc Natl Acad Sci USA 99:4256-4261.
Lee, et al., "Ordering of Quantum Dots Using Genetically Engineered Viruses" 2002 Science 296:892-895.
Lin, et al., "The unique hetero-oligomeric nature of the subunits in the catalytic cooperatively . . . " 1997 Proc Natl Acad Sci USA 94: 10780-10785.
Marco, et al., "The molecular chaperone TF55" 1994 FEBS 341: 152-155.
McMillan, et al., "Ordered nanoparticle arrays formed on engineered chaperonin protein templates" 2002 Nature Materials 1:247-252.
Naik et at, "Biomimetic synthesis and patterning of silver nanoparticles" 2002 Nature Materials 1: 169-172.
Patterson "Fluorescent protein spectra" 2001 Cell Sci 114:837-838.
Peng, et al., "Shape control of CdSe nanocrystals" 2000 Nature 404: 59-61.
Quaite-Randall, et al., "Conformational cycle of the archaeosome, a TCP1- like chaperonin from *Sulfolobus shibatae*" 1995 J. Biol. Chem. 270: 28818-28823.
Rizzo, et al., "An improved cyan fluorescent protein variant useful for FRET" 2004 Nature Biotechnology 22:445-449.
Sarikaya, et al., "Molecular biomimetics: nanotechnology through biology" 2003 Nature Materials 2:577-585.
Shaner "Improved monomeric red, orange and yellow fluorescent proteins derived from Discosoma sp. red fluorescent protein" 2004 Nature Biotechnology 22:1567-1572.
Sleytr, et al., "Crystalline bacterial cell surface layers (S layers)" 1999 Angew Chem Int Edn 38:1034-1054.
Slocik, et al., "Monoclonal antibody recognition of histidine-rich peptide encapsulated nanoclusters" 2002 Nanoletters 2:169-173.
Su, Wei-Wen "Fluorescent proteins as tools to aid protein production" 2005 Microbial Cell Fractions 4:12.
Trent, et al., "A molecular chaperone from a thermophilic archaebacterium is related to the eukaryotic protein t-complex polypeptide-1" 1991 Nature 354: 490-493.
Trent, et al., "Chaperone filaments" The archaeal cytoskeleton ? 1997 Proc. Nat. Acad. Sci USA 94: 5383-5388.
Whaley, et al., "Selection of peptides with semiconductor binding specificity for directed nanocrystal assembly" 2000 Nature 405: 665-668.
Yamashita "Fabrication of a two-dimensional array of nano-particles using ferritin molecule" 2001 Thin Solid Films 393:12-18.
Yaoi, et al., "Chaperonin Filaments: their formation and an evaluation of methods for studying them" 1998 Arch of Biochem and Biophys 356: 55-62.
Bosch, et al., Crystal structure of the beta-apical domain of the thermosome reveals structual plasticity in the protrusion region, J. Molecular Biology, Aug. 4, 2000, 19-25.
Kramer, et al., Engineered protein cages for nanomaterial synthesis, J. Am. Chem. Soc., 2004, 13282-13286, 126-41.
Llorca, et al., 3D reconstruction of the ATP-bound form of CCT reveals the asymmetric folding conformation of a type I . . . , Nature Structural Biology, Jul. 1999, 639-642, 6-7.
Pazirandeh, et al., Metallized nanotubes derived from bacteria, Biomimetics, 1992, 41-50, 1-1.
Schoehn, et al., Three conformations of an archael chaperonin, TF55 from *Sulfolobus shibatae*, J. Molecular Biology, Feb. 2000, 813-819, 296.
Shpigel, et al., Production and Purification of a Recombinant Human hsp60 Epitope Using the Cell . . . , Protein Expression and Purification, 1998, 185-191, 14, Academic Press.
Ursic, et al., The essential yeast Tcp1 protein affects actin and microtubules, Molecular Biology of the Cell, Oct. 1994, 1065-1080, 5, American Society for Cell Biology.
Van Bommel, et al., Organic Templates for the Generation of Inorganic Materials, Angew. Chem. Int. Ed., 2003, 980-999, 42-9.
Weiss, et al., A Mutant at Position 87 of the GroEL Chaperonin is Affected in Protein Binding and ATP Hydrolysis, J. Biological Chemistry, 13956-13960, 1995, 270-23.
Office Action, dated Mar. 13, 2006, from U.S. Appl. No. 10/494,853, filed May 6, 2004.
Office Action, dated Dec. 14, 2006, from U.S. Appl. No. 10/494,853, filed May 6, 2004.
Dat, et al., Mimicking a conformational B cell epitope of the heat shock protein PfHsp70-1 antigen of Plasmodium falciparum using a multiple antigenic peptide, Parasite Immunology 22(11):535-543, 2000, Blackwell Science Ltd.
Ishii, et al., Novel Protein—Forming Nanocluster Hybrid System: Stabilization of CdS Nanocluster Using Nanopore of Tubular Protein, The Chemical Society of Japan, 80th Fall Meeting, Sep. 7, 2001, 222, 1C1-04.
Jiang, et al., Formation of Huge Rotaxane by Encapsulating Luminescent Dendrimer Rod in Nanopore of Tubular Protein, The Chemical Society of Japan, 80th Fall Meeting, Sep. 7, 2001, 209, 3BC-07.
Miklos, et al., Primary structure and function of a second essential member of the heterooligomeric TCP1 chaperonin complex of yeast, TCP1β, Proc. Natl. Acad. Sci., 91:2743-2747, 1994, USA.
Shipway, et al., Nanoparticles as structural and functional units in surface-confined architectures, Chem. Commun., The Royal Society of Chemistry 2001, 20:2035-2045.
Response to Nonfinal Action, dated Mar. 13, 2006, in U.S. Appl. No. 10/494,853, filed May 6, 2004. Response filed Sep. 13, 2006.
Response to Final Rejection, dated Dec. 14, 2006, in U.S. Appl. No. 10/494,853, filed May 6, 2004. Response filed Jun. 7, 2007.
Nonfinal Action, dated May 28, 2008, in U.S. Appl. No. 10/494,853, filed May 6, 2004.
Response to Nonfinal Action, dated May 28, 2008, in U.S. Appl. No. 10/494,853, filed May 6, 2004. Response filed Nov. 26, 2008.
Final Rejection, dated Feb. 20, 2009, in U.S. Appl. No. 10/494,853, filed May 6, 2004.
Response to Final Rejection, dated Feb. 20, 2009, in U.S. Appl. No. 10/494,853, filed May 6, 2004. Response filed Aug. 19, 2009.
Nonfinal Rejection mailed Oct. 19, 2009 in related U.S. Appl. No. 11/653,479.

* cited by examiner

|  | (375) 375 | 380 | 390 | | Section 12 408 |
|---|---|---|---|---|---|
| TF55 beta – S. shibatae | (349) | – – – – – – | D L G Y A L V E E R K V G E D K M V F V E G A K N P |  |  |
| GroEL – E. coli | (341) | A I Q G R V A Q | D L G T A E R V E Q V K V G E D Y M T F V T G C K N P |  |  |
| thermosome beta – T. acidophilum | (341) | – – – – – – | D L G T A E R V E Q V K V G E D Y M T F V T G C K N P |  |  |
| cyanobacterial HSP60 synechococcus | (339) | A V K A R V D Q | R R Q I E T E S S Y D K E K L Q E N F V F I T – V K D K |  |  |
| HSP60-4 M. acetivorans | (356) | – – – – – – | C D L G R A G S I K L E K K N G E N F V F I T – V K D K |  |  |
| HSP65 – M. tuberculosis | (339) | A I A G R V A Q | R Q E I E N S D S D Y D R E K L Q E D K M V F I E G A K L A G |  |  |
| thermosome alpha – A. pernix | (345) | – – – – – – | Y L G Y A E L V E E R K V G E D K M V F I E G A K N P |  |  |
| thermosome alpha – M. mazei | (341) | – – – – – – | D L G Y A G M V E E K D V T G S R M T F V T G C K D S |  |  |
| mitochondrial HSP60 – A. thaliana | (371) | G I E E R C E Q | R S A I E L S T S D Y D K E K L Q E R L A K L S G |  |  |
| TCP1 alpha – YEAST | (350) | F – – – E S S Y | L G L C D E V Q A K F S D D E C I L L K G T S K H |  |  |
| mitochondrial HSP60 – HUMAN | (311) | – – – – – – | – – – – – – – – – – – – – – – – – – – – – – – – – – D |  |  |
| mitochondrial HSP60 – MOUSE | (366) | H I E K R I Q E | T E Q L D I T T S E Y E K E K L N E R L A K L S D |  |  |
| TCP1 alpha – HUMAN | (340) | F – – – E A A M | G Q A E E V Q E R I C D D E L I L K N T K A R |  |  |
| TCP1 alpha – MOUSE | (340) | F – – – E V T M | L G Q A E E V Q E R I C D D E L I L K N T K A R |  |  |
| Consensus | (375) |  | L G A E V K D K L I A K A |  |  |

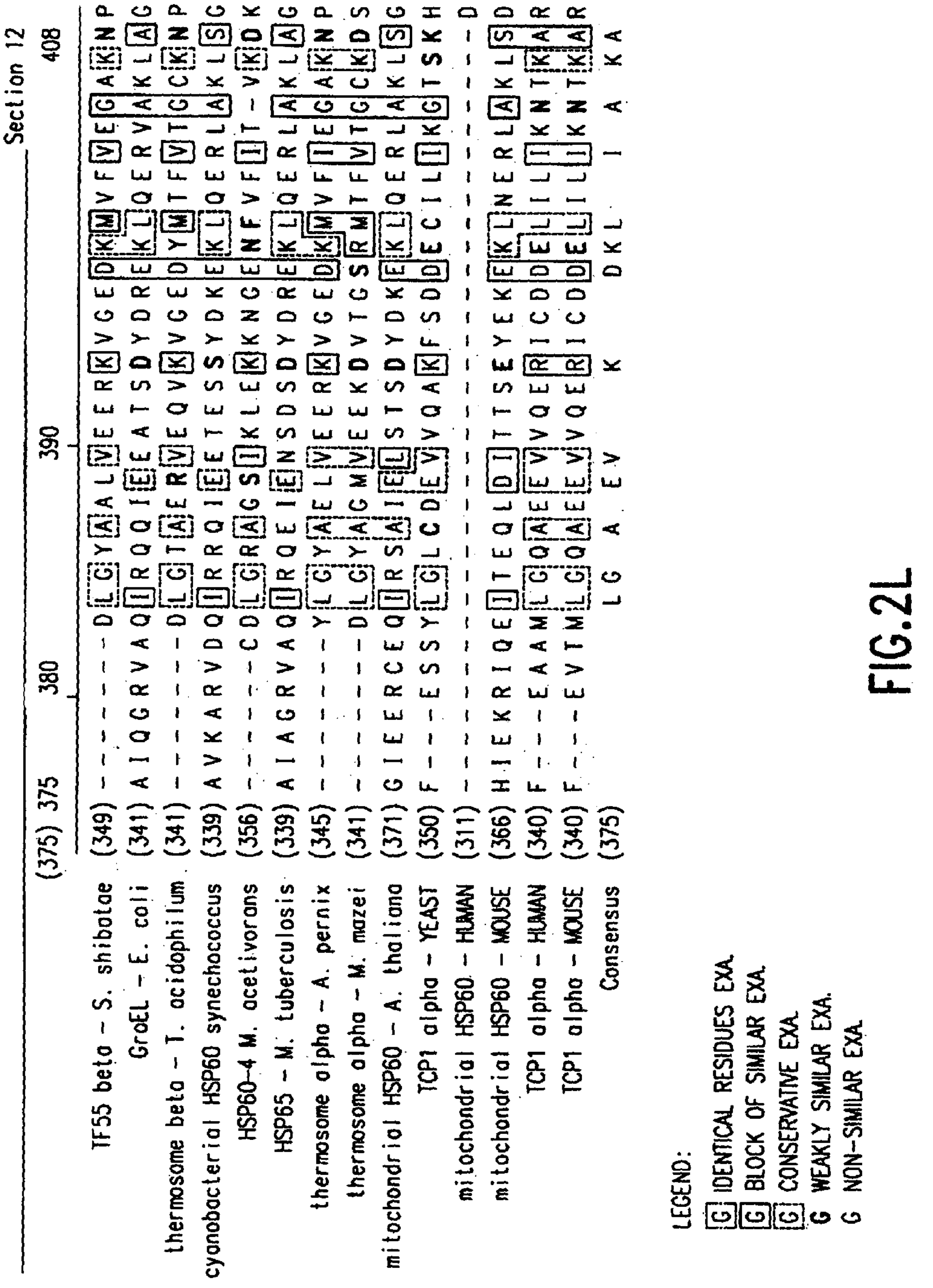

FIG.2L

LEGEND:
G IDENTICAL RESIDUES EXA.
G BLOCK OF SIMILAR EXA.
G CONSERVATIVE EXA.
G WEAKLY SIMILAR EXA.
G NON-SIMILAR EXA.

Section 15

| | | (477) 477 … 490 … 500 … 510 |
|---|---|---|
| TF55 beta - S. shibatae | (444) | E A Y A N A I E G L I M I L A E N A G L D P I D K L M Q L R S L H E |
| GroEL - E. coli | (441) | K V A L R A M E A P L R Q I V L N C G E E P S V V A N T V K G G D - |
| thermosome beta - T. acidophilum | (436) | E K F A D A I E E I P R A L A E N A G L D P I D I L L K L R A E H A |
| cyanobacterial HSP60 synechococcus | (441) | Q I V A R A L T A R L K R I A E N A G L N G A V I S E R V K E L P - |
| HSP60-4 M. acetivorans | (451) | Q A Y A E A L E K I P V I L A R N I G M N E I D A M A Q M R N S Y A |
| HSP65 - M. tuberculosis | (438) | N I V K V A L E A P L K Q I A F N S G L E P G V V A E K V R N L P - |
| thermosome alpha - A. pernix | (440) | E A Y A E A L E T I P T V L A E S A G M D A L E A L L K L R S L H S |
| thermosome alpha - M. mazei | (436) | T K F A E S L E V I P Q T L A E N A G L D P I D M L V E M R S Q H E |
| mitochondrial HSP60 - A. thaliana | (471) | Q I I Q N A L K T P V Y T I A S N A G V E G A V I V G K L L E Q D N |
| TCP1 alpha - YEAST | (449) | A E F A A A L L I I P K T L A V N A A K D S S E L V A K L R S Y H A |
| mitochondrial HSP60 - HUMAN | (378) | E I I K K T L K F P A M T I A K N A G V E V S L I V E K I M Q S S - |
| mitochondrial HSP60 - MOUSE | (466) | E I I K R A L K I P A M T I A K N A G V E G S L I V E K I L Q S S - |
| TCP1 alpha - HUMAN | (439) | A E F A R S L L V I P N T L A V N A A Q D S T D L V A K L R A F H N |
| TCP1 alpha - MOUSE | (439) | A E F A R S L L V I P N T L A V N A A Q D S T D L V A K L R A F H N |
| Consensus | (477) | F A A L E I P T L A N A G L D D I V K L R S H |

LEGEND:

G IDENTICAL RESIDUES EXA.
G BLOCK OF SIMILAR EXA.
G CONSERVATIVE EXA.
G WEAKLY SIMILAR EXA.
G NON-SIMILAR EXA.

FIG. 20

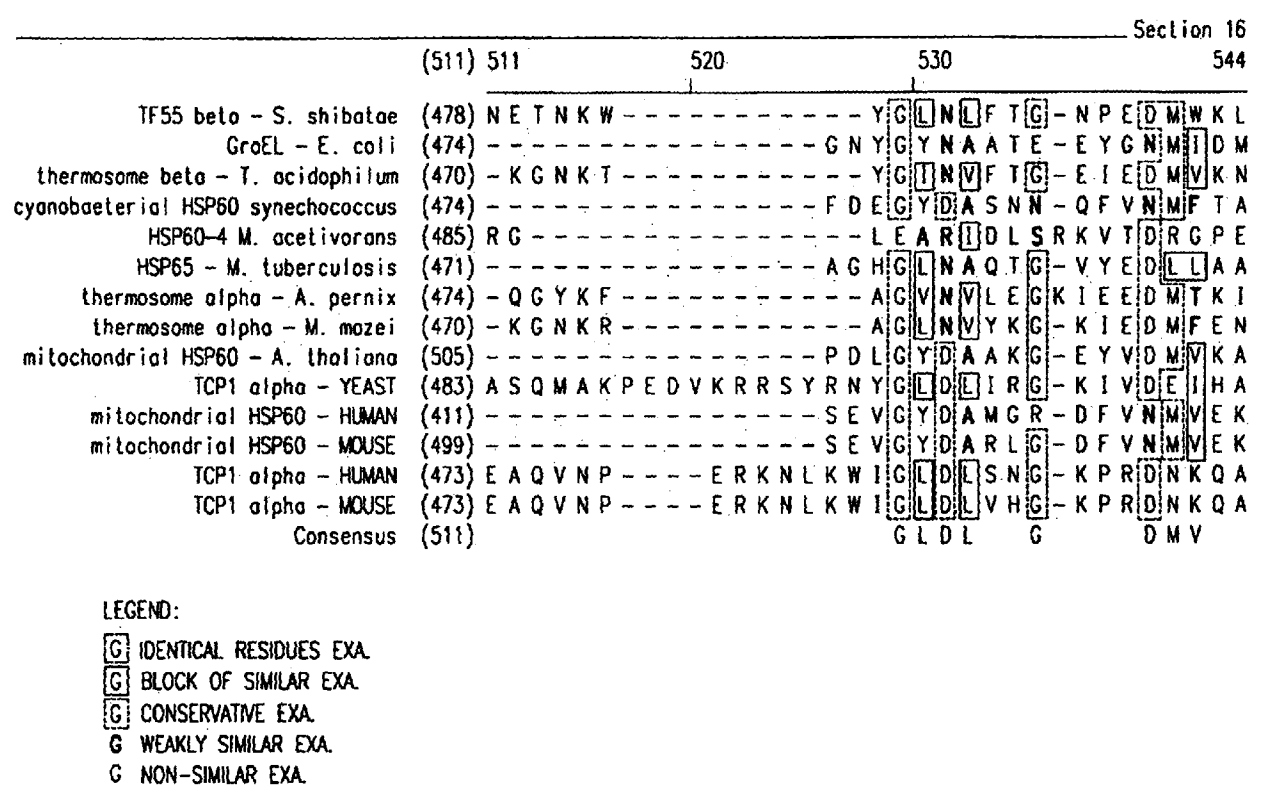

Section 16

| | | |
|---|---|---|
| | (511) | 511 520 530 544 |
| TF55 beta - S. shibatae | (478) | N E T N K W - - - - - - - - - - - Y G L N L F T G - N P E D M W K L |
| GroEL - E. coli | (474) | - - - - - - - - - - - - - - - G N Y G Y N A A T E - E Y G N M I D M |
| thermosome beta - T. acidophilum | (470) | - K G N K T - - - - - - - - - - - Y G I N V F T G - E I E D M V K N |
| cyanobacterial HSP60 synechococcus | (474) | - - - - - - - - - - - - - - - F D E G Y D A S N N - Q F V N M F T A |
| HSP60-4 M. acetivorans | (485) | R G - - - - - - - - - - - - - - - L E A R I D L S R K V T D R G P E |
| HSP65 - M. tuberculosis | (471) | - - - - - - - - - - - - - - - A G H G L N A Q T G - V Y E D L L A A |
| thermosome alpha - A. pernix | (474) | - Q G Y K F - - - - - - - - - - - A G V N V L E G K I E E D M T K I |
| thermosome alpha - M. mazei | (470) | - K G N K R - - - - - - - - - - - A G L N V Y K G - K I E D M F E N |
| mitochondrial HSP60 - A. thaliana | (505) | - - - - - - - - - - - - - - - P D L G Y D A A K G - E Y V D M V K A |
| TCP1 alpha - YEAST | (483) | A S Q M A K P E D V K R R S Y R N Y G L D L I R G - K I V D E I H A |
| mitochondrial HSP60 - HUMAN | (411) | - - - - - - - - - - - - - - - S E V G Y D A M G R - D F V N M V E K |
| mitochondrial HSP60 - MOUSE | (499) | - - - - - - - - - - - - - - - S E V G Y D A R L G - D F V N M V E K |
| TCP1 alpha - HUMAN | (473) | E A Q V N P - - - - E R K N L K W I G L D L S N G - K P R D N K Q A |
| TCP1 alpha - MOUSE | (473) | E A Q V N P - - - - E R K N L K W I G L D L V H G - K P R D N K Q A |
| Consensus | (511) | G L D L G D M V |

LEGEND:

- [G] IDENTICAL RESIDUES EXA.
- [G] BLOCK OF SIMILAR EXA.
- [G] CONSERVATIVE EXA.
- G WEAKLY SIMILAR EXA.
- G NON-SIMILAR EXA.

FIG.2P

|                                          |       | 545                  | 550              | 560                | Section 17 578     |
|------------------------------------------|-------|----------------------|------------------|--------------------|--------------------|
| TF55 beta – S. shibatae                  | (545) | G V I E P            | A L V K M N A I  | K A A T E A V      | T L V L R I D D T  | V A A G K          |
| GroEL – E. coli                          | (500) | G V I T E P          | A L V K M N A I  | K A A I E A V      | T L V L R I D D I  | V A A G K          |
| thermosome beta – T. acidophilum         | (492) | G V I E P P          | T K V I T R S A L | Q Y A A S V A G L  | M T T E C M V T D L | P                 |
| cyanobacterial HSP60 synechococcus       | (491) | G V I E P P          | A K V T R S A L Q | E S A S V A G L    | M I T R I D D V I  | A T K S            |
| HSP60-4 M. acetivorans                   | (492) | G I V D P P          | A K V T R S A L Q | N A A S I A A M    | V L T T E C I V D K | P                 |
| HSP65 – M. tuberculosis                  | (504) | – V Y D S            | A T V K K L A L   | I A G T G N A A S  | V L F L T T E A V  | V A D K P          |
| thermosome alpha – A. pernix             | (489) | G V A D P            | V K V T R S A L Q | V T K S A S E A A  | I S L K I D D V I  | A A A P            |
| thermosome alpha – M. mozei              | (496) | N V I Y E            | P V L V K I K Q V | I L N A A V D A L  | I M V L R I D D V  | I A S T G          |
| mitochondrial HSP60 – A. tholiana        | (491) | N V E P L            | R I K T Q A I N   | A A A I E A A I    | M V L T T E A V V  | V D L P            |
| TCP1 alpha – YEAST                       | (523) | G I L D P            | L K V I R T A L L | D K S A L E A C V  | A I L L T T A E V  | L V T E I P        |
| mitochondrial HSP60 – HUMAN              | (516) | G V L E P T          | I S K V K S L K F | A L L D D A S G V  | A S L L T T A E V  | V T E I P          |
| mitochondrial HSP60 – MOUSE              | (429) | G L I D P            | T K F V R T A L L | D K S A L E A C V  | A I L L T T A E V  | V T E I P          |
| TCP1 alpha – HUMAN                       | (517) | G L L D P T          | K V V R T A L L   | D A A G V A S L    | L T T A E A V V T E | I P                |
| TCP1 alpha – MOUSE                       | (502) | G V F E P T          | I V K V K S L K F | A T E A A I T      | I L R I D D L I K L | H P                |
| Consensus                                | (502) | G V F E P T          | I V K V K S L K F | A T E A A I T      | I L R I D D L I K L | H P                |
|                                          | (545) | G V I D P            | K V K R           | A L   A T E A A    | L I L R I D D V V   | P                  |

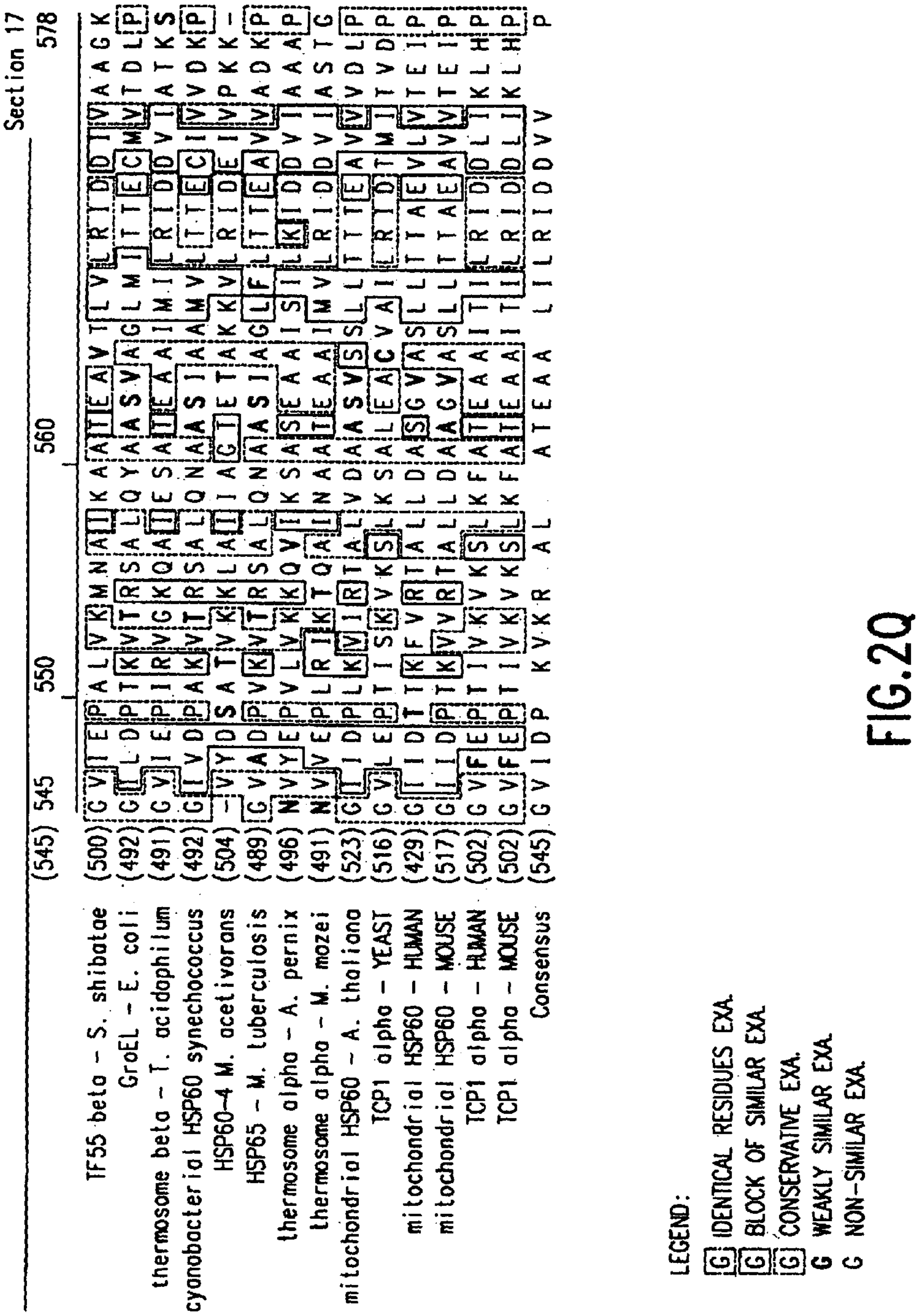

FIG.2Q

LEGEND:
- [G] IDENTICAL RESIDUES EXA.
- [G] BLOCK OF SIMILAR EXA.
- [G] CONSERVATIVE EXA.
- G WEAKLY SIMILAR EXA.
- G NON-SIMILAR EXA.

```
                                                               Section 18
                                     (579) 579        590              606
TF55 beta - S. shibatae              (534) KGGSEPGGKKEKEEKSSED----------
GroEL - E. coli                      (526) K-----NDAADLGAAGGMGGMGGMGGMM
thermosome beta - T. acidophilum     (525) SSSSSNPPKSGSSSESSED----------
cyanobacterial HSP60 synechococcus   (526) EP----KEKAPAGAGGGMGDFDY-----
HSP60-4 M. acetivorans               (536) ----------------------------
HSP65 - M. tuberculosis              (523) E-----KEKASVPGGGDMGGMDF-----
thermosome alpha - A. pernix         (530) PKKKEKKGKTGEEEEEEGGGSKFEF---
thermosome alpha - M. mazei          (525) GGRAAPGGMPGGDMEDMM----------
mitochondrial HSP60 - A. thaliana    (557) KDE--SESGAAGAGMGGMGGMDY-----
TCP1 alpha - YEAST                   (550) EPPKEDPHDH------------------
mitochondrial HSP60 - HUMAN          (463) KEEKDPGMGAMDGMGGGMGGGMF-----
mitochondrial HSP60 - MOUSE          (551) KEEKDPGMGAMGGMGGGMGGSML-----
TCP1 alpha - HUMAN                   (536) ES-KDDKHGSYEDAVHSGALND------
TCP1 alpha - MOUSE                   (536) ES-KDDKHGSYENAVHSGALDD------
Consensus                            (579)     D    A       MG
```

LEGEND:

G IDENTICAL RESIDUES EXA.

G BLOCK OF SIMILAR EXA.

G CONSERVATIVE EXA.

G WEAKLY SIMILAR EXA.

G NON-SIMILAR EXA.

FIG.2R

```
  1  MAS..........PVL LLKEGTSRTTGR DAL RNNI LAAK T LAEMLR   Alpha
  1  MATATVATTPEGI PVI ILKEGSSRT YGK EAL RANI AAVKAI EEALK   Beta
  1  MA...............YLL REGT CRSTGN EVI LNNI AVAKI LLEMLK  Gamma

 37  SSLGPKGLDKMLI DSF GDV TI TNDGATI VKDMEI QHPAAKLLVEAA    Alpha
 47  STYGPRGMDKMFV DSL GDI TI TNDGATI LDK MDL QHPTGKLLVQI A  Beta
 34  SSLGPKGLDKMLV EG- QDI TI TNDGATI VKNMEV QHPTAKLLI ETA   Gamma

 83  KAQDAEVGDGTTSAVVLAGA LLEKAESLLDQNI HPTI III EGYKKAY     Alpha
 93  KGQDEET ADGTKTAVI LAGEL AKKAEDLLYK EI HPTI VSGYKKAE     Beta
 79  KTVDTEVGDGTTSVVVLAGL LLEKAEDLLNQKI HPTVI IEGYRKAL       Gamma

129  TKAL ELL PQL GTRI DI RDL NSSVARDTL RKI AFTTL ASKFI AEGAE Alpha
139  EI ALKTI QDI AQPVSI ND-.....TDVL RKVAL TSL GSKAVAGARE   Beta
125  SSSL ELL KSI ADKI SP ED-.....RKI VHDL VYTTL SSKF FSTEHT Gamma

175  LNKI I DMVI DAI VNVAEP LPNGGY NVSL DL I KI DKKK GGSI EDSVL Alpha
179  Y--LADL VVKAVAQVAE- LRGDKWY VDL DNVQI VKKHGGSI NDTQL    Beta
165  LEKI I NL VI EASL AVL D- KRDGT YDL DI KNI KI VKVNGGEFDDSEL Gamma

221  VKGL VL DKEVVHPGMPRRV TKAKI AVL DAAL EVEKPEI SAKI SI TS Alpha
222  VYGI VVDKEVVHPGMPKRI ENAKI ALL DASL EVEKPEL DAEI RI ND  Beta
210  VNGI VVDKEPTNENMPKRA ENVKVML ADFPL KL EKTEI SMKL GI SD  Gamma

267  PEQI KAFL DEESKYL KDMVDKL ASI GANVVI CQKGI DDI AQHFL AK Alpha
268  PTQMHKFL EEEENI L KEKVDKI AAT GANVVI CQKGI DEVAQHYL AK  Beta
256  PTQI KGYL DEQT AYVKQMVDKI KAMGVKL FI TQKDI DEVASYL MGK  Gamma

313  KGI LAVRRVKRSDI EKLEKAL GARI I SSI KDATP DDL GYAEL VEER Alpha
314  KGI LAVRRAKKSDLEKLARATGGRVI SNI DELTS QDL GYAAL VEER    Beta
302  SGI I ALKNVKRSDI ELL SRATGAKI ASSMKDANE SDL GEAKL VEVR  Gamma

359  RVGNDKMVFI EGAKNL KAVNI LL RGSNDMAL DEAERSI NDAL HALR   Alpha
360  KVGEDKMVFVEGAKNP KSVSI LI RGGL ERVVDETERAL RDAL GTVA    Beta
348  NLGKNKYLFI QSDKA- KAVTVI I KGSNNMVT DEAERSL NDAFNSI R   Gamma

405  NI LLEPVI LPGGGAI EL EL AMKL REYARSVGGKEQL AI EAFADAL E Alpha
406  DVI RDGRAVAGGGAVEI EI AKRL RKYAP QVGGKEQL AI EAYANAI E  Beta
393  NLLLEPYI VAGGGAVEEEL AKRL RENAGKVP GKEQL AFNAFADAL E    Gamma

451  EI PTI LAETAGLEAI SALMDL RARHAKGLTN- TGVDVI GQKI VDDV   Alpha
452  GLI MI LAENAGLDPI DKL MQL RSLHENETNKWYGL NL FTGN- PEDM  Beta
439  EYVSI LSETAGMDPI SALTEI RHKHANGLKN- AGI DI VKARI YDNM   Gamma

496  YAL NI I EPI RVKA QVL KSATEAATAI LKI DDL I AAAPL KSEKKGGE Alpha
497  WKL GVI EPAL VKMNAI KAATEAVTL VL RI DDI VAAGKKGGSEPGGK  Beta
484  LELKVI DSLKVKE QVLKSATEAATAI LKI DDMI AAAPAKQQPQ...    Gamma

542  GSKEESGGEGGAGTPSLGD                                     Alpha
543  KEKEEKSSE.........D                                     Beta
527  - PQQPNPYL.........G                                    Gamma
```

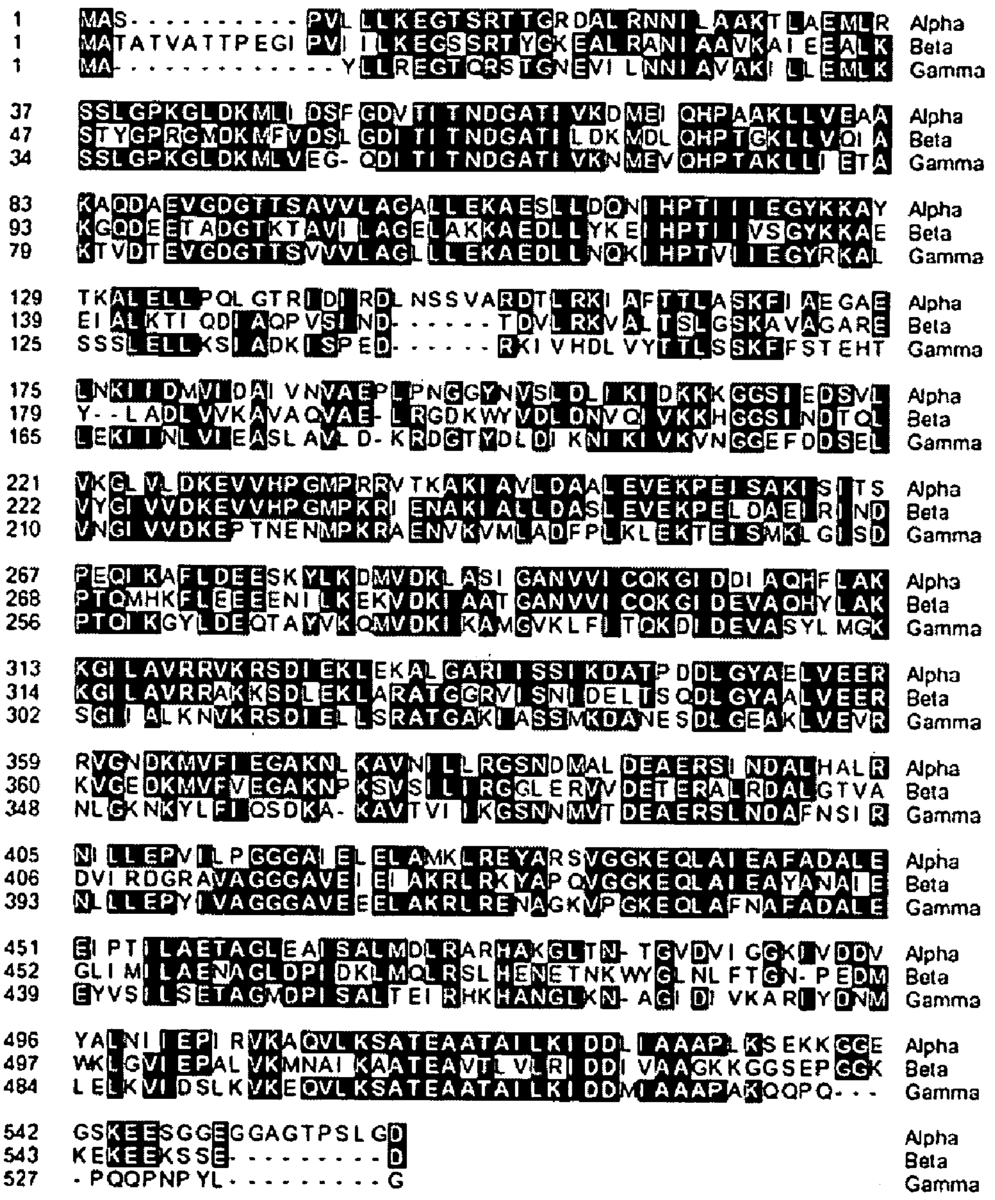

FIG. 15 atg gcc tat tta tta aga gaa gga aca cag aga tct act gga aac gag 48
Met Ala Tyr Leu Leu Arg Glu Gly Thr Gln Arg Ser Thr Gly Asn Glu
1 5 10 15 gta ata cta aac aac ata gct gta gcc aaa ata tta ctg gaa atg cta 96
Val Ile Leu Asn Asn Ile Ala Val Ala Lys Ile Leu Leu Glu Met Leu
20 25 30 aag tca agc cta ggt cct aag ggt tta gac aag atg tta gtt gag ggg 144
Lys Ser Ser Leu Gly Pro Lys Gly Leu Asp Lys Met Leu Val Glu Gly
35 40 45 caa gac att aca ata act aat gac ggt gcg aca ata gtt aaa aac atg 192
Gln Asp Ile Thr Ile Thr Asn Asp Gly Ala Thr Ile Val Lys Asn Met
50 55 60 gaa gtg cag cat cct act gca aaa tta ctc att gaa acc gct aaa act 240
Glu Val Gln His Pro Thr Ala Lys Leu Leu Ile Glu Thr Ala Lys Thr
65 70 75 80 gtt gat acc gag gta gga gat ggg aca act tca gta gtc gtt ctt gcc 288
Val Asp Thr Glu Val Gly Asp Gly Thr Thr Ser Val Val Val Leu Ala
85 90 95 ggg tta cta tta gaa aaa gct gag gat ttg ctg aat cag aag atc cat 336
Gly Leu Leu Leu Glu Lys Ala Glu Asp Leu Leu Asn Gln Lys Ile His
100 105 110 cca act gtc ata ata gaa ggt tat agg aag gct cta agt tca tca tta 384
Pro Thr Val Ile Ile Glu Gly Tyr Arg Lys Ala Leu Ser Ser Ser Leu
115 120 125 gaa ttg tta aaa agt att gca gat aag att agt cca gaa gat agg aag 432
Glu Leu Leu Lys Ser Ile Ala Asp Lys Ile Ser Pro Glu Asp Arg Lys
130 135 140 ata gtt cac gat cta gta tat act act cta tcg agt aag ttc ttc tca 480
Ile Val His Asp Leu Val Tyr Thr Thr Leu Ser Ser Lys Phe Phe Ser
145 150 155 160 aca gag cat act cta gag aag ata ata aat cta gtt att gaa gct tca 528
Thr Glu His Thr Leu Glu Lys Ile Ile Asn Leu Val Ile Glu Ala Ser
165 170 175 ttg gcg gta ttg gat aaa aga gat gga acc tat gat ctg gat att aag 576
Leu Ala Val Leu Asp Lys Arg Asp Gly Thr Tyr Asp Leu Asp Ile Lys
180 185 190 aat ata aag att gta aaa gtc aat ggt ggg gaa ttt gat gat agt gag 624
Asn Ile Lys Ile Val Lys Val Asn Gly Gly Glu Phe Asp Asp Ser Glu
195 200 205 ctt gta aat ggg atc gtt gta gat aag gag ccc acc aat gag aat atg 672
Leu Val Asn Gly Ile Val Val Asp Lys Glu Pro Thr Asn Glu Asn Met
210 215 220 ccg aaa agg gcg gaa aac gtt aag gta atg tta gct gac ttc cca tta 720
Pro Lys Arg Ala Glu Asn Val Lys Val Met Leu Ala Asp Phe Pro Leu
225 230 235 240 aaa ctt gaa aaa acg gaa att agc atg aag ctg gga ata agt gac ccc 768
Lys Leu Glu Lys Thr Glu Ile Ser Met Lys Leu Gly Ile Ser Asp Pro
245 250 255 act cag ata aag gga tac ttg gat gaa caa acg gca tat gtt aag caa 816
Thr Gln Ile Lys Gly Tyr Leu Asp Glu Gln Thr Ala Tyr Val Lys Gln
260 265 270

FIG. 16A

```
atg gtg gat aag ata aag gct atg ggc gtt aaa ttg ttt att aca caa        864
Met Val Asp Lys Ile Lys Ala Met Gly Val Lys Leu Phe Ile Thr Gln
        275                 280                 285
aag gac att gat gaa gtc gct tca tat tta atg gga aaa agt ggg ata        912
Lys Asp Ile Asp Glu Val Ala Ser Tyr Leu Met Gly Lys Ser Gly Ile
    290                 295                 300
ata gcg tta aag aac gta aag agg agt gac ata gag tta ctg agt aga        960
Ile Ala Leu Lys Asn Val Lys Arg Ser Asp Ile Glu Leu Leu Ser Arg
305                 310                 315                 320
gct act ggt gcg aaa att gca agt agc atg aaa gac gct aat gag agt       1008
Ala Thr Gly Ala Lys Ile Ala Ser Ser Met Lys Asp Ala Asn Glu Ser
                325                 330                 335
gat tta ggg gaa gct aaa tta gtg gag gtt aga aat tta gga aag aac       1056
Asp Leu Gly Glu Ala Lys Leu Val Glu Val Arg Asn Leu Gly Lys Asn
            340                 345                 350
aaa tac ctc ttc att caa tct gat aaa gct aaa gcg gtg act gta atc       1104
Lys Tyr Leu Phe Ile Gln Ser Asp Lys Ala Lys Ala Val Thr Val Ile
        355                 360                 365
ata aag ggc tcg aat aac atg gta act gat gaa gca gaa agg agt tta       1152
Ile Lys Gly Ser Asn Asn Met Val Thr Asp Glu Ala Glu Arg Ser Leu
    370                 375                 380
aat gac gcc ttt aac tcc ata aga aac ttg tta cta gaa ccc tat att       1200
Asn Asp Ala Phe Asn Ser Ile Arg Asn Leu Leu Leu Glu Pro Tyr Ile
385                 390                 395                 400
gtg gct ggt ggt ggt gct gta gag gag gag ttg gct aag agg tta agg       1248
Val Ala Gly Gly Gly Ala Val Glu Glu Glu Leu Ala Lys Arg Leu Arg
                405                 410                 415
gag aac gct gga aaa gtt ccc gga aag gag caa ttg gca ttt aat gca       1296
Glu Asn Ala Gly Lys Val Pro Gly Lys Glu Gln Leu Ala Phe Asn Ala
            420                 425                 430
ttt gcg gat gct ttg gag gag tac gtt tca ata cta tca gaa act gct       1344
Phe Ala Asp Ala Leu Glu Glu Tyr Val Ser Ile Leu Ser Glu Thr Ala
        435                 440                 445
ggc atg gat ccc ata agt gcg tta acc gaa ata aga cat aaa cat gca       1392
Gly Met Asp Pro Ile Ser Ala Leu Thr Glu Ile Arg His Lys His Ala
    450                 455                 460
aac ggg tta aag aat gct ggg att gac ata gtt aag gct aga att tac       1440
Asn Gly Leu Lys Asn Ala Gly Ile Asp Ile Val Lys Ala Arg Ile Tyr
465                 470                 475                 480
gat aac atg ctt gag ctt aaa gta atc gat tct cta aag gtt aag gaa       1488
Asp Asn Met Leu Glu Leu Lys Val Ile Asp Ser Leu Lys Val Lys Glu
                485                 490                 495
caa gtt tta aag agc gcc aca gaa gcc gct act gcg att tta aag atc       1536
Gln Val Leu Lys Ser Ala Thr Glu Ala Ala Thr Ala Ile Leu Lys Ile
            500                 505                 510
gac gac atg ata gca gca gct cct gca aag caa caa cct caa cca caa       1584
Asp Asp Met Ile Ala Ala Ala Pro Ala Lys Gln Gln Pro Gln Pro Gln
        515                 520                 525
cag cca aat cca tac tta ggt ta                                        1607
Gln Pro Asn Pro Tyr Leu Gly
    530                 535
```

FIG. 16B

ATGGCAataaatgatactgacgtacttaggaaagtagcattaacatcctt
aggcagtaaggcagtagcaggcgcacgagagtatttagctgaccttgtgg
ttaaagcagtggcacaagtagcagaattaagaggagataagtggtatgtt
gatctagataatgtacaaatagttaaaaaacatggtggtagcattaatga
tactcaattagtatacggcatagtagttgataaggaagttgtacatccgg
gcatgccaaagaggattgaaaatgctaagatagccctttagacgcttca
ttagaagttgagaaacccgaattggatgcagaaataagaattaacgatcc
aacacagatgcacaaattcttggaagaagaagaaaacatattgaaagaaa
aagtagataagattgcagctactggtgctaacgttgtaatagcgcagaaa
ggtatcgatgaagttgcacaacactatttagctaagaaaggtatattagc
tgttaggagagccaagaagagtgatttagagaaattagctagagctaccg
gaggtagagtcatatcaaatattgatgaattaacttcacaagatctaggt
tatgccgcattagtggaagagagaaaagtaggtgaagacaagatcgtatt
cgtagaaggtgcaaagaatccaaaatcagttagtatactaataagaggag
gattagagagagtagtagatgagactgaaagagctcttagggacgcttta
ggtacagtggcagatgtaataagggatggtagagcagtagctggtggtgg
agctgttgagatagagatagctaagagattaagaaagtatgccccacaag
ttggtggtaaagagcaattagcaattgaagcatatgctaatgcaatagag
ggtctcattatgatattggcggaaaacgcaggattagatcctatagacaa
attaatgcaattaagaagtcttcacgagaatgagaccaataaatggtatg
gacttaatttatttactggaaatccagaggatatgtggaaattaggtgtt
attgaaccggcactagtgaaaatgaatgcaattaaggctgcaacagaagc
agtaacattagtgttaagaatagatgatattgtaGGTGGTTCTGGTGGTA
CCatacctgtaataattttaaaagagggatcaagtagaacatatggaaaa
gaagctttaagggctaatattgctgcagtgaaagcaattgaagaggcatt
aaaaagcacctatggtccacgtggaatggataagattcttgttgatagct
taggagatattacaataacaaatgatggagccactattcttgataaaatg
gatttacaacacccaacaggtaagcttttagttcagatagctaaaggaca
agacgaggaaacagctgatggcactaaaactgctgtaattcttgctggag
aattagctaaaaaagcagaagatcttttatataaggagattcacccaaca
ataattgtaagcggatataagaaggcagaagaaattgcattaaagaccat
ccaagatatagcacaaccggtcagc

FIGURE 21A

MAINDTDVLRKVALTSLGSKAVAGAREYLADLVVKAVAQVAELRGDKWYV
DLDNVQIVKKHGGSINDTQLVYGIVVDKEVVHPGMPKRIENAKIALLDAS
LEVEKPELDAEIRINDPTQMHKFLEEEENILKEKVDKIAATGANVVIAQK
GIDEVAQHYLAKKGILAVRRAKKSDLEKLARATGGRVISNIDELTSQDLG
YAALVEERKVGEDKIVFVEGAKNPKSVSILIRGGLERVVDETERALRDAL
GTVADVIRDGRAVAGGGAVEIEIAKRLRKYAPQVGGKEQLAIEAYANAIE
GLIMILAENAGLDPIDKLMQLRSLHENETNKWYGLNLFTGNPEDMWKLGV
IEPALVKMNAIKAATEAVTLVLRIDDIVGGSGGTIPVIILKEGSSRTYGK
EALRANIAAVKAIEEALKSTYGPRGMDKILVDSLGDITITNDGATILDKM
DLQHPTGKLLVQIAKGQDEETADGTKTAVILAGELAKKAEDLLYKEIHPT
IIVSGYKKAEEIALKTIQDIAQPVS

FIGURE 21B

ATGGCAgatccaacacagatgcacaaattcttggaagaagaagaaaacat
attgaaagaaaaagtagataagattgcagctactggtgctaacgttgtaa
tagcgcagaaaggtatcgatgaagttgcacaacactatttagctaagaaa
ggtatattagctgttaggagagccaagaagagtgatttagagaaattagc
tagagctaccggaggtagagtcatatcaaatattgatgaattaacttcac
aagatctaggttatgccgcattagtggaagagagaaaagtaggtgaagac
aagatcgtattcgtagaaggtgcaaagaatccaaaatcagttagtatact
aataagaggaggattagagagagtagtagatgagactgaaagagctctta
gggacgctttaggtacagtggcagatgtaataagggatggtagagcagta
gctggtggtggagctgttgagatagagatagctaagagattaagaaagta
tgccccacaagttggtggtaaagagcaattagcaattgaagcatatgcta
atgcaatagagggtctcattatgatattggcggaaaacgcaggattagat
cctatagacaaattaatgcaattaagaagtcttcacgagaatgagaccaa
taaatggtatggacttaatttatttactggaaatccagaggatatgtgga
aattaggtgttattgaaccggcactagtgaaaatgaatgcaattaaggct
gcaacagaagcagtaacattagtgttaagaatagatgatattgtaGGTGG
TTCTGGTGGTACCatacctgtaataattttaaaagagggatcaagtagaa
catatggaaaagaagctttaagggctaatattgctgcagtgaaagcaatt
gaagaggcattaaaaagcacctatggtccacgtggaatggataagattct
tgttgatagcttaggagatattacaataacaaatgatggagccactattc
ttgataaaatggatttacaacacccaacaggtaagcttttagttcagata
gctaaaggacaagacgaggaaacagctgatggcactaaaactgctgtaat
tcttgctggagaattagctaaaaaagcagaagatcttttatataaggaga
ttcacccaacaataattgtaagcggatataagaaggcagaagaaattgca
ttaaagaccatccaagatatagcacaaccggtcagcataaatgatactga
cgtacttaggaaagtagcattaacatccttaggcagtaaggcagtagcag
gcgcacgagagtatttagctgaccttgtggttaaagcagtggcacaagta
gcagaattaagaggagataagtggtatgttgatctagataatgtacaaat
agttaaaaaacatggtggtagcattaatgatactcaattagtatacggca
tagtagttgataaggaagttgtacatccgggcatgccaaagaggattgaa
aatgctaagatagccctttagacgcttcattagaagttgagaaacccga
attggatgcagaaataagaattaac

FIGURE 22A

MADPTQMHKFLEEEENILKEKVDKIAATGANVVIAQKGIDEVAQHYLAKK
GILAVRRAKKSDLEKLARATGGRVISNIDELTSQDLGYAALVEERKVGED
KIVFVEGAKNPKSVSILIRGGLERVVDETERALRDALGTVADVIRDGRAV
AGGGAVEIEIAKRLRKYAPQVGGKEQLAIEAYANAIEGLIMILAENAGLD
PIDKLMQLRSLHENETNKWYGLNLFTGNPEDMWKLGVIEPALVKMNAIKA
ATEAVTLVLRIDDIVGGSGGTIPVIILKEGSSRTYGKEALRANIAAVKAI
EEALKSTYGPRGMDKILVDSLGDITITNDGATILDKMDLQHPTGKLLVQI
AKGQDEETADGTKTAVILAGELAKKAEDLLYKEIHPTIIVSGYKKAEEIA
LKTIQDIAQPVSINDTDVLRKVALTSLGSKAVAGAREYLADLVVKAVAQV
AELRGDKWYVDLDNVQIVKKHGGSINDTQLVYGIVVDKEVVHPGMPKRIE
NAKIALLDASLEVEKPELDAEIRIN

FIGURE 22B

ATGGCAatattagctgttaggagagccaagaagagtgatttagagaaatt
agctagagctaccggaggtagagtcatatcaaatattgatgaattaactt
cacaagatctaggttatgccgcattagtggaagagagaaaagtaggtgaa
gacaagatcgtattcgtagaaggtgcaaagaatccaaaatcagttagtat
actaataagaggaggattagagagagtagtagatgagactgaaagagctc
ttagggacgctttaggtacagtggcagatgtaataagggatggtagagca
gtagctggtggtggagctgttgagatagagatagctaagagattaagaaa
gtatgccccacaagttggtggtaaagagcaattagcaattgaagcatatg
ctaatgcaatagagggtctcattatgatattggcggaaaacgcaggatta
gatcctatagacaaattaatgcaattaagaagtcttcacgagaatgagac
caataaatggtatggacttaatttatttactggaaatccagaggatatgt
ggaaattaggtgttattgaaccggcactagtgaaaatgaatgcaattaag
gctgcaacagaagcagtaacattagtgttaagaatagatgatattgtaGG
TGGTTCTGGTGGTACCatacctgtaataattttaaaagagggatcaagta
gaacatatggaaaagaagctttaagggctaatattgctgcagtgaaagca
attgaagaggcattaaaaagcacctatggtccacgtggaatggataagat
tcttgttgatagcttaggagatattacaataacaaatgatggagccacta
ttcttgataaaatggatttacaacacccaacaggtaagcttttagttcag
atagctaaaggacaagacgaggaaacagctgatggcactaaaactgctgt
aattcttgctggagaattagctaaaaaagcagaagatcttttatataagg
agattcacccaacaataattgtaagcggatataagaaggcagaagaaatt
gcattaaagaccatccaagatatagcacaaccggtcagcataaatgatac
tgacgtacttaggaaagtagcattaacatccttaggcagtaaggcagtag
caggcgcacgagagtatttagctgaccttgtggttaaagcagtggcacaa
gtagcagaattaagaggagataagtggtatgttgatctagataatgtaca
aatagttaaaaaacatggtggtagcattaatgatactcaattagtatacg
gcatagtagttgataaggaagttgtacatccgggcatgccaaagaggatt
gaaaatgctaagatagccctttagacgcttcattagaagttgagaaacc
cgaattggatgcagaaataagaattaacgatccaacacagatgcacaaat
tcttggaagaagaagaaaacatattgaaagaaaaagtagataagattgca
gctactggtgctaacgttgtaatagcgcagaaaggtatcgatgaagttgc
acaacactatttagctaagaaaggt

FIGURE 23A

MAILAVRRAKKSDLEKLARATGGRVISNIDELTSQDLGYAALVEERKVGE
DKIVFVEGAKNPKSVSILIRGGLERVVDETERALRDALGTVADVIRDGRA
VAGGGAVEIEIAKRLRKYAPQVGGKEQLAIEAYANAIEGLIMILAENAGL
DPIDKLMQLRSLHENETNKWYGLNLFTGNPEDMWKLGVIEPALVKMNAIK
AATEAVTLVLRIDDIVGGSGGTIPVIILKEGSSRTYGKEALRANIAAVKA
IEEALKSTYGPRGMDKILVDSLGDITITNDGATILDKMDLQHPTGKLLVQ
IAKGQDEETADGTKTAVILAGELAKKAEDLLYKEIHPTIIVSGYKKAEEI
ALKTIQDIAQPVSINDTDVLRKVALTSLGSKAVAGAREYLADLVVKAVAQ
VAELRGDKWYVDLDNVQIVKKHGGSINDTQLVYGIVVDKEVVHPGMPKRI
ENAKIALLDASLEVEKPELDAEIRINDPTQMHKFLEEEENILKEKVDKIA
ATGANVVIAQKGIDEVAQHYLAKKG

FIGURE 23B

ATGGCAaataaatggtatggacttaatttatttactggaaatccagagga
tatgtggaaattaggtgttattgaaccggcactagtgaaaatgaatgcaa
ttaaggctgcaacagaagcagtaacattagtgttaagaatagatgatatt
gtaGGTGGTTCTGGTGGTACCatacctgtaataattttaaaagagggatc
aagtagaacatatggaaaagaagctttaagggctaatattgctgcagtga
aagcaattgaagaggcattaaaaagcacctatggtccacgtggaatggat
aagattcttgttgatagcttaggagatattacaataacaaatgatggagc
cactattcttgataaaatggatttacaacacccaacaggtaagcttttag
ttcagatagctaaaggacaagacgaggaaacagctgatggcactaaaact
gctgtaattcttgctggagaattagctaaaaagcagaagatcttttata
taaggagattcacccaacaataattgtaagcggatataagaaggcagaag
aaattgcattaaagaccatccaagatatagcacaaccggtcagcataaat
gatactgacgtacttaggaaagtagcattaacatccttaggcagtaaggc
agtagcaggcgcacgagagtatttagctgaccttgtggttaaagcagtgg
cacaagtagcagaattaagaggagataagtggtatgttgatctagataat
gtacaaatagttaaaaacatggtggtagcattaatgatactcaattagt
atacggcatagtagttgataaggaagttgtacatccgggcatgccaaaga
ggattgaaaatgctaagatagccctttagacgcttcattagaagttgag
aaacccgaattggatgcagaaataagaattaacgatccaacacagatgca
caaattcttggaagaagaagaaaacatattgaaagaaaaagtagataaga
ttgcagctactggtgctaacgttgtaatagcgcagaaaggtatcgatgaa
gttgcacaacactatttagctaagaaaggtatattagctgttaggagagc
caagaagagtgatttagagaaattagctagagctaccggaggtagagtca
tatcaaatattgatgaattaacttcacaagatctaggttatgccgcatta
gtggaagagagaaaagtaggtgaagacaagatcgtattcgtagaaggtgc
aaagaatccaaaatcagttagtatactaataagaggaggattagagagag
tagtagatgagactgaaagagctcttagggacgctttaggtacagtggca
gatgtaataagggatggtagagcagtagctggtggtggagctgttgagat
agagatagctaagagattaagaaagtatgccccacaagttggtggtaaag
agcaattagcaattgaagcatatgctaatgcaatagagggtctcattatg
atattggcggaaaacgcaggattagatcctatagacaaattaatgcaatt
aagaagtcttcacgagaatgagacc

FIGURE 24A

MANKWYGLNLFTGNPEDMWKLGVIEPALVKMNAIKAATEAVTLVLRIDDI
VGGSGGTIPVIILKEGSSRTYGKEALRANIAAVKAIEEALKSTYGPRGMD
KILVDSLGDITITNDGATILDKMDLQHPTGKLLVQIAKGQDEETADGTKT
AVILAGELAKKAEDLLYKEIHPTIIVSGYKKAEEIALKTIQDIAQPVSIN
DTDVLRKVALTSLGSKAVAGAREYLADLVVKAVAQVAELRGDKWYVDLDN
VQIVKKHGGSINDTQLVYGIVVDKEVVHPGMPKRIENAKIALLDASLEVE
KPELDAEIRINDPTQMHKFLEEEENILKEKVDKIAATGANVVIAQKGIDE
VAQHYLAKKGILAVRRAKKSDLEKLARATGGRVISNIDELTSQDLGYAAL
VEERKVGEDKIVFVEGAKNPKSVSILIRGGLERVVDETERALRDALGTVA
DVIRDGRAVAGGGAVEIEIAKRLRKYAPQVGGKEQLAIEAYANAIEGLIM
ILAENAGLDPIDKLMQLRSLHENET

FIGURE 24B

```
ATGGCAttaggtgttattgaaccggcactagtgaaaatgaatgcaattaa
ggctgcaacagaagcagtaacattagtgttaagaatagatgatattgtaG
GTGGTTCTGGTGGTACCatacctgtaataattttaaaagagggatcaagt
agaacatatggaaaagaagctttaagggctaatattgctgcagtgaaagc
aattgaagaggcattaaaaagcacctatggtccacgtggaatggataaga
ttcttgttgatagcttaggagatattacaataacaaatgatggagccact
attcttgataaaatggatttacaacacccaacaggtaagcttttagttca
gatagctaaaggacaagacgaggaaacagctgatggcactaaaactgctg
taattcttgctggagaattagctaaaaagcagaagatcttttatataag
gagattcacccaacaataattgtaagcggatataagaaggcagaagaaat
tgcattaaagaccatccaagatatagcacaaccggtcagcataaatgata
ctgacgtacttaggaaagtagcattaacatccttaggcagtaaggcagta
gcaggcgcacgagagtatttagctgaccttgtggttaaagcagtggcaca
agtagcagaattaagaggagataagtggtatgttgatctagataatgtac
aaatagttaaaaaacatggtggtagcattaatgatactcaattagtatac
ggcatagtagttgataaggaagttgtacatccgggcatgccaaagaggat
tgaaaatgctaagatagccctttttagacgcttcattagaagttgagaaac
ccgaattggatgcagaaataagaattaacgatccaacacagatgcacaaa
ttcttggaagaagaagaaaacatattgaaagaaaaagtagataagattgc
agctactggtgctaacgttgtaatagcgcagaaaggtatcgatgaagttg
cacaacactatttagctaagaaaggtatattagctgttaggagagccaag
aagagtgatttagagaaattagctagagctaccggaggtagagtcatatc
aaatattgatgaattaacttcacaagatctaggttatgccgcattagtgg
aagagagaaaagtaggtgaagacaagatcgtattcgtagaaggtgcaaag
aatccaaaatcagttagtatactaataagaggaggattagagagagtagt
agatgagactgaaagagctcttagggacgctttaggtacagtggcagatg
taataagggatggtagagcagtagctggtggtggagctgttgagatagag
atagctaagagattaagaaagtatgccccacaagttggtggtaaagagca
attagcaattgaagcatatgctaatgcaatagagggtctcattatgatat
tggcggaaaacgcaggattagatcctatagacaaattaatgcaattaaga
agtcttcacgagaatgagaccaataaatggtatggacttaatttatttac
tggaaatccagaggatatgtggaaa
```

FIGURE 25A

MALGVIEPALVKMNAIKAATEAVTLVLRIDDIVGGSGGTIPVIILKEGSS
RTYGKEALRANIAAVKAIEEALKSTYGPRGMDKILVDSLGDITITNDGAT
ILDKMDLQHPTGKLLVQIAKGQDEETADGTKTAVILAGELAKKAEDLLYK
EIHPTIIVSGYKKAEEIALKTIQDIAQPVSINDTDVLRKVALTSLGSKAV
AGAREYLADLVVKAVAQVAELRGDKWYVDLDNVQIVKKHGGSINDTQLVY
GIVVDKEVVHPGMPKRIENAKIALLDASLEVEKPELDAEIRINDPTQMHK
FLEEEENILKEKVDKIAATGANVVIAQKGIDEVAQHYLAKKGILAVRRAK
KSDLEKLARATGGRVISNIDELTSQDLGYAALVEERKVGEDKIVFVEGAK
NPKSVSILIRGGLERVVDETERALRDALGTVADVIRDGRAVAGGGAVEIE
IAKRLRKYAPQVGGKEQLAIEAYANAIEGLIMILAENAGLDPIDKLMQLR
SLHENETNKWYGLNLFTGNPEDMWK

FIGURE 25B

ATGGCAgatccaacacagatgcacaaattcttggaagaagaagaaacat
attgaaagaaaaagtagataagattgcagctactggtgctaacgttgtaa
tagcgcagaaaggtatcgatgaagttgcacaacactatttagctaagaaa
ggtatattagctgttaggagagccaagaagagtgatttagagaaattagc
tagagctaccggaggtagagtcatatcaaatattgatgaattaacttcac
aagatctaggttatgccgcattagtggaagagagaaaagtaggtgaagac
aagatcgtattcgtagaaggtgcaaagaatccaaaatcagttagtatact
aataagaggaggattagagagagtagtagatgagactgaaagagctctta
gggacgctttaggtacagtggcagatgtaataagggatggtagagcagta
gctggtggtggagctgttgagatagagatagctaagagattaagaaagta
tgccccacaagttggtggtaaagagcaattagcaattgaagcatatgcta
atgcaatagagggtctcattatgatattggcggaaaacgcaggattagat
cctatagacaaattaatgcaattaagaagtcttcacgagaatgagaccaa
taaatggtatggacttaatttatttactggaaatccagaggatatgtgga
aattaggtgttattgaaccggcactagtgaaaatgaatgcaattaaggct
gcaacagaagcagtaacattagtgttaagaatagatgatattgtaGGTGG
TTCTGGTGGTACCatacctgtaataattttaaaagagggatcaagtagaa
catatggaaaagaagctttaagggctaatattgctgcagtgaaagcaatt
gaagaggcattaaaaagcacctatggtccacgtggaatggataagattct
tgttgatagcttaggagatattacaataacaaatgatggagccactattc
ttgataaaatggatttacaacacccaacaggtaagcttttagttcagata
gctaaaggacaagacgaggaaacagctgatggcactaaaactgctgtaat
tcttgctggagaattagctaaaaagcagaagatcttttatataaggaga
ttcacccaacaataattgtaagcggatataagaaggcagaagaaattgca
ttaaagaccatccaagatatagcacaaccggtcagcataaatgatactga
cgtacttaggaaagtagcattaacatccttaggcagtaaggcagtagcag
gcgcacgagagtatttagctgaccttgtggttaaagcagtggcacaagta
gcagaattaagaggagataagtggtatgttgatctagataatgtacaaat
agttaaaaaacatggtggtagcattaatgatactcaattagtatacggca

FIGURE 26A-1 tagtagttgataaggaagttgtacatccgggcatgccaaagaggattgaa
aatgctaagatagcccttttagacgcttcattagaagttgagaaacccga
attggatgcagaaataagaattaacggcagcggcggatccggggtgagca
agggcgaggagctgttcaccggggtggtgcccatcctggtcgagctggac
ggcgacgtaaacggccacaagttcagcgtgtccggcgagggcgagggcga
tgccacctacggcaagctgaccctgaagttcatctgcaccaccggcaagc
tgcccgtgccctggcccaccctcgtgaccaccttcggctacggcctgcag
tgcttcgcccgctaccccgaccacatgaagcagcacgacttcttcaagtc
cgccatgcccgaaggctacgtccaggagcgcaccatcttcttcaaggacg
acggcaactacaagacccgcgccgaggtgaagttcgagggcgacaccctg
gtgaaccgcatcgagctgaagggcatcgacttcaaggaggacggcaacat
cctggggcacaagctggagtacaacGGCGGTACCGGATCTGGAGGTGAGC
TCaacagccacaacgtctatatcatggccgacaagcagaagaacggcatc
aaggtgaacttcaagatccgccacaacatcgaggacggcagcgtgcagct
cgccgaccactaccagcagaacacccccatcggcgacggccccgtgctgc
tgcccgacaaccactacctgagctaccagtccgccctgagcaaagacccc
aacgagaagcgcgatcacatggtcctgctggagttcgtgaccgccgccgg
gatcactctcggcatggacgagctgtacaagcaccaccatcaccatcac

FIGURE 26A-2

MADPTQMHKFLEEEENILKEKVDKIAATGANVVIAQKGIDEVAQHYLAKK
GILAVRRAKKSDLEKLARATGGRVISNIDELTSQDLGYAALVEERKVGED
KIVFVEGAKNPKSVSILIRGGLERVVDETERALRDALGTVADVIRDGRAV
AGGGAVEIEIAKRLRKYAPQVGGKEQLAIEAYANAIEGLIMILAENAGLD
PIDKLMQLRSLHENETNKWYGLNLFTGNPEDMWKLGVIEPALVKMNAIKA
ATEAVTLVLRIDDIVGGSGGTIPVIILKEGSSRTYGKEALRANIAAVKAI
EEALKSTYGPRGMDKILVDSLGDITITNDGATILDKMDLQHPTGKLLVQI
AKGQDEETADGTKTAVILAGELAKKAEDLLYKEIHPTIIVSGYKKAEEIA
LKTIQDIAQPVSINDTDVLRKVALTSLGSKAVAGAREYLADLVVKAVAQV
AELRGDKWYVDLDNVQIVKKHGGSINDTQLVYGIVVDKEVVHPGMPKRIE
NAKIALLDASLEVEKPELDAEIRINGSGGSGVSKGEELFTGVVPILVELD
GDVNGHKFSVSGEGEGDATYGKLTLKFICTTGKLPVPWPTLVTTFGYGLQ
CFARYPDHMKQHDFFKSAMPEGYVQERTIFFKDDGNYKTRAEVKFEGDTL
VNRIELKGIDFKEDGNILGHKLEYNGGTGSGGELNSHNVYIMADKQKNGI
KVNFKIRHNIEDGSVQLADHYQQNTPIGDGPVLLPDNHYLSYQSALSKDP
NEKRDHMVLLEFVTAAGITLGMDELYKHHHHHH

FIGURE 26B

ATGGCAaataaatggtatggacttaatttatttactggaaatccagagga
tatgtggaaattaggtgttattgaaccggcactagtgaaaatgaatgcaa
ttaaggctgcaacagaagcagtaacattagtgttaagaatagatgatatt
gtaGGTGGTTCTGGTGGTACCatacctgtaataattttaaaagagggatc
aagtagaacatatggaaaagaagctttaagggctaatattgctgcagtga
aagcaattgaagaggcattaaaaagcacctatggtccacgtggaatggat
aagattcttgttgatagcttaggagatattacaataacaaatgatggagc
cactattcttgataaaatggatttacaacacccaacaggtaagcttttag
ttcagatagctaaggacaagacgaggaaacagctgatggcactaaaact
gctgtaattcttgctggagaattagctaaaaagcagaagatcttttata
taaggagattcacccaacaataattgtaagcggatataagaaggcagaag
aaattgcattaaagaccatccaagatatagcacaaccggtcagcataaat
gatactgacgtacttaggaaagtagcattaacatccttaggcagtaaggc
agtagcaggcgcacgagagtatttagctgaccttgtggttaaagcagtgg
cacaagtagcagaattaagaggagataagtggtatgttgatctagataat
gtacaaatagttaaaaacatggtggtagcattaatgatactcaattagt
atacggcatagtagttgataaggaagttgtacatccgggcatgccaaaga
ggattgaaaatgctaagatagccctttagacgcttcattagaagttgag
aaacccgaattggatgcagaaataagaattaacgatccaacacagatgca
caaattcttggaagaagaagaaaacatattgaaagaaaaagtagataaga
ttgcagctactggtgctaacgttgtaatagcgcagaaaggtatcgatgaa
gttgcacaacactatttagctaagaaaggtatattagctgttaggagagc
caagaagagtgatttagagaaattagctagagctaccggaggtagagtca
tatcaaatattgatgaattaacttcacaagatctaggttatgccgcatta
gtggaagagagaaaagtaggtgaagacaagatcgtattcgtagaaggtgc
aaagaatccaaaatcagttagtatactaataagaggaggattagagagag
tagtagatgagactgaaagagctcttagggacgctttaggtacagtggca
gatgtaataagggatggtagagcagtagctggtggtggagctgttgagat
agagatagctaagagattaagaaagtatgccccacaagttggtggtaaag
agcaattagcaattgaagcatatgctaatgcaatagagggtctcattatg

FIGURE 27A-1 atattggcggaaaacgcaggattagatcctatagacaaattaatgcaatt
aagaagtcttcacgagaatgagaccggctctggcggatccggatccgggg
tgagcaagggcgaggagctgttcaccggggtggtgcccatcctggtcgag
ctggacggcgacgtaaacggccacaagttcagcgtgtccggcgagggcga
gggcgatgccacctacggcaagctgaccctgaagttcatctgcaccaccg
gcaagctgcccgtgccctggcccaccctcgtgaccaccttcggctacggc
ctgcagtgcttcgcccgctaccccgaccacatgaagcagcacgacttctt
caagtccgccatgcccgaaggctacgtccaggagcgcaccatcttcttca
aggacgacggcaactacaagacccgcgccgaggtgaagttcgagggcgac
accctggtgaaccgcatcgagctgaagggcatcgacttcaaggaggacgg
caacatcctggggcacaagctggagtacaacGGCGGTACCGGATCTGGAG
GTGAGCTCaacagccacaacgtctatatcatggccgacaagcagaagaac
ggcatcaaggtgaacttcaagatccgccacaacatcgaggacggcagcgt
gcagctcgccgaccactaccagcagaacacccccatcggcgacggccccg
tgctgctgcccgacaaccactacctgagctaccagtccgccctgagcaaa
gaccccaacgagaagcgcgatcacatggtcctgctggagttcgtgaccgc
cgccgggatcactctcggcatggacgagctgtacaagcaccaccatcacc
atcac

FIGURE 27A-2

MANKWYGLNLFTGNPEDMWKLGVIEPALVKMNAIKAATEAVTLVLRIDDI
VGGSGGTIPVIILKEGSSRTYGKEALRANIAAVKAIEEALKSTYGPRGMD
KILVDSLGDITITNDGATILDKMDLQHPTGKLLVQIAKGQDEETADGTKT
AVILAGELAKKAEDLLYKEIHPTIIVSGYKKAEEIALKTIQDIAQPVSIN
DTDVLRKVALTSLGSKAVAGAREYLADLVVKAVAQVAELRGDKWYVDLDN
VQIVKKHGGSINDTQLVYGIVVDKEVVHPGMPKRIENAKIALLDASLEVE
KPELDAEIRINDPTQMHKFLEEEENILKEKVDKIAATGANVVIAQKGIDE
VAQHYLAKKGILAVRRAKKSDLEKLARATGGRVISNIDELTSQDLGYAAL
VEERKVGEDKIVFVEGAKNPKSVSILIRGGLERVVDETERALRDALGTVA
DVIRDGRAVAGGGAVEIEIAKRLRKYAPQVGGKEQLAIEAYANAIEGLIM
ILAENAGLDPIDKLMQLRSLHENETGSGGSGSGVSKGEELFTGVVPILVE
LDGDVNGHKFSVSGEGEGDATYGKLTLKFICTTGKLPVPWPTLVTTFGYG
LQCFARYPDHMKQHDFFKSAMPEGYVQERTIFFKDDGNYKTRAEVKFEGD
TLVNRIELKGIDFKEDGNILGHKLEYNGGTGSGGELNSHNVYIMADKQKN
GIKVNFKIRHNIEDGSVQLADHYQQNTPIGDGPVLLPDNHYLSYQSALSK
DPNEKRDHMVLLEFVTAAGITLGMDELYKHHHHHH

FIGURE 27B

ATGGcgagcccggtcttgttattgaaagagggaacgagtagaactactgg
tagagatgcgttaaggaataatatacttgctgcaaagacactagccgaaa
tgttaaggagtagtttaggtcctaaaggtcttgataaaatgttaattgat
agtttcggtgacgtaaccataactaatgatggtgctacaatagtaaagga
tatggagatacagcatccagcagcaaagctattagtagaagcagctaaag
cacaagatgctgaagtaggtgatggtactacaagcgctgtagtattagct
ggtgctctattggagaaagctgaaagtttattggatcaaaatatacatcc
aacaataattattgaggggtataagaaggcatataccaaggccttggagt
tacttccacagttaggaactaggatcgatataagggatttgaattcttca
gttgctagggatactctaagaaaaatagcatttactacactagcaagtaa
gtttattgcagaaggtgctgaattaaataaaataattgacatggtaatag
acgcaatagttaatgttgcagaacctctacctaatggtgggtacaatgtg
agtttagacttaataaagatagataagaagaaaggtggaagtatagagga
tagcgtcttagttaaaggactagtattagataaggaggttgtgcaccctg
gaatgcctagaagagtcactaaagccaagatagctgttttggatgcagca
ttagaggtagaaaagcctgaaatctcagctaagataagtataacatcacc
agagcaaatcaaggctttcttagatgaggaatccaaatatcttaaggaca
tggttgataaactagcgtcaataggcgctaacgttgtaatatgccagaaa
ggtattgatgatatcgcacagcacttcttagctaagaaaggtatattggc
tgtaagaagggttaagaggagcgatatagagaaattagagaaggcattag
gcgcgagaataataagcagtattaaagacgctactcccgatgatttagga
tacgccgaattagttgaggaaaggagagttggaaatgacaaaatggtatt
tatagaaggtgctaagaatctgaaggccgtgaatatcttgttaagaggtt
caaatgatatggcattagatgaggctgagaggagtataaatgatgcattg
catgctctgaggaacatattattagagccagtaatattgccaggtggtgg
cgctatcgagttagaattagcgatgaaattaagagagtatgctagaagtg
taggaggtaaggagcaattagctatagaagcatttgcagatgcattagag
gagatacctatgattttagctgaaactgcagggctggaggctatatctgc
actaatggacttaagagctagacacgctaagggattaaccaatactggtg
tagatgtaataggtgggaagatcgtagacgatgtatatgccttaaacatc
attgagcctataagagtaaaggctcaagtgttaaagagcgcaacagaggc
ggctacagcaatattaaagattgatgacctaatagctgcagctccattaa
agagcgagaagaaaggtggagaaggaagtaaagaagaaagtggtggagaa
ggaggagctggtactccatctttaggagac

FIGURE 28A

MASPVLLLKEGTSRTTGRDALRNNILAAKTLAEMLRSSLGPKGLDKMLID
SFGDVTITNDGATIVKDMEIQHPAAKLLVEAAKAQDAEVGDGTTSAVVLA
GALLEKAESLLDQNIHPTIIIEGYKKAYTKALELLPQLGTRIDIRDLNSS
VARDTLRKIAFTTLASKFIAEGAELNKIIDMVIDAIVNVAEPLPNGGYNV
SLDLIKIDKKKGGSIEDSVLVKGLVLDKEVVHPGMPRRVTKAKIAVLDAA
LEVEKPEISAKISITSPEQIKAFLDEESKYLKDMVDKLASIGANVVICQK
GIDDIAQHFLAKKGILAVRRVKRSDIEKLEKALGARIISSIKDATPDDLG
YAELVEERRVGNDKMVFIEGAKNLKAVNILLRGSNDMALDEAERSINDAL
HALRNILLEPVILPGGGAIELELAMKLREYARSVGGKEQLAIEAFADALE
EIPMILAETAGLEAISALMDLRARHAKGLTNTGVDVIGGKIVDDVYALNI
IEPIRVKAQVLKSATEAATAILKIDDLIAAAPLKSEKKGGEGSKEESGGE
GGAGTPSLGD

FIGURE 28B atggtattcgtagaaggtgcaaagaatccaaaatcagttagtatactaat
aagaggaggattagagagagtagtagatgagactgaaagagctcttaggg
acgctttaggtacagtggcagatgtaataagggatggtagagcagtagct
ggtggtggagctgttgagatagagatagctaagagattaagaaagtatgc
cccacaagttggtggtaaagagcaattagcaattgaagcatatgctaatg
caatagaaggacttatcatgatattggcggaaaacgcaggattagatcct
atagacaaattaatgcaattaagaagtcttcacgagaatgagaccaataa
atggtatggacttaatttatttactggaaatccagaggatatgtggaaat
taggtgttattgaaccggcactagtgaaaatgaatgcaattaaggctgca
acagaagcagtaacattagtgttaagaatagatgatattgtaGGTGGTTC
TGGTGGTACCatacctgtaataattttaaaagagggatcaagtagaacat
atggaaaagaagctttaagggctaatattgctgcagtgaaagcaattgaa
gaggcattaaaaagcacctatggtccacgtggaatggataagatgcttgt
tgatagcttaggagatattacaataacaaatgatggagccactattcttg
ataaaatggatttacaacacccaacaggtaagcttttagttcagatagct
aaaggacaagacgaggaaacagctgatggcactaaaactgctgtaattct
tgctggagaattagctaaaaaagcagaagatcttttatataaggagattc
acccaacaataattgtaagcggatataagaaggcagaagaaattgcatta
aagaccatccaagatatagcacaaccggtcagcataaatgatactgacgt
acttaggaaagtagcattaacatccttaggcagtaaggcagtagcaggcg
cacgagagtatttagctgaccttgtggttaaagcagtggcacaagtagca
gaattaagaggagataagtggtatgttgatctagataatgtacaaatagt
taaaaaacatggtggtagcattaatgatactcaattagtatacggcatag
tagttgataaggaagttgtacatccgggcatgccaaagaggattgaaaat
gctaagatagccctttagacgcttcattagaagttgagaaacccgaatt
ggatgcagaaataagaattaac

FIGURE 29A

MVFVEGAKNPKSVSILIRGGLERVVDETERALRDALGTVADVIRDGRAVA
GGGAVEIEIAKRLRKYAPQVGGKEQLAIEAYANAIEGLIMILAENAGLDP
IDKLMQLRSLHENETNKWYGLNLFTGNPEDMWKLGVIEPALVKMNAIKAA
TEAVTLVLRIDDIVGGSGGTIPVIILKEGSSRTYGKEALRANIAAVKAIE
EALKSTYGPRGMDKMLVDSLGDITITNDGATILDKMDLQHPTGKLLVQIA
KGQDEETADGTKTAVILAGELAKKAEDLLYKEIHPTIIVSGYKKAEEIAL
KTIQDIAQPVSINDTDVLRKVALTSLGSKAVAGAREYLADLVVKAVAQVA
ELRGDKWYVDLDNVQIVKKHGGSINDTQLVYGIVVDKEVVHPGMPKRIEN
AKIALLDASLEVEKPELDAEIRIN

FIGURE 29B

ATGGCAACAGCTACAGTTGCAACTACACCCGAAGGTATACCTGTAATAAT
TTTAAAAGAGGGATCAAGTAGAACATATGGAAAAGAAGCTTTAAGGGCTA
ATATTGCTGCAGTGAAAGCAATTGAAGAGGCATTAAAAAGCACCTATGGT
CCACGTGGAATGGATAAGATGTTCGTTGATAGCTTAGGAGATATTACAAT
AACAAATGATGGAGCCACTATTCTTGATAAAATGGATTTACAACACCCAA
CAGGTAAGCTTTTAGTTCAGATAGCTAAAGGACAAGACGAGGAAACAGCT
GATGGCACTAAAACTGCTGTAATTCTTGCTGGAGAATTAGCTAAAAAAGC
AGAAGATCTTTTATATAAGGAGATTCACCCAACAATAATTGTAAGCGGAT
ATAAGAAGGCAGAAGAAATTGCATTAAAGACCATCCAAGATATAGCACAA
CCGGTCAGCATAAATGATACTGACGTACTTAGGAAAGTAGCATTAACATC
CTTAGGCAGTAAGGCAGTAGCAGGCGCACGAGAGTATTTAGCTGACCTTG
TGGTTAAAGCAGTGGCACAAGTAGCAGAATTAAGAGGAGATAAGTGGTAT
GTTGATCTAGATAATGTACAAATAGTTAAAAAACATGGTGGTAGCATTAA
TGATACTCAATTAGTATACGGCATAGTAGTTGATAAGGAAGTTGTACATC
CGGGCATGCCAAAGAGGATTGAAAATGCTAAGATAGCCCTTTTAGACGCT
TCATTAGAAGTTGAGAAACCCGAATTGGATGCAGAAATAAGAATTAACGA
TCCAACACAGATGCACAAATTCTTGGAAGAAGAAGAAAACATATTGAAAG
AAAAAGTAGATAAGATTGCAGCTACTGGTGCTAACGTTGTAATATGCCAG
AAAGGTATCGATGAAGTTGCACAACACTATTTAGCTAAGAAAGGTATATT
AGCTGTTAGGAGAGCCAAGAAGAGTGATTTAGAGAAATTAGCTAGAGCTA
CCGGAGGTAGAGTCATATCAAATATTGATGAATTAACTTCACAAGATCTA
GGTTATGCCGCATTAGTGGAAGAGAGAAAAGTAGGAGAGGATAAGATGGT
ATTCGTAGAAGGTGCAAAGAATCCAAAATCAGTTAGTATACTAATAAGAG
GAGGATTAGAGAGAGTAGTAGATGAGACTGAAAGAGCTCTTAGGGACGCT
TTAGGTACAGTGGCAGATGTAATAAGGGATGGTAGAGCAGTAGCTGGTGG
TGGAGCTGTTGAGATAGAGATAGCTAAGAGATTAAGAAAGTATGCCCCAC
AAGTTGGTGGTAAAGAGCAATTAGCAATTGAAGCATATGCTAATGCAATA
GAAGGACTTATCATGATATTGGCGGAAAACGCAGGATTAGATCCTATAGA
CAAATTAATGCAATTAAGAAGTCTTCACGAGAATGAGACCAATAAATGGT
ATGGACTTAATTTATTTACTGGAAATCCAGAGGATATGTGGAAATTAGGT
GTTATTGAACCGGCACTAGTGAAAATGAATGCAATTAAGGCTGCAACAGA
AGCAGTAACATTAGTGTTAAGAATAGATGATATTGTAGCAGCTGGAAAGA
AGGGTGGAAGTGAGCCAGGCGGTAAGAAAGAGAAAGAAGAAAAGTCCTCT
GAAGAC

FIG. 30

ATGGCAACAGCTACAGTTGCAACTACACCCGAAGGTATACCTGTAATAAT
TTTAAAAGAGGGATCAAGTAGAACATATGGAAAAGAAGCTTTAAGGGCTA
ATATTGCTGCAGTGAAAGCAATTGAAGAGGCATTAAAAAGCACCTATGGT
CCACGTGGAATGGATAAGATGTTCGTTGATAGCTTAGGAGATATTACAAT
AACAAATGATGGAGCCACTATTCTTGATAAAATGGATTTACAACACCCAA
CAGGTAAGCTTTTAGTTCAGATAGCTAAAGGACAAGACGAGGAAACAGCT
GATGGCACTAAAACTGCTGTAATTCTTGCTGGAGAATTAGCTAAAAAAGC
AGAAGATCTTTTATATAAGGAGATTCACCCAACAATAATTGTAAGCGGAT
ATAAGAAGGCAGAAGAAATTGCATTAAAGACCATCCAAGATATAGCACAA
CCGGTCAGCATAAATGATACTGACGTACTTAGGAAAGTAGCATTAACATC
CTTAGGCAGTAAGGCAGTAGCAGGCGCACGAGAGTATTTAGCTGACCTTG
TGGTTAAAGCAGTGGCACAAGTAGCAGAATTAAGAGGAGATAAGTGGTAT
GTTGATCTAGATAATGTACAAATAGTTAAAAAACATGGTGGTAGCATTAA
TGATACTCAATTAGTATACGGCATAGTAGTTGATAAGGAAGTTGTACATC
CGGGCATGCCAAAGAGGATTGAAAATGCTAAGATAGCCCTTTTAGACGCT
TCATTAGAAGTTGAGAAACCCGAATTGGATGCAGAAATAAGAATTAACGA
TCCAACACAGATGCACAAATTCTTGGAAGAAGAAGAAAACATATTGAAAG
AAAAAGTAGATAAGATTGCAGCTACTGGTGCTAACGTTGTAATATGCCAG
AAAGGTATCGATGAAGTTGCACAACACTATTTAGCTAAGAAAGGTATATT
AGCTGTTAGGAGAGCCAAGAAGAGTGATTTAGAGAAATTAGCTAGAGCTA
CCGGAGGTAGAGTCATATCAAATATTGATGAATTAACTTCACAAGATCTA
GGTTATGCCGCATTAGTGGAAGAGAGAAAAGTAGGAGAGGATAAGATGGT
ATTCGTAGAAGGTGCAAAGAATCCAAAATCAGTTAGTATACTAATAAGAG
GAGGATTAGAGAGAGTAGTAGATGAGACTGAAAGAGCTCTTAGGGACGCT
TTAGGTACAGTGGCAGATGTAATAAGGGATGGTAGAGCAGTAGCTGGTGG
TGGAGCTGTTGAGATAGAGATAGCTAAGAGATTAAGAAAGTATGCCCCAC
AAGTTGGTGGTAAAGAGCAATTAGCAATTGAAGCATATGCTAATGCAATA
GAAGGACTTATCATGATATTGGCGGAAAACGCAGGATTAGATCCTATAGA
CAAATTAATGCAATTAAGAAGTCTTCACGACAATGAGACCAATAAATGGT
ATGGACTTAATTTATTTACTGGAAATCCAGAGGATATGTGGAAATTAGGT
GTTATTGAACCGGCACTAGTGAAAATGAATGCAATTAAGGCTGCAACAGA
AGCAGTAACATTAGTGTTAAGAATAGATGATATTGTAGCAGCTGGAAAGA
AGGGTGGAAGTGAGCCAGGCGGTAAGAAAGAGAAAGAAGAAAAGTCCTCT
GAAGAC

FIG. 31

VERSATILE PLATFORM FOR NANOTECHNOLOGY BASED ON CIRCULAR PERMUTATIONS OF CHAPERONIN PROTEIN

This application is a continuation-in-part of U.S. Ser. No. 10/494,853, which is based on PCT/US02/35889, filed Nov. 8, 2002, which claims priority of a provisional application, U.S. Ser. No. 60/340,538, filed Nov. 8, 2001, the contents of all of which are hereby incorporated by reference in their entirety into this application.

Throughout this application various publications are referenced. The disclosures of these publications in their entireties are hereby incorporated by reference into this application in order to more fully describe the state of the art to which this invention pertains.

The work described here was supported, at least in part, by grants from: The National Aeronautics and Space Administration. The United States government may, therefore, have certain rights in the invention.

FIELD OF INVENTION

The present invention relates to the field of bio-nanotechnology. The present invention provides compositions and methods for making chaperonin subunit polypeptides which are modified by relocating the N-terminal and C-terminal to different positions. The modified chaperonin subunit polypeptides can assemble as part of chaperonin structures, and the relocated N- and C-terminal ends can be linked to or bind with organic or inorganic molecules. The assembled chaperonin structures are useful for producing nanoscale filaments or two-dimensional crystals having functions produced by the linked or bound organic or inorganic molecule.

BACKGROUND

The controlled organization of inorganic materials into multi-dimensional addressable arrays is the foundation for both logic and memory devices, as well as other nonlinear optical and sensing devices (Zhirnov et al., 2001 Computer 34: 34-43; Xia et al., 2000 Adv. Mater. 12: 693-713). Many of these devices are currently fabricated using lithographic patterning processes that have progressively developed toward greater integration densities and smaller sizes. At submicron scales, however, conventional lithographic processes are approaching their practical and theoretical limits. At scales below 100 nm, ion and electron beam lithography becomes prohibitively expensive and time consuming, and more importantly, at these scales quantum effects fundamentally change the properties of devices (Sato et al., 1997 J. Appl. Phys. 82: 696).

Nanoscale templates for constrained synthesis, in situ deposition, or direct patterning of nanometer scale inorganic arrays are being developed using both artificial and natural materials. Artificial materials such as microphase separated block copolymers (Park et al., 2001 Appl. Phys. Lett. 79: 257-259) and hexagonally close-packed spheres (Hulteen et al., 1995 J. Vac. Sci. Technol. A, 1553-1558) have been used for nanoscale fabrication. Natural materials such as DNA (Richter et al., 2000 Adv. Mater. 12: 507-510; Keren et al., 2002 Science 297: 72-75), bacterial and archaeal surface layer proteins (S-layer proteins) (Sleytr et al., 1999 Angew. Chem. Int. Ed. 38: 1034-1054; Douglas et al., Appl. Phys. Lett. 48: 676-678; Hall et al., 2001 CHEMPHYSCHEM 3: 184-186), virus capsids (Shenton et al., 1999 Adv. Mater. 11: 253-256; Douglas et al., 1999 Adv. Mater., 679-681; Douglas et al., Nature 393: 152-155; Wang et al., 2002 Angew. Chem. Int. Ed. 41: 459-462), phage (Lee et al., 2002 Science 296: 892-895), and some globular proteins (Yamashita, I., 2001 Thin Solid Films 393: 12-18) have been used as templates and in other nanoscale applications.

Various nanometer scale objects, including arrays of nanoparticles formed by non-conventional methods are being explored for use as viable alternatives to standard lithographically patterned devices. Individual nanoparticles, also known as quantum dots (QDs), have been shown to behave as isolated device components such as single electron transistors (Likharev, K. K., 1999 Proc. IEEE 87: 606-632; Thelander et al., 2001 Appl. Phys. Lett. 79: 2106-2108). Theoreticians have postulated that two-dimensional arrays of QDs with nanoscale resolution could form the basis of future generations of electronic and photonic devices. The function of these devices will be based on phenomena such as coulomb charging, inter-dot quantum tunneling and other coherent properties derived from the electronic consequences of confinement and nanoparticle surface area to volume ratios (Maier, S. A. et al., 2001 Adv. Mater. 13: 1501-1505; Maier et al., Phys. Rev. B 65, 193408; Zrenner, A. et al., 2002 Nature 418: 612-614; Berven et al., 2001 Adv. Mater. 13: 109-113).

Traditional techniques for patterning ordered arrays of materials onto inorganic substrates and manufacturing devices currently used are ion beam lithography and molecular beam epitaxy. These techniques possess inherent limitations due to the use of polymeric light masks for pattern formation, however, there is a theoretical limitation of patterning that could ultimately limit the processes in the hundreds of nanometers.

While there are strong incentives to develop nanoscale architectures, these developments require alternate fabrication methods and new insights into the behavior of materials on nanometer scales (Nalwa, H. S., 2000 "Handbook of Materials and Nanotechnology", Academic Press, San Diego).

Development of methods for ordering nanoscale materials through "bottom up" assembly will provide new tools for creating nanostructured materials and devices that self-assemble or self-repair. Synthetic and biological polymers have gained attention because of their inherent ability to form structures on the nanometer scale with little or no mechanical processing. Self-assembly and phase separation of these natural or synthetic polymers have been successfully used for nanoscale ordering of materials. Biopolymers form especially well-defined structures and assemblies with highly specific chemical functionalities. Nucleic acids (J Richter, et al., 2000 Advanced Materials 12:507-510; M G Warner and J E Hutchison 2003 Nature Materials 2:272-277; and K Keren, et al., 202 Science 297:72-75), proteins (K Douglas and N A Clark 1986 Appl Phys Lett 48:676-678; U B Sleytr, et al., 1999 Angew Chem Int Edn 38:1034-1054; I Yamashita 2001 Thin Solid Films 393:12-18; M Allen, et al., 2002 14:1562-1565; R A McMillan, et al., 2002 Nature Materials 1:247-252), virions and virus capsids (W Shenton, et al., 1999 Adv Mater 11:253-256; S-W Lee, et al., 2002 Science 296:892-895; Q Wang, et al., 2002 Angew Chem Int Ed Engl 41:459-462) have all been used to create nanostructured materials with unique properties.

A number of protein complexes have been developed as nanoscale templates. These templates can be functionalized by genetic modification to add chemically reactive sites that bind inorganic materials. For example, chaperonin complexes can be functionalized to bind soft metals. In nature, chaperonins are protein complexes having two stacked rings each comprising 7, 8 or 9 HSP60 subunits. The HSP60 subunits were mutated to include single cysteine residues placed at different solvent-exposed sites, including the apical pore. The thiols of these cysteine residues provide binding sites for gold or zinc (PCT/US02/35889). The chaperonin complexes comprising these mutant HSP60 subunits bind gold or zinc and assemble into two-dimensional crystals.

Protein complexes can also be modified to include peptide sequences having desirable binding or catalytic functions. These protein complexes comprise subunits having inserted peptide sequences. However, the mutant subunits may fail to fold, assemble into complexes or organize into higher-order structures. Furthermore, insertion as a loop may render the peptide sequence inactive and fusion to one of the native termini may not provide sufficient surface accessibility. To overcome this challenge, circular permutation has been used to join peptide sequences within a protein template. Circular permutation is a reordering of the polypeptide chain such that the original N- and C-terminal ends are joined and new termini are created elsewhere in the protein. New peptide sequences can be joined to either of the new termini without perturbing subunit assembly. Published studies of protein circular permutation demonstrate that, for proteins in which the native amino and carboxyl termini are near in space, many relocated positions for the new termini are viable (P T Beernink, et al., 2001 Protein Sci 10:528-537; U Heinemann and M Hahn 1995 Prog Biophys Mol Biol 64:121-143; M Iwakura, et al., 2000 Nat Struct Biol 7:580-585).

The present invention provides chaperonin subunit polypeptides which are modified to relocate the native N-terminal and C-terminal ends from the central pore region to various new positions on the exterior of the folded modified chaperonin polypeptide. The relocated N- and C-terminal ends are joined with a peptide sequence that behaves as a reporter. The modified chaperonin polypeptides fold into subunits that self-assemble into double-ringed chaperonin structures, and the chaperonin structures organize into higher order structures such as two-dimensional crystals and filaments. Additionally, the reporter peptide is functional. These chaperonin structures are useful for producing ordered nanoscale materials and devices.

SUMMARY

The present invention provides chaperonin polypeptides which are modified to include N-terminal and C-terminal ends that are relocated from the central pore region to various different positions in the polypeptide which are located on the exterior of the folded modified chaperonin polypeptide.

The relocated N-terminal or C-terminal ends can be covalently joined to, or bound with, a nucleic acid molecule, a lipid, a carbohydrate, a second polypeptide, or a nanoparticle.

In the modified chaperonin polypeptide, the naturally-occurring N-terminal and C-terminal ends are joined together directly or with an intervening linker peptide sequence. In one embodiment, the intervening linker sequence comprises the amino acid sequence Gly-Gly-Ser-Gly-Gly-Thr.

The modified chaperonin polypeptide is based on a Group I or Group II chaperonin polypeptide.

The Group I chaperonin polypeptides are from *Escherichia, Cyanobacteria, Mycobacteria, Coxiella, Rickettsia, Chlamydia, Thermotoga*, chloroplast, mammalian mitochondria, or yeast mitochondria. The Group II chaperonin polypeptides are from *Sulfolobales, Methanopyrus, Pyrodictium, Thermoplasma, Thermoplasma, Thermococus, Pyrococus, Mathanococus*, or yeast cytosol.

In one embodiment, the modified chaperonin polypeptide from *Sulfolobus* is an alpha, beta, or gamma polypeptide.

In one embodiment, the modified chaperonin polypeptide comprises a *Sulfolobus shibatae* TF55 beta polypeptide comprising the N-terminal and C-terminal ends relocated after any amino acid position in the range 149-158, in particular relocated to position 153.

In another embodiment, the modified chaperonin polypeptide comprises a *Sulfolobus shibatae* TF55 beta polypeptide comprising the N-terminal and C-terminal ends relocated after any amino acid position in the range 263-270, in particular relocated to position 267.

In another embodiment, the modified chaperonin polypeptide comprises a *Sulfolobus shibatae* TF55 beta polypeptide comprising the N-terminal and C-terminal ends relocated after any amino acid position in the range 311-330, in particular relocated to position 316.

In another embodiment, the modified chaperonin polypeptide comprises a *Sulfolobus shibatae* TF55 beta polypeptide comprising the N-terminal and C-terminal ends relocated after any amino acid position in the range 472-487, in particular relocated to position 480.

In yet another embodiment, the modified chaperonin polypeptide comprises a *Sulfolobus shibatae* TF55 beta polypeptide comprising the N-terminal and C-terminal ends relocated after any amino acid position in the range 494-508, in particular relocated to position 499.

The present invention also provides assembled chaperonin structures, comprising at least one of the modified chaperonin subunits of the invention.

The assembled chaperonin structures can have one or more of 2-, 3-, 4-, 5-, 6-, 7-, 8-, 9-, and 10-fold symmetry.

The present invention further provides: nucleic acid molecules encoding the modified chaperonin polypeptide of the invention; vectors comprising these nucleic acid molecules; and host cells carrying these vectors.

The present invention provides in vivo methods for producing modified chaperonin polypeptides, comprising culturing the host/vector systems under conditions suitable for the host to produce the modified chaperonin polypeptide.

The present invention also provides in vitro methods for producing the assembled chaperonin structures of the invention, comprising reacting the modified chaperonin polypeptides under conditions suitable for self-assembly of the modified chaperonin polypeptide into the assembled chaperonin structures.

The present invention provides chaperonin structures that organize into higher order structures such as nanofilaments or nanoarrays. These nanofilaments and nanoarrays can be used to produce nanodevices or nanocoatings.

BRIEF DESCRIPTION OF FIGURES

FIG. 10(D) shows XEDS spectra of bare carbon film (solid line) and the gold nanoparticle nanoarray (dashed line) from the probed area outlined by a circle in FIG. 10(B), as indicated by the arrow.

FIG. 15 shows the protein sequence alignment of *S. shibatae* TF55 alpha subunit (SEQ ID NO: 39), beta subunit (SEQ ID NO: 1) and gamma subunit (SEQ ID NO: 38).

FIGS. 16A and 16B show the DNA sequence (SEQ ID NO: 37) and amino-acid sequence for *S. shibatae* gamma subunit (SEQ ID NO: 38).

FIG. 21 shows the full (A) DNA (SEQ ID NO:66) and (B) amino acid (SEQ ID NO:67) sequence of a position 153 circular permutant chaperonin protein.

FIG. 22 shows the full (A) DNA (SEQ ID NO:68) and (B) amino acid (SEQ ID NO:69) sequence of a position 267 circular permutant chaperonin protein.

FIG. 23 shows the full (A) DNA (SEQ ID NO:70) and (B) amino acid (SEQ ID NO:71) sequence of a position 316 circular permutant chaperonin protein.

FIG. 24 shows the full (A) DNA (SEQ ID NO:72) and (B) amino acid (SEQ ID NO:73) sequence of a position 480 circular permutant chaperonin protein.

FIG. 25 shows the full (A) DNA (SEQ ID NO:74) and (B) amino acid (SEQ ID NO:75) sequence of a position 499 circular permutant chaperonin protein.

FIG. 26 shows the full (A) DNA (SEQ ID NO: 76) and (B) amino acid (SEQ ID NO:77) sequence of a position 267 circular permutant chaperonin-EYFP fusion protein.

FIG. 27 shows the full (A) DNA (SEQ ID NO:78) and (B) amino acid (SEQ ID NO:79) sequence of a position 480 circular permutant chaperonin-EYFP fusion protein.

FIG. 28 shows the full (A) DNA (SEQ ID NO:80) and (B) amino acid (SEQ ID NO:1) sequence of wild-type TF55 alpha subunit from *Sulfolobus shibatae.*

FIGS. 29A and 29B show the full (A) DNA (SEQ ID NO:81) and (B) amino acid (SEQ ID NO:82) sequence of a position 267 "dwarf" deletion circular permutant chaperonin protein.

FIG. 30 shows the DNA sequence (SEQ ID NO:85) of TF55 beta subunit from Sulfolobus shibatae.

FIG. 31 shows a different DNA sequence (SEQ ID NO:86) of TF55 beta subunit from Sulfolobus shibatae.

DETAILED DESCRIPTION OF THE INVENTION

Definitions

Figure 1:
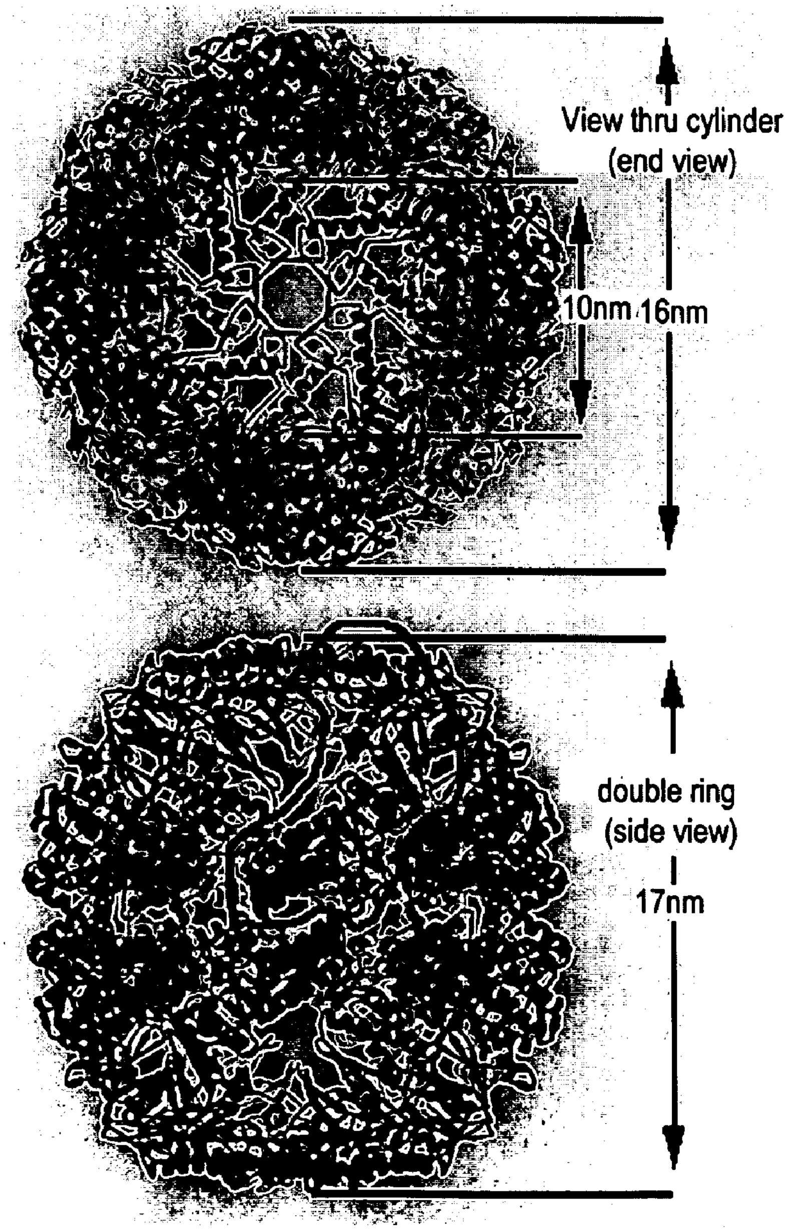
FIG. 1 illustrates an end and side view of a model of an HSP60 chaperonin at 2.3 Å resolution. The outlined region of the side view shows a single subunit of HSP60.

All scientific and technical terms used in this application have meanings commonly used in the art unless otherwise specified. As used in this application, the following words or phrases have the meanings specified.

As used herein, the term "isolated" refers to a specific nucleic acid or polypeptide, or a fragment thereof, in which contaminants (i.e. substances that differ from the specific nucleic acid or polypeptide molecule) have been separated from the specific nucleic acid or polypeptide.

As used herein, the term "purified" refers to a specific isolated nucleic acid or polypeptide, or a fragment thereof, in which substantially all contaminants (i.e. substances that differ from the specific nucleic acid or polypeptide molecule) have been separated from the specific nucleic acid or polypeptide.

As used herein, the term "naturally-occurring" refers to a nucleic acid or polypeptide molecule found in nature.

As used herein, the term "wild type" refers to a nucleic acid or polypeptide molecule having the same nucleotide and/or amino acid sequence as a naturally-occurring, non-mutant molecule, respectively.

As used herein, the term "modified" refers to molecules with amino acid or nucleotide sequences differing (mutated) from a naturally-occurring i.e., wild-type, amino acid or nucleotide, sequence. The modified molecules can retain the same structural properties as a wild-type molecule.

As used herein, the term "derivative" means any modification or alteration of a wild-type molecule. Derivatives include, but are not limited to: a substitution, conservative or non-conservative, in a amino acid and/or nucleotide sequence including substitutions by other amino acids, nucleotides, amino acid analogs or nucleotide analogs; a deletion of one or more amino acids and/or nucleotides; an insertion of one or more amino acids and/or nucleotides; and pre- and/or post-translational modifications. A derivative molecule can share sequence similarity and/or activity with its parent molecule.

As used herein, a first nucleotide or amino acid sequence is said to have sequence "identity" to a second nucleotide or amino acid sequence, respectively, when a comparison of the first and the second sequences shows that they are exactly alike.

As used herein, a first nucleotide or amino acid sequence is said to be "similar" to a second sequence when a comparison of the two sequences shows that they have few sequence differences (i.e., the first and second sequences are nearly identical). For example, two sequences are considered to be similar to each other when the percentage of nucleotides or amino acids that differ between the two sequences can be between about 60% to 99.99%.

As used herein, the term "complementary" refers to nucleic acid molecules having purine and pyrimidine nucleotide bases which have the capacity to associate through hydrogen bonding to form base pairs thereby mediating formation of double stranded nucleic acid molecules. The following base pairs are related by complementarity: guanine and cytosine; adenine and thymine; and adenine and uracil. Complementary applies to all base pairs comprising two single-stranded nucleic acid molecules, or to all base pairs comprising a single-stranded nucleic acid molecule folded upon itself.

As used herein, the term "conservative" refers to substituting an amino acid residue for a different amino acid residue that has similar chemical properties. A conservative amino acid substitution includes: substituting any hydrophobic (e.g., nonpolar) amino acid for any other hydrophobic amino acid; or substituting any hydrophilic (polar, uncharged) amino acid for any other hydrophilic amino acid; or substituting any positively charged amino acid for any other positively charge amino acid; or substituting any negatively charge amino acid for any other negatively charged amino acid (TE Creighton, "Proteins" WH Freeman and Company, New York). The amino acid substitutions include, but are not limited to, substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A), or glycine (G) and serine (S) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered conservative in particular environments.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The single-letter codes for amino acid residues include the following: A=alanine, R=arginine, N=asparagine, D=aspartic acid, C=cysteine, Q=Glutamine, E=Glutamic acid, G=glycine, H=histidine, I=isoleucine, L=leucine, K=lysine, M=methionine, F=phenylalanine, P=proline, S=serine, T=threonine, W=tryptophan, Y=tyrosine, V=valine.

In order that the invention herein described can be more fully understood, the following description is set forth.

The Modified Chaperonin Polypeptides

In its various aspects, the present invention provides: modified chaperonin polypeptides, and fragments and derivatives thereof; assembled chaperonins comprising the modified chaperonin polypeptides of the present invention; nucleic acid molecules encoding the modified chaperonin polypeptides, or fragments and derivatives thereof; recombinant DNA molecules; transformed host cells; host-vector systems; methods for producing the modified chaperonin polypeptides; methods for using the modified chaperonin polypeptides including producing bio-nano scale devices and coatings.

In nature, chaperonins are ubiquitous and essential subcellular structures having 14, 16, or 18 heat shock protein subunits (e.g., HSP60), arranged as two stacked rings and measuring approximately 16 to 18 nm tall by approximately 15 to 17 nm wide, depending on their species of origin (Hartl et al., 2002 Science 295: 1852-8). Chaperonins have a central pore, as well as apical, intermediate and equatorial domains. In a wild-type HSP60 protein subunit, the naturally-occurring N- and C-terminal ends occur in a region that forms part of the central pore in the assembled chaperonin. FIG. 1 illustrates an end and side view of a chaperonin that comprises 16 subunits, i.e., eight subunits per ring.

The present invention provides chaperonin subunit polypeptides, and fragments or derivatives thereof, which are modified to include N-terminal and C-terminal ends that are relocated from their naturally-occurring positions to different positions in the polypeptide.

In the modified chaperonin polypeptide, the N- and C-terminal ends are relocated from the central pore region to a new position on the exterior of the folded modified chaperonin polypeptide. The positions of the relocated N- and C-terminal ends are selected to circumvent the space constraints of the central pore, thereby permitting joining or binding other molecules to the modified chaperonin polypeptide.

The modified chaperonin polypeptides of the present invention are mutant chaperonin polypeptides. The modified chaperonin polypeptides exhibit the same structural properties as naturally-occurring wild-type chaperonin subunit polypeptides, which includes folding into a subunit structure having the same or similar shape compared to a wild-type chaperonin subunit polypeptide. The folded modified chaperonin subunit structure can self-assemble with other chaperonin subunit structures (folded wild-type and/or modified subunit polypeptides) to form a double-ringed chaperonin structure. The folded modified chaperonin subunit structure can self-assemble in vivo or in vitro to form a double-ringed chaperonin structure. The double-ringed chaperonin structure, comprising at least one modified polypeptide of the present invention, can be organized into two-dimensional crystals or filaments which are useful for producing nanodevices such as logic and memory devices, non-linear optical devices, and sensing devices.

The present invention provides modified chaperonin polypeptides, or fragments or derivatives thereof, derived or isolated from any source whether natural, synthetic, semi-synthetic, or recombinant.

The terms "modified chaperonin subunit polypeptides", "modified chaperonin polypeptides", and "modified polypeptides" refer to chaperonin subunit polypeptides which are modified by relocating the N- and C-terminal ends. These terms are used interchangeable herein.

Group I and II Chaperonin Polypeptides

The modified polypeptides can be produced using any Group I or Group II chaperonin polypeptide. Chaperonins have been classified into two groups, Group I and Group II, based on sequence and structural comparisons. (See, e.g., Trent et al., 1991 Nature 354: 490-493; Horwich et al., 1993 Phil. Trans R. Soc. Lond. 339: 313-326).

Group I chaperonins are from bacteria and the bacterial-derived organelles of Eukarya (mitochondria and chloroplasts), while Group II chaperonins are from Archaea and eukaryotic cytosol. A description of the expression of endogenous, wild-type TF55 *Sulfolobus shibatae*, and a comparison of a Group I chaperonin (GroEL) to the Group II chaperonin TF55 is disclosed by Trent (U.S. Pat. No. 5,428,131).

Any of the Group I chaperonin subunit proteins can be used to produce the modified chaperonin polypeptides of the present invention. Wild-type Group I chaperonins are composed of seven subunits in each of the two rings of the double-ring structure. The wild-type cpn60 subunit proteins, which comprise about 550 to about 580 amino acid residues, have been described by different names in different species, including, but not limited to *Escherichia coli* GroEL protein, *Cyanobacterial* groEL analogues, *Mycobacterium tuberculosis* and *leprae* 65 Kd antigen, *Coxiella burnetti* heat shock protein B (gene htpB), *Rickettsia tsutsugamushi* major antigen 58, *Chlamydial* 57 Kd hypersensitivity antigen (gene hypB), Chloroplast RuBisCO subunit binding-protein alpha and beta chains, Mammalian mitochondrial matrix protein P1 (mitonin or P60), and yeast HSP60 protein.

In one embodiment, e.g., when utilizing Group I chaperonins, chaperonin polypeptides, and/or mutant chaperonins and/or mutant chaperonin polypeptides, a co-chaperonin can be utilized in forming the higher order structures of the invention. As such, in one example of such an embodiment, a composition or device of the invention further comprises a co-chaperonin. Co-chaperonins are well known to those of skill in the art (Harris et al., 1995 J. Structural Biol. 115: 68-77). In another, non-limiting example of such an embodiment, a co-chaperonin can be utilized in producing nanofilaments. For example, the cpn60 in the bacterium *E. coli* (GroEL) in nature is associated with a single ring structure composed of 10 kDa proteins (co-chaperonin or cpn10) called "GroES." As such, a GroES polypeptide represents an exemplary, non-limiting species of co-chaperonin that can be utilized in conjunction with Group I chaperonins, e.g., GroEL or GroEL-derived chaperonins, chaperonin polypeptides, and/or mutant chaperonins or chaperonin polypeptides. In different embodiments of the invention, the compositions, e.g., nanotemplates or nanostructures, are formed from one or more chaperonins with the co-chaperonin on one or both ends of the chaperonin.

Any of the Group II chaperonins subunit proteins can be used to produce the modified chaperonin polypeptides of the present invention. Group II chaperonins are composed of identical or diverse subunits arranged in rings of eight or nine subunits, depending on the organism. In the yeast *Saccharomyces cerevisiae*, for example, there is evidence for eight different subunits in each ring (Lin et al., 1997 Proc. Natl. Acad. Sci. USA 94: 10780-10785). Among the Archaea some thermophilic methanogens (e.g., *Methanopyrus kandleri, Methanococcus jannaschii, Methanococcus thermolithotrophicus*) have chaperonins with identical subunits (Furutani et al., 1998 J. Biol. Chem. 273: 28399-28407), while in the mesophilic methanogen *Methanosarcina acetivorans* there are five different subunits (Galagan et al., 2002 Genome Research 12: 532-542). Of the 50 archaeal chaperonin sequences in the databases most have >40% amino acid sequence identity.

The majority of Group II chaperonins in Archaea have eight subunits per ring and are referred to as "thermosomes" (Klumpp, M., and Baumeister, W., 1998, FEBS Letters 430: 73-77), but the chaperonins in the thermoacidophilic Archaea in the family Sulfolobales have nine subunits per ring (Trent et al., 1991 Nature 354: 490-493; Marco et al., 1994 FEBS 341: 152-155). These *Sulfolobus* octadecameric chaperonins are referred to as "rosettasomes" (Kagawa et al., 1995 J. Mol. Biol. 253: 712-725) to distinguish them from thermosomes. Other examples of thermosomes include chaperonins from *Pyrodictium occultum, Thermoplasma acidophilum* and *Methanopyrus kandleri* (Ellis et al., 1998 J. Struc. Biol. 123: 30-36). It has previously been reported that rosettasomes are composed of two types of HSP60s known as TF55 alpha and beta, that TF55 alpha and beta are among the most abundant proteins in *S. shibatae* grown at optimal temperatures (75-83° C.), and that their synthesis increases at heat-shock temperatures (85-88° C.) (Kagawa et al., 1995 J. Mol. Biol. 253: 712-725). A third related subunit of *S. shibatae*, has also been identified by sequence analyses (Archibald et al., 1999 Current Biology 9: 1053-1056). Sequence information from *S. solfataricus* (Charlebois et al., 1998 Current Opinion in Microbiology 1: 584-588) allowed TF55 alpha, beta, and gamma expression to be predicted based on codon usage (Karlin et al., 2001 J. Bacteriol. 183: 5025-5040). Chaperonins from eukaryotic cytosol are referred to as "TCP1," which identifies one of the proteins comprising the ring structure, "TriC" which means TCP1 ring chaperonin, or "CCT" which means chaperonin containing TCP1. Any of these chaperonins subunit proteins can be used to produce the modified chaperonin polypeptides of the present invention.

Sources of gene sequences encoding chaperonin polypeptides include but are not limited to bacterial chaperonin genes encoding such proteins as Gro ES/Gro EL; archaeal chaperonin genes encoding such proteins as TF55, TF56, alpha, beta, gamma, and cpn60s; mammalian chaperonins such as Hsp60, Hsp10, TCP-1, cpn60 and the homologues of these chaperonin genes in other species (J. G. Wall and A. Pluckthun, Current Biology, 6:507-516 (1995); Hartl, Nature, 381:571-580 (1996)). Additionally, heterologous genomic or cDNA libraries can be used as libraries to select or screen for chaperonins.

Figure 2A:
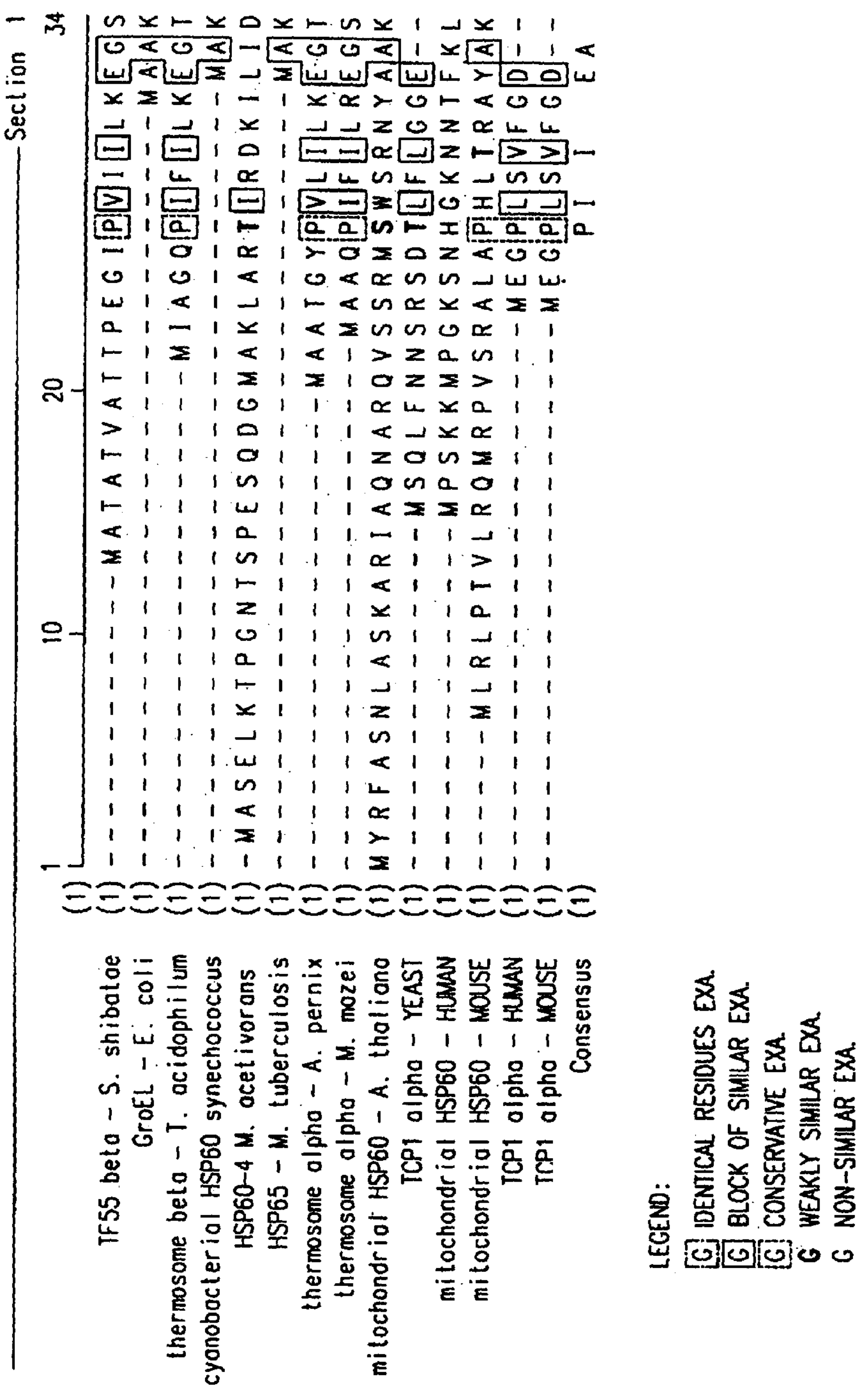
FIGS. 2A-2R show the protein sequence alignment of *S. shibatae* TF55 beta subunit (SEQ ID NO: 1), bacterial *E. coli* GroEL (SEQ ID NO:2), thermosome *T. acidophilum* beta subunit (SEQ ID NO:3), cyanobacterial synechococcus HSP60 (SEQ ID NO:4), *M. acetivorans* HSP60-4 (SEQ ID NO:5), *M. tuberculosis* HSP65 (SEQ ID NO:6), thermosome *A. pernix* alpha subunit (SEQ ID NO:7), thermosome *M. mazei* alpha subunit (SEQ ID NO:8), mitochondrial *A. thaliana* HSP60 (SEQ ID NO:9), yeast TCP1 alpha subunit (SEQ ID NO:10), human mitochondrial HSP60 (SEQ ID NO:11), mouse mitochondrial HSP60 (SEQ ID NO:12), human TCP1 alpha subunit (SEQ ID NO:13), mouse TCP1 alpha subunit (SEQ ID NO:14), and the consensus (SEQ ID NO:15). Identical residues are enclosed in a dot-dashed box, blocks of similar residues are enclosed in a solid box, and conservative matches are enclosed in a dashed box.

FIGS. 2A-2R show protein sequence alignments covering a representative set of Groups I (bacteria) and Group II (archaea and eukarya) chaperonins. The protein sequence are sequences for *S. shibatae* TF55 beta subunit (SEQ ID NO: 1), bacterial *E. coli* GroEL (SEQ ID NO:2), thermosome *T. acidophilum* beta subunit (SEQ ID NO:3), cyanobacterial synechococcus HSP60 (SEQ ID NO:4), *M. acetivorans* HSP60-4 (SEQ ID NO:5), *M. tuberculosis* HSP65 (SEQ ID NO:6), thermosome *A. pernix* alpha subunit (SEQ ID NO:7), thermosome *M. mazei* alpha subunit (SEQ ID NO:8), mitochondrial *A. thaliana* HSP60 (SEQ ID NO:9), yeast TCP1 alpha subunit (SEQ ID NO:10), human mitochondrial HSP60 (SEQ ID NO:11), mouse mitochondrial HSP60 (SEQ ID NO:12), human TCP1 alpha subunit (SEQ ID NO:13), mouse TCP1 alpha subunit (SEQ ID NO:14), and the consensus (SEQ ID NO:15). White letters on a black background, solid lines, and dashed lines surround the regions of the sequence alignment containing identical residues, a block of similar residues, and conservative matches, respectively.

Folded Structure

Figure 3:
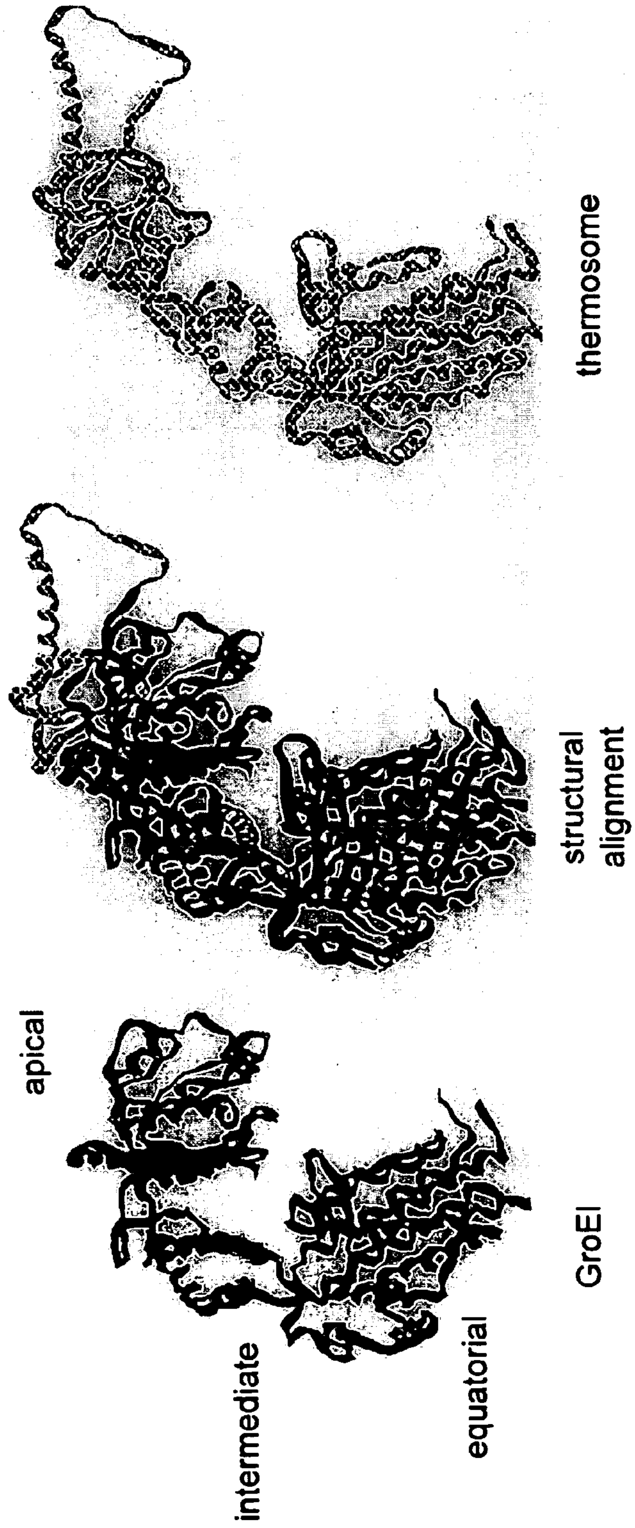
FIG. 3 shows a structural alignment of the archaeal chaperonin (thermosome) and the bacterial chaperonin (GroEL), indicating the structural similarities between group I and group II chaperonins. The black areas of the structural alignment indicate where the features of the two chaperonin subunits overlap.

While Group I chaperonin subunit proteins can have greater than 50% sequence identity, sequence identity among Group II chaperonin subunit proteins can be on the order of less than 33%. Despite the sequence variations among the cpn60 subunits from the different species, however, Group I and Group II cpn60 subunits share significant structural similarity. FIG. 3 shows a structural comparison between a subunit of the archaeal (*Thermoplasma acidophilum*) thermosome and the bacterial (*E. coli*) GroEL chaperonins.

The alignment was performed using an algorithm based on the iterative dynamic programming approach (Gerstein, M. & Levitt, M., Protein Science 7: 445-456, 1998; and Gerrstein, M. & Levitt, M, Proc. of ISMB-96, pp. 59-67, 1996).

For purposes of wild-type chaperonins and chaperonin polypeptides, such three dimensional structural similarity serves to illustrate that fact that any chaperonin or chaperonin polypeptide routinely can be utilized as part of the compositions and devices of the present invention, either alone or combination. For purposes of modified chaperonins and chaperonin polypeptides, as discussed in detail in the next section, such sequence similarity serves to provide teaching that allows for routine manipulation of sequences in producing the modified chaperonin polypeptides of the present invention.

The two subunits exhibit very similar structures, in that both possess an equitorial, an intermediate and an apical region. Even though these two examples of cpn60 subunits are farther apart by sequence than most cpn60 subunits, as evidenced by the very little similarity in their sequence alignments (see FIGS. 2A-2R), the crystal structures for each reveal that they share considerable structural identity—most all helical, sheet, and random coil regions correspond, as shown in black in the center panel. Variations in structure are tolerated in the apical domain, as evidenced by the loop of the thermosome, while the equatorial domains adopt similar conserved folding motifs.

It is noted that, while the chaperonins observed to date comprise seven, eight or nine subunits per ring, the present invention provides methods and compositions of exploiting chaperonins with any number of subunits per ring (e.g., 7, 8, 9 or 10).

Chaperonins from the different species can comprise only a single type of subunit or they can have different types of subunits (e.g., archeal chaperonins comprising alpha, beta, gamma, etc.). These subunits are called alpha subunits, beta subunits, or gamma subunits, due to some differences in the protein sequences of the subunits of a given species. As is known to one of ordinary skill in the art, in some species yet more varieties of subunits exist. The structure of chaperonins (Ellis et al., 1998, J. Struc. Biol. 123, 30-36) describes a chaperonin from *Sulfolobus solfataricus* with a 2:1 ratio of alpha:beta subunit composition of the nine-membered ring (rosettasomes). The present invention provides means of assembling chaperonins from only a single type of wild-type or modified chaperonin polypeptides, or from various proportions of the different wild-type or modified chaperonin polypeptides.

In a specific embodiment, HSP60s (heat-shock proteins) in organisms living at high temperatures, called "thermophiles," are the source of the wild-type and mutated chaperonin polypeptides of the present invention. These proteins are present in all organisms and are among the most abundant proteins in extreme thermophiles, e.g., in one of the highest temperature thermophiles *Pyrodictium occultum*, they reportedly account for 73% of total protein (Phipps et al., 1991 The EMBO Journal 10(7): 1711-1722).

Selecting the Position of Relocated Terminal Ends

Using the amino acid sequence and/or the predicted folded structure of any Group I or II wild-type chaperonin subunit polypeptide as a guide (FIGS. 2A-R and 15), one skilled in the art can select the amino acid position to relocate the N- and C-terminal ends. The new terminal end positions can be selected based on the following criteria: the position is not buried within the folded modified chaperonin polypeptide; the new position is not near the subunit interface; and the new position is not part of the regular secondary structure.

In one embodiment, the N-terminal and C-terminal ends are relocated to any position on the exterior of the folded polypeptide that occurs in the apical, intermediate or equatorial domain.

In another embodiment, any chaperonin subunit polypeptide can be modified by relocating the N- and C-terminal ends to produce the modified polypeptides of the present invention, including: TF55 alpha, beta or gamma subunits from *Sulfolobales shibatae*. For example, the N- and C-terminal ends can be relocated to any position 1-560 for TF55 alpha subunit, position 1-552 for TF55 beta subunit, or position 1-535 for TF55 gamma subunit (FIG. 15).

In another embodiment, using the amino acid sequence of wild-type TF55 beta subunit from *Sulfolobus shibatae* as a guide, the N- and C-terminal ends are relocated to any amino acid positions within or about a region having a consensus sequence, a conserved folded structure, or non-conserved sequence (FIG. 15). Many positions can be modified. In one embodiment, the N- and C-terminal ends can be relocated to amino acid positions within or about the ranges: 149-158; 263-270; 311-330; 472-487; or 494-508. In yet another embodiment, the N- and C-terminal ends are relocated to amino acid positions 153, 267, 316, 480 or 499, based on wild-type HSP60 beta subunit from *Sulfolobus shibatae*.

Linker Sequences

The modified chaperonin polypeptides also comprise the naturally-occurring N- and C-terminal ends linked directly together or linked with an intervening linker sequence. The intervening linker does not interfere with the ability of the modified chaperonin polypeptide to fold and assemble into double-ringed chaperonin structures. In the modified chaperonin polypeptide, the intervening linker can maintain the same or similar spatial organization or distance as that found in a folded wild type chaperonin polypeptide. The intervening linker can be a flexible or helical linker sequence (Arai, et al., 2001 Protein Engineering 14:529-532; Waldo, et al., 1999 Nature Biotechnology 17:691-695). The intervening linker sequence comprises between 1 to about 10 amino acid residues or derivatives thereof. The intervening linker sequence comprises amino acid residues such as glycine, serine, alanine and/or threonine, or derivatives thereof, in any combination and in any order. In principle, the linker sequence can include any amino acid residue, however, large and/or hydrophobic residues are more likely to cause problems. In one embodiment, the linker sequence comprises the amino acid sequence Gly-Gly-Ser-Gly-Gly-Thr (SEQ ID NO:64). In another embodiment, the modified chaperonin polypeptide comprises an additional linker sequence. For example, the chaperonin-EYFP fusion protein which is modified at position 267 comprises an additional linker comprising the sequence Gly-Ser-Gly-Gly-Ser-Gly (SEQ ID NO:83) which joins the yellow fluorescent protein to the chaperonin protein (FIG. 26B). In another example, the chaperonin-EYFP fusion protein which is modified at position 480 comprises an additional linker comprising the sequence Gly-Ser-Gly-Gly-Ser-Gly-Ser-Gly (SEQ ID NO:84) which joins the yellow fluorescent protein to the chaperonin protein (FIG. 27B).

Joined or Bound Molecules

In one embodiment, the modified chaperonin polypeptides comprise relocated N- and C-terminal ends that are covalently joined with an organic molecule, or an inorganic molecule or compound.

In a different embodiment, the modified chaperonin polypeptides comprise relocated N- and C-terminal ends that bind non-covalently with an organic molecule, or an inorganic molecule or compound.

The organic molecule or inorganic molecule/compound is joined or bound to the modified polypeptide in such a way that it does not disrupt the structure of the modified polypeptide. The modified polypeptide can fold into a structure that resembles a wild-type folded chaperonin subunit polypeptide. The folded modified polypeptide can self-assemble into a double-ringed chaperonin structure. The assembled chaperonin structure can be organized into nanodevices or coatings.

The organic molecule can be a second polypeptide molecule, including but not limited to a: protein; peptide fragment; reporter molecule; metal-binding peptide; enzyme; hormone; growth factor; trophic factor; antibody; antigen; receptor; toxin; fluorescent protein; or luminescent protein.

The second polypeptide can be from any organism including bacterial, viral, mammalian (e.g., bovine, porcine, murine, equine, canine, feline, monkey, ape, ovine or human), piscine, avian or insect.

The second polypeptide includes metal-binding peptide sequences that bind selectively to specific faces of gallium arsenide, silicon or indium phosphide. An exemplary, non-limiting list of partial amino-acid sequences from clones that bind to different surfaces of GaAs and/or InP (Whaley et al., 2000 Nature 405: 665-668) includes:

```
VTSPDSTTGAMA        (SEQ ID NO: 16)

AASPTQSMSQAP        (SEQ ID NO: 17)

AQNPSDNNTHTH        (SEQ ID NO: 18)
```

-continued

```
ASSSRSHFGQTD        (SEQ ID NO: 19)

WAHAPQLASSST        (SEQ ID NG:20)

ARYDLSIPSSES        (SEQ ID NO: 21)

TPPRPIQYNHTS        (SEQ ID NO: 22)

SSLQLPENSFPH        (SEQ ID NO: 23)

GTLANQQIFLSS        (SEQ ID NO: 24)

HGNPLPMTPFPG        (SEQ ID NO: 25)

RLELAIPLQGSG        (SEQ ID NO: 26)
```

Whaley et al. also describes amino-acid sequences that bind silicon and not silicon dioxide. An example of an amino-acid sequence that binds to ZnS(102) (Lee et al., 2002 Science 296: 892-895) is:

```
CNNPMHQNC        (SEQ ID NO: 27)
```

A list of partial amino-acid sequences from clones that bind to Ag (Naik et al., 2002 Nature Materials 1: 169-172) includes:

```
AYSSGAPPMPPF        (SEQ ID NO: 28)

NPSSLFRYLPSD        (SEQ ID NO: 29)

SLATQPPRTPPV        (SEQ ID NO: 30)
```

A list of partial amino acid sequences from clones that bind to Au (Brown et al., 2000 J. Mol. Biol. 299, 725-735; Brown, S., 1997,Nature Biotechnol. 15, 269-272) includes:

```
MHGKTQATSGTIQS        (SEQ. ID. NO: 31)

ALVPTAHRLDGNMH        (SEQ. ID. NO: 32)
```

Further examples of peptide sequences that bind inorganic molecules or compounds have been discovered using bacterial cell surface or phage display procedures, as reviewed by Sarikaya (2003 Nature Materials 2:577-7585).

A list of amino acid sequences from clones that bind to Au (Sarikaya, et al., 2003 Nature Materials 2:577-585) includes:

```
SKTSLGQSGASLQGSEKLTNG        (SEQ ID NO: 40)

QATSEKLVRGMEGASLHPAKT        (SEQ ID NO: 41)
```

A list of amino acid sequences from clones that bind to Pt (Sarikaya, et al., 2003 Nature Materials 2:577-585) includes:

```
DRTSTWR        (SEQ ID NO: 42)

QSVTSTK        (SEQ ID NO: 43)

SSSHLNK        (SEQ ID NO: 44)
```

A list of amino acid sequences from clones that bind to Pd (Sarikaya, et al., 2003 Nature Materials 2:577-585) includes:

| | |
|---|---|
| SVTQNKY | (SEQ ID NO: 45) |
| SPHPGPY | (SEQ ID NO: 46) |
| HAPTPML | (SEQ ID NO: 47) |

A list of amino acid sequences from clones that bind to $SiO_2$ (Sarikaya, et al., 2003 Nature Materials 2:577-585) includes:

| | |
|---|---|
| MSPHPHPRHHHT | (SEQ ID NO: 48) |
| RGRRRRLSCRLL | (SEQ ID NO: 49) |
| KPSHHHHHTGAN | (SEQ ID NO: 50) |

A list of amino acid sequences from clones that bind to zeolites (Sarikaya, et al., 2003 Nature Materials 2:577-585) includes:

| | |
|---|---|
| VKTQATSREEPPRLPSKHRPG | (SEQ ID NO: 51) |
| MDHGKYRQKQATPG | (SEQ ID NO: 52) |

A list of amino acid sequences from clones that bind to ZnO (Sarikaya, et al., 2003 Nature Materials 2:577-585) includes:

| | |
|---|---|
| NTRMTARQHRSANHKSTQRA | (SEQ ID NO: 53) |
| YDSRSMRPH | (SEQ ID NO: 54) |

A list of amino acid sequences from clones that bind to $CaCO_3$ (Sarikaya, et al., 2003 Nature Materials 2:577-585) includes:

| | |
|---|---|
| HTQNMRMYEPWF | (SEQ ID NO: 55) |
| DVFSSFNLKHMR | (SEQ ID NO: 56) |

A list of amino acid sequences from clones that bind to $Cr_2O_3$ (Sarikaya, et al., 2003 Nature Materials 2:577-585) includes:

| | |
|---|---|
| WRPKAATN | (SEQ ID NO: 57) |
| RIRHRLVGQ | (SEQ ID NO: 58) |

A list of an amino acid sequence from clones that bind to $Fe_2O_3$ (Sarikaya, et al., 2003 Nature Materials 2:577-585) includes:

| | |
|---|---|
| RRTVKHHVN | (SEQ ID NO: 59) |

A list of amino acid sequences from clones that bind to GaAs (Sarikaya, et al., 2003 Nature Materials 2:577-585) includes:

| | |
|---|---|
| AQNPSDNNTTH | (SEQ ID NO: 60) |
| RLELAIPLQGSG | (SEQ ID NO: 61) |
| TPPRPIQYNHTS | (SEQ ID NO: 62) |

A list of an amino acid sequences from clones that bind to ZnS (Sarikaya, et al., 2003 Nature Materials 2:577-585) includes:

| | |
|---|---|
| NNPMHQN | (SEQ ID NO: 63) |

The second polypeptide includes a reporter molecule, such as yellow fluorescent protein (EYFP) (SEQ M NO:91), green fluorescent protein (GFP), red fluorescent protein (RFP), DS red from coral, auto-fluorescent proteins including blue fluorescent protein (BFP), cerulean fluorescent protein (CFP), luciferase, glutathione-S-transferase (GST), horseradish peroxidase (HRP), chloramphenicol acetyltransferase (CAT) beta-galactosidase, beta-glucuronidase, and any derivatives of these reporter molecules (Labas, 2002 Proc Natl Acad Sci USA 99:4256-4261; Shaner 2004 Nature Biotechnology 22:1567-1572; Patterson 2001 Cell Science 114: 837-838; Wei Wen Su 2005 Microbiol Cell Factories 4:12; Rizzo 2004 Nature Biotechnology 22:445-449; Griesbeck 2001 Journal Biological Chemistry 276:29188-29194).

The second polypeptide includes an epitope tag, such as histidine (His) tags, or V5 tags, FLAG tags, influenza hemagglutinin (HA) tags, Myc tags, VSV-G tags, or thioredoxin (Trx) tags. The tagged-fusion molecules are useful for facilitating isolation and/or purification of the modified chaperonin polypeptides (Marshak, D. R., et al., 1996 in: "Strategies for Protein Purification and Characterization" pp 396).

The second polypeptide can include maltose binding protein (MBP), S-tag, Lex A DNA binding domain (DBD) fusions, GAL4 DNA binding domain fusions, and herpes simplex virus (HSV) BP16 protein.

The second polypeptide can be engineered to include a cleavage site located between the modified chaperonin polypeptide and the second polypeptide so that the modified chaperonin polypeptide can be cleaved and purified away from the second polypeptide. The cleavage site can include recognition sequences for the following enzymes: enterokinase, corin, MT-SP/matryptase, trypsin, chymotrypsin, human airway trypsin-like protease (HAT), mast cell tryptase, elastase, plasmin, kallikrein, TMPRSS2, MBL-associated serine proteases (MASP-1 and MASP-2), Stubble-stubbloid, furin, thrombin or factor Xa.

The organic molecule can be a nucleic acid molecule, including but not limited to: DNA; RNA; DNA/RNA hybrids; or derivatized nucleic acid molecules. The organic molecule can be a lipid or a carbohydrate.

The inorganic molecule or compound is a nanoparticle which includes: gallium arsenide; silicon; silicon dioxide; indium phosphide; ZnS; gold; silver; CdSe—ZnS; CdS; CdSe; InP; InGaAs; CuCl; InAs quantum dots; silicon nanocrystals and nanopyramids; silver nanoparticles; magnetic quantum dots (e.g., nanomagnets, such as CoCu, FeCu, NiFe/Ag, and CoAg); transition metals (e.g., gold, silver, zinc, cadmium, platinum, palladium, cobalt, mercury or nickel); alkali or alkaline earth metals (e.g., sodium, potassium, calcium or cesium); group III elements (e.g., aluminum, gallium or indium); group IV elements (e.g., silicon, germanium, tin or lead); group V elements (e.g., phosphorous, arsenic, antimony, or bismuth); or group VI elements (e.g., sulfur, selenium or tellurium). The inorganic molecules or compounds also include any given combination, such as III-V compounds like GaAs or AlGaAs. The inorganic molecules or compounds also include: a fullerene; a carbon nanotube; or a dielectric, polymeric, or semiconducting nanoparticle.

Amino Acid Analogs and Altered Polypeptides

The present invention further provides modified chaperonin polypeptides, or fragments or derivatives thereof, comprising amino acid analogs. The amino acid analogs can be chemically synthesized, and include dextro or levo forms, or peptidomimetics.

The modified chaperonin polypeptides can include any combination of amino acids from natural and/or or non-natural sources. The amino acid residues can include L-amino acids and/or D-amino acids. The amino acid residues can include rare amino acids such as 4-hydroxyproline or hydroxylysine. The amino acid can include organic acids or amides. The amino acid can include derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation). The amino acids can include side-chain modifications and/or substitutions (e.g., methylation, benzylation, t-butylation, tosylation, alkoxycarbonylation, and the like). The amino acids can include derivatives having an N-acetyl group such that the amino group that represents the N-terminus of the linear peptide prior to cyclization is acetylated, and/or a C-terminal amide group (i.e., the carboxy terminus of the linear peptide prior to cyclization is amidated). The amino acids can include, but are not limited to, penicillamine, beta-beta-tetramethylene cysteine, beta-beta-pentamethylene cysteine, beta-mercaptopropionic acid, beta-beta-pentamethylene-beta-mercaptopropionic acid, 2-mercaptobenzene, 2-mercaptoaniline, 2-mercaptoproline, omithine, diaminobutyric acid, alpha-aminoadipic acid, m-aminomethylbenzoic acid, and alpha-beta-diaminopropionic acid.

The present invention also provides modified chaperonin polypeptides which are altered, for example, by post-translational pathways or by chemical synthesis, including N- or O-glycosylated amino acid residues. The N-terminal end of the polypeptides can be altered to include acylated or alkylated residues. The C-terminal end of the polypeptides can be altered to include esterified or amidated residues. The non-terminal amino acid residues can be altered, including but not limited to, alterations of the amino acids, arginine, aspartic acid, asparagine, proline, glutamic acid, lysine, serine, threonine, tyrosine, histidine, and cysteine.

Sequence Variants

The present invention provides modified chaperonin polypeptides, or fragments or derivatives thereof, comprising sequence variations of any naturally-occurring chaperonin polypeptide (FIG. 2A-R, 15, 16, or 28B). As persons skilled in the art understand, any number of amino acids can be varied alone, or in combination with other amino acids and yet the modified chaperonin polypeptides will retain their functional activity (e.g., folding into a subunit structure that self-assembles into a double-ringed chaperonin structure). Sequence variants of the modified chaperonin polypeptides include: amino acid substitutions, amino acid insertions, amino acid deletions, mutant forms, allelic forms, and homologs.

The sequence variants also includes chaperonin polypeptides from naturally-occurring or laboratory strains, where the amino acid sequence of the chaperonin polypeptide differs from that of any of the Group I or II chaperonin polypeptides disclosed herein (see also FIGS. 2A-R, 15, 16 and 21-29)

Amino Acid Substitutions

The modified chaperonin polypeptides, or fragments or derivatives thereof, can include amino acid substitutions, including conservative and/or non-conservative amino acid substitutions. Guidance in determining which and how many amino acid residues can be substituted in the modified chaperonin polypeptides can be found in the properties of a naturally-occurring, chaperonin polypeptide. These properties include the amino acid length, the physical length, the folded conformation, or the ability to self-assemble into a chaperonin. These properties can be derived by prediction (e.g., based on amino acid sequence) and/or experiment (e.g., based on X-ray crystallography or transmission electron microscopy (TEM)). The substituted amino acids are selected so that the properties of the variant, modified chaperonin polypeptides is identical or similar to that of a naturally-occurring chaperonin subunit polypeptides. In one embodiment, the modified chaperonin polypeptides comprise a cysteine substituted with another amino acid. For example the cysteine at position 258 is substituted with alanine, as shown in FIG. 28B.

Mutant Forms

The present invention also provides modified chaperonin polypeptides, or fragments or derivatives thereof, having a mutation. The mutant variant has an amino sequence that differs from that of the wild-type, naturally-occurring chaperonin polypeptide. The mutations include amino acid substitutions, deletions, insertions, additions, truncations, or processing or cleavage errors of the protein. The mutant variants can have the same or similar functional activity of a wild-type chaperonin polypeptide.

In one embodiment, the modified chaperonin polypeptides comprise deletions of up to 10, 20, 30, 40, 50, 60 or 70 amino acids from the N- or C-terminal end. In another embodiment, the modified chaperonin polypeptides comprise additional deleted amino acids. For example, a "dwarf" modified chaperonin polypeptide (modified at position 267) comprises an additional 52 amino acids deleted from the N-terminal end of (e.g., FIG. 29B) compared to the 267 'non-dwarf' modified polypeptide (FIG. 22B). These deletion variants retain the ability to fold and assemble into double-ringed chaperonin structures. FIG. 29A shows the corresponding DNA sequence.

Designing Modified Chaperonin Polypeptides

The present invention provides methods for producing modified chaperonin polypeptides through selective mutation of the polypeptide, and then exploiting the ability of these variants to self-assemble into higher-order structures under various conditions for forming the compositions and devices, e.g., nanotemplates, nanostructures, nanoarrays and nanodevices, of the invention.

The compositions and devices of the invention, e.g., the nanotemplates, nanostructures, nanoarrays and nanodevices of the invention, comprise, unless otherwise indicated, at least one mutant chaperonin, which comprises at least one mutant chaperonin polypeptide. Non-limiting examples of mutant chaperonins and mutant chaperonin polypeptides that can be utilized as part of the methods and compositions of the present invention are described herein.

In referring to mutant chaperonins and mutant chaperonin polypeptides, the term "mutant" refers to a difference relative to what is considered a wild-type sequence. Representative, non-limiting examples of wild-type chaperonin polypeptide sequences are presented in FIGS. 2A-2R. Generally, a mutant chaperonin sequence refers to a sequence that does not occur in nature at a greater than 10% (±10%) allelic frequency, as measured by standard methods and available data. For example, an example of a mutant *S. shibatae* chaperonin polypeptide is one that is expressed by an allele that is present in the organism at no greater than 10% (±10%) allelic frequency.

It is appreciated by those skilled in the art that the sequence and three dimensional structural similarities between chaperonins and chaperonin polypeptides from different organisms can be used as a guide to utilize any chaperonin polypeptide to produce the modified chaperonin polypeptides and assembled structures of the present invention. The sequence and three dimensional structural similarity of the subunits among the different types of chaperoning, which is illustrated by the sequence alignment depicted in FIGS. 2A-2R and the structural overlap as illustrated in a representative comparison depicted in FIG. 3, provides the basis for the production of the modified chaperonin polypeptides and assembled chaperonins of the invention.

Further, the details of the structure of chaperonins can be solved at atomic-resolution (2.3-2.8 Å) (See, e.g., FIG. 1, and Xu, Z. et al., 1997 Nature 388: 741-750; and Ditzel, L., J. Lowe, et al., 1998 Cell 93: 125-138). This provides detailed information about the location of every atom of every amino acid in the double ring structure (e.g., FIG. 4), and can be used to routinely select positions for modification and can routinely assess the properties of the modified chaperoning.

Utilizing the sequence and three dimensional structural similarities among chaperonins and chaperonin polypeptides, as well as the ability to solve at atomic-resolution the structure of particular chaperonins and chaperonin polypeptides, the structure of the chaperonin polypeptides can be manipulated to influence, for example, their folding, assembly, strength, and binding properties, as well as the assembly, strength and binding properties of the resulting chaperoning.

Such structural similarities can be utilized in a number of different ways in designing appropriate mutants. For example, a mutant in one species that exhibits a desirable characteristic can be introduced into a corresponding position in another chaperonin by utilizing the sequence similarity and/or the three dimensional structural similarity between the chaperoning. In one such embodiment, for example, the mutant *S. shibatae* sequences successfully utilized in the examples presented below can routinely be introduced into other chaperonin polypeptides by these techniques.

Standard methods well known in the art which allow changing specific amino acids in chaperonin polypeptides, such as the method of site-directed mutagenesis, regions of the subunits can be modified, and the resulting chaperonin polypeptides can routinely be tested for their ability to produce chaperonins and, for example, nanotemplates, nanostructures, nanoarrays and nanodevices, e.g., their ability to assemble into tubes and filaments or two-dimensional crystals can be tested. In one embodiment, for example, amino acid tails can be attached to chaperonin polypeptide subunits that do not inhibit their ability to assemble into rings and tubes, and that allow the binding of various nanoscale materials, such as metals, at various locations of the chaperonins, including inside the chaperonin structure. In one embodiment, one of the three HSP60 subunits (beta) from *Sulfolobus shibatae*, an organism that lives in geothermal hot-springs and grows at temperatures of up to 85° C./pH 2.0 is used to form mutant chaperonins. The chaperonins in *S. shibatae* are octadecameric with nine subunits per ring. FIG. 15 shows the protein sequence alignment of *S. shibatae* TF55 alpha subunit (SEQ ID NO: 39), beta subunit (SEQ ID NO: 1) and gamma subunit (SEQ ID NO: 38). The beta subunit can be chosen for a particular application based on such factors as its thermostability, which makes it easy to purify as a recombinant protein, and its propensity to form desirable structures.

Figure 4:
FIG. 4 shows the detailed structure of a Group II chaperonin subunit.
Figure 5A:
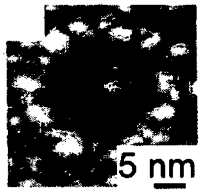
FIGS. 5A-D shows individual HSP60 (heat-shock protein) chaperonins and filaments as observed in the electron microscope.
Figure 5B:
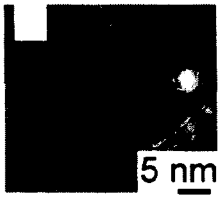
Figure 5C:
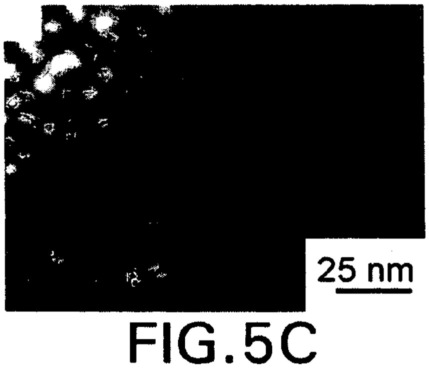
Figure 5D:
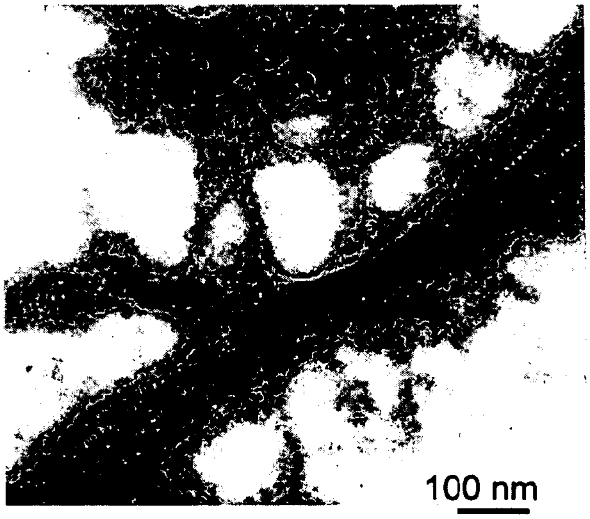

In general, the chaperonin subunits have many regions that can accommodate relocated N- and C-terminal ends in each of their three domains-equatorial, intermediate, and apical domains, as illustrated in FIG. 3. FIG. 4 shows the detailed structure of a Group II chaperonin subunit that can be used in selecting the relocated terminal positions.

Other modified chaperonin polypeptides have been previously described. These modified chaperonin polypeptides comprise mutations having single cysteine residues placed at various solvent-exposed sites on the polypeptide. The thiol moiety of these cysteine residues provides binding sites for soft metals (see PCT/US02/35889). These mutations also change the dimensions of the resulting chaperonin subunit, such as length, inner pore diameter, outer diameter, and the like. The mutant chaperonin polypeptides described in PCT/US02/35889 can be used as a guide to select the positions of the relocated N- and C-terminal ends in the modified chaperonin polypeptides of the present invention. The modified chaperonin polypeptides of the present invention can use any of the mutant chaperonin polypeptides described in PCT/US02/35889 as a basis, and relocate the N- and C-terminal ends therein.

The choice of mutation may also depend on the desired structure for the different applications of the present invention, including the formation of nanotemplates, nanostructures, nanoarrays and nanodevices.

The choice of mutations to make depends on the desired structure of the resulting chaperonin, and can routinely be ascertained. In a specific embodiment, the mutated chaperonin polypeptide subunits include ones that assemble into higher order structures with less than seven subunits per ring or more than nine subunits per ring, such as six to 10 subunits per ring. Mutations can be made to the subunit sequence such that the resulting subunit variants assemble into a structure with any number of subunits per ring. Mutations introduced that that change in number of subunits per ring can, for example, be used to modify the diameter of a resulting ring nanostructure.

Factors that affect the choice of which chaperonin polypeptides to manipulate (e.g., from what species, which subunit(s), etc.), and what mutations are to be made to them, include the desired dimensions, i.e., length, pore diameter, and outer diameter, of the resulting chaperonin product, or introduction of a selective binding site anywhere on the polypeptide. The subunits of both Group I and Group II chaperonins will tolerate a point mutation at almost any position. When sequence alignments are used in determining mutation positions, mutations at similar, non-identical residues, as determined by sequence alignment, being preferred, and non-conserved positions, as determined by sequence alignment being more preferred. When three dimensional structural alignments are used in determining mutation positions, a structural alignment of chaperonin subunits, such as that of FIG. 3, can serve as a guide in deciding where on the subunit to perform the mutation. The loops and turns from the two structures that do not directly superimpose can be choices of points to perform mutations, including deletions and insertions. The amino acid sequence alignment of various chaperonins can also be used in determining the mutation positions. For example, FIG. 15 depicts sequence alignment of TF55 alpha, beta and gamma subunits from *S. shibatae*. In the modified chaperonin polypeptides of the present invention, the N- and C-terminal ends can be relocated to any position 1-560 for TF55 alpha subunit, position 1-552 for TF55 beta subunit, or position 1-535 for TF55 gamma subunit (FIG. 15).

In one embodiment, a choice of deletion of the amino acid loop at the apical domain of a group II chaperonin is made through comparison of the structural alignment of FIG. 3, and with the observation that the loopless group I chaperonin subunit assembles into the double-ring structure of the chaperonin. In another embodiment, the N- or C-terminus is removed. In yet another embodiment, the N- or C-terminus is modified by inserting a sequence. The sequence can be inserted for binding specificity, such as by introducing cysteine or tyrosine which can be modified chemically.

In one embodiment, the mutant chaperonin comprises one more mutated chaperonin polypeptide sequences with one or more point mutations. An exemplary point mutation in TF55-beta from *Sulfolobus shibatae* results from residue 298 being changed from cysteine to alanine and residue 270 changed from glutamine to cysteine (see PCT/US02/35889). In another embodiment, the mutant chaperonin comprises one more mutated chaperonin polypeptide sequences with one or more sequences deleted. An exemplary deletion in TF55-beta results from *Sulfolobus shibatae* with residues 254 to 281 deleted (see PCT/US02/35889). In another embodiment, the mutant chaperonin comprises one or more mutated chaperonin polypeptide sequences with one or more polypeptide sequences inserted. An exemplary insertion in TF55-beta results from *Sulfolobus shibatae* with peptides that possess binding specificity inserted. As discussed above, corresponding mutations can be routinely introduced into any other chaperonin polypeptide.

In another embodiment, the peptides are designed to bind nanoscale materials such as nanoparticles and quantum dots. In yet another embodiment, the peptides are designed to bind only to specific surfaces. Still other modifications can also be made in the equatorial domains that include deletions, substitutions and additions to the N- and C-termini with little effect on the formation of chaperonins or nanotemplates such as filaments. For example, up to about 5, 10, 15, 20, 25, or 30 amino acids of the N- and/or C-terminus of the chaperonin polypeptide can be modified, e.g., deleted. For example, GroEL can be modified by removing up to about 27 amino acids from the C-terminus without impairing its ability to assemble into double rings.

Additional references that describe possible mutations of specific residues of the polypeptides are contained in the review article by Fenton (1997 Protein Science 6: 743-760).

The sequence alignment of FIGS. 2A-2R indicates that the regions that have been manipulated in *S. shibatae* also exist in other species. Whatever mutations have been successfully made in one species may be successfully others species, whether bacterial, other archea or eukarya. The corresponding regions of the sequence alignments can therefore serve as a guide in choice of manipulations to produce variants in other species, combined with the knowledge of the region of the chaperonin subunit that the given mutated sequence is located. A successful mutation of the chaperonin polypeptide from any given species is indicated if the mutated chaperonin polypeptide retains its ability to assemble into the higher order structures of the invention, including the nanotemplates, nanostructures, nanoarrays and nanodevices.

Figure 7A:
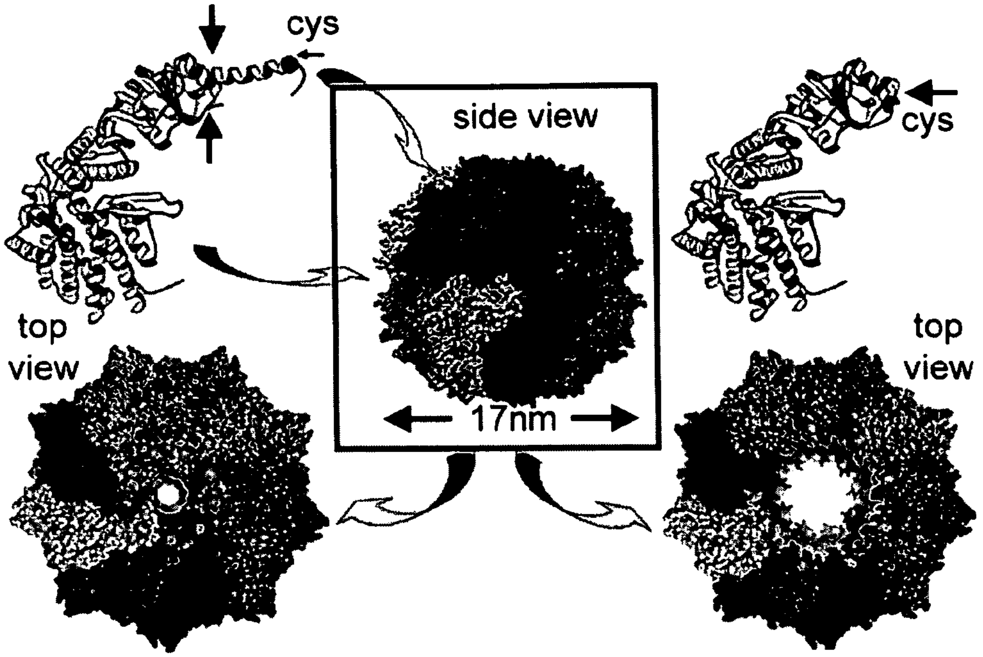
FIGS. 7A-E show the assembly of engineered HSP60s (heat-shock proteins) into nanotemplates for the production of nanoarrays comprising nanoscale materials such as nanoparticles.
Figure 7B:
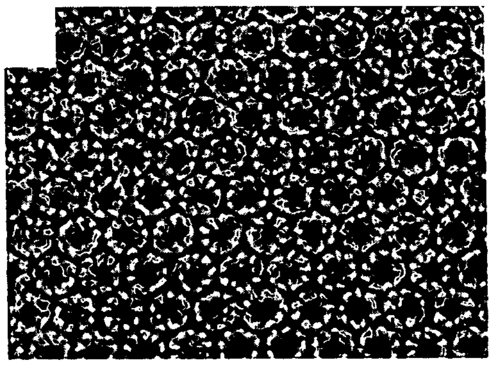
Figure 7C:
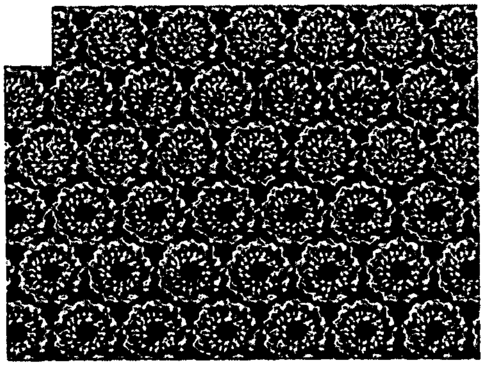
Figure 7D:
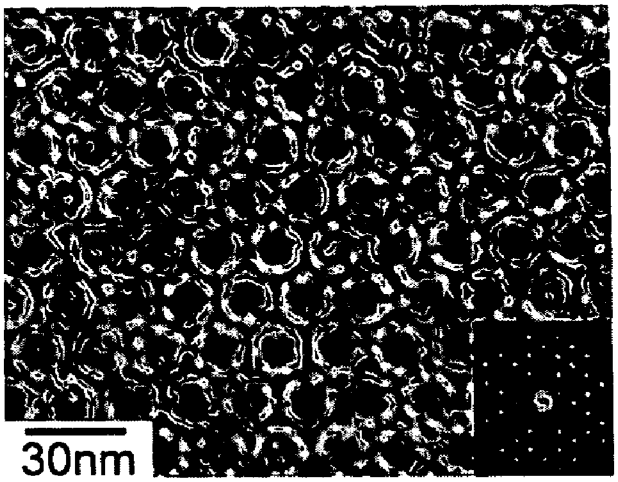

In a specific embodiment, guided by structural information, the beta subunit of *Sulfolobus shibatae* is genetically modified to add chemically reactive sites without destroying its ability to assemble into chaperonins and 2D crystals. While a detailed three-dimensional structure of *S. shibatae* beta is not known, X-ray structures for homologous chaperonin subunits are known (See, e.g., Xu et al. And Diztel et al., supra.). Detailed transmission electron microscopic (TEM) analyses of *S. shibatae* chaperonins have also been reported (Trent et al., 1997 Proc. Nat. Acad. Sci 94: 5383-5388). Using X-ray structures of homologous subunits and TEM analyses of *Sulfolobus* chaperonins, a hypothetical three-dimensional model for the beta chaperon can be produced, and used to guide genetic manipulations (See, e.g., Peitsch, M. C., 1995 Bio/Technology 13: 658; Guex, N., Peitsch, M. C., 1997 Electrophoresis 18: 2714; Guex, N., Diemand, A., Peitsch, M. C., 1999 TiBS 24: 364). At least two classes of beta mutants can be created using site-directed mutagenesis, many of which retain their ability to assemble into chaperonins that form 2D crystals (FIGS. 7B and 7D).

The present invention provides at least five different modified chaperonin polypeptides which retain the ability to assemble into chaperonin structures. These modified polypeptides can be used as a guide to other modified chaperonin polypeptides.

Figure 7E:
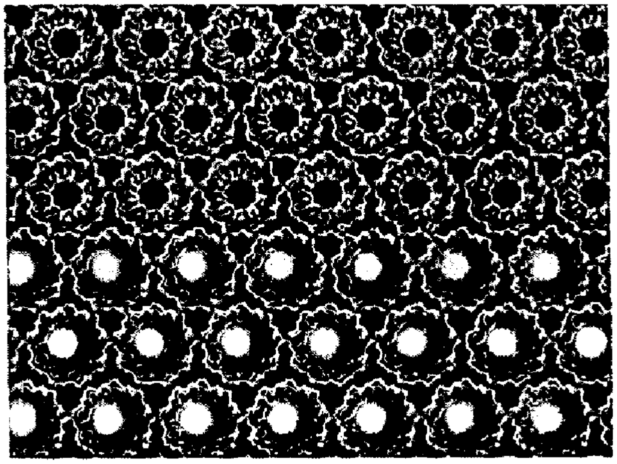
Figure 8A:
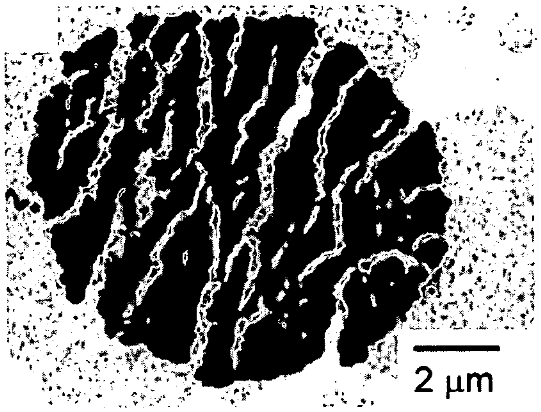
FIGS. 8A-D show gold nanoparticles binding to engineered chaperonins and chaperonin nanotemplates.
Figure 8B:
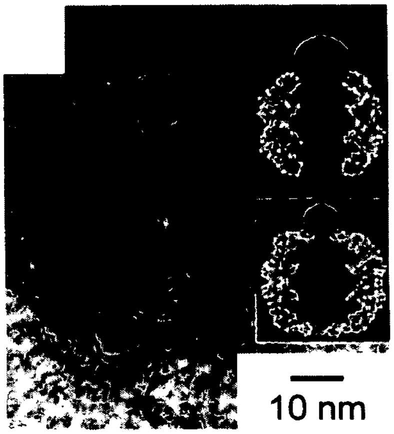
Figure 8C:
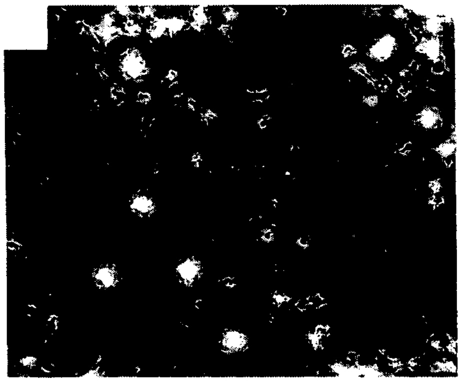
Figure 8D:
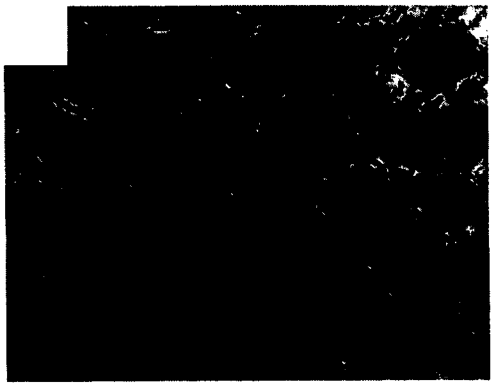

In two classes of beta mutants of *S. shibatae*, the single native cysteine residue in beta can be changed to a nonreactive residue, for example, an alanine residue, e.g., to prevent potential issues with folding and with assembly of mutant subunits. A cysteine can then placed at different solvent-exposed sites. The thiols of these cysteines can provide binding sites for soft metals including gold and zinc (see PCT/US02/35889). In one class of beta mutants of *S. shibatae*, the exposed cysteine is placed near the tip of a 28 amino acid loop on the apical domain of beta, which in the assembled chaperonin protrudes into the central cavity. This mutant chaperonin has a ring of reactive thiols with a diameter of approximately 3 nm on both ends (FIG. 7A). In the other class of beta mutants of *S. shibatae*, the protruding 28 amino acid loop was removed and placed the exposed cysteine on the apical domain itself. The mutant chaperonin assembled from this subunit has a ring of reactive thiols with a diameter of approximately 9 nm and an open pore into its central cavity (FIGS. 7D, 7E).

The beta subunit of *S. shibatae* proves to have sufficient structural plasticity in its apical domain to accommodate both the amino acid substitutions and deletions can be made without loss of its ability to form chaperonins and 2D crystals. Under reducing conditions both classes of beta mutants formed chaperonins that assembled into disk-shaped, hexagonally packed 2D crystals up to 20 μm in diameter (FIGS. 7B and 7D), the crystalline lattice ordering of which is confirmed by fast Fourier transformation (FFT) of the TEM images FIG. 7D, inset).

Figure 2B:
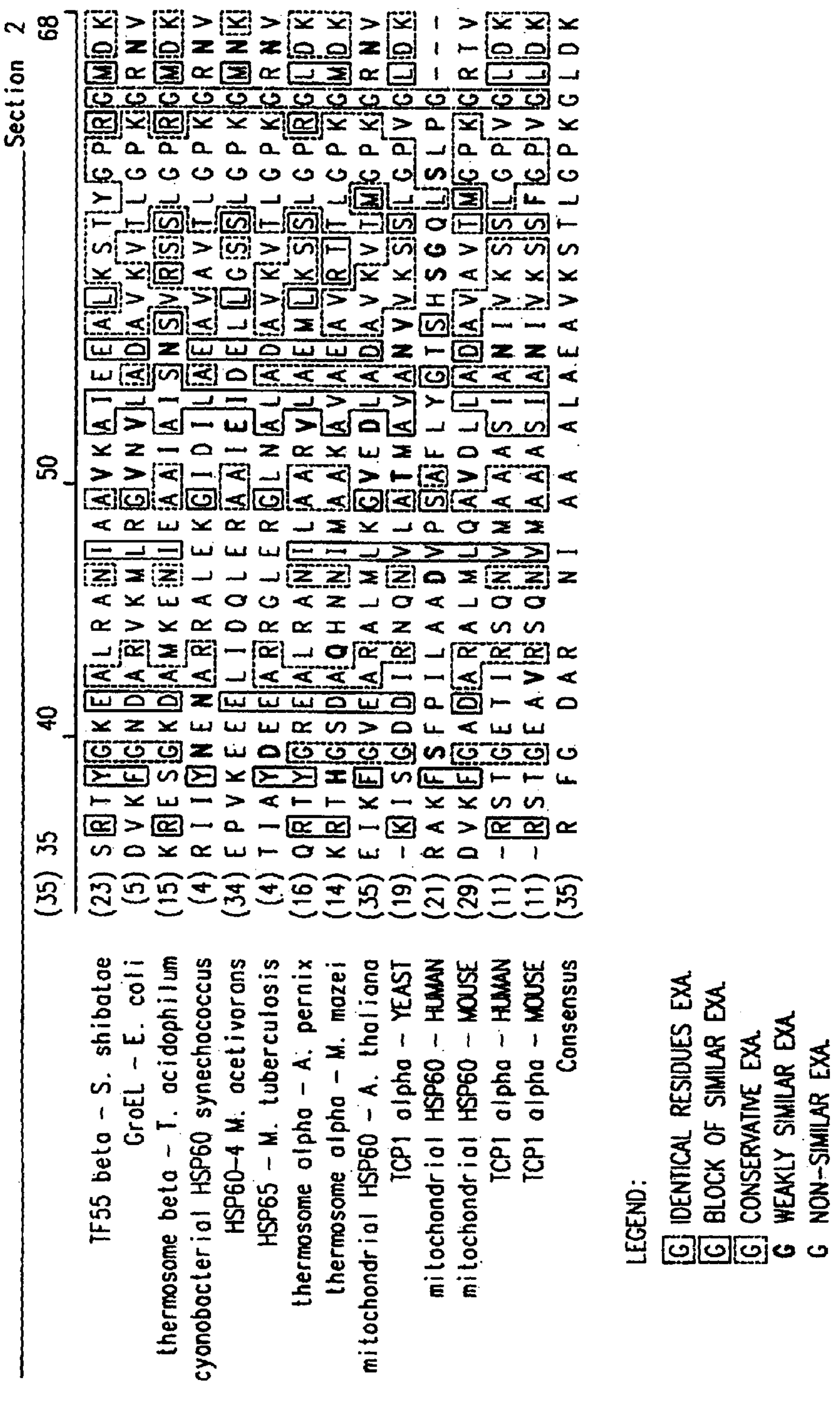
Figure 2C:
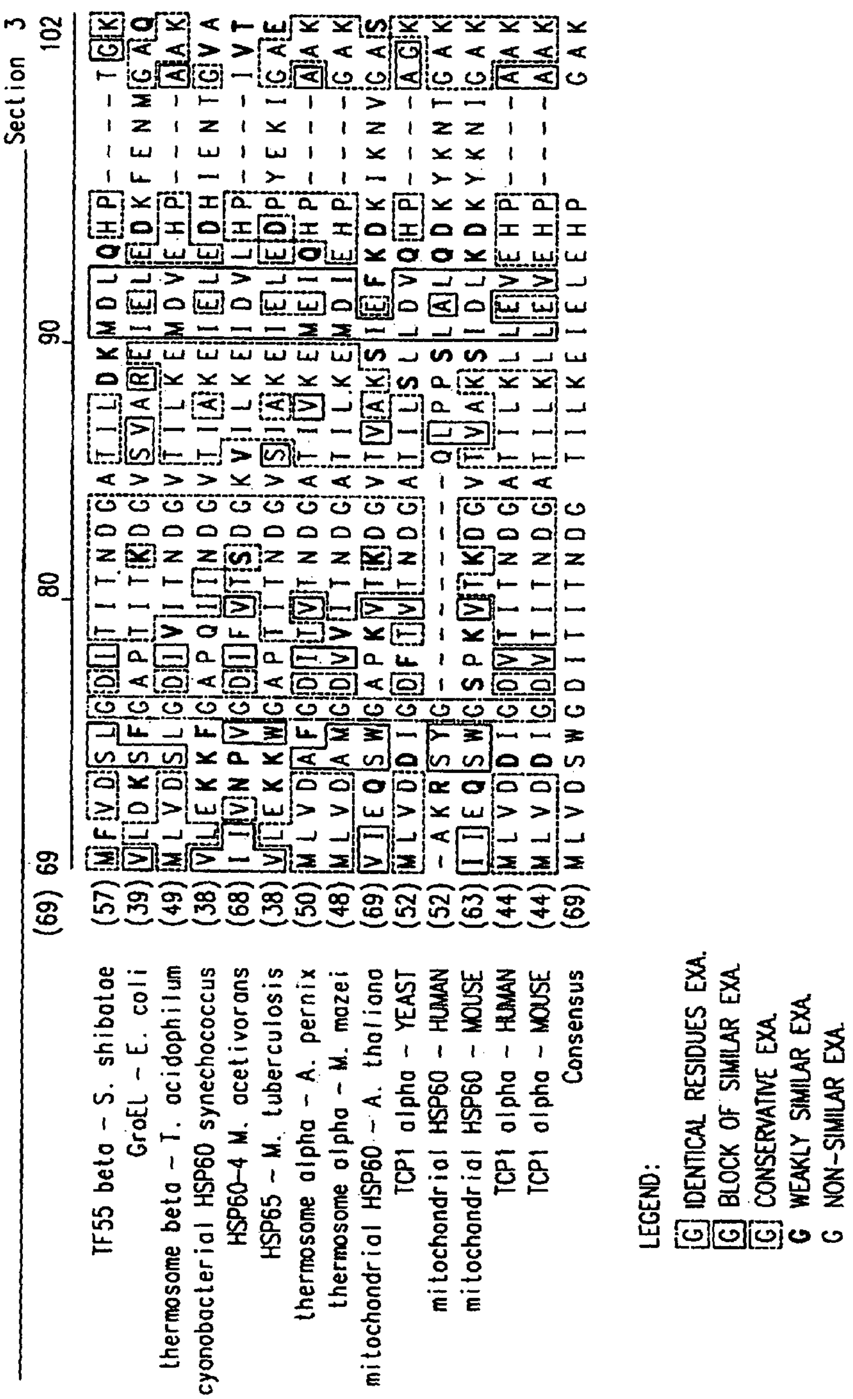
Figure 2D:
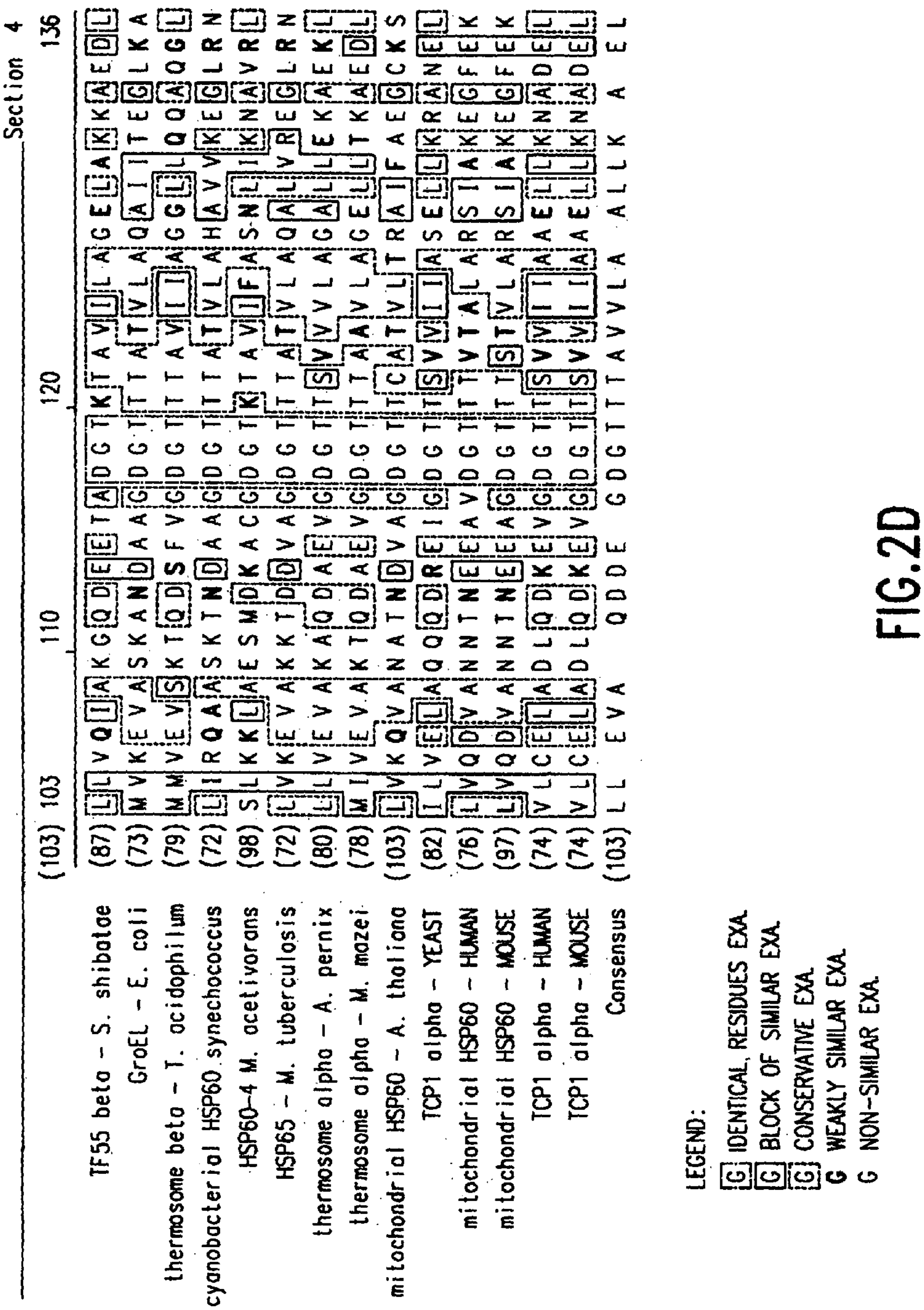
Figure 2E:
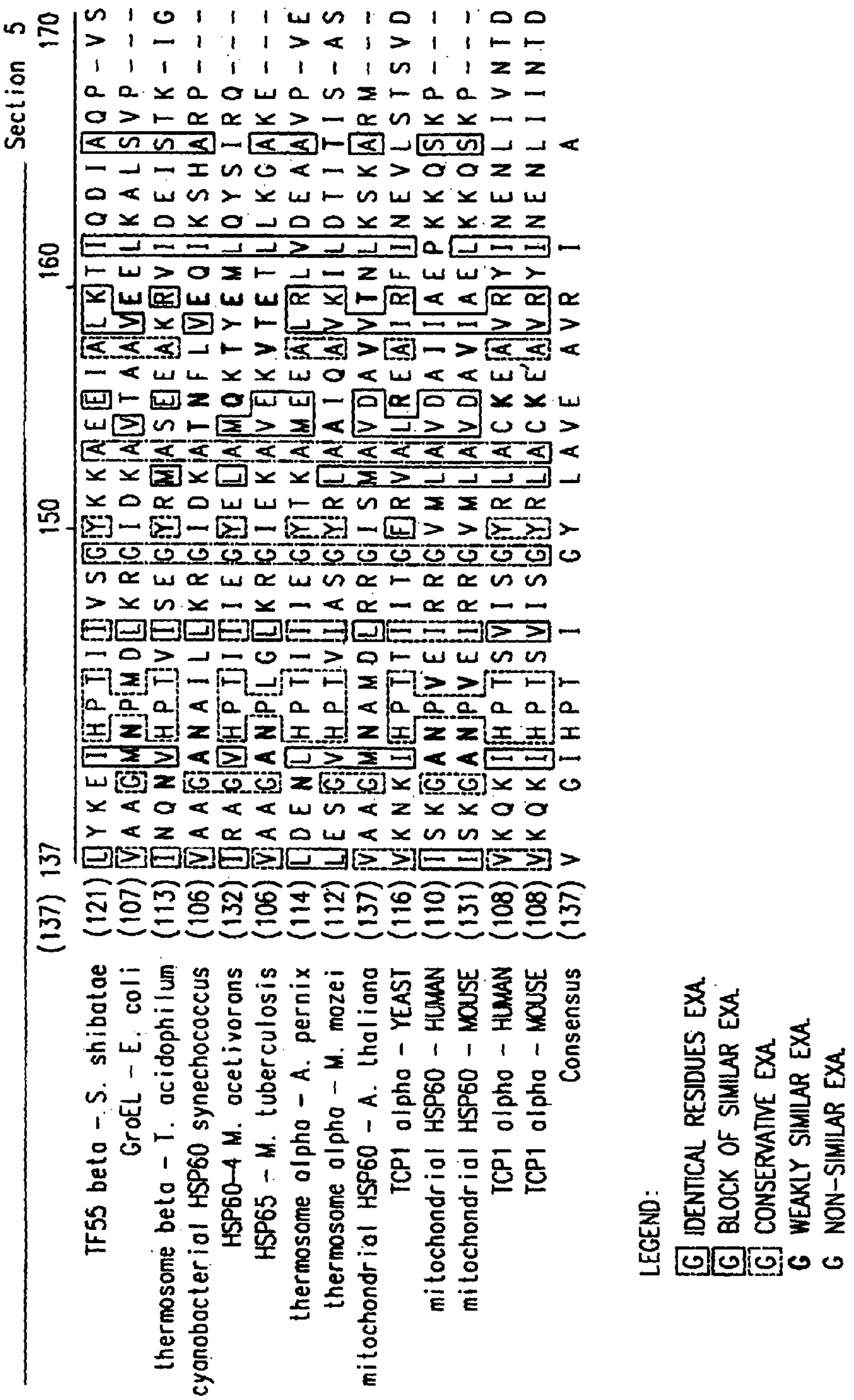
Figure 2F:
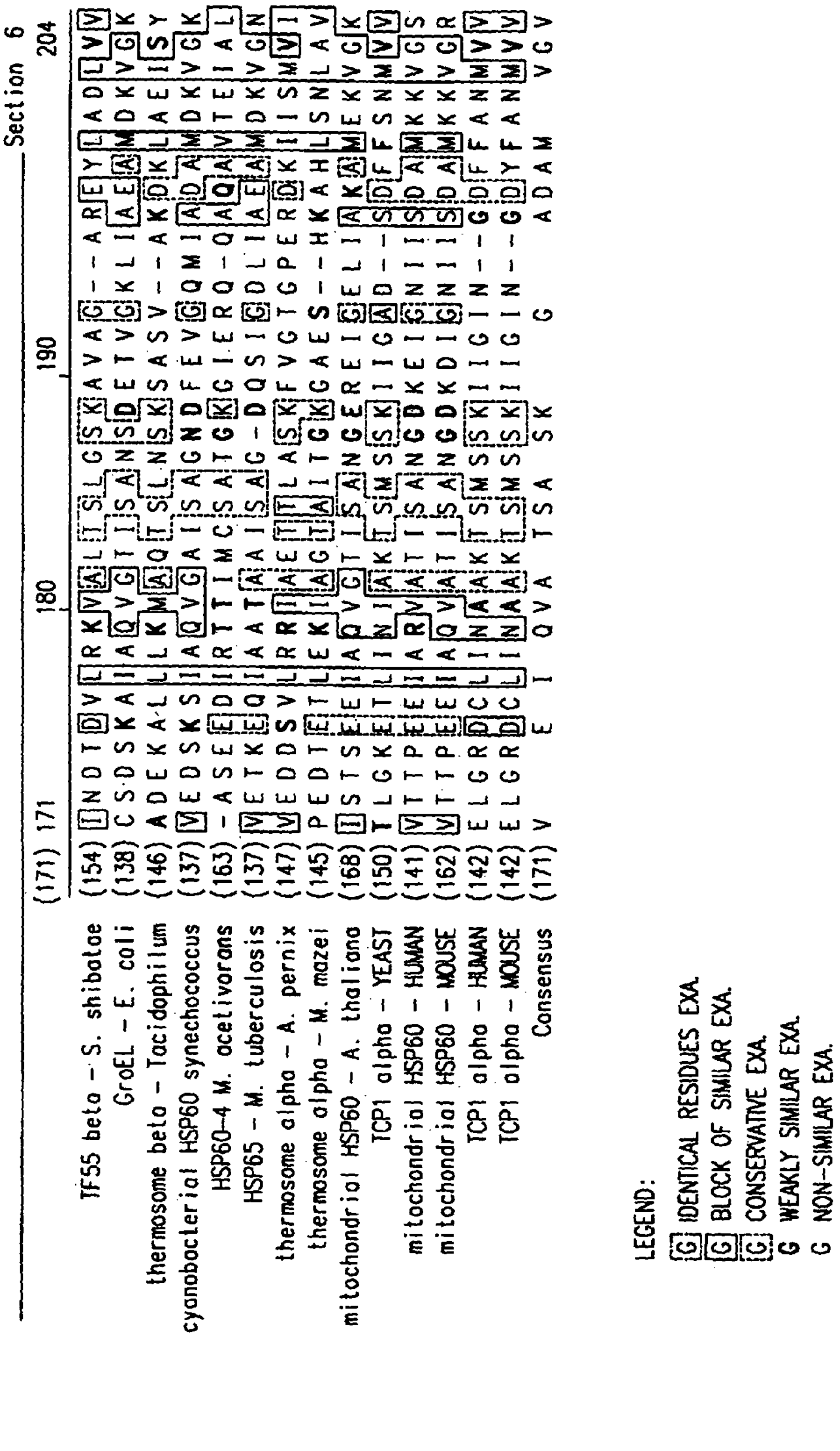
Figure 2G:
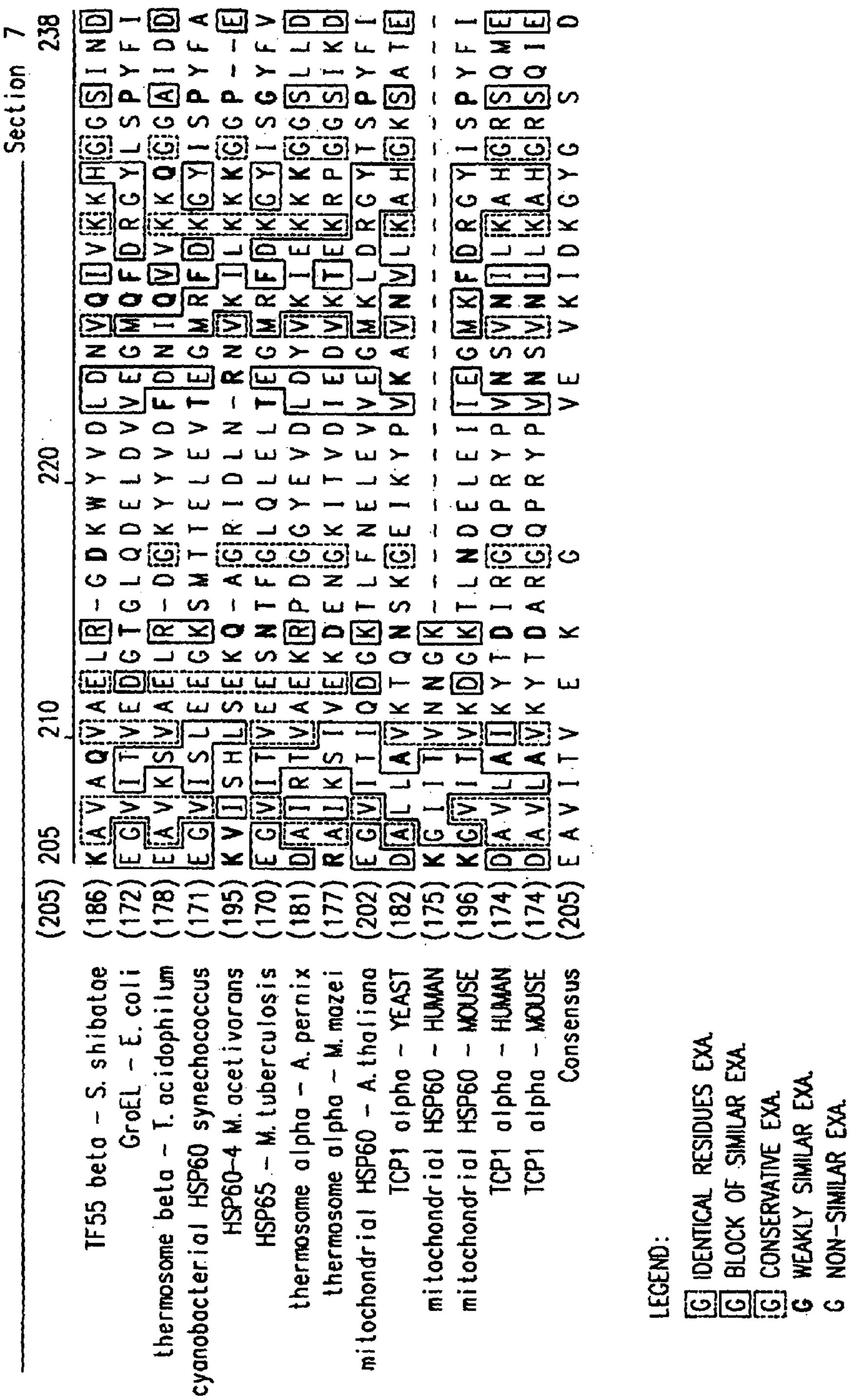
Figure 2H:
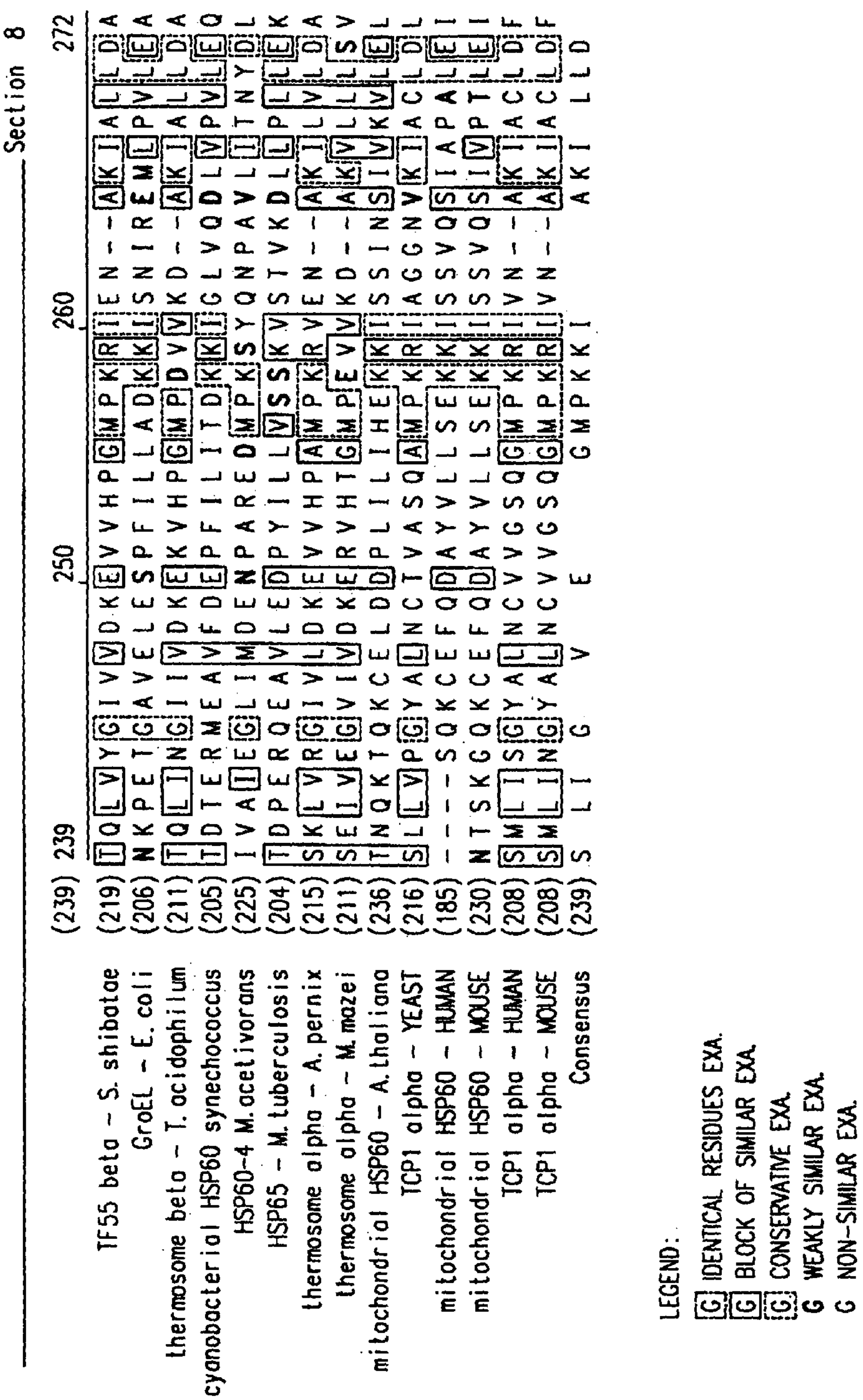
Figure 2I:
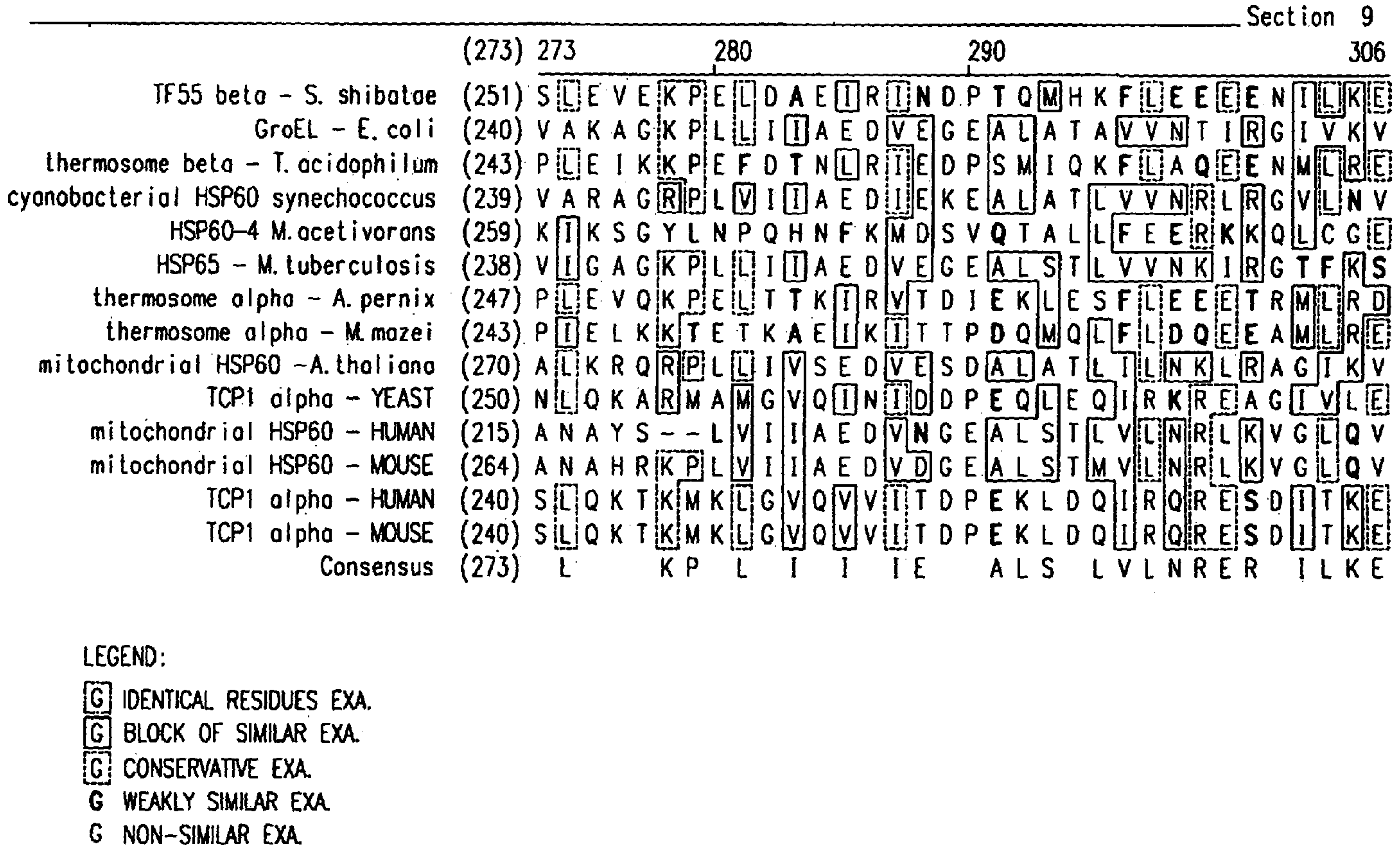
Figure 2J:
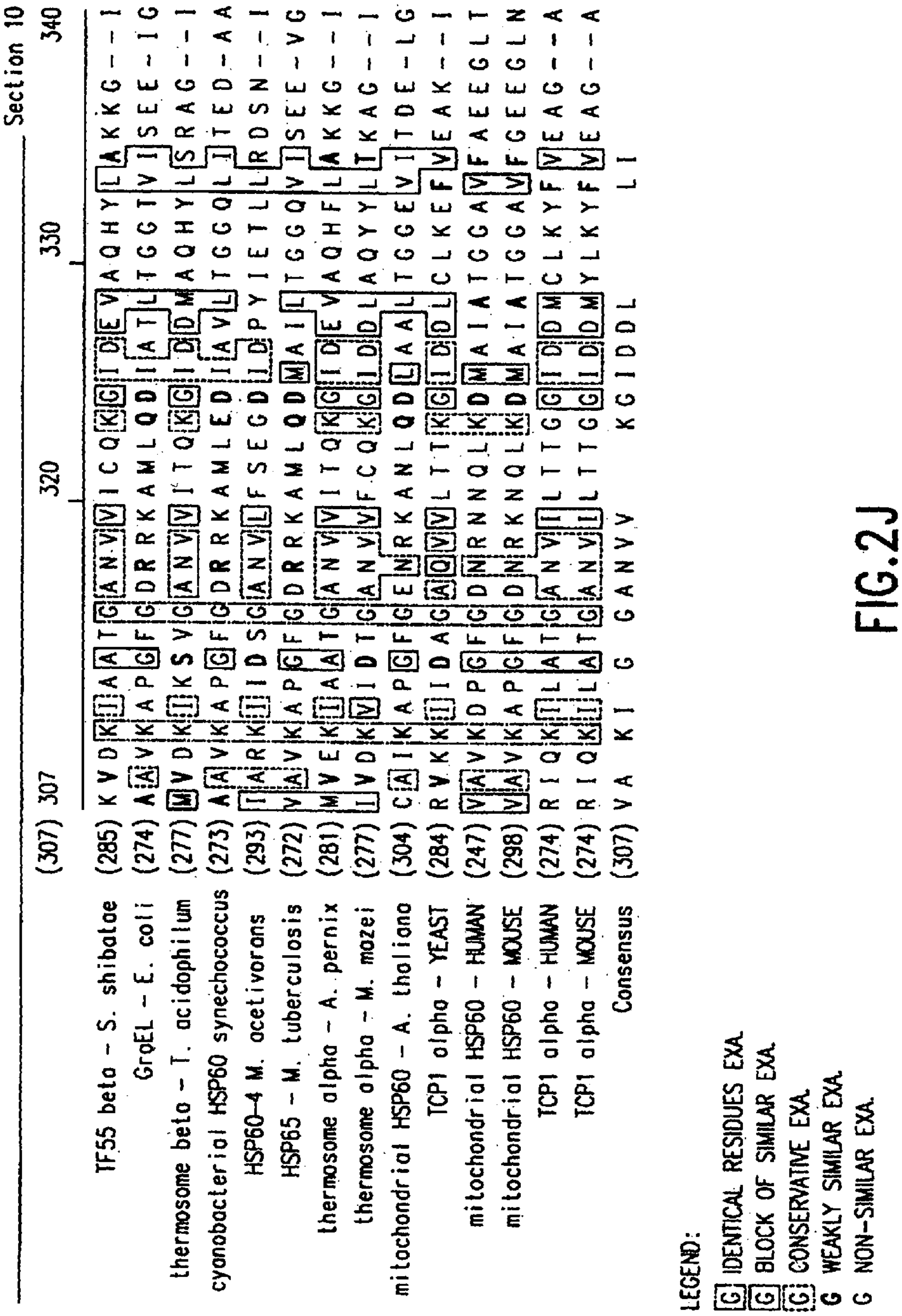
Figure 2K:
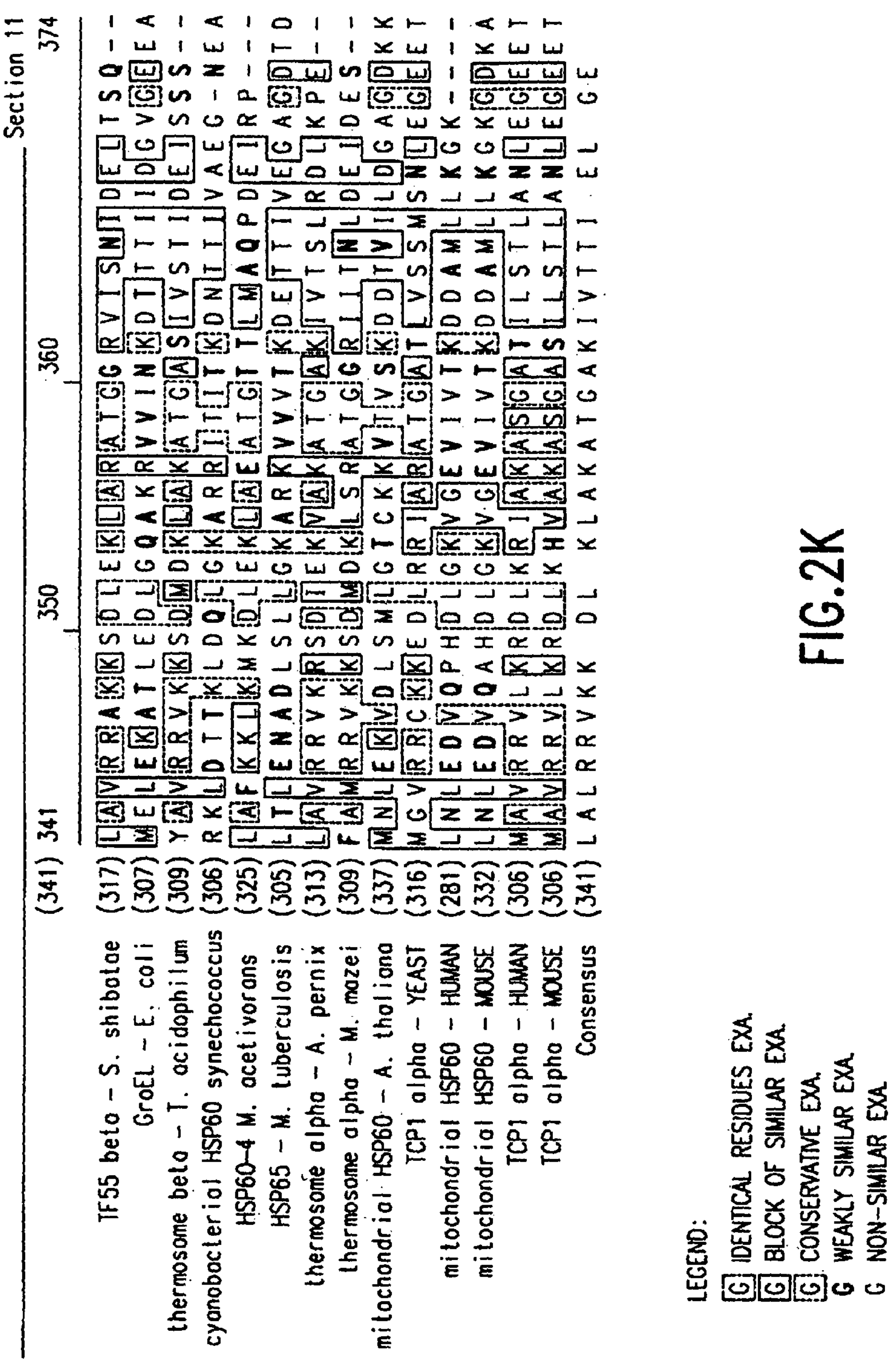
Figure 2M:
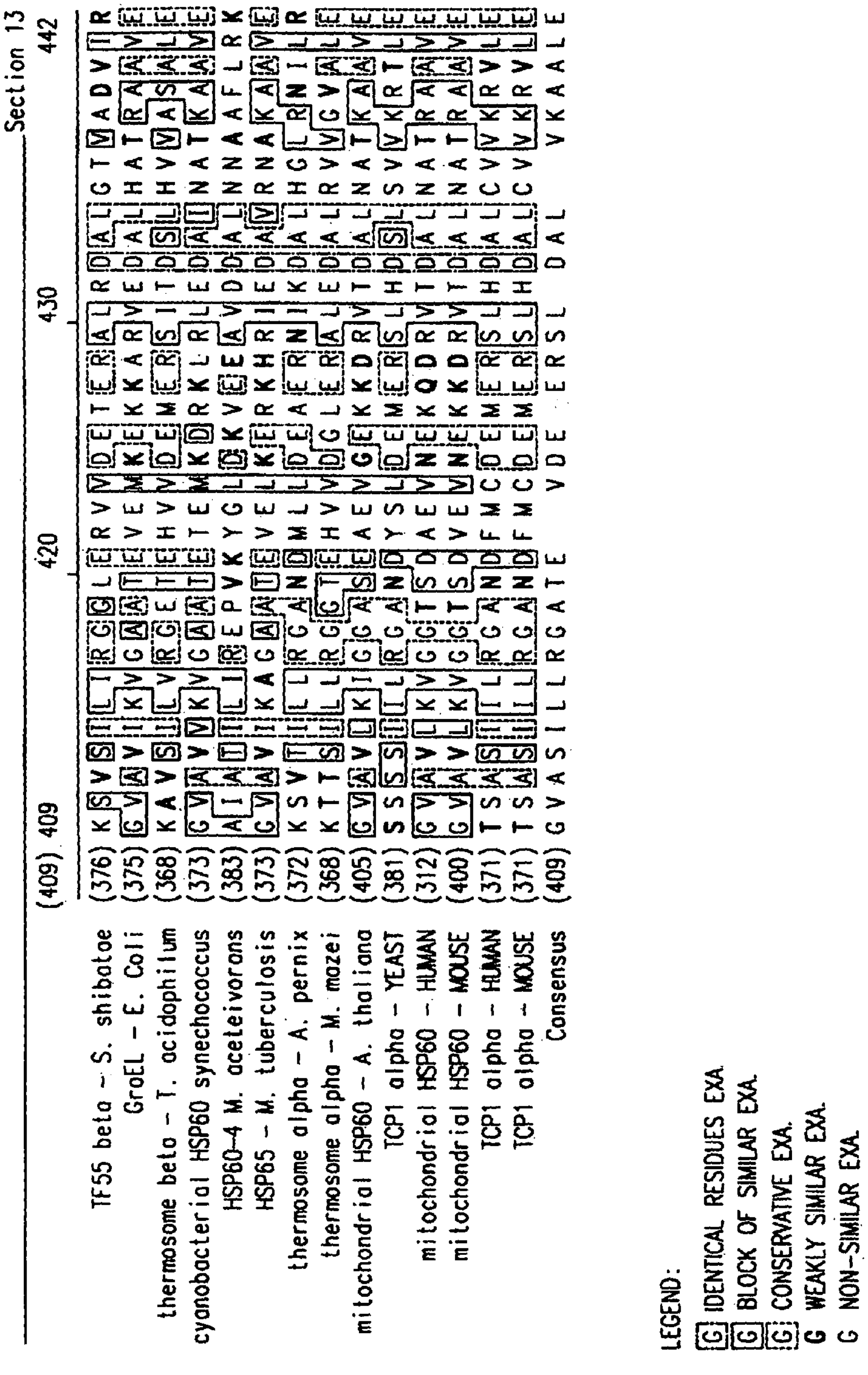
Figure 2N:
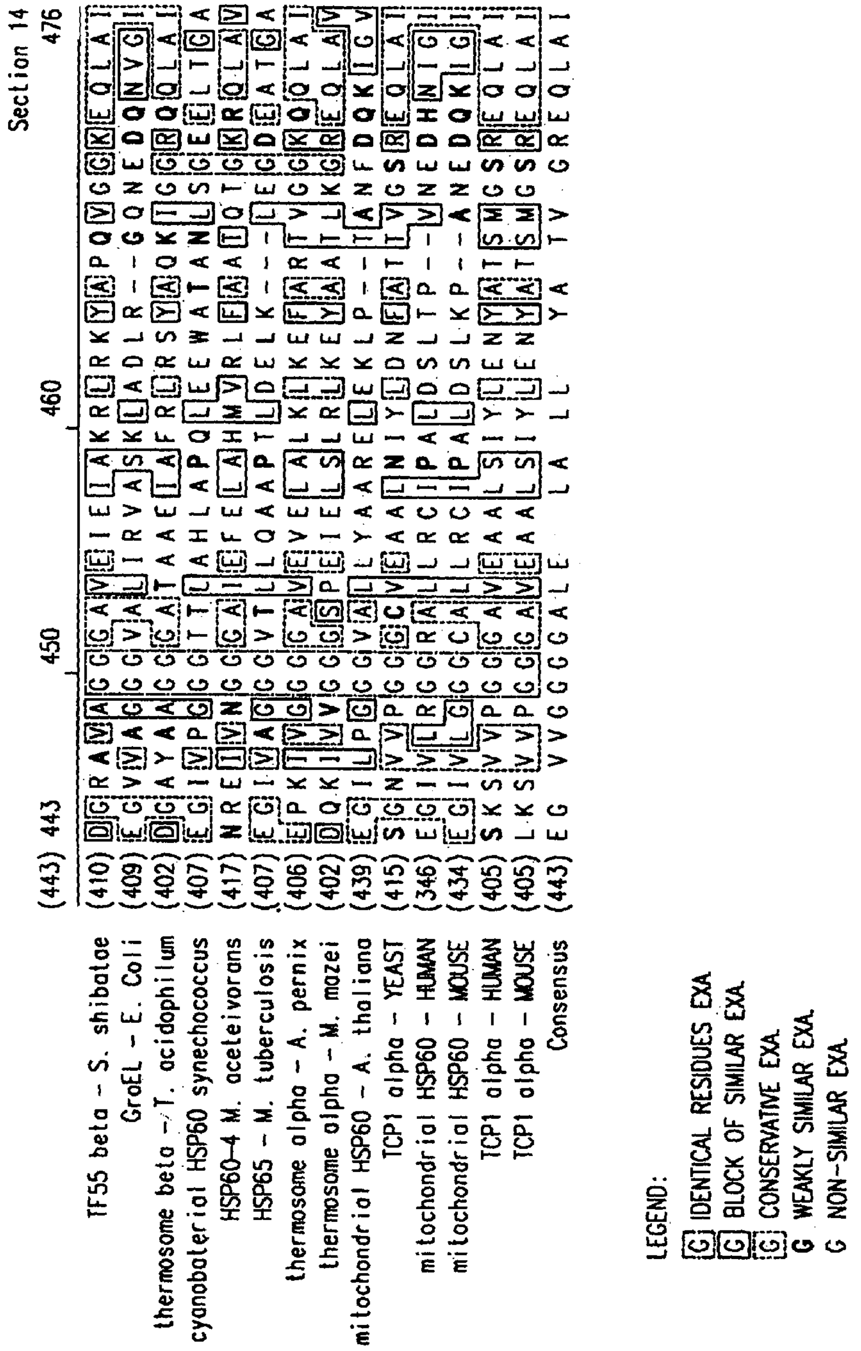

With knowledge of the sequences of the group I or group II chaperonin polypeptide, any number of mutations can be judiciously placed at one or more areas of the apical, intermediate and/or equatorial domains of the chaperonin polypeptide. As evidenced by the sequence alignment of FIGS. 2A-2B, the regions that have been manipulated in *S. shibatae* also exist in other species. Whatever mutations work in one species can be made to work in others. These corresponding regions of the sequence alignments can therefore serve as a guide in choice of manipulations to produce variants in other species. Thus, the many different varieties of binding sites that can be placed at different locations on a chaperonin can be exploited in the formation of the nanotemplates, nanostructures, nanoarrays and nanodevices of the present invention.

Nucleic Acid Molecules

The present invention provides various isolated nucleic acid molecules, or fragments or derivatives thereof, comprising polynucleotide sequences encoding the modified chaperonin subunit polypeptides of the present invention. The nucleic acid molecules of the present invention are also termed "nucleic acid molecules encoding the modified polypeptides" or "nucleic acid molecules of the present invention". For example, the polynucleotide sequence of a nucleic acid molecule encoding the modified chaperonin subunit polypeptide is shown in FIGS. 21A, 22A, 23A, 24A, 25A, 26A, 27A and 29A.

The present invention further provides related polynucleotide molecules, such as complementary modified chaperonin subunit polypeptides, or a part thereof, and those that hybridize to the nucleic acid molecules of the invention.

The polynucleotide sequences encoding the modified chaperonin subunit polypeptides, are preferably in isolated form, and include, but are not limited to, DNA, RNA, DNA/RNA hybrids, and related molecules, and fragments thereof. Specifically contemplated are genomic DNA, cDNA, ribozymes, and antisense RNA or DNA molecules, as well as nucleic acids molecules based on an alternative backbone or including alternative bases, whether derived from natural sources or synthesized.

In accordance with the practice of the invention, the nucleic acid molecules of the invention can be isolated full-length or partial length molecules. The nucleotide sequence of the invention can encode all or portions of the modified chaperonin subunit polypeptides of the invention.

Isolated Nucleic Acid Molecules

The nucleic acid molecules of the invention are preferably in isolated form, where the nucleic acid molecules are substantially separated from contaminant nucleic acid molecules having sequences other than modified chaperonin subunit sequences. A skilled artisan can readily employ nucleic acid isolation procedures to obtain isolated, modified chaperonin subunit sequences (Sambrook et al., in: "Molecular Cloning" (1989)). The present invention also provides for isolated modified chaperonin subunit sequences generated by recombinant DNA technology or chemical synthesis methods. The present invention also provides nucleotide sequences isolated from various organisms including bacterial, viral, mammalian (e.g., bovine, porcine, murine, equine, canine, feline, monkey, ape, ovine or human), piscine, avian or insect.

The isolated nucleic acid molecules include DNA, RNA, DNA/RNA hybrids, and complementary sequences, or a fragment or derivative thereof, and those which hybridize to the nucleic acid molecules encoding the modified chaperonin subunit polypeptides. The preferred nucleic acid molecules have nucleotide sequences identical to or similar to the nucleotide sequences disclosed herein. Specifically contemplated are genomic DNA, RNA e.g., small interfering RNA, cDNA, ribozymes and antisense molecules.

Linker Sequences

The present invention provides nucleic acid molecules encoding the modified polypeptides having the naturally-occurring N- and C-terminal ends linked directly together or linked with an intervening linker sequence. The nucleic acid molecule can encode the intervening linker sequence comprising 1 to about 10 amino acid residues. The nucleic acid molecules encode a flexible or helical linker peptide. The intervening linker sequence comprises amino acid residues such as glycine, serine, alanine, and/or threonine, or derivatives thereof. In one embodiment, the nucleic acid molecule encodes a linker sequence comprising the amino acid sequence Gly-Gly-Ser-Gly-Gly-Thr (SEQ ID NO:64). In another embodiment, the nucleic acid molecule comprises the nucleotide sequence GGTGGTTCTGGTGGTACC (SEQ ID NO:65) shown as part of the sequences in FIGS. 21A, 22A, 23A, 24A, 25A 26A, 27A and 29A.

The Second Polypeptide Sequences

The present invention provides nucleic acid molecules encoding the modified polypeptides joined with a second polypeptide sequence. The modified chaperonin subunit sequence is operatively joined, in-frame, to the second polypeptide sequence.

The nucleotide sequence encoding the second polypeptide can encode a: protein; peptide fragment; reporter molecule; metal-binding peptide; enzyme; hormone; growth factor; trophic factor; antibody; receptor; toxin; fluorescent protein; luminescent protein; or metal-binding peptide. These second polypeptides are described above.

Sequence Identity and Similarity

The present invention provides isolated nucleic acid molecules having a polynucleotide sequence identical or similar to the modified chaperonin subunit sequences disclosed herein.

One embodiment of the invention provides nucleic acid molecules that exhibit sequence identity or similarity with the modified chaperonin subunit nucleotide sequences, such as molecules that have at least 60% to 99.9% sequence similarity and up to 100% sequence identity with the sequences of the invention as shown in FIG. 21A, 22A, 23A, 24A, 25A, 26A, 27A, or 29A. Another embodiment provides nucleic acid molecules that exhibit between about 75% to 99.9% sequence similarity, and another embodiment provides molecules that have between about 86% to 99.9% sequence similarity. Yet another embodiment provides molecules that have 100% sequence identity with the modified chaperonin subunit sequences of the invention as shown in FIG. 21A, 22A, 23A, 24A, 25A, 26A, 27A, or 29A.

Complementary Nucleotide Sequences

The present invention also provides nucleic acid molecules that are complementary to the sequences as described in FIG. 21A, 22A, 23A, 24A, 25A, 26A, 27A, or 29A. Complementarity can be full or partial. A nucleotide sequence that is fully complementary is complementary to the entire modified chaperonin subunit sequence as described in any one of FIG. 21A, 22A, 23A, 24A, 25A, 26A, 27A, or 29A. A nucleotide sequence that is partially complementary is complementary to only a portion of sequences as described in any one of FIG. 21A, 22A, 23A, 24A, 25A, 26A, 27A, or 29A. The complementary molecules include anti-sense nucleic acid molecules.

Hybridizing Nucleic Acid Molecules

The present invention further provides nucleic acid molecules having polynucleotide sequences that selectively hybridize to the nucleotide sequence of the invention as shown in any one of FIG. 21A, 22A, 23A, 24A, 25A, 26A, 27A, or 29A. The nucleic acid molecules that hybridize can hybridize under high stringency hybridization conditions. Typically, hybridization under standard high stringency conditions will occur between two complementary nucleic acid molecules that differ in sequence complementarity by about 70% to about 100%. It is readily apparent to one skilled in the art that the high stringency hybridization between nucleic acid molecules depends upon, for example, the degree of identity, the stringency of hybridization, and the length of hybridizing strands. The methods and formulas for conducting high stringency hybridizations are well known in the art (Sambrook, et al., in: "Molecular Cloning" (1989)).

In general, stringent hybridization conditions are those that: (1) employ low ionic strength and high temperature for washing, for example, 0.015M NaCl/0.0015M sodium citrate/0.1% SDS at 50 degrees C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42 degrees C.

Another example of stringent conditions include the use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42 degrees C., with washes at 42 degrees C. in 0.2×SSC and 0.1% SDS. A skilled artisan can readily determine and vary the stringency conditions appropriately to obtain a clear and detectable hybridization signal.

Nucleic Acid Fragments

The present invention further provides nucleic acid molecules having fragments of the modified chaperonin subunit sequences of the invention, such as a portion of the sequences shown in any one of FIGS. 21A, 22A, 23A, 24A, 25A, 26A, 27A, or 29A. The size of the fragment will be determined by its intended use. For example, if the fragment is chosen to encode a full-length modified chaperonin subunit polypeptide, then the skilled artisan shall select the polynucleotide fragment that is large enough to encode this polypeptide. If the fragment is to be used as a nucleic acid probe or PCR primer, then the fragment length is chosen to obtain a relatively small number of false positives during a probing or priming procedure.

The nucleic acid molecules, fragments thereof, and probes and primers of the present invention are useful for a variety of molecular biology techniques including, for example, hybridization screens of libraries, or detection and quantification of mRNA transcripts as a means for analysis of gene transcription and/or expression. The probes and primers can be DNA, RNA or derivatives of DNA or RNA molecules. A probe or primer length of at least 15 base pairs is suggested by theoretical and practical considerations (Wallace, B. and Miyada, G. 1987 in: "Oligonucleotide Probes for the Screening of Recombinant DNA Libraries" in: *Methods in Enzymology,* 152:432-442, Academic Press).

Fragments of the modified chaperonin nucleotide sequences that are particularly useful as selective hybridization probes or PCR primers can be readily identified from the modified chaperonin nucleotide sequences, using art-known methods. For example, sets of PCR primers that bind and/or detect a portion of nucleic acid molecule encoding the modified chaperonin subunit polypeptides can be made by PCR methods (described in U.S. Pat. No. 4,965,188). The probes and primers of this invention can be prepared by methods well known to those skilled in the art (Sambrook, et al. supra). The probes and primers can be synthesized by chemical synthesis methods (ed: Gait, M. J. 1984 in: "Oligonucleotide Synthesis", IRL Press, Oxford, England).

One embodiment of the present invention provides nucleic acid primers that are complementary to any of the sequences shown in FIGS. 21A, 22A, 23A, 24A, 25A, 26A, 27A, or 29A, which allow specific amplification of nucleic acid molecules of the invention or of any specific portions thereof.

Alternatively, a fragment of the modified chaperonin subunit molecule sequence can be used to construct a recombinant fusion gene having the modified chaperonin subunit sequence fused to a different sequence.

Codon Usage Variants

The present invention provides isolated codon-usage variants that differ from the disclosed modified chaperonin subunit nucleotide sequences, yet do not alter the predicted polypeptide sequence or biological activity of the encoded modified chaperonin subunit polypeptide. For example, a number of amino acids are designated by more than one triplet codon. Codons that specify the same amino acid can occur due to degeneracy in the genetic code. Examples include nucleotide codons CGT, CGG, CGC, and CGA encoding the amino acid, arginine (R); or codons GAT, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The codon-usage variants can be generated by recombinant DNA technology. Codons can be selected to optimize the level of production of the RNA transcripts encoding the modified chaperonin subunit polypeptides in a particular prokaryotic or eukaryotic expression host. Codons can be selected to extend the half-life or increased stability of the transcript encoding the modified chaperonin subunit polypeptide. The present invention provides selecting every possible triplet codon to generate every possible combination of nucleotide sequences that encode the modified chaperonin subunit polypeptides of the present invention. This particular embodiment provides isolated nucleotide sequences that vary from the sequences as described in described in any one of FIGS. 21A, 22A, 23A, 24A, 25A, 26A, 27A, or 29A, such that each variant nucleotide sequence encodes a molecule having sequence identity with the amino acid sequence described in FIGS. 21B, 22B, 23B, 24B, 25B, 26B, 27B, or 29B.

Variant Nucleotide Sequences

The present invention provides nucleic acid molecules comprising polynucleotide sequences encoding variant forms of any of the modified chaperonin subunit polypeptides having the same or similar structure to a naturally-occurring, wild-type chaperonin subunit polypeptide.

The variant nucleotide sequences of the present invention include conservative or non-conservative amino acid substitutions. The variant nucleotide sequences include mutations such as amino acid substitutions, deletions, insertions, additions, truncations, or processing or cleavage errors of the protein. The variant nucleotide sequences include allelic or homolog variants of the naturally-occurring modified chaperonin subunit polypeptides. In one embodiment, the variant nucleic acid molecule, which encodes a modified chaperonin polypeptide, comprises silent mutations where the nucleotide sequence in certain regions differs from that of a wild type sequence but still encodes the same amino acids. The silent mutations can be useful for suppressing Shine-Dalgarno sequences when expressed in bacteria.

Derivative Nucleic Acid Molecules

The nucleic acid molecules of the invention also include derivative nucleic acid molecules which differ from DNA or RNA molecules, and anti-sense molecules.

Derivative molecules include peptide nucleic acids (PNAs), and non-nucleic acid molecules including phosphorothioate, phosphotriester, phosphoramidate, and methylphosphonate molecules, that bind to single-stranded DNA or RNA in a base pair-dependent manner (P C Zamecnik, et al., 1978 Proc. Natl. Acad. Sci. 75:280284; P C Goodchild, et al., 1986 Proc. Natl. Acad. Sci. 83:4143-4146). Peptide nucleic acid molecules comprise a nucleic acid oligomer to which an amino acid residue, such as lysine, and an amino group have been added. These small molecules, also designated anti-gene agents, stop transcript elongation by binding to their complementary (template) strand of nucleic acid (P E Nielsen, et al., 1993 Anticancer Drug Des 8:53-63). Reviews of methods for synthesis of DNA, RNA, and their analogues can be found in: Oligonucleotides and Analogues, eds. F Eckstein, 1991, IRL Press, New York; Oligonucleotide Synthesis, ed. M J Gait, 1984, IRL Press, Oxford, England. Additionally, methods for antisense RNA technology are described in U.S. Pat. Nos. 5,194,428 and 5,110,802. A skilled artisan can readily obtain these classes of derivative nucleic acid molecules using the herein described modified chaperonin polynucleotide sequences, see for example "Innovative and Perspectives in Solid Phase Synthesis" (1992) Egholm, et al. pp 325-328 or U.S. Pat. No. 5,539,082.

Labeled Nucleic Acid Molecules

The present invention provides nucleic acid molecules of the invention linked or labeled with a detectable marker. Examples of a detectable marker include, but are not limited to, a radioisotope, a fluorescent compound, a bioluminescent compound, a chemiluminescent compound, a metal chelator or an enzyme. Technologies for generating labeled nucleic acid molecules are well known (Sambrook et al., in Molecular Cloning (1989)).

Recombinant Nucleic Acid Molecules

The present invention provides recombinant nucleic acid molecules (e.g., DNA or RNA) comprising nucleotide sequences encoding the modified chaperonin subunit polypeptides, or a fragment or derivative thereof, as described herein. As used herein, a recombinant nucleic acid molecule has been subjected to molecular manipulation in vitro. Methods for generating recombinant nucleic acid molecules are well known in the art (Sambrook et al., Molecular Cloning (1989)). In one embodiment, the recombinant DNA molecules of the present invention are operably linked to one or more expression control sequences and/or vector sequences.

Vectors

The recombinant nucleic acid molecules of the present invention each comprise the polynucleotide sequence, or fragments or derivatives thereof, encoding the modified chaperonin subunit polypeptides joined to a vector to generate a recombinant vector molecule.

The term vector includes, but is not limited to, plasmids, cosmids, BACs, YACs, PACs and phagemids. The vector can be an autonomously replicating vector comprising a replicon that directs the replication of the rDNA within the appropriate host cell. Alternatively, the vector directs integration of the recombinant vector into the host cell. Various viral vectors can also be used, such as, for example, a number of well known retroviral and adenoviral vectors (Berkner 1988 Biotechniques 6:616-629).

The vectors of the invention permit expression of the modified chaperonin subunit polypeptides, or fragments or derivatives thereof, in prokaryotic or eukaryotic host cells. The vectors can be expression vectors, comprising an expression control element, such as a promoter sequence, which enables transcription of the inserted modified chaperonin subunit nucleotide sequence and can be used for regulating the expression (e.g., transcription and/or translation) of a linked modified chaperonin subunit nucleotide sequence in an appropriate host cell.

The expression control elements can be of various origins, including naturally-occurring and synthetic. The naturally-occurring elements can be cellular or viral in origin. Expression control elements are known in the art and include, but are not limited to, inducible promoters, constitutive promoters, secretion signals, enhancers, transcription terminators, and other transcriptional regulatory elements.

Other expression control elements that are involved in translation are known in the art, and include the Shine-Dalgarno sequence (e.g., prokaryotic host cells), and initiation and termination codons. Exogenous transcriptional elements and initiation codons can be of various origins, both natural and synthetic.

The promoters can be inducible which are regulated by environmental stress (e.g., heat, oxidizing conditions, or toxic compounds), environmental stimuli or the growth medium of the cells (IPTG), including those from the genes for heat shock proteins (e.g., hsp60), alcohol dehydrogenase 2, isocytochrome C, acid phosphatase, enzymes associated with nitrogen catabolism, and enzymes responsible for maltose and galactose utilization.

The promoters can be constitutive including yeast beta-factor, alcohol oxidase, cytomegalovirus, and PGH. For reviews, see Ausubel et al (1987 Current Protocols in Molecular Biology, John Wiley & Sons, New York N.Y.) and Grant et al (1987 Methods in Enzymology 153:516-544).

The promoter can be plac (with a laci$^q$ on the vector to reduce background expression), which can be regulated by the addition of isopropylthiogalactoside (IPTG), another promoter pT7Φ10, which is specific to T7 RNA polymerase and is not recognized by *E. coli* RNA polymerase. T7 RNA polymerase, which is resistant to rifamycin, is encoded on the defective lambda DE lysogen in the *E. coli* BL21 chromosome. T7 polymerase in BL21(DE3) is super-repressed by the laci$^q$ gene in the plasmid and is induced and regulated by IPTG.

The efficiency of transcription can be augmented by the inclusion of enhancers appropriate to the cell system in use (Scharf, D., et al, 1994 Results Probl. Cell. Differ. 20:125-62; Bittner, et al., 1987 Methods in Enzymol. 153:516-544). Viral promoters include SV40 early promoter or the promoter included within the LTR of a retroviral vector. Other viral promoters include the cytomegalovirus promoter (M Boshart, et al., 1985 Cell 41:521-530).

Commonly used eukaryotic control sequences for use in expression vectors include promoters and control sequences compatible with mammalian cells such as, for example, CMV promoter and avian sarcoma virus (ASV) (πLN vector). Other commonly used promoters include the early and late promoters from Simian Virus 40 (SV40) (Fiers, et al., 1973

Nature 273:113), or other viral promoters such as those derived from polyoma, Adenovirus 2, and bovine papilloma virus. An inducible promoter, such as hMTII (Karin, et al., 1982 Nature 299:797-802) can also be used.

Transcriptional control sequences for yeast vectors include promoters for the synthesis of glycolytic enzymes (Hess et al., 1968) J Adv Enzyme Reg. 7:149; Holland et al., 1978 Biochemistry 17:4900). Additional promoters known in the art include the CMV promoter provided in the CDM8 vector (Toyama and Okayama 1990 FEBS 268:217-221); the promoter for 3-phosphoglycerate kinase (Hitzeman et al., 1980 J Biol Chem 255:2073), and those for other glycolytic enzymes.

Specific translation initiation signals can also be required for efficient translation of a modified chaperonin subunit polypeptide. These signals include the ATG-initiation codon and adjacent sequences. The ATG-initiation sequences or upstream sequences of a naturally-occurring modified chaperonin subunit polypeptides can be inserted into the appropriate expression vector. Alternatively, a synthetic ATG-initiation codon and other sequences can be used. The ATG-initiation codon must be in the correct reading-frame to ensure translation of the insert sequence.

The expression control elements can be placed at the 3' end of the coding sequences.

These sequences can act to stabilize messenger RNA. Such terminators are found in the 3' untranslated region following the coding sequences in several yeast-derived and mammalian genes.

The expression vector can include at least one selectable marker gene encoding a gene product that confers drug resistance such as resistance to kanamycin, ampicillin, chloramphenicol or tetracycline.

The expression vector can include any marker gene. These include, but are not limited to, the herpes simplex virus thymidine kinase (M Wigler et al., 1977 Cell 11:223-32) and adenine phosphoribosyltransferase (I Lowy et al., 1980 Cell 22:817-23) genes which can be employed in tk-minus or aprt-minus cells, respectively. Also, antimetabolite, antibiotic or herbicide resistance can be used as the basis for selection; for example, dhfr which confers resistance to methotrexate (M Wigler et al., 1980 Proc Natl Acad Sci 77:3567-70); npt, which confers resistance to the aminoglycosides neomycin and G-418 (F Colbere-Garapin et al., 1981 J. Mol. Biol. 150:1-14) and als or pat, which confer resistance to chlorsulfuron and phosphinotricin acetyltransferase, respectively (L E Murry, in: McGraw Yearbook of Science and Technology (1992) McGraw Hill New York N.Y., pp 191-196). Additional selectable genes have been described, for example, trpB, which allows cells to utilize indole in place of tryptophan, or hisD, which allows cells to utilize histinol in place of histidine (Hartman, and Mulligan 1988 Proc. Natl. Acad. Sci. 85:8047-51). Recently, the use of visible markers has gained popularity with such markers as anthocyanins, β-glucuronidase and its substrate, GUS, and luciferase and its substrate, luciferin, being widely used not only to identify transformants, but also to quantify the amount of transient or stable protein expression attributable to a specific vector system (C A Rhodes et al., 1995 Methods Mol. Biol. 55:121-131).

The vector also comprises multiple endonuclease restriction sites that enable convenient insertion of exogenous DNA sequences. Methods for generating a recombinant expression vector encoding the modified chaperonin subunit polypeptides are well known in the art (T Maniatis, et al., 1989 Molecular Cloning, A Laboratory Manual, Cold Spring Harbor Laboratory, Cold Spring Harbor; N.Y.; F Ausubel, et al. 1989 Current Protocols in Molecular Biology, John Wiley & Sons, New York N.Y.).

The expression vectors can include expression control elements for expression in bacterial host cells. These expression control elements can be induced by environmental conditions such as heat-shock, or by addition of agents such as isopropyl-β-D-thiogalactopyranoside (e.g., IPTG) (N Yamaguchi, et al. 2002 The J of Biol Chem 277:6806-6812). Prokaryotic cell expression vectors are well known in the art and are available from several commercial sources. For example, pET19b (Novagen, Madison, Wis.), Superlinker vectors pSE280 and pSE380 (Invitrogen, San Diego, Calif.), pGEX vector (Promega, Madison, Wis.), pTrcHisB vector (Invitrogen), pET vector (e.g., pET-21, Novagen Corp.), BLUESCRIPT phagemid (Stratagene, LaJolla, Calif.), pSPORT (Gibco BRL, Rockville, Md.), or ptrp-lac hybrids can be used to express the modified chaperonin subunit polypeptides in bacterial host cells.

The expression vectors used for generating modified chaperonin subunit polypeptides can be compatible with eukaryotic host cells. The vectors can be compatible with vertebrate cells. These vectors can include expression control elements such as promoters and/or enhancers from mammalian genes or mammalian viruses. Other expression vectors can include tissue-specific or cell-specific promoters and/or enhancers from mammalian genes or mammalian viruses.

The expression vectors can be compatible with other eukaryotic host cells, including insect, plant, or yeast cells. The expression vectors can include expression control elements, such as the baculovirus polyhedrin promoter for expression in insect cells. The promoters and/or enhancers derived from plant cells (e.g., heat shock, RUBISCO, storage protein genes), viral promoters or leader sequences or from plant viruses can also be used.

Eukaryotic cell expression vectors are well known in the art and are available from several commercial sources, including PSVL and pKSV-10 (Pharmacia), pBPV-1/pML2d (International Biotechnologies, Inc.), pTDT1 (ATCC, #31255), and similar eukaryotic expression vectors. Examples of expression vectors for eukaryotic host cells include, but are not limited to, vectors for mammalian host cells including: BPV-1; pHyg; pRSV; pSV2; pTK2 (Maniatis); pIRES (Clontech); pRc/CMV2; pRc/RSV; pSFV1 (Life Technologies); pVPakc Vectors; pCMV vectors; pSG5 vectors (Stratagene); retroviral vectors (e.g., pFB vectors (Stratagene)); pCDNA-3 (Invitrogen) or modified forms thereof; adenoviral vectors; Adeno-associated virus vectors; baculovirus vectors. Other expression vectors for eukaryotic host cells include pESC vectors (Stratagene) for yeast and pFastBac for expression in insect cells (Gibco/BRL, Rockville, Md.).

Host-Vector Systems

The present invention further provides a host-vector system comprising a vector comprising a modified chaperonin subunit nucleotide sequence, or a fragment or derivative thereof, introduced into a suitable host cell.

The host-vector system can be used to transcribe and/or express (e.g., produce) the modified chaperonin subunit polypeptides of the invention. The host cell can be either prokaryotic or eukaryotic.

Prokaryotic Host Cells

Examples of suitable prokaryotic host cells include bacteria strains from genera such as *Escherichia, Bacillus, Pseudomonas, Streptococcus*, and *Streptomyces*. In one embodiment, *E. coli* strain BL21(DE3) and BL21(DE3/ pLysS) (Novagen, Madison, Wis.), although other compatible recA strains, such as HMS174(DE3) and HMS174(DE3/pLysS) can be used.

In bacterial systems, a number of expression vectors can be selected depending upon the use intended for the modified chaperonin subunit polypeptides. For example, when large quantities of the modified chaperonin subunit polypeptides are desired, vectors that direct high level expression of fusion proteins that are soluble and readily purified can be desirable. Such vectors include, but are not limited to, the multifunctional *E. coli* cloning and expression vectors such as BLUESCRIPT (Stratagene), in which the modified chaperonin subunit nucleotide sequence can be ligated into the vector in-frame with sequences for the amino-terminal Met and the subsequent 7 residues of galactosidase so that a hybrid protein is produced. Other vectors include the pET19b (Novagen), pIN vectors (Van Heeke & Schuster 1989 J Biol Chem 264: 5503-5509), and the like. The pGEX vectors (Promega, Madison Wis.) can also be used to express foreign proteins as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor Xa protease cleavage sites so that the cloned protein of interest can be released from the GST moiety at will.

The methods for introducing the modified chaperonin subunit nucleotide sequences into the host cells are well-known methods that depend on the type of vector used and host system employed. For example, prokaryotic host cells are typically introduced (e.g., transformed) with nucleic acid molecules by electroporation or salt treatment methods (Cohen et al., 1972 Proc Acad Sci USA 69:2110; Maniatis, T., et al., 1989 in: Molecular Cloning, A Laboratory Manual, Cold Spring Harbor Laboratory, Cold Spring Harbor, N.Y.

Eukaryotic Host Cells

Examples of suitable eukaryotic host cells include insect cells, yeast cells, plant cells, or animal cells such as mammalian cells.

An expression system that can be used to express modified chaperonin subunit polypeptides is an insect system. In one such system, *Autographa californica* nuclear polyhedrosis virus (AcNPV) can be used as a vector to express foreign genes in *Spodoptera frugiperda* insect cells or in *Trichoplusia larvae*. The sequence encoding a modified chaperonin subunit polypeptides can be cloned into a nonessential region of the virus, such as the polyhedrin gene, and placed under control of the polyhedrin promoter. Successful insertion of a modified chaperonin subunit sequence will render the polyhedrin gene inactive and produce recombinant virus lacking coat protein. The recombinant viruses can then used to infect *S. frugiperda* cells or *Trichoplusia larvae* in which the modified chaperonin subunit polypeptides can be expressed (Smith et al 1983 J Virol 46:584; E K Engelhard, et al, 1994 Proc Nat Acad Sci 91:3224-3227).

In mammalian host cells, a number of viral-based expression systems can be utilized. In cases where an adenovirus is used as an expression vector, a modified chaperonin subunit nucleotide sequence can be ligated into an adenovirus transcription/translation vector having the late promoter and tripartite leader sequence. Insertion in a nonessential E1 or E3 region of the viral genome results in a viable virus capable of expressing a modified chaperonin subunit polypeptides in infected host cells (Logan and Shenk 1984 Proc Natl Acad Sci 81:3655-59). In addition, transcription enhancers, such as the rous sarcoma virus (RSV) enhancer, can be used to increase expression in mammalian host cells.

In yeast, *Saccharomyces cerevisiae*, a number of vectors including constitutive or inducible promoters such as beta-factor, alcohol oxidase and PGH can be used. For reviews, see Ausubel et al (Current Protocols in Molecular Biology, John Wiley & Sons, New York N.Y.) and Grant et al (1987 Methods in Enzymology 153:516-544).

In cases where plant expression vectors are used, the expression of a sequence encoding a modified chaperonin subunit polypeptides can be driven by any of a number of promoters. For example, viral promoters such as the 35S and 19S promoters of CaMV (Brisson, et al., 1984 Nature 310: 511-514) can be used alone or in combination with the omega leader sequence from TMV (Takamatsu, et al., 1987 EMBO J 6:307-311). Alternatively, plant promoters such as the small subunit of RUBISCO (Coruzzi et al 1984 EMBO J 3:1671-1680; Broglie et al 1984 Science 224:838-843); or heat shock promoters (J Winter and R M Sinibaldi 1991 Results Probl Cell Differ. 17:85-105) can be used.

In addition, a host cell strain can be chosen for its ability to modulate the expression of the inserted modified chaperonin subunit nucleotide sequences or to process the expressed protein in the desired fashion. Such modifications of the expressed modified chaperonin subunit polypeptides include, but are not limited to, acetylation, carboxylation, glycosylation, phosphorylation, lipidation and acylation. Post-translational processing which cleaves a precursor form of the protein (e.g., a pre-pro protein) can also be important for correct insertion, folding and/or function. Different host cells such as CHO, HeLa, MDCK, 293, WI38, etc. have specific cellular machinery and characteristic mechanisms for such post-translational activities and can be chosen to ensure the correct modification and processing of the introduced, foreign protein.

The methods for introducing the modified chaperonin subunit nucleotide sequences into eukaryote host cells are well-known methods that depend on the type of vector used and host system employed. For example, in vertebrate cells, the nucleic acid sequences are introduced with vectors using various methods, including calcium phosphate-mediated DNA transfection (Graham and Van der Eb 1973 Virology 52:456-467; M Wigler, et al 1977 Cell 11:223-232) or other cationic-mediated transfection methods, electroporation (E Neuman, et al 1982 EMBO J 1:841-845), microinjection (W F Anderson, et al 1980 Proc Natl Acad Sci USA 77:5399-5403; M R Cappechi 1980 Cell 22:479-488; A Graessman, et al 1979 J Virology 32:989-994), or lipid methods including encapsulation of DNA in lipid vesicles (M Schaefer-Ridder 1982 Science 215:166-168). Other methods include the particle gun method. Still other methods include using an adenovirus transcription/translation vector comprising the late promoter and tripartite leader sequence. A nucleic acid sequence can be inserted in a nonessential E1 or E3 region of the adenoviral genome to create a viable virus capable of expressing the protein encoded by the nucleic acid sequence (Logan and Shenk 1984 Proc Natl Acad Sci 81:3655-59). Alternatively, retroviral transfer methods can be used (E Gibloa, et al 1986 BioTechniques 4:504-512).

Plant cells can be introduced by direct DNA transformation or pathogen-mediated transfection. For reviews of such techniques, see Hobbs, S. in: "McGraw Yearbook of Science and Technology" (1992) McGraw Hill New York N.Y., pp 191-196; or Weissbach and Weissbach (1988) in: "Methods for Plant Molecular Biology", Academic Press, New York N.Y., pp 421-463. Alternatively, plant cells can be introduced via a particle-gun method using metal particles.

Selection of Transformed Cells

The host cells introduced with the modified chaperonin subunit nucleotide sequences can be identified by techniques well known in the art. The cells can be selected, lysed and their DNA content examined for the presence of the introduced sequences using a DNA gel blot method or similar method (Southern 1975 J Mol Biol 98:503; Berent et al., 1985 Biotech 3:208). Alternatively, the proteins produced from the cells of the invention can be assayed via a biochemical assay or immunological method.

Any number of selection systems can be used to recover the introduced (e.g, transformed or transfected) cells. The introduced cells can be selected based on expression of herpes simplex virus thymidine kinase (Wigler, M., et al., 1977 Cell 11:223-32), or adenine phosphoribosyltransferase (Lowy, I. et al., 1980 Cell 22:817-23) genes which can be employed in tk-minus or aprt-minus cells, respectively. Also, antimetabolite, antibiotic or herbicide resistance can be used as a basis for selection; for example, dhfr which confers resistance to methotrexate (Wigler, M., et al., 1980 Proc Natl Acad Sci 77:3567-70); npt, which confers resistance to the aminoglycosides neomycin and G-418 (Colbere-Garapin, F., et al., 1981 J. Mol. Biol. 150:1-14) and als or pat, which confer resistance to chlorsulfuron and phosphinotricin acetyltransferase, respectively. Additional selectable genes have been described, for example, trpB, which allows cells to utilize indole in place of tryptophan, or hisD, which allows cells to utilize histinol in place of histidine (S C Hartman and R C Mulligan 1988 Proc. Natl. Acad. Sci. 85:8047-51). Recently, the use of visible markers has gained popularity with such markers as anthocyanins, beta-glucuronidase and its substrate, GUS, and luciferase and its substrate, luciferin, being widely used not only to identify transformants, but also to quantify the amount of transient or stable protein expression attributable to a specific vector system (C Rhodes, et al., 1995 Methods Mol. Biol. 55:121-131).

Producing Modified Polypeptides

The present invention provides methods for producing the modified chaperonin subunit polypeptides. The modified polypeptides of the invention, or fragments or derivatives thereof, can be produced as recombinant molecules produced in prokaryote or eukaryote host cells, or generated as synthetic molecules.

The modified polypeptides can be produced using standard recombinant technology techniques. For example, expression vectors comprising nucleotide sequences encoding the modified chaperonin subunit polypeptides can be introduced into a prokaryote or eukaryote host cell (i.e., a host-vector system), the host-vector system can be cultured under conditions suitable for the host cell to produce the modified polypeptides, and the polypeptides so produced can be isolated. The isolated modified polypeptides can be enriched to further separate the modified polypeptides away from other non-desirable polypeptides or cellular fractions. The isolated modified polypeptides can be purified to produce a sample of modified polypeptides having very little or no contaminating non-desirable polypeptide or cellular fractions.

In one embodiment, the host-vector system can be cultured at non-heat stress temperatures (e.g., 75 degrees C.). In another embodiment, the host-vector system can be cultured at heat stress temperatures (e.g., 86 degrees C.).

In a non-limiting example, a sequence encoding a thermostable chaperonin, e.g. a thermostable HSP60, can be transferred into *E. coli* and grown at temperatures standard for the cell. The expressed polypeptide can then be easily purified from *E. coli* proteins by heating and centrifugation. The thermolabile *E. coli* proteins precipitate leaving the thermostable polypeptide greater than 90% pure after a centrifugation.

In an embodiment where the chaperonin polypeptides are thermostable extremophiles, the cell extracts can be heated for easier purification of the chaperonin subunits. For example, the purification of the chaperonin beta subunit of *Sulfolobus shibatae* expressed in *E. coli* involves heating total cell extracts to 85° C. for 30 minutes, which precipitates most *E. coli* proteins, but the thermostable beta remains soluble. Therefore, heating and centrifuging cell extracts separates the beta subunit from most *E. coli* proteins, which simplifies further purification using ion exchange chromatography (Kagawa, H. K. et al., 1995 The 60 kDa heat shock proteins in the hyperthermophilic archaeon *Sulfolobus shibatae*. J Mol Biol 253:712-25).

In one non-limiting example, a purification procedure comprises, either alone or in combination: 1) chromatography on molecular sieve, ion-exchange, and/or hydrophobic matrices; 2) preparative ultracentrifugation; and 3) affinity chromatography.

Assembled Chaperonin Structures

The present invention provides assembled chaperonin structures comprising at least one of the modified chaperonin polypeptides of the invention from Group I or Group II subunit polypeptides, or any combination and any proportion of Group I and II. The chaperonin structures comprise at least one of the modified chaperonin polypeptides from alpha, beta, or gamma subunits, or any combination or in any proportion thereof. The chaperonin structures comprise at least one modified chaperonin polypeptide from one organism, or from different organisms (chimeric chaperonin structure). The chaperonin structures comprise at least one modified polypeptide which are based on HSP60, TCP-1, thermal factor 55 (TF55), thermal factor 56 (TF56), or GroEL subunits. The choice of subunits can be made depending on factors such as operating conditions. For example, if the subunits or chaperonin structures are to experience high operating temperatures, then one skilled in the art could select a modified polypeptide from extremophiles. The chaperonin structures comprise 7, 8, 9 or 10 subunits per ring. The chaperonin structures can have 2-, 3-, 4-, 5-, 6-, 7-, 8- 9-, or 10-fold symmetry. The chaperonin structures comprise at least on of the modified chaperonin polypeptides and a co-chaperonin (e.g., GroEL and GroES).

Production In Vivo

The present invention provides methods for producing the double-ringed chaperonin structures in vivo, comprising: culturing a host cell carrying an expression vector (host-vector system) under conditions suitable for the cell to produce the modified chaperonin polypeptide in the cell and permitting self-assembly of the chaperonin structure in the cell; and isolating the assembled chaperonin structure from the cell.

In one embodiment, the host cell co-expresses the modified chaperonin polypeptide (e.g., GroEL) and a co-chaperonin polypeptide (e.g., GroES) so as to self-assemble in the cell the chaperonin structure comprising the modified chaperonin polypeptide and the co-chaperonin.

Production In Vitro

The present invention provides methods for producing the double-ringed chaperonin structures in vitro. In one embodiment, the methods comprise: reacting isolated modified chaperonin polypeptides under conditions suitable to permit self-assembly of the modified chaperonin polypeptides to form the chaperonin structures. In another embodiment, the methods comprise: reacting isolated modified chaperonin polypeptides with wild-type chaperonin polypeptides under conditions suitable to permit self-assembly of the modified chaperonin polypeptides and the wild-type chaperonin polypeptides to form the chaperonin structures.

The assembly reaction can be performed using modified and/or wild-type chaperonin polypeptides that are enriched or purified. Alternatively, the assembly reaction can be performed using modified and/or wild-type chaperonin polypeptides from crude cell extracts. The assembly reaction can be allowed to proceed prior to purification of the assembled chaperonin structures.

The conditions suitable to permit self-assembly of the modified chaperonin polypeptides (with modified chaperonin polypeptides or with wild-type chaperonin polypeptides) includes $Mg^{2+}$, in the presence of ATP, ADP, AMP-PNP, GTP or ATPγS. The temperature or pH for formation will depend on the type and thermostability of the modified or wild-type chaperonin polypeptides or the chaperonin structures. For example, for the thermostable chaperonin beta subunit of *S. shibatae*, the temperature can be 4° C.-85° C., while it may be lower for other types of polypeptides (e.g., less than 40° C.). For a given modified chaperonin polypeptide, optimal conditions for self-assembly (i.e., concentration and proportion of $Mg^{2+}$ to ATP, ADP, AMP-PNP, GTP or ATPγS) are easily determined by routine experimentation, such as by changing each variable individually and monitoring formation of the appropriate products. For formation of the chaperonins any of $Mg^{2+}$, ATP, ADP, AMP-PNP, GTP or ATPγS can be present in an amount ranging from 1 mM, up to 10 mM, 20 mM, 30 mM or higher. For example, filaments can be formed in 5 mM HEPES buffer with 25 mM $MgCl_2$ and 1 mM ATP (total volume 300 μl) (Yoai et al., 1998 Archives of Biochemistry and Biophysics 356: 55-62). While it has been shown that the formation of chaperonins from alpha and beta subunits of *S. shibatae* does not depend on the presence of $K^+$, formation of the higher order structures from the subunits of other organisms may require the presence of $K^+$.

In another embodiment, the chaperonins are formed in the absence of introduction of any of $Mg^{2+}$, ATP, ADP, AMP-PNP, GTP or ATPγS. At sufficiently high concentrations of the chaperonins, e.g., at concentrations of 2-5 mg/ml, or up to 30 mg/ml or more, some of the higher order structures can spontaneously assemble (Quaite-Randall et al., 1995, J. Biol. Chem. 270, 28818-28823). The concentration of the chaperonins or chaperonin polypeptides in different embodiments is 0.1 mg/ml, 0.5 mg/ml, 1 mg/ml, 2, mg/ml, 5 mg/ml, 10 mg/ml, 20 mg/ml, 30 mg/ml, 50 mg/ml or higher.

Higher Order Structures

The present invention provides higher order structures comprising the modified chaperonin polypeptides of the invention. The higher order structures include rings, tubes, filaments, and sheets (2-D crystals). The nanorings can have rectangular, pentagonal, hexagonal or heptagonal architectural arrangements of chaperonins.

The present invention also provides methods for producing the higher order structures. In one embodiment, the methods comprise: reacting isolated modified chaperonin polypeptides under conditions suitable to permit self-assembly of the modified chaperonin polypeptides to form assembled chaperonin structures which can form the higher order structures. In another embodiment, the methods comprise: reacting isolated modified chaperonin polypeptides with wild-type chaperonin polypeptides under conditions suitable to permit self-assembly of the modified chaperonin polypeptides and the wild-type chaperonin polypeptides to form assembled chaperonin structures which can form the higher order structures.

The conditions suitable to permit formation of the higher order structures include: the presence or absence of ATP, ADP, AMP-PNP, GTP or ATPγS in the reaction; and/or the concentration of the modified and/or wild-type chaperonin polypeptides. The presence of ATP induces the formation of an extensive network of filaments, while using ADP, AMP-PNP, GTP or ATPγS induces the formation of shorter filaments. For example, with respect to reactions comprising mutant and/or mutant and wild-type TF55 α and β subunits of *S. shibatae*, chaperonin structures can be formed at concentrations of approximately 0.1 mg/ml, while filaments are formed at approximately 0.5 mg/ml. Longer aligned filaments can be formed at concentrations of approximately 1.0 mg/ml. Other conditions are known for forming structures like filaments of differing average lengths or two-dimensional arrays (Yaoi et al., 1998 Archives of Biochemistry and Biophysics 356: 55-62; and Trent et al., 1997 Proc. Natl. Acad. Sci 94: 5383-5388). Thus, the length of filaments can be controlled through manipulation and choice of reaction conditions, with certain concentrations necessary for particular structures being routinely attainable.

The architectural symmetry of the chaperonin structures and higher order structures can be dictated by varying the reaction conditions, or through directed binding or arrangement of the chaperonins relative to each other. The architectural symmetry includes—1, 2-, 3-, 4-, 5-, 6-, 7-, 8-, 9- or 10-fold symmetry. For example, nanofilaments having one-dimensional architectural symmetry can be formed using certain mutant chaperonin polypeptides in the presence of $Mg^{2+}$ and nucleotides. These nanofilaments can cluster to form bundles of filaments that are microns in length and with bundle diameters of up to microns in thickness.

Figure 6A:
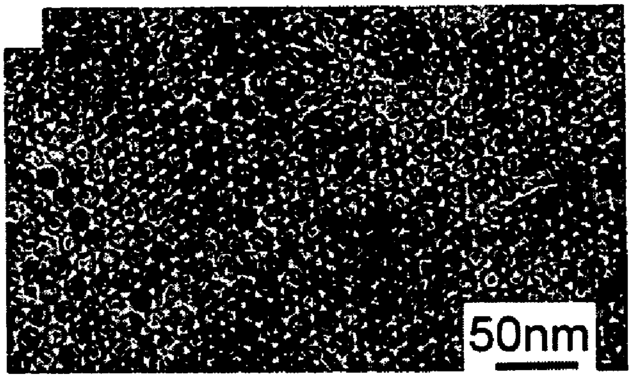
FIGS. 6A and 6B show the organization of HSP60 rings into 2-dimensional crystals on a metal grid coated with lipid (6A) and filament bundles arranged on a bed of rings (visible as spots in background) (6B).
Figure 6B:
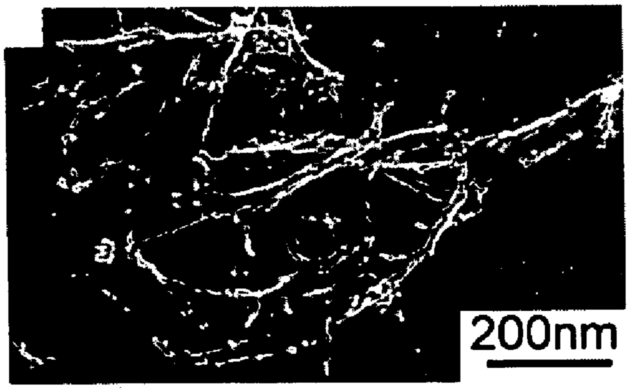

FIG. 5 shows that in the electron microscope individual HSP60s in the double-rings appear as black "blobs" (A, end view) or alternating dark and light bands (B, side view). These double-rings self-assemble into chains or porous tubes (C) and the tubes associate into filaments (D). FIG. 6 shows the organization of HSP60 rings into 2-dimensional crystals on a metal grid coated with lipid (A) and filament bundles arranged on a bed of rings (visible as spots in background) (B). In general, the choice of proportion of ATP to $Mg^{2+}$ affects the formation of higher order structures, such as filaments or arrays. The higher order structures can have long range two- or three-dimensional ordering as in an array with trigonal or hexagonal close packed architectural arrangement of the chaperonins through self-assembly (FIG. 6).

The various architectural symmetries can also be dictated through directed arrangement of the chaperonins onto a substrate either through a masking technique or by directed binding (Whaley et al., 2000 Nature 405: 665-668, which describes peptides that bind to selectively to specific faces gallium arsenide, silicon or indium phosphide). An exemplary, non-limiting list of partial amino-acid sequences from clones that bind to different surfaces of GaAs and/or InP (Whaley et al., 2000 Nature 405: 665-668) includes:

| | |
|---|---|
| VTSPDSTTGAMA | (SEQ ID NO: 16) |
| AASPTQSMSQAP | (SEQ ID NO: 17) |
| AQNPSDNNTHTH | (SEQ ID NO: 18) |
| ASSSRSHFGQTD | (SEQ ID NO: 19) |
| WAHAPQLASSST | (SEQ ID NO: 20) |
| ARYDLSIPSSES | (SEQ ID NO: 21) |

-continued

| | |
|---|---|
| TPPRPIQYNHTS | (SEQ ID NO: 22) |
| SSLQLPENSFPH | (SEQ ID NO: 23) |
| GTLANQQIFLSS | (SEQ ID NO: 24) |
| HGNPLPMTPFPG | (SEQ ID NO: 25) |
| RLELAIPLQGSG | (SEQ ID NO: 26) |

Whaley et al. also describes amino-acid sequences that bind silicon and not silicon dioxide. An example of an amino-acid sequence that binds to ZnS(102) (Lee et al., 2002 Science 296: 892-895) is:

CNNPMHQNC (SEQ ID NO: 27)

A list of partial amino-acid sequences from clones that bind to Ag (Naik et al., 2002 Nature Materials 1: 169-172) includes:

| | |
|---|---|
| AYSSGAPPMPPF | (SEQ ID NO: 28) |
| NPSSLFYRLPSD | (SEQ ID NO: 29) |
| SLATQPPRTPPV | (SEQ ID NO: 30) |

A list of partial amino-acid sequences from clones that bind to Au (Brown et al., 2000 J. Mol. Biol. 299: 725-735; Brown, S, 1997 Nature Biotechnol. 15: 269-272) includes:

| | |
|---|---|
| MHGKTQATSGTIQS | (SEQ ID NO: 31) |
| ALVPTAHRLDGNMH | (SEQ ID NO: 32) |

Another advantage is that HSP60 nanotemplate structures such as rings, tubes, and filaments (to be described in detail below) bind to DNA and RNA using the method of "gel shift," to proteins by the method of autoradiography, and to liposomes and lipid monolayers.

Nanostructures, Nanoarrays, Nanodevices

The modified polypeptides can self-assemble into chaperonin structures which can be used as the basis for producing nanotemplates, nanostructures, nanoarrays and nanodevices.

The term "nanotemplate" as used herein, unless otherwise indicated, refers to a composition comprising at least one modified chaperonin polypeptide The term "nanostructure" as used herein, unless otherwise indicated, refers to a composition comprising at least one modified chaperonin polypeptide and one or more nanoscale materials, such as nanoparticles and/or quantum dots.

The term "nanoarray" as used herein, unless otherwise indicated, refers an ordered arrangement of at least one modified chaperonin polypeptide and/or nanostructures.

The term "nanodevice" as used herein, unless otherwise indicated, refers to a device comprising at least one modified chaperonin polypeptide, at least one nanostructure, and/or at least one nanoarray. Exemplary devices include, but are not limited to, electronic, semiconductor, mechanical, nanoelectromechanical, magnetic, photonic, optical, optoelectronic or biomedical devices.

The term "nanounit" as used herein, unless otherwise indicated, refers any of the components or "basic building blocks" of a nanostructure, including, for example: a nanscale object, such as a nanoparticle or a quantum dot; a modified chaperonin polypeptide; and a wild-type chaperonin; a wild-type chaperonin polypeptide; a mutant chaperonin; or a chaperonin polypeptide.

In a specific embodiment, the nanotemplate can comprise a chaperonin structure comprising at least one modified chaperonin polypeptide, which serve as "spacers" in the nanotemplates. The spacer chaperonins can be confined to specific regions of the nanotemplate, and would not present specific binding sites for any of polypeptides, nanoscale materials or linker molecules. The spacers can therefore serve a similar function as a mask in semiconductor fabrication.

The generation of several different mutations of a given subunit can result in differences in dimension of the resulting chaperonins that comprise the nanotemplate. For example, a variant produced through the removal of a 28 amino acid loop at the apical end from of the β subunit of *S. shibatae* resulted in a chaperonin with an expanded internal pore diameter of from 2.5 nm to 9 nm (see FIGS. 7B-D). This can be exploited in forming a nanotemplate with different mixtures of chaperonin subunit variants to present pores with different pore diameters for the binding of nanosale objects such as nanoparticles and/or quantum dots.

The chaperonins and/or nanotemplates can differ according to the types of subunits and also the combinations of types of subunits used in formation. For example, in vitro alpha and beta subunits of *S. shibatae* form homo-oligomeric rosettasomes, while mixtures of alpha, beta, and gamma form hetero-oligomeric rosettasomes. It has also been found that beta homo-oligomeric rosettasomes and all hetero-oligomeric rosettasomes of *S. shibatae* associate into filaments. FIG. 15 shows the protein sequence alignment of *S. shibatae* TF55 alpha subunit (SEQ ID NO: 39), beta subunit (SEQ ID NO: 1) and gamma subunit (SEQ ID NO: 38). In vivo rosettasomes are hetero-oligomeric with an average subunit-ratio of 1α:1β:0.1γ in cultures grown at 75° C., a ratio of 1α:3β:1γ in cultures grown at 60° C., and a ratio of 2α:3β:0γ after 86° C. heat shock. Additionally, it has been observed that rosettasomes containing gamma were relatively less stable than those with alpha and/or beta subunits. A protein sequence alignment of the alpha, beta, gamma subunits of *S. shibatae* (see Figure), also provides useful information for positioning mutations on the chaperonin polypeptides. FIGS. 16A and 16B provide the DNA and amino-acid sequences of isolated *S. shibatae* TF55-γ.

The isolated chaperonin polypeptide subunits from a given organism can assemble into different types of nanotemplates and other higher order structures (Kagawa et al., 2003 Molecular Microbiology 48:143-156). The isolated *S. shibatae* TF55 alpha subunit (SEQ ID NO: 39) alone forms discrete homo-oligomeric rosettasomes with the characteristic nine-fold ring member symmetry, and arrays of rosettasomes. The isolated *S. shibatae* TF55 beta subunit (SEQ ID NO: 1) forms filaments of rosettasomes and bundles of filaments. The isolated *S. shibatae* TF55 gamma subunit (SEQ ID NO: 38) does not assemble into rosettasomes, but forms amorphous aggregates and non-uniform round objects, which were seen in the TEM (FIG. 6C). Varying the proportions of the different subunits from a given organism can also result in the assembly of different higher order structure being formed (Kagawa et al., 2003 Molecular Microbiology 48:143-156). A 1:1:1 mixture of *S. shibatae* TF55 alpha, beta, and gamma subunits results in hetero-oligomeric rosettasomes and filaments that were less bundled than the ones formed from isolated beta subunits. The 1:1 mixture of *S. shibatae* TF55 alpha and beta subunits results in filaments that are indistinguishable from filaments formed by the 1:1:1 mixtures of alpha, beta and gamma.

In one embodiment, the higher order structures, such as the nanotemplates and nanostructures, comprise at least one isolated *S. shibatae* TF55 gamma subunit. This embodiment of the invention can comprise mutated or wild-type chaperonin polypeptides. In a specific embodiment, the higher order structures, comprise at least one isolated *S. shibatae* TF55 gamma subunit and wild-type chaperonin polypeptides.

In another embodiment, the nanotemplate forms part of a coating or a nanofabric. Due to the capability of the chaperonins to self-assemble in an ordered arrangement on a fairly large length scale as compared to their pore diameters, they can be applied in these areas that could take advantage of the capability. Additionally, the resulting coating or nanofabric can be made to include optical, electric, magnetic, catalytic, or enzymatic moieties as functional units. These are produced through the selected placement of different nanoscale materials the apical domain of the chaperonin, e.g., near the pores of the nanotemplates, or on other binding sites of the chaperonin, or in between chaperoning. The inclusion of nanoscale material with the nanotemplates is discussed further in the section on nanostructures.

Changes in the subunit composition that can influence volume and reactivity of the central cavity of a chaperonin can also be exploited for various applications of the nanotemplates. While not wishing to be limited to a particular theory or mechanism, it is noted that the N- and C-termini of chaperonin subunits are believed to project into and occlude the central cavity. As such, because these termini can differ between subunits of a given species (e.g., rosettasome of *S. shibatae*), changes in subunit composition of the chaperonin can be used to impact on the central cavity. Changes in the volume and binding properties of the central cavity of the chaperonin can therefore be dictated based on the composition of the chaperonin, which can be exploited in the formation of nanostructures which present different types of binding sites for nanoscale materials. In certain embodiments the N- and C-termini are deleted.

The assembly of chaperonin polypeptides, for example HSP60s, into such structures as rings, tubes, filaments, and sheets (2-D crystals) can be regulated chemically. The assembly can be manipulated by, for example, the proportion of ATP/$Mg^{2+}$ and/or by manipulating the concentration of these regions. HSP60-rings, tubes, and filaments can, for example, function as nano-vessels if they are able to absorb, retain, protect and release gases or chemical reagents, including reagents of medical or pharmaceutical interest. On a nanoscale, the filamentous structures, preferably HSP60 structures, are hollow and chemicals that are diffused or bound inside can be bound or released under programmed conditions at targeted locations.

The structures, e.g., rings, tubes, and filaments, can be induced to form ordered structures on surfaces. Under controlled conditions the chaperonins are observed to form 2-dimensional crystals on surfaces and the filament bundles may be oriented on surfaces. In an alternate embodiment, the nanotemplate functions as a multi-nanowell assay plate, or a single-molecule probe for DNA detection and hybridization.

Layers of interwoven chaperonin filaments may form a nano-fabric. Such fabrics may be induced to form on lipid layers and may ultimately be used to coat surfaces of materials. This may be of value in medical transplants in which the material could be coated with, e.g., an HSP60 (derived from the host organism) fabric from the host and thereby limit the immune response against the transplant.

Fabrics or two-dimensional crystals of chaperonins comprising HSP60 can form nano-arrays of DNA or RNA by taking advantage of the intrinsic affinity of HSP60s for nucleic acids. Such arrays would represent an unprecedented density of DNA probes and thereby greatly amplify the density of information per unit area. Other kinds of probes based on other molecules that associate with HSP60 can also be developed.

For characterization, electron microscopy and electron probing methods (EDAX) can be used for investigating the contents of nano vessels, the continuity of nano-wires, the product of template experiments, and the nature of nanofabrics. Atomic force microscope (AFM) can be used in imaging and analyzing features of these nanotemplates. The DNA nano-arrays can be tested by hybridization methods.

The present invention provides methods for forming nanostructures. The chaperonins offer many advantages over other molecules for the controlled assembly of complex architectures, in their ability to self-assemble. A nanostructure can be formed from a selective placement process involving self-assembly, or directed binding, depending on the desired resulting architectural arrangement. The steps in the formation of a nanostructure can include adding one or more nanounits comprising (i) at least one nanotemplate, (ii) at least one wild-type chaperonin, or (iii) a mixture of (i) and (ii) to a surface, and adding one or more nanounits comprising (i) at least one nanoparticle, (ii) at least one quantum dot, or (iii) a combination of (i) and (ii) to said surface. Any unbound nanounits are removed in order to maintain the desired architecture. Each of the addition steps are repeated as many times as necessary to result in a nanostructure. Optimal conditions for assembly (i.e., concentration and proportion of $Mg^{2+}$ to ATP, ADP, AMP-PNP, GTP or ATPγS) are easily determined by routine experimentation, such as by changing each variable individually and monitoring formation of the appropriate products. In alternate embodiment, the nanostructures assemble in the absence of any of $Mg^{2+}$, ATP, ADP, AMP-PNP, GTP or ATPγS. In yet other embodiments, assembly may require the presence of $K^+$.

The resulting nanostructures utilize proteins to control the assembly of structures that may, in certain embodiments, incorporate organic materials or inorganic materials such as metallic, semiconducting or magnetic nanoparticles (Bruchez et al., 1998 Science 281: 2013-16; Peng et al., 2000 Nature 404(6773): 59-61; Whaley et al., 2000 Nature 405: 665-68).

For the formation of a nanostructure, nanoscale materials can be combined with the chaperonin polypeptides and/or chaperonins under suitable conditions (e.g., concentration and proportion of $Mg^{2+}$, $K^+$, ATP, ADP, AMP-PNP, GTP or ATPγS). The nanoscale material (i.e., the nanoparticle or quantum dot) can be attached to the chaperonin and/or the polypeptide subunits at specific binding sites prior to assembly of the nanostructure. The nanoscale materials can be introduced before the formation of the nanotemplates, e.g., by being directly bound to a subunit, prior to assembly of the various subunits and/or chaperonins into the nanostructures. In an alternate embodiment, the nanoscale material is attached to specific binding sites after the nanotemplate is assembled. In such an embodiment, a nanotemplate is first formed, with the selected sites for binding of the nanostructures present on pre-determined locations of the nanotemplates, and then the nanostructures are introduced.

Figure 10A:
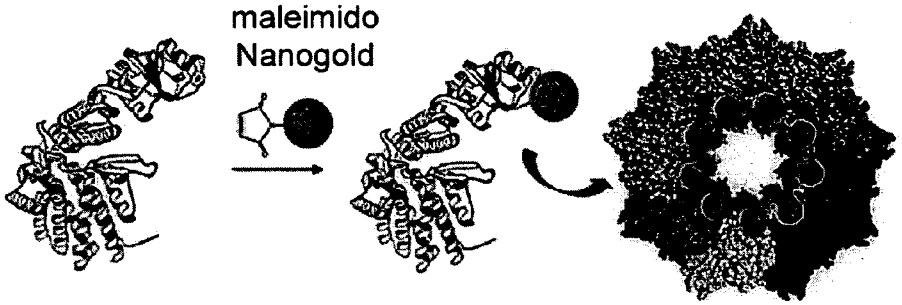
FIGS. 10A-D show the formation of a nanoarray of gold nanoparticles.

In another embodiment, the nanoparticles are coated with a coating that allows specific binding of the nanostructures to the pre-determined locations on the nanotemplates. FIG. 10A shows a gold particle derivatized with surface-accessible, thiol-reactive maleimide groups (monomaleimido Nanogold, Nanoprobes, Inc.). The nanogold quantum dots were covalently bound to the mutant beta subunit of *S. shibatae* with a cysteine presented as a binding site.

In other embodiments, the nanoscale materials are coated with an inorganic and/or organic compounds, a polymer, a protein, a peptide, hormones, antibodies, nucleic acids, receptors, reactive chemical groups, binding agents and the like. For example, the nanoscale materials can be coated with a polyethylene glycol compound containing chemically reactive amine groups.

In yet another embodiment, the nanoscale materials are coated with biotin or streptavidin. In a specific embodiment, the nanoscale materials are coated with bovine serum albumin (BSA) and biotin, and the streptavidin is located at one or more binding sites of the nanotemplate. In another example, amino acids, or small peptides are coated directly on the surface of the nanoscale materials, or are chemically linked to polymers or other type of macromolecules.

Examples of nanoscale materials include, but are not limited to, nanoparticles, such as gold, silver and other metal nanoparticle or composite nanoparticles of the metals; quantum dots (QD), including CdSe—ZnS, CdS, ZnS, CdSe, InP, InGaAs, CuCl, and InAs quantum dots, silicon nanocrystals and nanopyramids, silver nanoparticles; or magnetic quantum dots, e.g., nanomagnets, such as CoCu, FeCu, NiFe/Ag, and CoAg nanomagnets. The nanoscale materials can comprise one or more materials, or combinations of materials, such as transition metals, including gold, silver, zinc, cadmium, platinum, palladium, cobalt, mercury or nickel; alkali or alkaline earth metals, including sodium, potassium, calcium or cesuim; group III elements, including, aluminum, gallium or indium; group IV elements, including, silicon, germanium, tin or lead; group V elements, including, phosphorous, arsenic, antimony, or bismuth; or group VI elements, including, sulfur, selenium or tellurium. The listed materials can be in any given combination. Examples of III-V compounds include GaAs or AlGaAs. The nanoscale material could also be a fullerene, a carbon nanotube, or a dielectric, polymeric, or semiconducting nanoparticle. In an alternate embodiment, flexible protein joints may be added to rigid carbon nanotubes to increase the diversity of possible forms while maintaining the functional features inherent in both kinds of nano-structures.

The size of the nanoscale material can be about 0.5 nm, 1 nm, about 10 nm, about 50 nm, about 100 nm, about 200 nm, or about 500 nm, or more. The size of the nanoparticles can depend on the location of the binding site on the nanotemplate. If the binding site is at an apical domain, or within the internal cavity of the chaperonin, then the size of nanoscale material may correlate with the pore diameter of the chaperonin to which it binds. FIGS. 7C and 7E show that the size of the nanoscale material that bind at the apical domain of chaperonins formed from variants of the beta subunits of *S. shibatae*. FIG. 7C shows an illustration of the 3-nm-pore 2D crystal (p312) indicating how 5 nm gold binds within the engineered pores. FIG. 7E shows an illustration of the 9-nm-pore 2D crystal (p312) indicating how 10 nm gold binds within the engineered pores. The nanoscale materials may also be located in interstitial regions of the nanotemplate, i.e., between the chaperonins. The nanoscale materials may be bound to more than one chaperonin, such as when the nanoscale material in present in an interstitial site. In another embodiment, the nanoscale material is located on top of a region of the nanotemplate, and serve as a type of "mask." In this embodiment, the nanoscale material can range up to 500 nm in size.

Morphologies of nanoparticles include, for example, nanopillars, nanocrystals, nanorods, nanotubes, nanowires, nanofilaments, nanofibers and composite metal/dielectric nanoshells.

In a specific embodiment, application of an electric field is used to disrupt the nanostructure or the template which may be reformed on addition of other reagents with the removal of the electric field.

In an alternate embodiment, differing amounts or proportions of ATP, ADP, AMP-PNP, GTP or ATPγS are used to disrupt the nanostructure or nanotemplates, or to cause the nanoscale material to become unbound from the nanostructure or nanotemplate.

In an embodiment, amino acid tails that do not inhibit their ability to assemble into rings and tubes are attached to the chaperonin polypeptides, e.g., HSP60s, and that allow the binding of the nanoscale materials inside the chaperonins structure, at an apical, equitorial or intermediate domain, or on other locations of the chaperonin.

Mutated chaperonin polypeptides, including HSP60s, can form nanometer or micron scale tubes and filaments or arrays containing metals or doped or undoped semiconductors, and could function as nano-wires, field-effect transistors, switches, diodes or logic devices. Given that metals can be attached to chaperonin polypeptides, their assembly into tubes would create a protein coated metal-cored conduit, i.e., a wire. By orienting and networking such wires nano-circuitry can potentially be created, which may be of value in the computer industry.

The nanostructures can also be incorporated into coatings with optical, electric, magnetic, catalytic, or enzymatic moieties as functional units.

A nanoarray is a nanoscale or microscale ordered arrangement of nanotemplates and/or nanostructures. A nanoarray, therefore comprises an ordered array of nanostructures. A nanoarray can have any type of long range packing symmetry, including 2-, 3-, 4-, or 6-fold packing symmetry. The nanoarray can be a one-dimensional structure, a two-dimensional array, or a three-dimensional array. In a specific embodiment, where the nanoparticles are dielectrics, a three-dimensional nanoarray can be a photonic bandgap crystal. Optimal conditions for assembly and crystallization of a nanoarray (i.e., concentration and proportion of $Mg^{2+}$ to ATP, ADP, AMP-PNP, GTP or ATPγS) are easily determined by routine experimentation, such as by changing each variable individually and monitoring formation of the appropriate products.

Assembly and higher order organization of mutant chaperonin polypeptides has been previously described (PCT/US02/35889) and can be used as a basis to select the optimal conditions for assembly and higher order organization using the modified chaperonin polypeptides of the present invention. For example, in a previous study (PCT/US02/35889), two classes of beta mutants of *S. shibatae* are described having a single native cysteine residue changed to a nonreactive alanine to prevent potential problems with folding and with assembly of mutant subunits. The cysteine is then placed at different solvent-exposed sites. The thiols of these cysteines provide binding sites for soft metals including gold and zinc. In one class of beta mutants, the exposed cysteine was placed near the tip of a 28 amino acid loop on the apical domain of beta, which in the assembled chaperonin protrudes into the central cavity. FIG. 7A-E shows an example of the assembly of engineered HSP60s into nanoparticle array templates of the preferred embodiment. This mutant chaperonin has a ring of reactive thiols with a diameter of approximately 3 nm on both ends (FIG. 7A, left). In the other class of beta mutants, the protruding 28 amino acid loop is removed and placed the exposed cysteine on the apical domain itself. The mutant chaperonin assembled from this subunit has a ring of reactive thiols with a diameter of approximately 9 nm and an open pore into its central cavity (FIG. 7A, right). FIG. 7A (top left) shows a model of a mutated HSP60 beta subunit indicating apical loop cysteine placement by an arrow. The side view is consistent with both classes of chaperonin variants assembled from mutated beta subunits into two symmetrically stacked nine-fold rings (FIG. 7A, center), while FIG. 7A (bottom left) shows a top view of beta chaperonin variant revealing 3 nm pore ringed by nine cysteines.

For the previously described mutants (PCT/US02/35889), the TEM image of a negatively stained 2D crystal of the beta chaperonin variant with cysteines substituted into the apical pores is shown in FIG. 7B. The two-sided plane group p312 was assigned to the lattice through image analysis of micrographs of beta chaperonin 2D crystals from *S. shibatae* (Koeck et al., 1998 Biochim. Biophys. Acta 1429: 40-44). FIG. 7A (top right). Result of genetic removal of the 28 residue apical loop of beta and substitution of cysteine at the site fusing the α-carbon backbone. Residue deletion choices were made based on the structural data from the model in FIG. 7A (left) as indicated by the arrows. FIG. 7B (bottom right) shows a top view of chaperonin variant with 9 nm pore ringed by cysteines. FIG. 7B shows the 2D crystal of 9-nm-pore variant detailing apparent increase in pore size by the change in electron density within the negatively stained rings. Both samples were imaged at the same condenser defocus setting. The ordering of the crystal is illustrated by the FFT of the image. FIG. 7C shows an illustration of the 3-nm-pore 2D crystal (p312) indicating how 5 nm gold binds within the engineered pores. FIG. 7E shows an illustration of the 9-nm-pore 2D crystal (p312) indicating how 10 nm gold binds within the engineered pores.

As shown in a previous study (PCT/US0235889) the beta subunit *S. shibatae* proves to have sufficient structural plasticity in its apical domain to accommodate both the amino acid substitutions and deletions can be made without loss of its ability to form chaperonins and 2D crystals. Under reducing conditions both classes of beta mutants formed chaperonins that assembled into disk-shaped, hexagonally packed 2D crystals up to 20 μm in diameter (PCT/US02/35889, and FIG. 7B, 7D). The order within the crystalline lattices is illustrated by fast Fourier transformation (FFT) of the TEM images (FIG. 7B, inset) which produced an optical diffractogram expressing the periodicity.

In a previous study (PCT/US02/35889) to determine whether the thiol-containing 2D crystals of chaperonins acts as templates to bind and order nanoparticle QDs into arrays, commercially available gold nanoparticles (Ted Pella, Inc, Redding, Calif.) of different diameters were used (FIG. 8). FIG. 8 shows gold quantum dot binding to engineered chaperonins and chaperonin templates. The uniform dispersion of these gold QDs in aqueous solution allows them to bind to hydrated chaperonin templates. To increase their likelihood of binding specifically to the reactive thiol of the cysteines, however, the nanoparticles can be passivated with the ligand bis(p-sulfonatophenyl)phenylphosphine (BSPP) (Loweth, C. J., Caldwell, W. B., Peng, X., Alivisatos, A. P. & Schultz, P. G. (1999) DNA-based assembly of gold nanocrystals. Angew. Chem. Int. Ed. 38: 1808-1812). BSPP displaces the citrate shell formed during synthesis of gold QDs (Novak, J. P., Nickerson, C., Franzen, S. & Feldheim, D. L. (2001) Purification of molecularly bridged metal nanoparticle arrays by centrifugation and size exclusion chromatography. Anal. Chem. 73: 5758-5761) and thereby reduces nonspecific binding of the QDs to the protein template. The passivated gold QDs were reacted with the chaperonin templates attached to formvar-coated TEM grids (see Example 6.6) and imaged in TEM mode at 60 kV. At low magnifications the chaperonin 2D crystals were visualized in the TEM using the electron density of the gold QDs themselves. FIG. 8A shows a low magnification TEM image of 10 μm diameter unstained 2D crystal of 9 nm chaperonin variant with 10 nm gold QDs bound. Contrast is from gold QDs bound to the crystalline lattice of the underlying protein template. Drying can cause significant cracking and contributes to distortions and separation of regions of order within the array. FIG. 8B Higher-magnification stained TEM image of side views of 5 nm gold QDs tethered at the apical pores of the 3-nm-pore mutant chaperonins. At high magnification the chaperonin-gold interactions were visualized in the TEM by negative-staining samples with uranyl acetate. FIG. 8B (inset) shows a slab-view cutaway diagram of postulated orientation of 5 nm and 10 nm gold QDs bound at the apical pores of the two chaperonin variants. FIG. 8C shows a stained image of 5 nm gold QDs bound within the pores of the 3-nm-pore crystalline template. Occupied rings show the QDs (dark areas) surrounded and held in place by the outer protein density of the chaperonin pores. Empty rings have a brighter, less electron dense appearance. FIG. 8D shows ordered region of 10 nm gold bound to a 9-nm-pore template with similar area coverage as in FIG. 8C. The protein holding the QDs in place is more difficult to see due to the larger size of the 10 nm QDs. Individual chaperonins in solution were observed to bind gold QDs on one or both ends. The QDs are presumably held in place by multiple dative bonds formed between the gold surface and the thiols within the pores (FIG. 8B).

In a previous study (see PCT/US02/35889), in control experiments using chaperonin 2D crystals without exposed cysteines and with or without the amino acid loop deletions, the gold QDs appeared randomly distributed with no specific binding to the chaperonin crystals. On the surface of chaperonin 2D crystals with cysteines, however, the gold QDs bound specifically onto the pores (FIG. 8C) forming regions of order on the protein (FIG. 8D) separated from one another by the cracked regions that resulted from drying, indicating that the engineered chaperonin crystals function as templates for gold QDs in solution. These chaperonin templates were size selective when attached to substrates and appeared to bind QDs only on the exposed side. Templates made from beta mutants with cysteines added to the apical loop that formed 3 nm rings of reactive thiols ordered 5 nm (±3 nm) gold QDs, but did not order 10 nm (±2 nm) or 15 nm (±1 nm) gold QDs, which bound randomly on the template surface. Variations in size distribution of gold QDs are a result of the manufacturer's method of synthesis. The chaperonin templates with the loop removed and cysteines on the apical domains that formed 9 nm rings of reactive thiols ordered 10 nm (±2 nm) gold QDs, but 5 nm (±nm) and 15 nm (±1 nm) QDs bound randomly. This size selectivity is due to the accessibility and positioning of cysteine residues within the pores of the templates.

As shown in a previous study (PCT/US02/35889), the precision of the center-to-center spacing of gold QDs ordered by the chaperonin templates was 16 nm (±2 nm, n=200) for both 5 and 10 nm gold QD arrays, as determined by TEM. This is consistent with the center-to-center spacing of the chaperonin pores in the underlying templates. The edge-to-edge spacing between QDs ranged from 6 to 10 nm for arrays made with 5 nm (±3 nm) QDs bound to 3-nm-pore chaperonin templates and from 4 to 6 nm for arrays made with 10 nm (±2 nm) QDs bound to 9-nm-pore chaperonin templates. This variation in spacing can be attributed to both the variation in the size of the gold QDs and to imperfections in the lattice of the chaperonin templates resulting from drying, cracking and dislocations within the arrays. The observed variation in QD spacing could be decreased with improved routes to QD synthesis having narrower size distributions. With more monodisperse QDs, the precision of center-to-center spacing in the gold nanoarrays should make it possible to tune the physical properties of the arrays by controlling the interparticle coupling using different sized QDs (Dujardin, et al., 2002 Adv. Mater. 14: 775-788).

Figure 12:
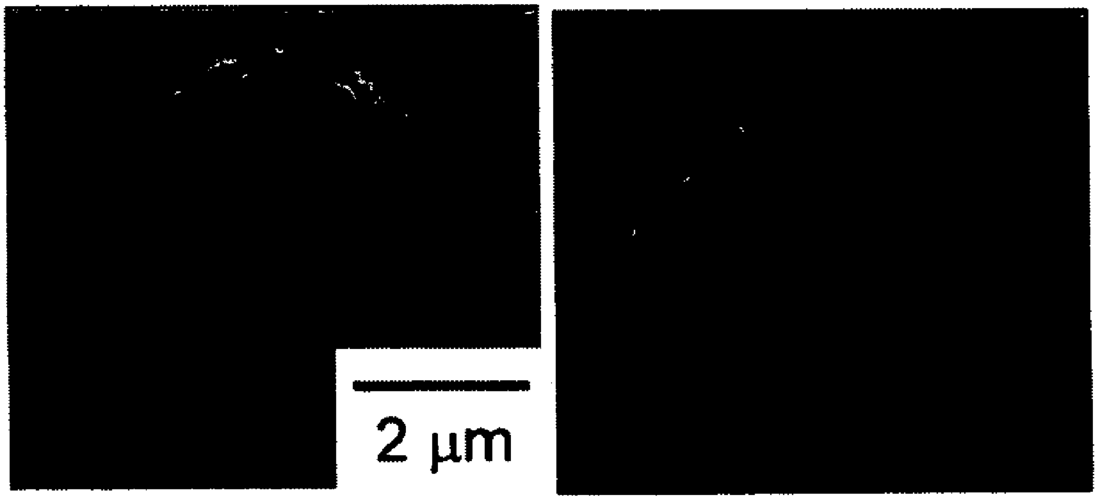
FIG. 12 shows a control experiment showing DIC (left) and fluorescent (right) images of non-cys-mutated chaperonin crystals after incubation with CdSe—ZnS QDs.
Figure 13:
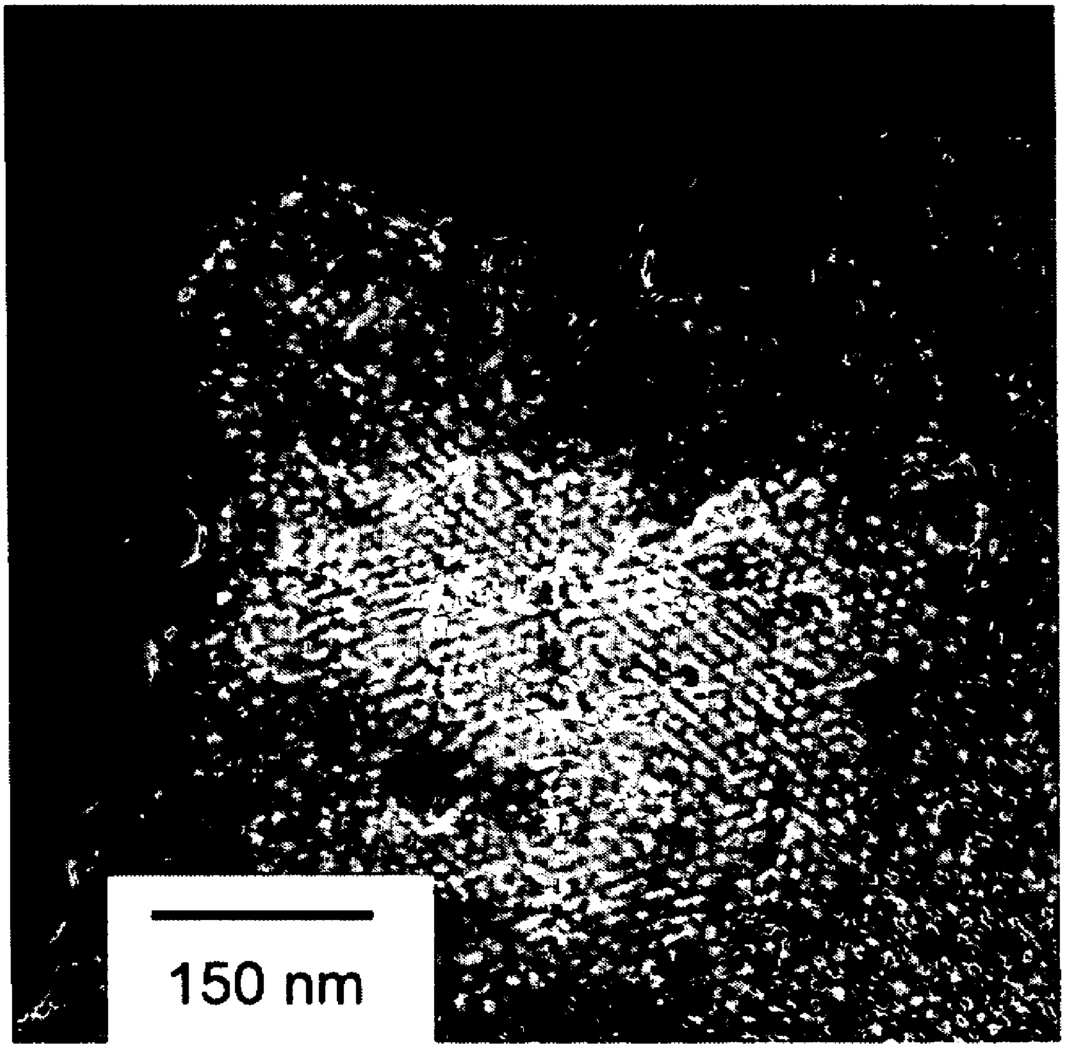
FIG. 13 shows an Energy Filtered TEM thickness map of a typical 2D protein crystal.

The chaperonin nanotemplate arrays can also bind and order semiconductor QDs to form nanoarrays. Quantum dots of size 4.5 nm luminescent core-shell (CdSe—ZnS QDs) were used (Dabbousi, B. O. et al. (1997) (CdSe)ZnS core-shell quantum dots: Synthesis and characterization of a size series of highly luminescent nanocrystallites. J. Phys. Chem. B 101: 9463-9475). These QDs were reacted with 3-nm-pore chaperonin templates attached to glass or formvar substrates. Semiconductor QDs have low solubility in aqueous solutions. A QD suspension in trioctylphosphine/trioctylphosphine oxide (TOP/TOPO) diluted with butanol was reacted with dried chaperonin templates. Under these conditions the QDs bound to the cysteine-containing chaperonin templates (see PCT/US02/35889, and FIG. 9), but not appreciably to chaperonin 2D crystals without exposed cyteines (FIGS. 12 and 13). This is consistent with observations that Zn in the outer ZnS shell of CdSe—ZnS QDs binds solvent-exposed thiols (Chan, W. C. & Nie, S. (1998) Quantum dot bioconjugates for ultrasensitive nonisotopic detection. Science 281: 2016-2018).

Figure 9A:
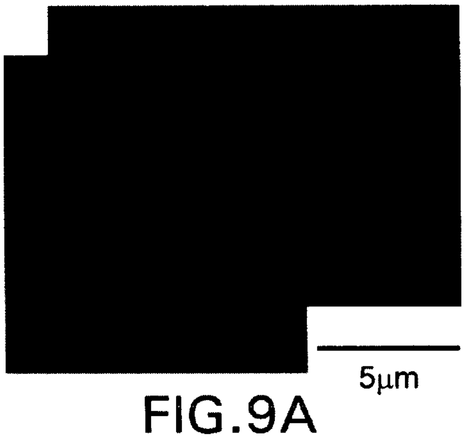
FIGS. 9A-D show semiconductor QD nanoarrays.
Figure 9B:
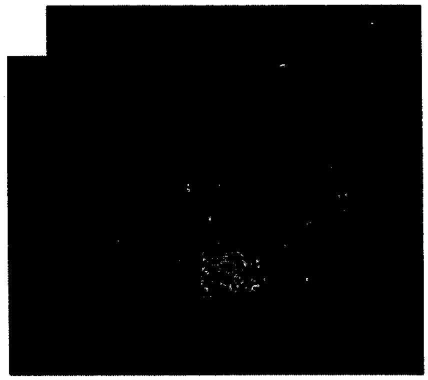
Figure 9C:
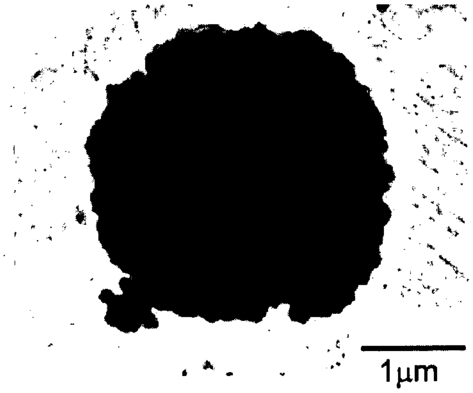
Figure 9D:
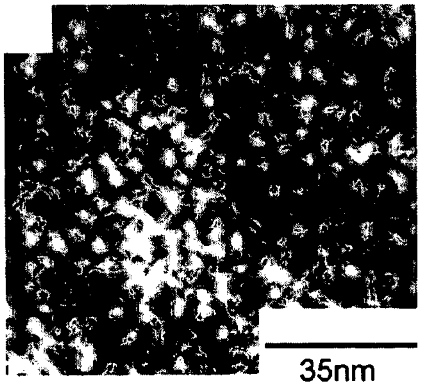

FIGS. 9A-D show the semiconductor QD nanoarray of a previously described mutant chaperonin polypeptide (PCT/US02/35889). FIG. 9A shows differential interference contrast (DIC) light micrograph of an 8 μm crystalline disc of 3-nm-pore template with 4.5 nm luminescent CdSe—ZnS QDs bound. The differential interference contrast (DIC) image of the QD-bound template (FIG. 9A) and the corresponding fluorescent image reveal that QDs bound to cysteine thiol retain their luminescent properties (Bruchez, M., Jr., Moronne, M., Gin, P., Weiss, S. & Alivisatos, A. P. (1998) Semiconductor nanocrystals as fluorescent biological labels. Science 281: 2013-2016). FIG. 9B shows both dry and rehydrated discs fluoresced indicating the QDs bound to the surface of the template. Selectivity for cysteine is confirmed using 2D crystals of beta variant without added cysteines which showed minimal QD binding (supporting information), while FIG. 9C shows low magnification TEM of an unstained array of CdSe—ZnS QDs. Image contrast is due to the bound semiconductor QDs. The mottled appearance of both the QD luminescence and the electron density of low magnification TEM images indicate that the QDs are unevenly distributed on the chaperonin templates. FIG. 9D shows higher-magnification image of same crystal revealing an ordered region of QDs bound to the protein lattice. At higher magnification of unstained samples, regions of ordered QDs are visible. These regions are separated by unoccupied regions where QDs did not bind to the protein template. This difference could be due to drying or to solvent effects of the butanol, both of which may alter the structure of the chaperonin template and the accessibility of the thiols. Water-soluble (silica-capped) CdSe—ZnS (Gerion, D. et al., 2001, "Synthesis and properties of biocompatible water-soluble silica-coated semiconductor nanocrystals," J. Phys. Chem. B 105: 8861-8871) QDs containing exposed thiol groups can bind more uniformly to hydrated chaperonin templates. The thiols on these QDs, however, can cause them to aggregate, which can result in the formation of defective arrays, in which case, it is preferable that the thiols be removed.

Figure 10B:
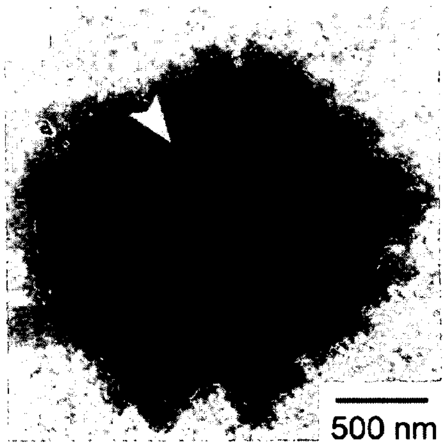
Figure 10C:
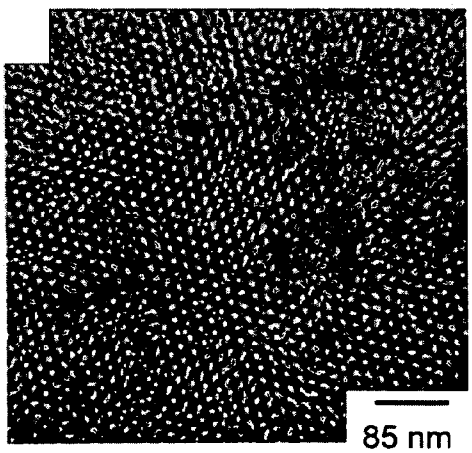
Figure 10D:
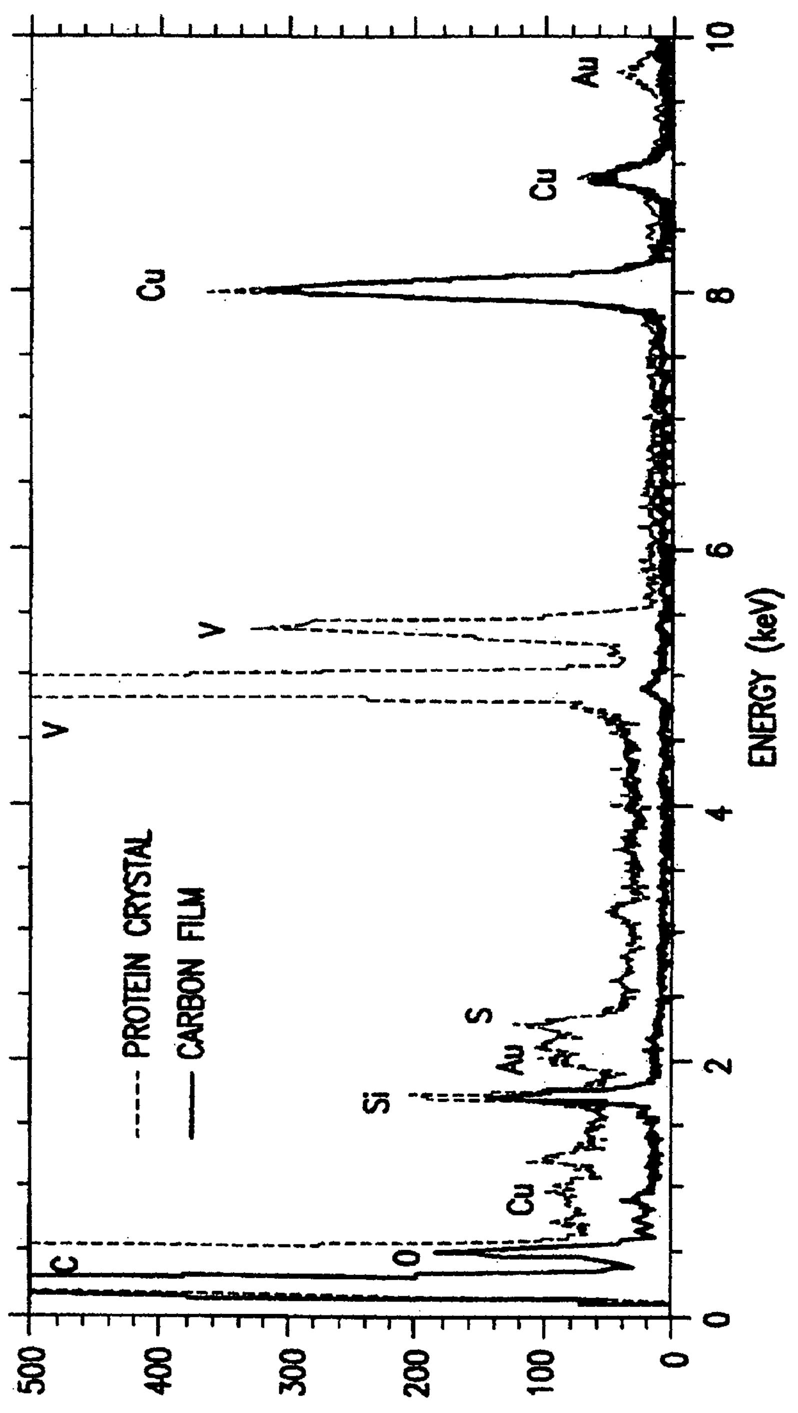

Nanoscale materials can be maneuvered into nanoarrays and nanostructures by first tethering them to chaperonin subunits and then ordered as the subunits assemble into chaperonins and 2D crystals (nanoarrays) or other nanostructures. As an example, commercially available 1.4 nm gold QDs derivatized with surface-accessible, thiol-reactive maleimide groups can be used (monomaleimido Nanogold, Nanoprobes, Inc., Yaphank, N.Y.). FIGS. 10A-D show an embodiment of a nanogold nanoarray comprising a previously described mutant chaperonin polypeptide (PCT/US02/35889). FIG. 10A shows a covalent attachment of 1.4 nm monomaleimido Nanogold to subunits of loop-minus beta variant of the beta subunit of *S. shibatae* through Michael addition of cysteine thiol to QD surface maleimide groups. FIG. 10A (right) shows possible arrangement of nine 1.4 nm covalently attached Nanogold QDs viewed at one end of a ring assembled from the derivatized subunit. FIG. 10B shows low magnification TEM image of a 2D crystalline array lightly stained with methylamine vanadate. The dark circular feature (arrow) demarks the analyzed area corresponding to the dashed-line spectrum in FIG. 10D and is the result of polymerization of mobile hydrocarbon which is attracted to the beam periphery. FIG. 10C shows higher-magnification brightfield EF-TEM image of the array revealing the ordered pattern of electron density that extends across the crystalline template. FIG. 10D shows XEDS spectra of bare carbon film (solid line) and Nanogold array (dashed line) from the probe outlined in FIG. 10B. Characteristic X-ray peaks from gold (Au $M_{\alpha}$~2 keV and Au $L_{\alpha}$~9.7 keV) confirm the presence of Nanogold within the array and the relative absence of Au on the support film.

Figure 11A:
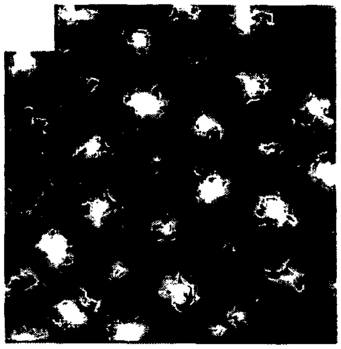
FIGS. 11A-C show HAADF STEM imaging of a nanogold array.
Figure 11B:
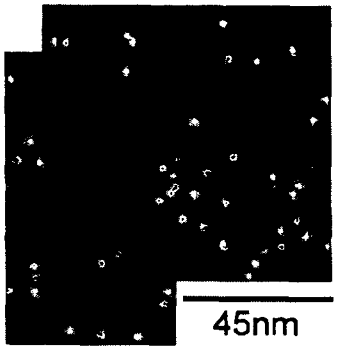
Figure 11C:
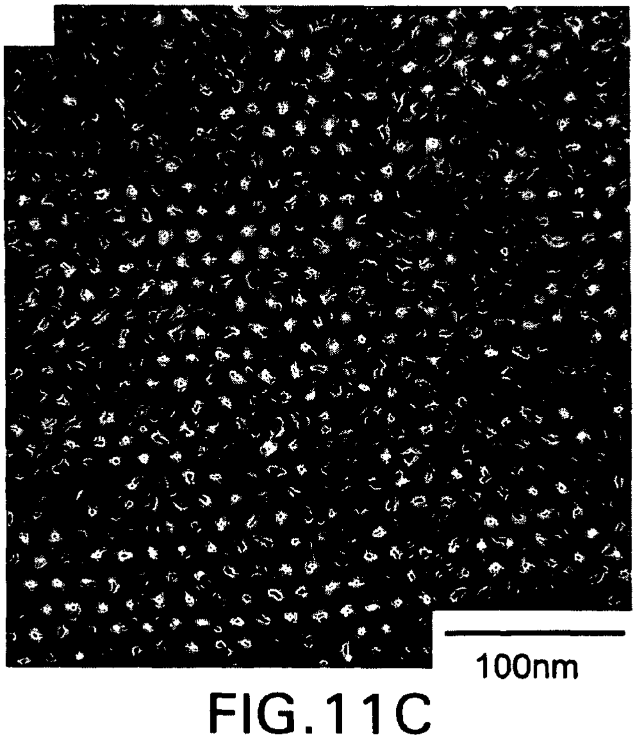

These Nanogold QDs were covalently bound to the mutant beta subunit with cysteine inserted in place of the 28 amino acid loop in the apical domain (see PCT/US02/35889, and FIGS. 10A-D). Subunits, with Nanogold attached, assembled into chaperonins in the presence of ATP/$Mg^{2+}$ (FIG. 10A); these chaperonins form 2D crystals (FIGS. 10B and 10C). The binding of the Nanogold QDs and localization within the pores of the chaperonin crystals was confirmed by analytical TEM (FIGS. 10 and 11A-11C). FIGS. 11A-11C show an HAADF STEM imaging of Nanogold array. FIGS. 11A-11C show the diameter of the features contributing to the array periodicity is consistent with multiple QDs localized within each ring. The diameter of electron density observed within the chaperonin rings forming the array (FIGS. 11A-11C) is approximately 8 to 12 times that observed for a single 1.4 nm Nanogold QD (FIGS. 11A-11C). FIGS. 11A-11C show the periodicity from the Nanogold QDs localized within the rings extends across the entire crystal.

In a previous study (PCT/US02/35889) ordered hexagonally spaced inclusions within the crystalline template were observed and determined to contain gold by imaging methylamine vanadate stained Nanogold samples in brightfield Energy Filtering (EFTEM) mode and by using X-ray Energy Dispersive Spectroscopy (XEDS) (FIG. 10B-D). Oxygen plasma-treated carbon support films were used because they are more stable in an electron beam than formvar. Because the protein templates do not adhere to plasma-treated carbon as well as to formvar, samples were stained with methylamine vanadate to enable identification of their location on the substrate. The XEDS spectrum of the Nanogold array reveals distinct peaks due to gold that are well separated from vanadium and copper peaks from the stain and carbon/copper support respectively (FIG. 10D).

High Angle Annular Dark Field (HAADF) Scanning/Transmission Electron Microscopy (STEM) was also used in a previous study (PCT/US02/35889) to image the gold localized and ordered within the Nanogold arrays (FIGS. 11A-C). Comparisons of bare Nanogold to Nanogold ordered into an array revealed that multiple Nanogold QDs were localized within the pores of the crystallized chaperonins (FIGS. 11A and 11B). The HAADF image of the Nanogold crystal also confirms the presence of gold within the chaperonin pores because contrast in HAADF imaging mode is atomic number dependent, and nearly independent of focus or thickness. An HAADF comparison of the diameter of bare Nanogold particles on carbon to the diameter of the gold nanoparticles contained within the central pores of the chaperonins that template the Nanogold into arrays reveals that the central diameters are approximately eight to twelve times that of the diameter of a single Nanogold QD. This observation is consistent with a model which suggests that each ring can contain up to nine Nanogold QDs (one per subunit). A lower magnification HAADF image of a similar area of an array reveals the ordering of the gold extends throughout the template (FIG. 11C). High resolution XEDS mapping attempts of the gold within the array were unsuccessful as the crystals were destroyed with the electron dose needed for such measurements. EELS (Electron Energy Loss Spectroscopy) mapping using the Au O shell was correspondingly unsuccessful because the V M shell edge lies in close proximity to the Au O shell and thus masks the gold signal. FIG. 12 shows a control experiment showing DIC (left) and fluorescent (right) images of non-cys-mutated chaperonin crystals after incubation with CdSe—ZnS QDs.

The luminescence intensity of the fluorescent image is barely visible indicating minimal QD binding. FIG. 13 shows an Energy Filtered TEM thickness map of a typical 2D protein crystal. The intensity in this image is the ratio of the inelastic signal to the elastic signal and is proportional to the ratio of t/λ where lambda is the mean free path for inelastic scattering and t is the local mass thickness. Regions of nominally uniform intensity indicate regions of nominally constant mass thickness. Increasing intensity indicates increased thickness. At the various regions and at the edges of the crystal one can observe clear transitions indicating that the crystal is composed of several layers.

In a previous study (PCT/US02/35889) crystal thickness measurements (AFM and TEM) suggest that these crystals can be multilayered (supporting information), and are observed as crystals ranging from 1 to 10 layers (approximately 20 to 200 nm). The assembly of QDs into arrays by first covalently attaching them to subunits may create more defect-tolerant arrays because each chaperonin is composed of 18 subunits and therefore there are 18 chances for each site in the array to contain at least one QD. Likewise, the regions of QD ordering within arrays assembled this way appear to span the dimensions of the crystalline template and with fewer defects than previously observed. These types of arrays may find use in applications that demand longer range ordering than the 5 and 10 nm gold and semiconductor nanoparticle binding protocols allow.

The present invention provides a hybrid bio/inorganic approach to nanophase materials organization where the functionality of proteins can be rationally engineered. Using structural information and recombinant biotechnology techniques, genetically engineered chaperonins can be made to function both as nanotemplates and as vehicles for controlled nanoscale organization of preformed QDs into ordered nanoarrays, e.g., arrays of nanomagnets. These nanotemplates, nanostructures, and nanoarrays can be "wired" together into functional nanodevices, for example by using genetics, as alternate binding sites may be engineered at different locations on the chaperonin.

The possibility to induce asymmetry within the arrays by engineering alternate facets of the protein crystal is exploited in forming the nanodevices of the present invention. A nanodevice comprises at least one nanotemplate, at least one nanostructure, at least one nanoarray or some combination thereof. A nanodevice can, for example, be an electronic, semiconductor, mechanical, nanoelectromechanical, magnetic, photonic, optical, optoelectronic or biomedical device formed from at least one nanostructure, at least one nanoarray, and/or at least one nanotemplate.

In a specific embodiment, the nanostructures are organized into a nanodevice that functions with the chaperonins still present. In an alternate embodiment, the chaperonins are removed before the functioning of the nanodevice. The nanotemplate and nanostructure provide an organizational basis for attached molecules, nanoparticles and quantum dots. The attached nanoscale materials can be equally spaced at, e.g., 15 nm intervals, or selectively place at pre-determined sites. Taking advantage of the fact that enzymes (such as proteases) can be used to specifically remove the chaperonin, the nanotemplates can serve to leave behind pure material accurately placed on a surface at nano-scale resolution.

The steps in the formation of a nanodevice are similar to those for forming a nanostructure, except that the building blocks are nanotemplates, nanostructures, and/or nanoarrays. The steps can include adding one or more nanotemplates, nanostructures, nanoarrays, or some combination thereof to a surface, and then removing any unbound nanotemplates, nanostructures, or nanoarrays. The steps are repeated any desired number of times, with the choice of material introduction being changed at each step to build the desired nanodevice. Other masking techniques, e.g., semiconductor fabrication can also be combined with the present invention in the construction of the nanodevice.

There is no direct parallel of the present invention in the semiconductor manufacturing industry. The use of protein-based templates that self assemble into highly ordered structures allow of the engineering of semiconductor materials on a size regime much smaller than that currently attainable. Further, given the diversity of the chaperonin system (e.g, its ability to bind other biomolecules such as lipid and DNA/RNA) the compositions and devices of the invention can also be utilized in a biomedical, e.g., biomedical device, context.

Figure 14:
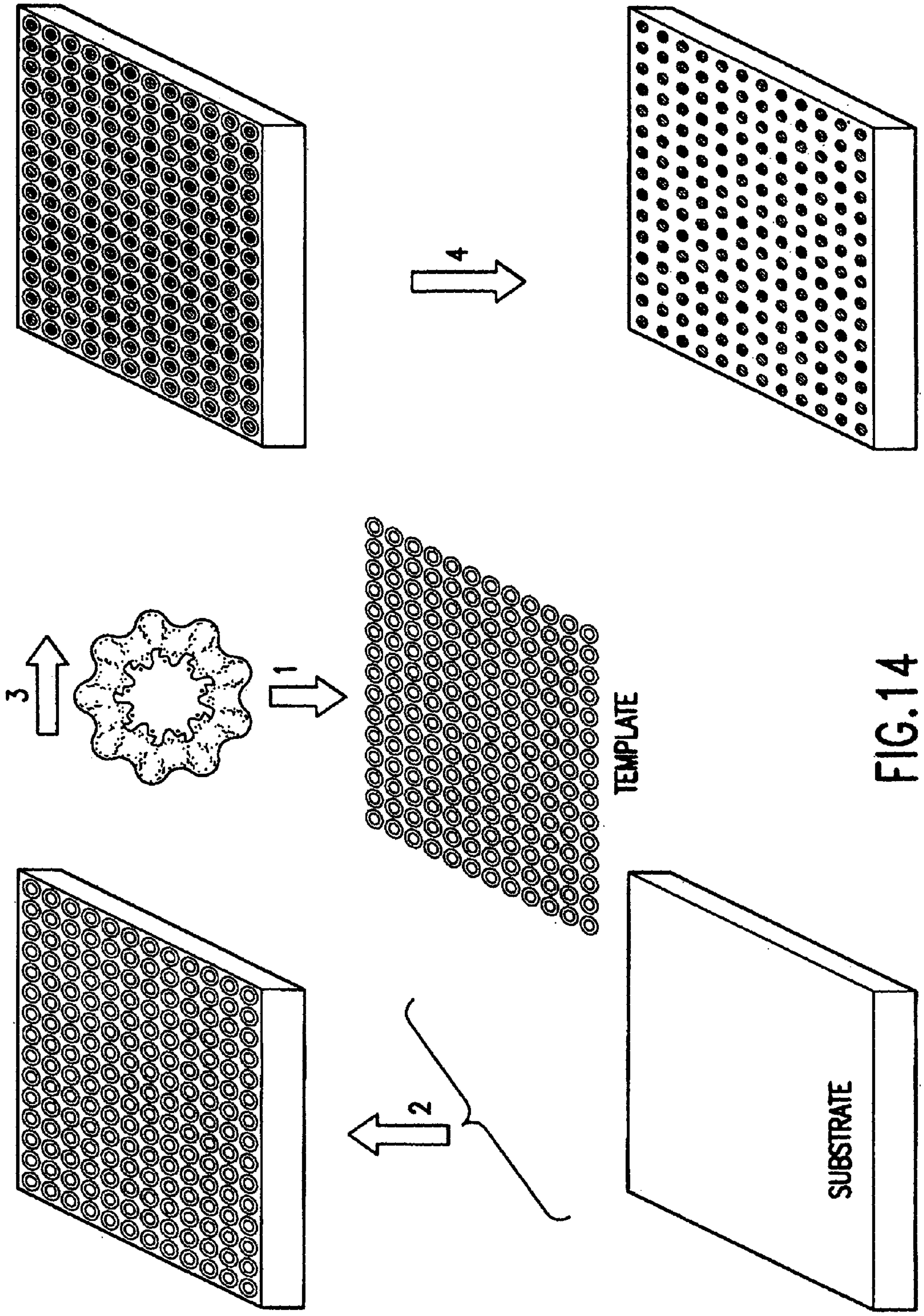
FIG. 14 illustrates steps in the formation of an ordered nanoarray of nanoparticles on a substrate.

The invention further provides methods to selectively deposit nanoparticles or quantum dots in an ordered array onto inorganic substrates. DNA manipulation and genetic engineering of the genes that code for chaperonins can be used to generate specificity in molecular recognition at defined sites within the protein. For example, by introducing cysteine residues into the protein, it can specifically bind colloidal gold molecules through dative bonding between the sulfhydryl (SH) moiety of Cys and Au0. This allows for the organization of gold nanoparticles into ordered arrays onto substrates. After organizing the gold onto the surface, the protein can be removed using a reactive ion cold plasma, leaving the patterned gold in place on a clean surface (FIG. 14), thereby producing a nanodevice of the invention. The HSP60s bound with proteins or peptides are capable of releasing the bound proteins or peptides in the presence of adenosine triphosphate (ATP) or acidic conditions (Udono and Srivastava, 1993 J. Exp. Med. 178:1391-1396).

With advances in microbial genetics, for example using phage and cell surface display to identify inorganic binding peptide sequences (Whaley et al., Nature 405: 665-668), the usefulness of this system extends beyond soft metals to other materials by, for example, the addition of sequences back into the loop region that was removed.

Examples of additional, non-limiting applications of the nanodevices include field emitters, sensors, optoelectronic and all-optical switches, lenses, probes, lasers, nanoelectromechanical systems (NEMS), circuitry and nanoelectronics, nanomachines (e.g., by attaching nanomotors), neural networks (nanoelectrodes for connections), nanocomputers, quantum computers, high-density magnetic memory or storage media, photonic crystals, nanocrystal antennas, multinanowell assay plates, nanocatalysts (e.g., palladium), nanopores for single-molecule DNA sequencing, amplifiers for telecommunications (approximately 7 nm PbSe and PbS quantum dots have a tunable gap near 1500 nm). Applications include, for example, memory or storage devices (e.g., hard-disk drive read heads, magnetic RAM), magnetic field sensors, magnetic logic devices, logic gates, and switches.

Further applications can also include, for example, biochip applications. Quantum dots in a biochip, for example, can each account for at least one or several data bits. The position of a single electron in a quantum dot can attain several states, so that a quantum dot can represent a byte of data. In an alternate embodiment, a quantum dot can be used in more than one computational instruction at a time.

Other applications of quantum dots include nanomachines, neural networks, and high-density memory or storage media.

In an alternate embodiment, the nanodevice, nanotemplate or nanoarray functions as a single-molecule probe for DNA detection, hybridization, and sequencing.

Polymer microspheres with uniformly embedded polymers have applications as, for example, active fluorescent building blocks in flat panel displays and luminescent labels in biological detection. This application is achieved by forming a nanodevice comprising a nanoarray of embedded polymer nanoparticles Still further applications relate to molecular motors, e.g., molecular motors in a biomedical context.

The following examples are presented to illustrate the present invention and to assist one of ordinary skill in making and using the same. The methodology and results may vary depending on the intended goal of treatment and the procedures employed. The examples are not intended in any way to otherwise limit the scope of the invention.

Example 1

The following provides a description of methods used to produce DNA sequences encoding the modified chaperonin polypeptides comprising relocated N-terminal and C-terminal ends, and encoding fusion proteins which are modified chaperonin polypeptide comprising relocate N- and C-terminal ends where the carboxy-terminal end is joined with a sequence encoding yellow fluorescent protein.

Materials and Methods

DNA Constructs

Genes encoding the permuted chaperonin proteins were created using a two-step polymerase chain reaction (PCR) method in which fragments of DNA before and after the permutation site are amplified with the flexible linked added to the beginning and end of the gene. The starting template DNA sequence encoding a TF55 beta subunit from *Sulfolobus shibatae* is shown in FIG. 28A. In the second step, the two fragments are annealed together at the flexible linker and the resulting template DNA was amplified by PCR. The DNA encoding the permuted protein was then cloned into an *E. coli* expression vector (pET19b, Novagen) at the Nco I and Xho I restrictions sites.

The resulting DNA sequences encoding the five different circular permutated TF55 polypeptides at positions 153, 267, 316, 480, or 499 are shown in FIGS. 22-26, respectively. Models of the five different circular permutated TF55 polypeptides in folded and assembled conformations are shown in FIGS. 17A-E.

Protein Expression

The expression vectors described above were transformed into *E. coli* BL21 DE3 cells containing a second vector that supplements rare tRNAs (BL21 DE3 CodonPlus RIL, Stratagene). This second vector was used because *E. coli* codon usage differs from *Sulfolobus*. Some tRNAs that are common in *Sulfolobus* (and therefore in *Sulfolobus* genes) are rare in *E. coli*. These cells were then culture in Luria Broth with 100 micrograms/liter ampicillin and 34 micrograms/liter chloramphenicol. IPTG was added to a final concentration of 1 mM when the culture reached an optical density of 0.4-0.8 at 600 nm. After four hours the cells were harvested by centrifugation. The resulting pellet was weighed, resuspended in 25 ml HEPES, 1 mM EDTA, pH 7.5 and stored at minus 80 degrees C.

Protein Purification

Cells were removed from storage at minus 80 degrees C. and thawed. Protease inhibitor cocktail (Sigma-Aldrich) was added during thawing at 0.25 ml per gram of wet pellet weight. When thawed, the cell suspension was placed on ice and sonicated 3 times for 2 minutes each with a one minute pause between sonications (Branson Sonifier 450, 60% duty cycle, output 6). The cell lysate was placed in a water bath at 70 degrees C. water bath for 30 minutes to precipitate heat-labile proteins. After heating, the lysate was cooled on ice for 10 minutes and then centrifuged at 17,000 g, at 4 degrees C., for 30 minutes. The supernatant was decanted and 2.5% (v/v) of a 5% (w/v) stock solution of polyethyleneimine (Sigma-Aldrich) at pH 7.8 was added to precipitate nucleic acids. After 10 minutes nice, the solution was again centrifuged at 17,000 g, at 4 degrees C., for 30 minutes. The supernatant from this step was filtered through a 0.45 micrometer pore membrane and diluted to 50 ml with 25 mM HEPES, 1 mM EDTA, pH 7.5. This protein solution was loaded onto a MonoQ 10/10 anion exchange column (Amersham Biosciences) and eluted by a linear gradient from 1 to 400 mM NaCl in 25 mM HEPES, 1 mM EDTA, pH 7.5. Peak fractions were confirmed by denaturing polyacrylamide gel electrophoresis, pooled and concentrated using Centriprep YM30 centrifugal concentrators (Millipore). Buffer was exchanged in the centrifugal concentrator with at least 10 volumes of 25 mM HEPES, 1 mM EDTA, pH 7.5. Protein concentration was determined by measuring absorbance at 280 nm using an estimated extinction coefficient of 56,820 $M^{-1}$ $cm^{-1}$.

Inclusion Body Preparation.

Cells were removed from storage at −80 degrees C. Reagents were added to a concentration of 25 mM HEPES, 100 mM NaCl, 0.5% TritonX-100 and 0.25 ml Protease Inhibitor Cocktail (Sigma-Aldrich) per gram wet pellet weight before thawing. Cells were lysed by sonication, 3 times for 2 minutes each with a 3 minute pause (Branson Sonifier 450, 40% duty cycle, output 5). Reagents were added to the cell lysate to a concentration of 10 mM MgSO4, 1 mg/ml Lysozyme (Sigma-Aldrich) and 1 microliter/10 ml Benzonase (Sigma-Aldrich) and incubated at room temperature for 20 minutes before centrifugation at 6000×G and 4 degrees C. for 15 min. The pellet was resuspended in 30 ml Buffer R (50 mM Tris-HCl pH 8.0, 100 mM NaCl, 5 mM EDTA, 0.5% Triton X-100), then sonicated for 1 minute at previous settings. Reagents for 10 mM MgSO4, 1 mg/ml Lysozyme and 1 microliterl/10 ml Benzonase were added, the lysate was incubated at room temperature for 20 minutes, then centrifuged at 6000×G, 4 degrees C., 10 min. The pellet was resuspended in 30 ml Buffer R, sonicated for 1 min and centrifuged 10 min. This last step was repeated (resuspended, sonicated, centrifuged). Next, the pellet was resuspended in 30 ml 25 mM HEPES pH 8.0, 100 mM NaCl, 5 mM EDTA, 0.1 NaN3, and centrifuged for 1 min at 6000×G, 4 degrees C. (This pellet was stored at −80° C. overnight).

The pellet was solubilized in 500 microliter 100 mM Tris-HCl pH 7.5, 50 mM Glycine, then denatured in a solution of 10 M Urea pH 7.5, 100 mM Tris, 50 mM Glycine to a final concentration of 8.5 M Urea. The protein was refolded by adding dropwise into 100 ml 50 mM Tris-HCl, 35 mM KCl, 2 mM MgCl2, 1 mM Beta mercaptoethanol pH 7.5.

This protein solution was purified by ion exchange chromatography as in the circular permutants.

Polyacrylamide Gel Electrophoresis

The purity of the proteins was evaluated using denaturing polyacrylamide gel electrophoresis (GeneMate 8-16% Express Gels, ISC BioExpress). The ability of each of the circular permutations to form double rings was assessed by non-denaturing 4-40% gradient polyacrylamide gel (FIG. 18) as previously described (J K Trent, et al., 1991 Nature 354: 490-493).

Formation of Crystals and Filaments

Crystal or filaments were formed from the circular permutant proteins by placing them in solution at concentrations of 1 to 5 mg/ml in 25 mM HEPES at pH7.5 with 1 mM ATP and 25 mM $MgCl_2$. The samples were stored at room temperature for 1 to 3 days before examination for higher order structure by light and electron microscopy.

Results

Transmission Electron Microscopy

Samples were prepared for the electron microscope by drop casting on carbon-coated formvar substrates (Ladd) and stained with 1% uranyl acetate. Samples were visualized using a Leo 912AB electron microscope in bright field TEM mode at 65 kV with a tungsten filament electron source.

Samples of the five different circular permutated chaperonin polypeptides (without the joined EYFP sequence) were analyzed at 1 hour or 24 hours after addition of 1 mM ATP and 25 mM $Mg^{2+}$ (FIG. 19A-J). All five circular permuted chaperonins analyzed formed double rings having the same structure as wild-type chaperonin double rings, with two rings of nine subunits each (FIG. 19A-E). The circular permutated chaperonin polypeptides 153, 267 and 316 formed predominantly crystalline structures. The circular permutated chaperonin polypeptides 480 and 499 formed predominantly filamentous structures. For permutants at positions 480 and 499, heating the sample to 70 degrees C. for 30 minutes immediately after addition of ATP and $Mg^{2+}$ produced longer filaments. This same heating regime did not improve crystallization of permutants 153, 267 or 316.

Figure 20:
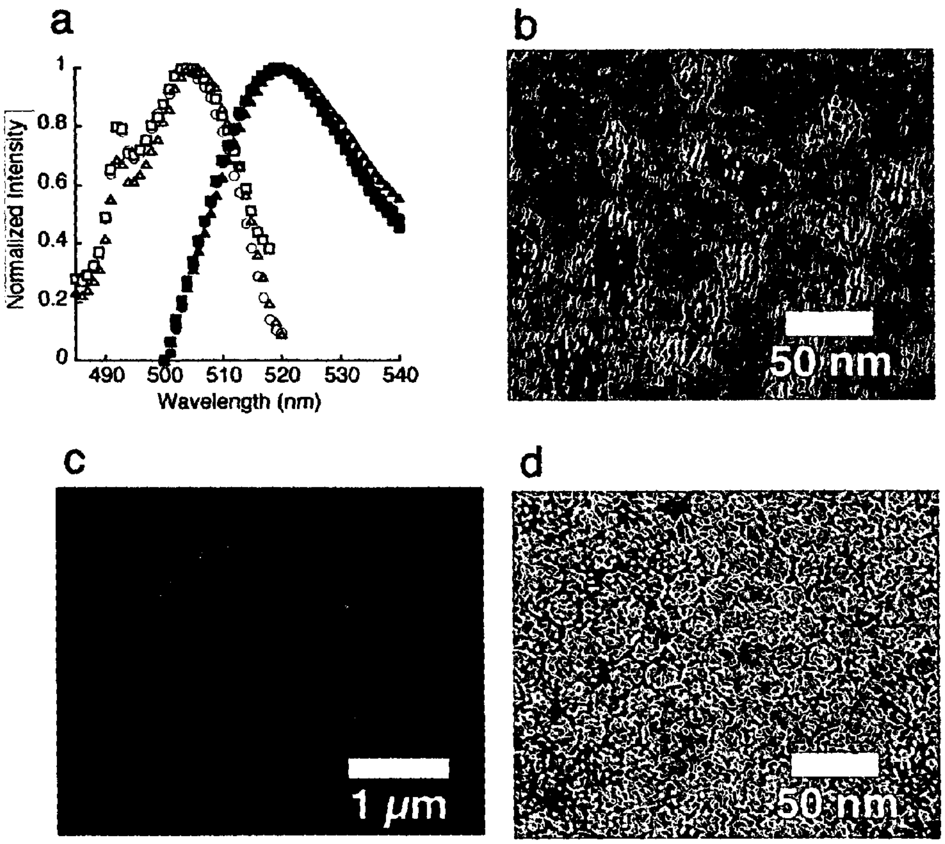
FIG. 20A-D shows circular permutant chaperonin proteins at positions 267 and 480 joined with yellow fluorescent protein (EYFP). A) Fluorescence excitation (open symbols) and emission (closed symbols) spectra for unmodified EYFP (circles), 267 permutant-EYFP fusion protein (squares), 480 permutant-EYFP fusion protein (triangles). B) TEM showing negatively stained rings formed by 480 permutant-EYFP fusion protein. C) Fluorescence microscopy of a crystal formed by the 267 permutant-EYFP fusion protein using Leica filter cube 13 (excitation 470 nm, emission 515 nm). D) TEM showing 2-dimensional crystal formed by 267 permutant-EYFP fusion protein.

The circular permutant EYFP fusion proteins −267 and −480 were analyzed via TEM. The 480 fusion protein assemble into chaperonin double rings having the same or similar form as wild-type chaperonins (FIG. 20B), and the 267 fusion protein organizes into a crystalline structure (FIG. 20D).

Fluorescence Analyses

The circular permutant fusion proteins (267 and 480) were analyzed using Leica filter cube I3 (excitation 470 nm, emission 515 nm). The chaperonin-EYFP fusion proteins (circular permutants 267 and 480) exhibit fluorescence similar excitation and emission spectra of EYFP (FIG. 20A). Additionally, fluorescence microscopy shows the 267 circular permutant fusion protein organizes into a crystalline structure (FIG. 20C).

Discussion

We present a general method for modifying protein templates using circular permutation so that additional peptide sequences can be added in a wide variety of specific locations. Circular permutation is a reordering of the polypeptide chain such that the original N- and C-terminal ends are joined and new end termini are created elsewhere in the protein. New protein sequences can be joined to the relocated termini without perturbing the protein structure and with minimal limitation on the size and conformation of the added sequence. We have used circular permutation to modify a chaperonin HSP60 protein template (TF55 beta subunit), by relocating the terminal ends at five different locations distributed across the surface of the protein complex.

Chaperonins are composed of 14, 16 or 18 subunits known as heat shock protein 60 (HSP60) (FU Hartl and M Hayer-Hartl 2002 Science 295:1852-1858), where 60 refers to their molecular mass of approximately 60 kilodaltons. In the presence of ATP and $Mg^{2+}$, these subunits assemble into a two-stacked ring structure. The modified chaperonin polypeptides of the present invention were based on an HSP60 from the hyperthermophilic archeon *Sulfolobus shibatae*, which lives in geothermal hot springs and thrives at pH 2 and temperatures up to 85 degrees C. *Sulfolobus shibatae* produces three related HSP60 proteins, designated alpha, beta and gamma. These three HSP60 proteins assemble in various stoichiometries, into octadecameric complexes with nine subunits per ring. These double ring structures are symmetric around a nine-fold axis and across a perpendicular two-fold axis. The surface adjacent to the interface between the rings is known as the equatorial surface and the surface of the ring most distant from the equator is the apical surface. Overall, the double rings are approximately 17 nm in diameter and 18 nm in length, and have a central pore. The *Sulfolobus shibatae* chaperonins are known to form higher order structures such as filaments (J D Trent, et al., 1997 Proc Natl Acad Sci USA 94:5383-5388) and two-dimensional crystals (J P Koeck, et al., 1998 Biochim Biophys Acta 1429:40-44; M J Ellis, et al., 1998 J Struct Biol 123:30-36). The filaments are based on interactions between the apical surfaces on one double ring with the apical surfaces of two adjacent double rings. The two dimensional crystals are based on interactions between the equatorial surface of one double ring with equatorial surfaces of six adjacent double rings. Bundled filaments have also been observed and are believed to contain both types of interactions.

We selected the HSP60 beta subunit (TF55, beta subunit) for our research because it forms homo-oligomeric rings that also assemble into filaments and two-dimensional crystals. We previously reported attaching nanoparticles to the chaperonin double rings using thiol chemistry provided by a single cysteine residue substituted into the HSP60 protein sequence (PCT/US02/35889). We report here creating a chaperonin circular permutant by joining a second peptide sequences having arbitrary length and topology (yellow fluorescent protein) onto the chaperonin protein sequence. The second peptide sequence is fused to the C-terminal end which is relocated from the central pore to a position on the exterior of the chaperonin polypeptide.

Circular permutant proteins have been reported using other proteins. Published studies of circular permutations in other proteins generally conclude that, for proteins where the native amino and carboxyl termini are near in space, many new locations for the termini are viable (P T Beernink, et al., 2001 Protein Sci 10:528-537; U Heinemann and M Hahn 1995 Prog Biophys Mol Biol 64:121-143; M Iwakura, et al., 2000 Nat Struct Biol 7:580-585). In one study, dihydrofolate reductase was permuted at each of the 158 possible positions, resulting in 85 permutants that are competent to fold (M Iwakura, et al., 2000 Nat Struct Biol 7:580-585).

Figure 17:
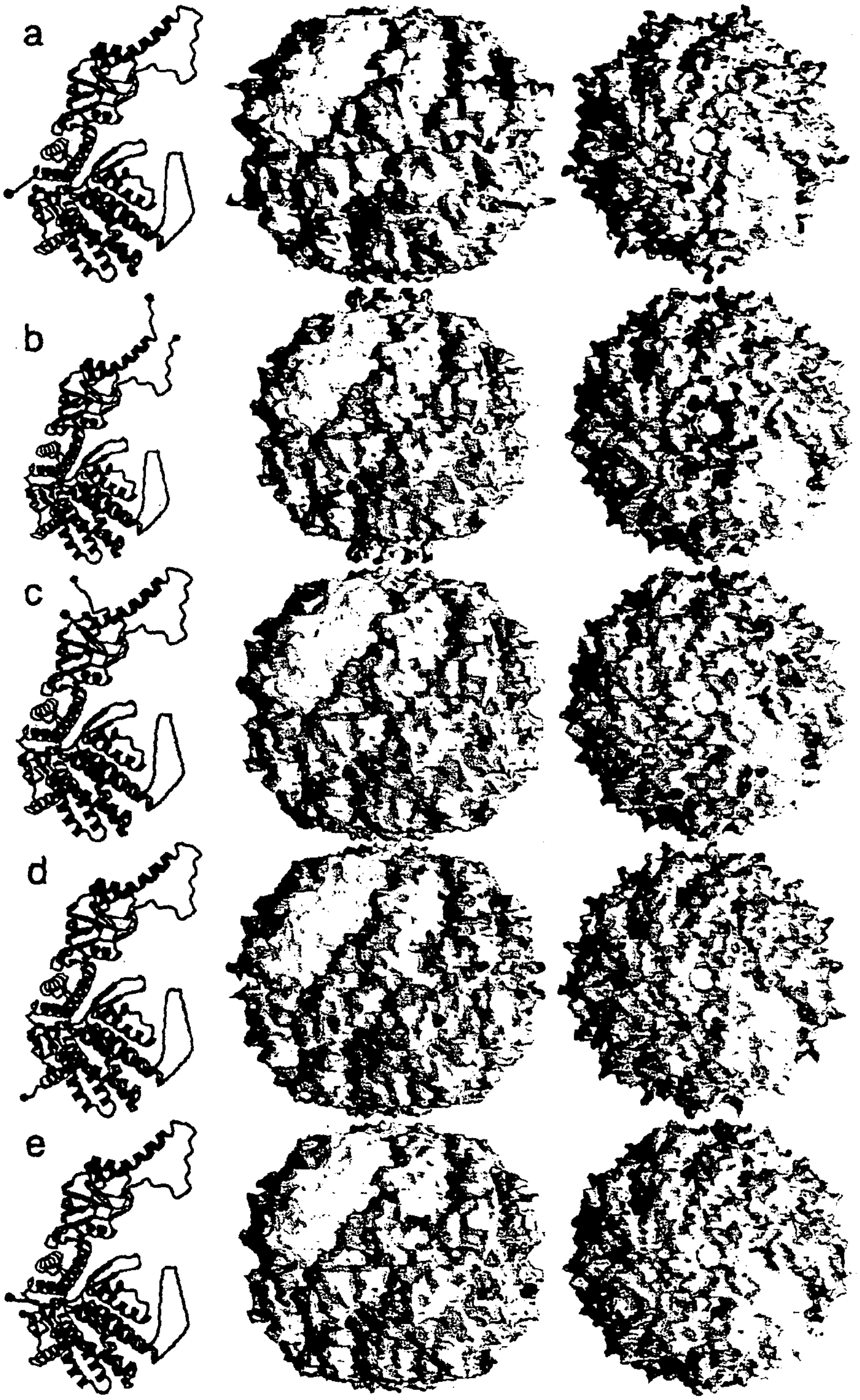
FIGS. 17A-E show models of circular permutant proteins at position: A) 153, B) 267, C) 316, D) 480, and E) 499. The left column shows ribbon representations of protein subunits. The center column shows side views of surface representations of the assembled rings. The right column shows top views of the surface representations of the assembled rings. Amino termini are labeled in blue. Carboxyl termini are labeled in red. The flexible linker sequences are labeled in green. In the assembled rings, a single subunit is highlighted in yellow.

We selected five sites for circular permutation that are distributed across the exterior surface of the double ring. These sites met the following criteria: (a) they are not buried; (b) they are not near the subunit interfaces; and (c) they are not part of regular secondary structure (alpha helices and beta sheets). In five different circular permutants, the new end termini are relocated after residues 153, 267, 316, 480 and 499 in the native TF55 beta subunit from *Sulfolobus shibatae*. The original end termini are linked by a flexible peptide sequence (GGSGGT). Models of the permuted proteins are shown in FIG. 17.

Figure 18:
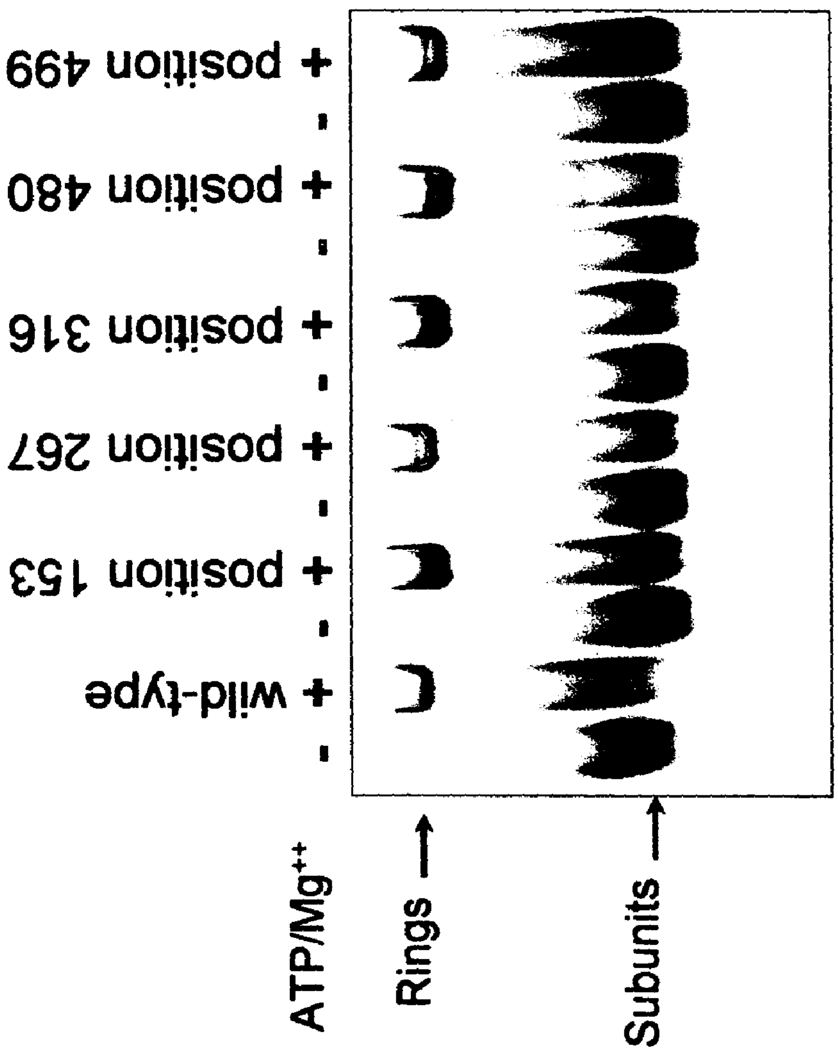
FIG. 18 shows a native polyacrylamide gel electrophoresis of wild-type chaperonin and circular permutants as unassembled protein subunits and assembled double rings in the presence and absence of ATP and magnesium ions.
Figure 19:
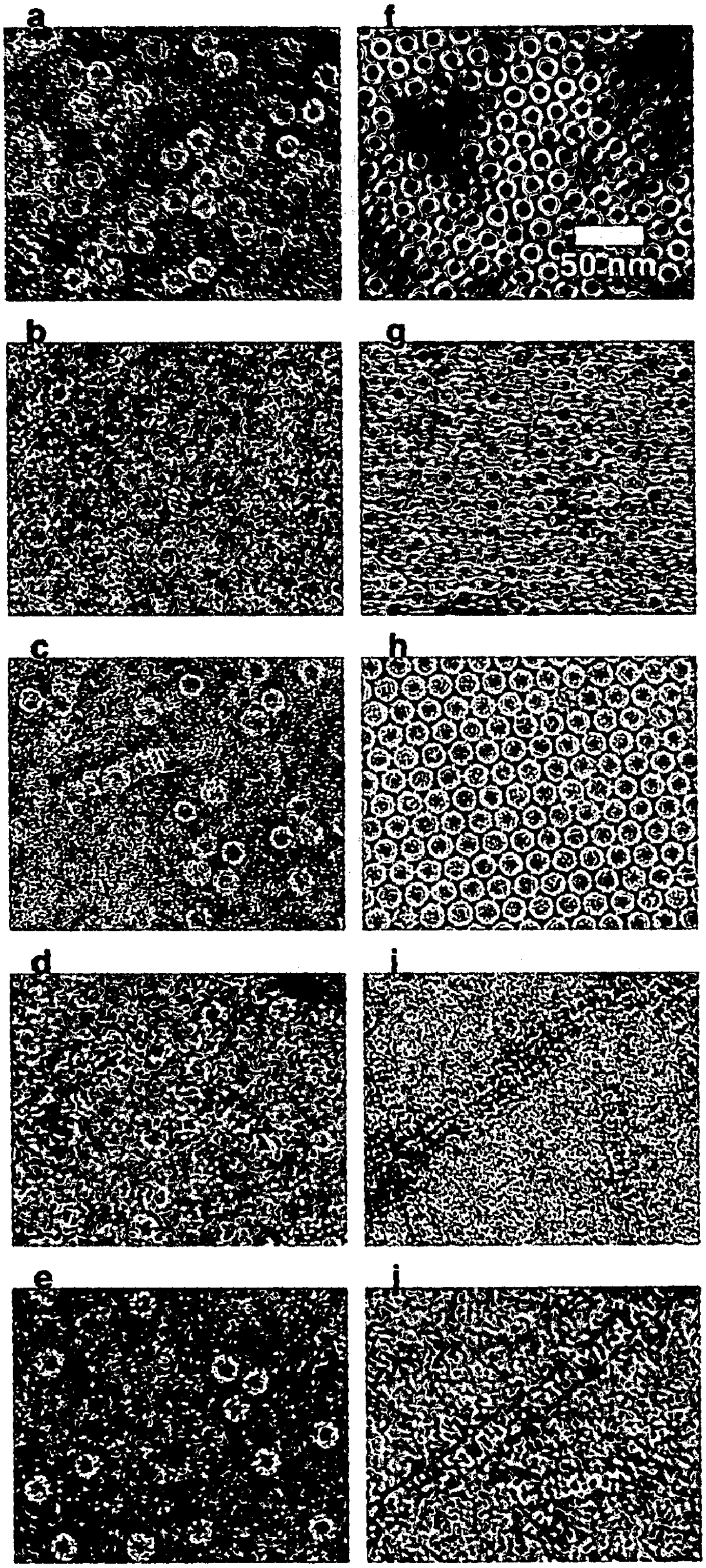
FIGS. 19A-J shows transmission electron microscopy (TEM) of assembled chaperonin double rings comprising circular permutant chaperonin proteins (lacking fused EYFP). Samples containing isolated double rings, shown in panels A-E were prepared 1 hour after addition of ATP and $MgCl_2$ to the protein samples. Samples containing higher-order structures, shown in panels F-J were prepared 24 hours after addition of ATP and $Mg^{2+}$ to the protein samples. A) Circular permutant at position 153 at 1 hour. F) Circular permutant at position 153 at 24 hours. B) Circular permutant at position 267 at 1 hour. G) Circular permutant at position 267 at 24 hours. C) Circular permutant at position 316 at 1 hour. H) Circular permutant at position 316 at 24 hours. D) Circular permutant at position 480 at 1 hour. J) Circular permutant at position 480 at 24 hours. E) Circular permutant at position 499 at 1 hour. J) Circular permutant at position 499 at 24 hours.

The circular permuted proteins were expressed at high levels in *E. coli* and were readily purified to better than 95% purity as determined by SDS-PAGE. The circular permuted proteins assemble into double rings with efficiency similar to wild-type protein, as demonstrated by non-denaturing gel electrophoresis (FIG. 18). Examination by transmission electron microscopy (TEM) indicates that the circular permuted chaperonin double rings have the same form as wild-type chaperonin double rings, with two rings of nine subunits each (FIG. 19A-E).

We expected circular permutation to affect the assembly of the resulting chaperonins into higher order structures. Specifically, perturbation of the peptide chain and addition of the new amino and carboxyl termini at different positions on the surface of the chaperonin double rings was expected to affect their propensity to form filamentous structures versus two-dimensional crystals. Changes to the apical surface of the chaperonin should destabilize the interactions necessary to form filaments, resulting in samples containing two-dimensional crystals with little or no filamentous material. On the other hand, changes on the equatorial surface of the chaperonin should destabilize interactions that are necessary to form two-dimensional crystals resulting in predominantly filamentous structures.

Examination of the assembled circular permutants using transmission electron microscopy confirms that permutations at positions 153, 267 or 316 results in predominantly crystalline samples. Conversely, permutations at positions 480 or 499 produce predominantly filamentous structures (FIGS. 19F-J). For permutants at positions 480 and 499, heating the sample to 70 degrees C. for 30 minutes immediately after addition of ATP and $Mg^{2+}$ produced longer filaments. This same heating regime did not improve crystallization of permutants 153, 267 or 316.

The fusion proteins were created by joining the circular permutant 267 and 480 with a sequence encoding the yellow fluorescent protein. Yellow fluorescent protein (EYFP) is a 28 kDa protein with a fluorescent excitation maximum at 512 nm and emission maximum at 529 nm. The fluorescent chromophore produced by EYFP is a result of cyclization and oxidation reactions, which require proper folding of the EYFP. The chaperonin-EYFP fusion proteins (circular permutants 267 and 480) exhibit fluorescence excitation and emission spectra typical of EYFP (FIG. 20A). This result indicates the EYFP assumed its correct structure to facilitate the reactions that produce the chromophore. Furthermore, the 480 fusion protein assemble into chaperonin double rings having the same or similar form as wild-type chaperonins (FIG. 20B), and the 267 fusion protein organizes into a crystalline structure (FIGS. 20C and D). These results indicate that fused EYFP is free in both fusion proteins to assume its most favorable conformation, and does not interfere with formation of double rings. Rings composed of the 267 fusion permutants readily form two-dimensional crystals of the same form as the 267 permutants lacking the fused EYFP. By contrast, the 480 fusion permutants do not form filaments under the same conditions as the 480 permutants lacking the fused EYFP. For example, filament formation by the 480 and 499 permutants (lacking EYFP) is improved upon heating to 70 degrees C. However, heating does not improve filament formation of the 480 fusion permutant because the heat unfolds the EYFP.

The chaperonin circular permutants described above are competent to form the double-ring structures typical of wild-type chaperonin proteins. We also fused a fluorescent protein (EYFP) to two representative permutants (267 and 480), and demonstrate that the fluorescent protein folds into its active structure and does not interfere with assembly of chaperonin double-rings.

The yellow fluorescent protein is a convenient reporter molecule. Other peptide sequences can also be used to provide desirable properties to the chaperonin circular permutants. For example, peptide sequences having catalytic, chemical reactivity, or binding specificity for inorganic materials are known. The peptide sequences can be a linear, constrained loop, or a fully structured protein. Some of these sequences have been discovered through studies of natural biomineralization (D E Morse, et al., 1993 Mat Res Soc Symp Proc 292:59-67; M L Paine and M L Snead 1997 J Bone Miner Res 12:221-227; N Kroger, et al., 1999 Science 286: 1129-1132; J M Slocik, et al., 2002 Nanoletters 2:169-173), while others have been isolated from large combinatorial libraries using phage display or bacterial cell-surface display (M Sarikaya, et al., 2003 Nat Mater 2:577-585). These sequences serve as an interface between the highly versatile structural properties of proteins, and the optical an electronic properties of inorganic nanoparticles.

What is claimed:

1. A circularly permuted chaperonin peptide molecule, comprising a new carboxyl-terminal amino acid and a new amino-terminal amino acid and a reordered chaperonin polypeptide sequence, wherein the circularly permuted chaperonin polypeptide molecule comprises a chaperonin polypeptide molecule which comprises a native carboxyl-terminal amino acid and a native amino-terminal amino acid, wherein the native terminal amino acids are joined directly together or joined via an intervening linker polypeptide sequence, and wherein the chaperonin polypeptide molecule, so joined, is cleaved at a location that differs from the location of the joined native terminal amino acids so as to generate a new carboxyl terminal amino acid and a new amino terminal amino acid and a reordered chaperonin polypeptide sequence, and wherein the chaperonin polypeptide molecule comprises a *Sulfolobus shibatae* thermophilic factor 55 (TF55) beta polypeptide according to any one of SEQ ID NOS:69, 67, 71, 73, or 75.

2. The circularly permuted chaperonin polypeptide molecule of claim 1 comprising an intervening linker polypeptide sequence which joins the native carboxyl terminal amino acid with the native amino terminal amino acid.

3. The circularly permuted chaperonin polypeptide molecule of claim 2, wherein the intervening linker polypeptide sequence comprises the amino acid sequence Gly-Gly-Ser-Gly-Gly-Thr according to SEQ ID NO:64.

4. The circularly permuted chaperonin polypeptide molecule of claim 1, which is a fusion protein, wherein said new carboxyl terminal amino acid or said new amino terminal amino acid is joined with a second polypeptide.

5. The circularly permuted chaperonin polypeptide molecule of claim 4, wherein said second polypeptide is a gold-binding peptide comprising the amino acid sequence SEQ ID NO:31.

6. The circularly permuted chaperonin polypeptide molecule of claim 4, wherein said second polypeptide is a yellow fluorescent protein (EYFP) according to SEQ ID NO: 91.

7. The circularly permuted chaperonin polypeptide molecule of claim 1, comprising a *Sulfolobus shibatae* TF55 beta polypeptide according to SEQ ID NO: 67.

8. The circularly permuted chaperonin polypeptide molecule of claim 1, comprising a *Sulfolobus shibatae TF*55 beta polypeptide according to SEQ ID NO: 71.

9. The circularly permuted chaperonin polypeptide molecule of claim 1, comprising a *Sulfolobus shibatae* TF55 beta polypeptide according to SEQ ID NO: 73.

10. The circularly permuted chaperonin polypeptide molecule of claim 1, comprising a Sulfolobus shibatae TF55 beta polypeptide according to SEQ ID NO:75.

* * * * *

SEQUENCE LISTING

```
<160> NUMBER OF SEQ ID NOS: 91

<210> SEQ ID NO 1
<211> LENGTH: 552
<212> TYPE: PRT
<213> ORGANISM: Sulfolobus shibatae
<220> FEATURE:
<221> NAME/KEY: MISC_FEATURE
<223> OTHER INFORMATION: TF55 beta subunit
```

-continued

<400> SEQUENCE: 1

```
Met Ala Thr Ala Thr Val Ala Thr Thr Pro Glu Gly Ile Pro Val Ile
1               5                   10                  15

Ile Leu Lys Glu Gly Ser Ser Arg Thr Tyr Gly Lys Glu Ala Leu Arg
            20                  25                  30

Ala Asn Ile Ala Ala Val Lys Ala Ile Glu Glu Ala Leu Lys Ser Thr
        35                  40                  45

Tyr Gly Pro Arg Gly Met Asp Lys Met Phe Val Asp Ser Leu Gly Asp
    50                  55                  60

Ile Thr Ile Thr Asn Asp Gly Ala Thr Ile Leu Asp Lys Met Asp Leu
65                  70                  75                  80

Gln His Pro Thr Gly Lys Leu Leu Val Gln Ile Ala Lys Gly Gln Asp
                85                  90                  95

Glu Glu Thr Ala Asp Gly Thr Lys Thr Ala Val Ile Leu Ala Gly Glu
            100                 105                 110

Leu Ala Lys Lys Ala Glu Asp Leu Leu Tyr Lys Glu Ile His Pro Thr
        115                 120                 125

Ile Ile Val Ser Gly Tyr Lys Lys Ala Glu Glu Ile Ala Leu Lys Thr
    130                 135                 140

Ile Gln Asp Ile Ala Gln Pro Val Ser Ile Asn Asp Thr Asp Val Leu
145                 150                 155                 160

Arg Lys Val Ala Leu Thr Ser Leu Gly Ser Lys Ala Val Ala Gly Ala
                165                 170                 175

Arg Glu Tyr Leu Ala Asp Leu Val Val Lys Ala Val Ala Gln Val Ala
            180                 185                 190

Glu Leu Arg Gly Asp Lys Trp Tyr Val Asp Leu Asp Asn Val Gln Ile
        195                 200                 205

Val Lys Lys His Gly Gly Ser Ile Asn Asp Thr Gln Leu Val Tyr Gly
    210                 215                 220

Ile Val Val Asp Lys Glu Val Val His Pro Gly Met Pro Lys Arg Ile
225                 230                 235                 240

Glu Asn Ala Lys Ile Ala Leu Leu Asp Ala Ser Leu Glu Val Glu Lys
                245                 250                 255

Pro Glu Leu Asp Ala Glu Ile Arg Ile Asn Asp Pro Thr Gln Met His
            260                 265                 270

Lys Phe Leu Glu Glu Glu Glu Asn Ile Leu Lys Glu Lys Val Asp Lys
        275                 280                 285

Ile Ala Ala Thr Gly Ala Asn Val Val Ile Cys Gln Lys Gly Ile Asp
    290                 295                 300

Glu Val Ala Gln His Tyr Leu Ala Lys Lys Gly Ile Leu Ala Val Arg
305                 310                 315                 320

Arg Ala Lys Lys Ser Asp Leu Glu Lys Leu Ala Arg Ala Thr Gly Gly
                325                 330                 335

Arg Val Ile Ser Asn Ile Asp Glu Leu Thr Ser Gln Asp Leu Gly Tyr
            340                 345                 350

Ala Ala Leu Val Glu Glu Arg Lys Val Gly Glu Asp Lys Met Val Phe
        355                 360                 365

Val Glu Gly Ala Lys Asn Pro Lys Ser Val Ser Ile Leu Ile Arg Gly
    370                 375                 380

Gly Leu Glu Arg Val Val Asp Glu Thr Glu Arg Ala Leu Arg Asp Ala
385                 390                 395                 400

Leu Gly Thr Val Ala Asp Val Ile Arg Asp Gly Arg Ala Val Ala Gly
```

-continued

```
            405                 410                 415

Gly Gly Ala Val Glu Ile Glu Ile Ala Lys Arg Leu Arg Lys Tyr Ala
            420                 425                 430

Pro Gln Val Gly Gly Lys Glu Gln Leu Ala Ile Glu Ala Tyr Ala Asn
        435                 440                 445

Ala Ile Glu Gly Leu Ile Met Ile Leu Ala Glu Asn Ala Gly Leu Asp
    450                 455                 460

Pro Ile Asp Lys Leu Met Gln Leu Arg Ser Leu His Glu Asn Glu Thr
465                 470                 475                 480

Asn Lys Trp Tyr Gly Leu Asn Leu Phe Thr Gly Asn Pro Glu Asp Met
                485                 490                 495

Trp Lys Leu Gly Val Ile Glu Pro Ala Leu Val Lys Met Asn Ala Ile
            500                 505                 510

Lys Ala Ala Thr Glu Ala Val Thr Leu Val Leu Arg Ile Asp Asp Ile
        515                 520                 525

Val Ala Ala Gly Lys Lys Gly Gly Ser Glu Pro Gly Gly Lys Lys Glu
    530                 535                 540

Lys Glu Glu Lys Ser Ser Glu Asp
545                 550


<210> SEQ ID NO 2
<211> LENGTH: 548
<212> TYPE: PRT
<213> ORGANISM: Escherichia coli
<220> FEATURE:
<221> NAME/KEY: MISC_FEATURE
<223> OTHER INFORMATION: GroEL

<400> SEQUENCE: 2

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205
```

-continued

```
Glu Thr Gly Ala Val Glu Leu Glu Ser Pro Phe Ile Leu Leu Ala Asp
    210                 215                 220

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
                245                 250                 255

Glu Ala Leu Ala Thr Ala Val Val Asn Thr Ile Arg Gly Ile Val Lys
            260                 265                 270

Val Ala Ala Val Lys Ala Pro Gly Phe Gly Asp Arg Arg Lys Ala Met
        275                 280                 285

Leu Gln Asp Ile Ala Thr Leu Thr Gly Gly Thr Val Ile Ser Glu Glu
    290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
            340                 345                 350

Ile Glu Glu Ala Thr Ser Asp Tyr Asp Arg Glu Lys Leu Gln Glu Arg
        355                 360                 365

Val Ala Lys Leu Ala Gly Gly Val Ala Val Ile Lys Val Gly Ala Ala
    370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
            420                 425                 430

Asn Glu Asp Gln Asn Val Gly Ile Lys Val Ala Leu Arg Ala Met Glu
        435                 440                 445

Ala Pro Leu Arg Gln Ile Val Leu Asn Cys Gly Glu Glu Pro Ser Val
    450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
            500                 505                 510

Leu Met Ile Thr Thr Glu Cys Met Val Thr Asp Leu Pro Lys Asn Asp
        515                 520                 525

Ala Ala Asp Leu Gly Ala Ala Gly Gly Met Gly Gly Met Gly Gly Met
    530                 535                 540

Gly Gly Met Met
545


<210> SEQ ID NO 3
<211> LENGTH: 543
<212> TYPE: PRT
<213> ORGANISM: Thermoplasma acidophilum
<220> FEATURE:
<221> NAME/KEY: MISC_FEATURE
<223> OTHER INFORMATION: beta subunit

<400> SEQUENCE: 3

Met Ile Ala Gly Gln Pro Ile Phe Ile Leu Lys Glu Gly Thr Lys Arg
1               5                   10                  15
```

-continued

```
Glu Ser Gly Lys Asp Ala Met Lys Glu Asn Ile Glu Ala Ala Ile Ala
            20                  25                  30

Ile Ser Asn Ser Val Arg Ser Ser Leu Gly Pro Arg Gly Met Asp Lys
        35                  40                  45

Met Leu Val Asp Ser Leu Gly Asp Ile Val Ile Thr Asn Asp Gly Val
    50                  55                  60

Thr Ile Leu Lys Glu Met Asp Val Glu His Pro Ala Ala Lys Met Met
65                  70                  75                  80

Val Glu Val Ser Lys Thr Gln Asp Ser Phe Val Gly Asp Gly Thr Thr
                85                  90                  95

Thr Ala Val Ile Ile Ala Gly Gly Leu Leu Gln Gln Ala Gln Gly Leu
            100                 105                 110

Ile Asn Gln Asn Val His Pro Thr Val Ile Ser Glu Gly Tyr Arg Met
        115                 120                 125

Ala Ser Glu Glu Ala Lys Arg Val Ile Asp Glu Ile Ser Thr Lys Ile
    130                 135                 140

Gly Ala Asp Glu Lys Ala Leu Leu Leu Lys Met Ala Gln Thr Ser Leu
145                 150                 155                 160

Asn Ser Lys Ser Ala Ser Val Ala Lys Asp Lys Leu Ala Glu Ile Ser
                165                 170                 175

Tyr Glu Ala Val Lys Ser Val Ala Glu Leu Arg Asp Gly Lys Tyr Tyr
            180                 185                 190

Val Asp Phe Asp Asn Ile Gln Val Val Lys Lys Gln Gly Gly Ala Ile
        195                 200                 205

Asp Asp Thr Gln Leu Ile Asn Gly Ile Ile Val Asp Lys Glu Lys Val
    210                 215                 220

His Pro Gly Met Pro Asp Val Val Lys Asp Ala Lys Ile Ala Leu Leu
225                 230                 235                 240

Asp Ala Pro Leu Glu Ile Lys Lys Pro Glu Phe Asp Thr Asn Leu Arg
                245                 250                 255

Ile Glu Asp Pro Ser Met Ile Gln Lys Phe Leu Ala Gln Glu Glu Asn
            260                 265                 270

Met Leu Arg Glu Met Val Asp Lys Ile Lys Ser Val Gly Ala Asn Val
        275                 280                 285

Val Ile Thr Gln Lys Gly Ile Asp Asp Met Ala Gln His Tyr Leu Ser
    290                 295                 300

Arg Ala Gly Ile Tyr Ala Val Arg Arg Val Lys Lys Ser Asp Met Asp
305                 310                 315                 320

Lys Leu Ala Lys Ala Thr Gly Ala Ser Ile Val Ser Thr Ile Asp Glu
                325                 330                 335

Ile Ser Ser Ser Asp Leu Gly Thr Ala Glu Arg Val Glu Gln Val Lys
            340                 345                 350

Val Gly Glu Asp Tyr Met Thr Phe Val Thr Gly Cys Lys Asn Pro Lys
        355                 360                 365

Ala Val Ser Ile Leu Val Arg Gly Glu Thr Glu His Val Val Asp Glu
    370                 375                 380

Met Glu Arg Ser Ile Thr Asp Ser Leu His Val Val Ala Ser Ala Leu
385                 390                 395                 400

Glu Asp Gly Ala Tyr Ala Ala Gly Gly Gly Ala Thr Ala Ala Glu Ile
                405                 410                 415

Ala Phe Arg Leu Arg Ser Tyr Ala Gln Lys Ile Gly Gly Arg Gln Gln
            420                 425                 430
```

-continued

```
Leu Ala Ile Glu Lys Phe Ala Asp Ala Ile Glu Glu Ile Pro Arg Ala
        435                 440                 445

Leu Ala Glu Asn Ala Gly Leu Asp Pro Ile Asp Ile Leu Leu Lys Leu
    450                 455                 460

Arg Ala Glu His Ala Lys Gly Asn Lys Thr Tyr Gly Ile Asn Val Phe
465                 470                 475                 480

Thr Gly Glu Ile Glu Asp Met Val Lys Asn Gly Val Ile Glu Pro Ile
                485                 490                 495

Arg Val Gly Lys Gln Ala Ile Glu Ser Ala Thr Glu Ala Ala Ile Met
            500                 505                 510

Ile Leu Arg Ile Asp Asp Val Ile Ala Thr Lys Ser Ser Ser Ser Ser
        515                 520                 525

Ser Asn Pro Pro Lys Ser Gly Ser Ser Ser Glu Ser Ser Glu Asp
    530                 535                 540


<210> SEQ ID NO 4
<211> LENGTH: 544
<212> TYPE: PRT
<213> ORGANISM: Cyanobacterial synechococcus
<220> FEATURE:
<221> NAME/KEY: MISC_FEATURE
<223> OTHER INFORMATION: Cyanobacterial HSP60

<400> SEQUENCE: 4

Met Ala Lys Arg Ile Ile Tyr Asn Glu Asn Ala Arg Arg Ala Leu Glu
1               5                   10                  15

Lys Gly Ile Asp Ile Leu Ala Glu Ala Val Ala Val Thr Leu Gly Pro
            20                  25                  30

Lys Gly Arg Asn Val Val Leu Glu Lys Lys Phe Gly Ala Pro Gln Ile
        35                  40                  45

Ile Asn Asp Gly Val Thr Ile Ala Lys Glu Ile Glu Leu Glu Asp His
    50                  55                  60

Ile Glu Asn Thr Gly Val Ala Leu Ile Arg Gln Ala Ala Ser Lys Thr
65                  70                  75                  80

Asn Asp Ala Ala Gly Asp Gly Thr Thr Thr Ala Thr Val Leu Ala His
                85                  90                  95

Ala Val Val Lys Glu Gly Leu Arg Asn Val Ala Ala Gly Ala Asn Ala
            100                 105                 110

Ile Leu Leu Lys Arg Gly Ile Asp Lys Ala Thr Asn Phe Leu Val Glu
        115                 120                 125

Gln Ile Lys Ser His Ala Arg Pro Val Glu Asp Ser Lys Ser Ile Ala
    130                 135                 140

Gln Val Gly Ala Ile Ser Ala Gly Asn Asp Phe Glu Val Gly Gln Met
145                 150                 155                 160

Ile Ala Asp Ala Met Asp Lys Val Gly Lys Glu Gly Val Ile Ser Leu
                165                 170                 175

Glu Glu Gly Lys Ser Met Thr Thr Glu Leu Glu Val Thr Glu Gly Met
            180                 185                 190

Arg Phe Asp Lys Gly Tyr Ile Ser Pro Tyr Phe Ala Thr Asp Thr Glu
        195                 200                 205

Arg Met Glu Ala Val Phe Asp Glu Pro Phe Ile Leu Ile Thr Asp Lys
    210                 215                 220

Lys Ile Gly Leu Val Gln Asp Leu Val Pro Val Leu Glu Gln Val Ala
225                 230                 235                 240

Arg Ala Gly Arg Pro Leu Val Ile Ile Ala Glu Asp Ile Glu Lys Glu
                245                 250                 255
```

-continued

```
Ala Leu Ala Thr Leu Val Val Asn Arg Leu Arg Gly Val Leu Asn Val
            260                 265                 270

Ala Ala Val Lys Ala Pro Gly Phe Gly Asp Arg Arg Lys Ala Met Leu
        275                 280                 285

Glu Asp Ile Ala Val Leu Thr Gly Gly Gln Leu Ile Thr Glu Asp Ala
    290                 295                 300

Ala Arg Lys Leu Asp Thr Thr Lys Leu Asp Gln Leu Gly Lys Ala Arg
305                 310                 315                 320

Arg Ile Thr Ile Thr Lys Asp Asn Thr Thr Ile Val Ala Glu Gly Asn
                325                 330                 335

Glu Ala Ala Val Lys Ala Arg Val Asp Gln Ile Arg Arg Gln Ile Glu
            340                 345                 350

Glu Thr Glu Ser Ser Tyr Asp Lys Glu Lys Leu Gln Glu Arg Leu Ala
        355                 360                 365

Lys Leu Ser Gly Gly Val Ala Val Val Lys Val Gly Ala Ala Thr Glu
    370                 375                 380

Thr Glu Met Lys Asp Arg Lys Leu Arg Leu Glu Asp Ala Ile Asn Ala
385                 390                 395                 400

Thr Lys Ala Ala Val Glu Glu Gly Ile Val Pro Gly Gly Gly Thr Thr
                405                 410                 415

Leu Ala His Leu Ala Pro Gln Leu Glu Glu Trp Ala Thr Ala Asn Leu
            420                 425                 430

Ser Gly Glu Glu Leu Thr Gly Ala Gln Ile Val Ala Arg Ala Leu Thr
        435                 440                 445

Ala Arg Leu Lys Arg Ile Ala Glu Asn Ala Gly Leu Asn Gly Ala Val
    450                 455                 460

Ile Ser Glu Arg Val Lys Glu Leu Pro Phe Asp Glu Gly Tyr Asp Ala
465                 470                 475                 480

Ser Asn Asn Gln Phe Val Asn Met Phe Thr Ala Gly Ile Val Asp Pro
                485                 490                 495

Ala Lys Val Thr Arg Ser Ala Leu Gln Asn Ala Ala Ser Ile Ala Ala
            500                 505                 510

Met Val Leu Thr Thr Glu Cys Ile Val Val Asp Lys Pro Glu Pro Lys
        515                 520                 525

Glu Lys Ala Pro Ala Gly Ala Gly Gly Gly Met Gly Asp Phe Asp Tyr
    530                 535                 540
```

```
<210> SEQ ID NO 5
<211> LENGTH: 535
<212> TYPE: PRT
<213> ORGANISM: Methanosarcina acetivorans
<220> FEATURE:
<221> NAME/KEY: MISC_FEATURE
<223> OTHER INFORMATION: acetivoran HSP60-4

<400> SEQUENCE: 5

Met Ala Ser Glu Leu Lys Thr Pro Gly Asn Thr Ser Pro Glu Ser Gln
1               5                   10                  15

Asp Gly Met Ala Lys Leu Ala Arg Thr Ile Arg Asp Lys Ile Leu Ile
            20                  25                  30

Asp Glu Pro Val Lys Glu Glu Glu Leu Ile Asp Gln Leu Glu Arg Ala
        35                  40                  45

Ala Ile Glu Ile Asp Glu Leu Leu Gly Ser Ser Leu Gly Pro Lys Gly
    50                  55                  60

Met Asn Lys Ile Ile Val Asn Pro Val Gly Asp Ile Phe Val Thr Ser
```

-continued

```
65                  70                  75                  80

Asp Gly Lys Val Ile Leu Lys Glu Ile Asp Val Leu His Pro Ile Val
                85                  90                  95

Thr Ser Leu Lys Lys Leu Ala Glu Ser Met Asp Lys Ala Cys Gly Asp
            100                 105                 110

Gly Thr Lys Thr Ala Val Ile Phe Ala Ser Asn Leu Ile Lys Asn Ala
        115                 120                 125

Val Arg Leu Ile Arg Ala Gly Val His Pro Thr Ile Ile Ile Glu Gly
    130                 135                 140

Tyr Glu Leu Ala Met Gln Lys Thr Tyr Glu Met Leu Gln Tyr Ser Ile
145                 150                 155                 160

Arg Gln Ala Ser Glu Glu Asp Ile Arg Thr Thr Ile Met Cys Ser Ala
                165                 170                 175

Thr Gly Lys Gly Ile Glu Arg Gln Gln Ala Gln Ala Val Thr Glu Ile
            180                 185                 190

Ala Leu Lys Val Ile Ser His Leu Ser Glu Lys Gln Ala Gly Arg Ile
        195                 200                 205

Asp Leu Asn Arg Asn Val Lys Ile Leu Lys Lys Lys Gly Gly Pro Glu
    210                 215                 220

Ile Val Ala Ile Glu Gly Leu Ile Met Asp Glu Asn Pro Ala Arg Glu
225                 230                 235                 240

Asp Met Pro Lys Ser Tyr Gln Asn Pro Ala Val Leu Ile Thr Asn Tyr
                245                 250                 255

Asp Leu Lys Ile Lys Ser Gly Tyr Leu Asn Pro Gln His Asn Phe Lys
            260                 265                 270

Met Asp Ser Val Gln Thr Ala Leu Leu Phe Glu Glu Arg Lys Lys Gln
        275                 280                 285

Leu Cys Gly Glu Ile Ala Arg Lys Ile Ile Asp Ser Gly Ala Asn Val
    290                 295                 300

Leu Phe Ser Glu Gly Asp Ile Asp Pro Tyr Ile Glu Thr Leu Leu Arg
305                 310                 315                 320

Asp Ser Asn Ile Leu Ala Phe Lys Lys Leu Lys Met Lys Asp Leu Glu
                325                 330                 335

Lys Leu Ala Glu Ala Thr Gly Thr Thr Leu Met Ala Gln Pro Asp Glu
            340                 345                 350

Ile Arg Pro Cys Asp Leu Gly Arg Ala Gly Ser Ile Lys Leu Glu Lys
        355                 360                 365

Lys Asn Gly Glu Asn Phe Val Phe Ile Thr Val Lys Asp Lys Ala Ile
    370                 375                 380

Ala Thr Ile Leu Ile Arg Glu Pro Val Lys Tyr Gly Leu Asp Lys Val
385                 390                 395                 400

Glu Glu Ala Val Asp Asp Ala Leu Asn Asn Ala Ala Phe Leu Arg Lys
                405                 410                 415

Asn Arg Glu Ile Val Asn Gly Gly Gly Ala Ile Glu Phe Glu Leu Ala
            420                 425                 430

His Met Val Arg Leu Phe Ala Ala Thr Gln Thr Gly Lys Arg Gln Leu
        435                 440                 445

Ala Val Gln Ala Tyr Ala Glu Ala Leu Glu Lys Ile Pro Val Ile Leu
    450                 455                 460

Ala Arg Asn Ile Gly Met Asn Glu Ile Asp Ala Met Ala Gln Met Arg
465                 470                 475                 480

Asn Ser Tyr Ala Arg Gly Leu Glu Ala Arg Ile Asp Leu Ser Arg Lys
                485                 490                 495
```

-continued

```
Val Thr Asp Arg Gly Pro Glu Val Tyr Asp Ser Ala Thr Val Lys Lys
            500                 505                 510

Leu Ala Ile Ile Ala Gly Thr Glu Thr Ala Lys Lys Val Leu Arg Ile
        515                 520                 525

Asp Glu Ile Val Pro Lys Lys
    530                 535


<210> SEQ ID NO 6
<211> LENGTH: 540
<212> TYPE: PRT
<213> ORGANISM: Methanosarcina tuberculosis
<220> FEATURE:
<221> NAME/KEY: MISC_FEATURE
<223> OTHER INFORMATION: tuberculosis HSP65

<400> SEQUENCE: 6

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro
            100                 105                 110

Leu Gly Leu Lys Arg Gly Ile Glu Lys Ala Val Glu Lys Val Thr Glu
        115                 120                 125

Thr Leu Leu Lys Gly Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Pro Glu Arg
        195                 200                 205

Gln Glu Ala Val Leu Glu Asp Pro Tyr Ile Leu Leu Val Ser Ser Lys
    210                 215                 220

Val Ser Thr Val Lys Asp Leu Leu Pro Leu Leu Glu Lys Val Ile Gly
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
```

-continued 305 310 315 320

Val Val Val Thr Lys Asp Glu Thr Thr Ile Val Glu Gly Ala Gly Asp
325 330 335

Thr Asp Ala Ile Ala Gly Arg Val Ala Gln Ile Arg Gln Glu Ile Glu
340 345 350

Asn Ser Asp Ser Asp Tyr Asp Arg Glu Lys Leu Gln Glu Arg Leu Ala
355 360 365

Lys Leu Ala Gly Gly Val Ala Val Ile Lys Ala Gly Ala Ala Thr Glu
370 375 380

Val Glu Leu Lys Glu Arg Lys His Arg Ile Glu Asp Ala Val Arg Asn
385 390 395 400

Ala Lys Ala Ala Val Glu Glu Gly Ile Val Ala Gly Gly Gly Val Thr
405 410 415

Leu Leu Gln Ala Ala Pro Thr Leu Asp Glu Leu Lys Leu Glu Gly Asp
420 425 430

Glu Ala Thr Gly Ala Asn Ile Val Lys Val Ala Leu Glu Ala Pro Leu
435 440 445

Lys Gln Ile Ala Phe Asn Ser Gly Leu Glu Pro Gly Val Val Ala Glu
450 455 460

Lys Val Arg Asn Leu Pro Ala Gly His Gly Leu Asn Ala Gln Thr Gly
465 470 475 480

Val Tyr Glu Asp Leu Leu Ala Ala Gly Val Ala Asp Pro Val Lys Val
485 490 495

Thr Arg Ser Ala Leu Gln Asn Ala Ala Ser Ile Ala Gly Leu Phe Leu
500 505 510

Thr Thr Glu Ala Val Val Ala Asp Lys Pro Glu Lys Glu Lys Ala Ser
515 520 525

Val Pro Gly Gly Gly Asp Met Gly Gly Met Asp Phe
530 535 540

<210> SEQ ID NO 7
<211> LENGTH: 554
<212> TYPE: PRT
<213> ORGANISM: Aeropyrum pernix
<220> FEATURE:
<221> NAME/KEY: MISC_FEATURE
<223> OTHER INFORMATION: Alpha subunit

<400> SEQUENCE: 7

Met Ala Ala Thr Gly Tyr Pro Val Leu Ile Leu Lys Glu Gly Thr Gln
1 5 10 15

Arg Thr Tyr Gly Arg Glu Ala Leu Arg Ala Asn Ile Leu Ala Ala Arg
20 25 30

Val Leu Ala Glu Met Leu Lys Ser Ser Leu Gly Pro Arg Gly Leu Asp
35 40 45

Lys Met Leu Val Asp Ala Phe Gly Asp Ile Thr Val Thr Asn Asp Gly
50 55 60

Ala Thr Ile Val Lys Glu Met Glu Ile Gln His Pro Ala Ala Lys Leu
65 70 75 80

Leu Val Glu Val Ala Lys Ala Gln Asp Ala Glu Val Gly Asp Gly Thr
85 90 95

Thr Ser Val Val Val Leu Ala Gly Ala Leu Leu Glu Lys Ala Glu Lys
100 105 110

Leu Leu Asp Glu Asn Leu His Pro Thr Ile Ile Ile Glu Gly Tyr Thr
115 120 125

-continued

```
Lys Ala Met Glu Glu Ala Leu Arg Leu Val Asp Glu Ala Ala Val Pro
    130                 135                 140

Val Glu Val Glu Asp Asp Ser Val Leu Arg Arg Ile Ala Glu Thr Thr
145                 150                 155                 160

Leu Ala Ser Lys Phe Val Gly Thr Gly Pro Glu Arg Asp Lys Ile Ile
                165                 170                 175

Ser Met Val Ile Asp Ala Ile Arg Thr Val Ala Glu Lys Arg Pro Asp
            180                 185                 190

Gly Gly Tyr Glu Val Asp Leu Asp Tyr Val Lys Ile Glu Lys Lys Lys
        195                 200                 205

Gly Gly Ser Leu Leu Asp Ser Lys Leu Val Arg Gly Ile Val Leu Asp
    210                 215                 220

Lys Glu Val Val His Pro Ala Met Pro Lys Arg Val Glu Asn Ala Lys
225                 230                 235                 240

Ile Leu Val Leu Asp Ala Pro Leu Glu Val Gln Lys Pro Glu Leu Thr
                245                 250                 255

Thr Lys Ile Arg Val Thr Asp Ile Glu Lys Leu Glu Ser Phe Leu Glu
            260                 265                 270

Glu Glu Thr Arg Met Leu Arg Asp Met Val Glu Lys Ile Ala Ala Thr
        275                 280                 285

Gly Ala Asn Val Val Ile Thr Gln Lys Gly Ile Asp Glu Val Ala Gln
    290                 295                 300

His Phe Leu Ala Lys Lys Gly Ile Leu Ala Val Arg Arg Val Lys Arg
305                 310                 315                 320

Ser Asp Ile Glu Lys Val Ala Lys Ala Thr Gly Ala Lys Ile Val Thr
                325                 330                 335

Ser Leu Arg Asp Leu Lys Pro Glu Tyr Leu Gly Tyr Ala Glu Leu Val
            340                 345                 350

Glu Glu Arg Lys Val Gly Glu Asp Lys Met Val Phe Ile Glu Gly Ala
        355                 360                 365

Lys Asn Pro Lys Ser Val Thr Ile Leu Leu Arg Gly Ala Asn Asp Met
    370                 375                 380

Leu Leu Asp Glu Ala Glu Arg Asn Ile Lys Asp Ala Leu His Gly Leu
385                 390                 395                 400

Arg Asn Ile Leu Arg Glu Pro Lys Ile Val Gly Gly Gly Gly Ala Val
                405                 410                 415

Glu Val Glu Leu Ala Leu Lys Leu Lys Glu Phe Ala Arg Thr Val Gly
            420                 425                 430

Gly Lys Gln Gln Leu Ala Ile Glu Ala Tyr Ala Glu Ala Leu Glu Thr
        435                 440                 445

Ile Pro Thr Val Leu Ala Glu Ser Ala Gly Met Asp Ala Leu Glu Ala
    450                 455                 460

Leu Leu Lys Leu Arg Ser Leu His Ser Gln Gly Tyr Lys Phe Ala Gly
465                 470                 475                 480

Val Asn Val Leu Glu Gly Lys Ile Glu Glu Asp Met Thr Lys Ile Asn
                485                 490                 495

Val Tyr Glu Pro Val Leu Val Lys Lys Gln Val Ile Lys Ser Ala Ser
            500                 505                 510

Glu Ala Ala Ile Ser Ile Leu Lys Ile Asp Asp Val Ile Ala Ala Ala
        515                 520                 525

Pro Pro Lys Lys Lys Glu Lys Lys Gly Lys Thr Gly Glu Glu Glu Glu
    530                 535                 540

Glu Glu Gly Gly Gly Ser Lys Phe Glu Phe
```

-continued 545 550

<210> SEQ ID NO 8
<211> LENGTH: 542
<212> TYPE: PRT
<213> ORGANISM: Aeropyrum mazei
<220> FEATURE:
<221> NAME/KEY: MISC_FEATURE
<223> OTHER INFORMATION: Alpha subunit

<400> SEQUENCE: 8

Met Ala Ala Gln Pro Ile Phe Ile Leu Arg Glu Gly Ser Lys Arg Thr
1 5 10 15

His Gly Ser Asp Ala Gln His Asn Asn Ile Met Ala Ala Lys Ala Val
20 25 30

Ala Glu Ala Val Arg Thr Thr Leu Gly Pro Lys Gly Met Asp Lys Met
35 40 45

Leu Val Asp Ala Met Gly Asp Val Val Ile Thr Asn Asp Gly Ala Thr
50 55 60

Ile Leu Lys Glu Met Asp Ile Glu His Pro Gly Ala Lys Met Ile Val
65 70 75 80

Glu Val Ala Lys Thr Gln Asp Ala Glu Val Gly Asp Gly Thr Thr Thr
85 90 95

Ala Ala Val Leu Ala Gly Glu Leu Leu Thr Lys Ala Glu Asp Leu Leu
100 105 110

Glu Ser Gly Val His Pro Thr Val Ile Ala Ser Gly Tyr Arg Leu Ala
115 120 125

Ala Ile Gln Ala Val Lys Ile Leu Asp Thr Ile Thr Ile Ser Ala Ser
130 135 140

Pro Glu Asp Thr Glu Thr Leu Glu Lys Ile Ala Gly Thr Ala Ile Thr
145 150 155 160

Gly Lys Gly Ala Glu Ser His Lys Ala His Leu Ser Asn Leu Ala Val
165 170 175

Arg Ala Ile Lys Ser Ile Val Glu Lys Asp Glu Asn Gly Lys Ile Thr
180 185 190

Val Asp Ile Glu Asp Val Lys Thr Glu Lys Arg Pro Gly Gly Ser Ile
195 200 205

Lys Asp Ser Glu Ile Val Glu Gly Val Ile Val Asp Lys Glu Arg Val
210 215 220

His Thr Gly Met Pro Glu Val Val Lys Asp Ala Lys Val Leu Leu Leu
225 230 235 240

Ser Val Pro Ile Glu Leu Lys Lys Thr Glu Thr Lys Ala Glu Ile Lys
245 250 255

Ile Thr Thr Pro Asp Gln Met Gln Leu Phe Leu Asp Gln Glu Glu Ala
260 265 270

Met Leu Arg Glu Ile Val Asp Lys Val Ile Asp Thr Gly Ala Asn Val
275 280 285

Val Phe Cys Gln Lys Gly Ile Asp Asp Leu Ala Gln Tyr Tyr Leu Thr
290 295 300

Lys Ala Gly Ile Phe Ala Met Arg Arg Val Lys Lys Ser Asp Met Asp
305 310 315 320

Lys Leu Ser Arg Ala Thr Gly Gly Arg Ile Ile Thr Asn Leu Asp Glu
325 330 335

Ile Asp Glu Ser Asp Leu Gly Tyr Ala Gly Met Val Glu Glu Lys Asp
340 345 350

-continued

```
Val Thr Gly Ser Arg Met Thr Phe Val Thr Gly Cys Lys Asp Ser Lys
        355                 360                 365

Thr Thr Ser Ile Leu Leu Arg Gly Gly Thr Glu His Val Val Asp Gly
    370                 375                 380

Leu Glu Arg Ala Leu Glu Asp Ala Leu Arg Val Val Gly Val Ala Leu
385                 390                 395                 400

Glu Asp Gln Lys Ile Val Val Gly Gly Gly Ser Pro Glu Ile Glu Leu
                405                 410                 415

Ser Leu Arg Leu Lys Glu Tyr Ala Ala Thr Leu Lys Gly Arg Glu Gln
            420                 425                 430

Leu Ala Val Thr Lys Phe Ala Glu Ser Leu Glu Val Ile Pro Gln Thr
        435                 440                 445

Leu Ala Glu Asn Ala Gly Leu Asp Pro Ile Asp Met Leu Val Glu Met
    450                 455                 460

Arg Ser Gln His Glu Lys Gly Asn Lys Arg Ala Gly Leu Asn Val Tyr
465                 470                 475                 480

Lys Gly Lys Ile Glu Asp Met Phe Glu Asn Asn Val Val Glu Pro Leu
                485                 490                 495

Arg Ile Lys Thr Gln Ala Ile Asn Ala Ala Thr Glu Ala Ala Ile Met
            500                 505                 510

Val Leu Arg Ile Asp Asp Val Ile Ala Ser Thr Gly Gly Gly Arg Ala
        515                 520                 525

Ala Pro Gly Gly Met Pro Gly Gly Asp Met Glu Asp Met Met
    530                 535                 540
```

<210> SEQ ID NO 9
<211> LENGTH: 577
<212> TYPE: PRT
<213> ORGANISM: Arabodopsis thaliana
<220> FEATURE:
<221> NAME/KEY: MISC_FEATURE
<223> OTHER INFORMATION: Mitochondrial thaliana HSP60

<400> SEQUENCE: 9

```
Met Tyr Arg Phe Ala Ser Asn Leu Ala Ser Lys Ala Arg Ile Ala Gln
1               5                   10                  15

Asn Ala Arg Gln Val Ser Ser Arg Met Ser Trp Ser Arg Asn Tyr Ala
            20                  25                  30

Ala Lys Glu Ile Lys Phe Gly Val Glu Ala Arg Ala Leu Met Leu Lys
        35                  40                  45

Gly Val Glu Asp Leu Ala Asp Ala Val Lys Val Thr Met Gly Pro Lys
    50                  55                  60

Gly Arg Asn Val Val Ile Glu Gln Ser Trp Gly Ala Pro Lys Val Thr
65                  70                  75                  80

Lys Asp Gly Val Thr Val Ala Lys Ser Ile Glu Phe Lys Asp Lys Ile
                85                  90                  95

Lys Asn Val Gly Ala Ser Leu Val Lys Gln Val Ala Asn Ala Thr Asn
            100                 105                 110

Asp Val Ala Gly Asp Gly Thr Thr Cys Ala Thr Val Leu Thr Arg Ala
        115                 120                 125

Ile Phe Ala Glu Gly Cys Lys Ser Val Ala Ala Gly Met Asn Ala Met
    130                 135                 140

Asp Leu Arg Arg Gly Ile Ser Met Ala Val Asp Ala Val Val Thr Asn
145                 150                 155                 160

Leu Lys Ser Lys Ala Arg Met Ile Ser Thr Ser Glu Glu Ile Ala Gln
                165                 170                 175
```

-continued

```
Val Gly Thr Ile Ser Ala Asn Gly Glu Arg Glu Ile Gly Glu Leu Ile
            180                 185                 190

Ala Lys Ala Met Glu Lys Val Gly Lys Glu Gly Val Ile Thr Ile Gln
        195                 200                 205

Asp Gly Lys Thr Leu Phe Asn Glu Leu Glu Val Val Glu Gly Met Lys
    210                 215                 220

Leu Asp Arg Gly Tyr Thr Ser Pro Tyr Phe Ile Thr Asn Gln Lys Thr
225                 230                 235                 240

Gln Lys Cys Glu Leu Asp Asp Pro Leu Ile Leu Ile His Glu Lys Lys
                245                 250                 255

Ile Ser Ser Ile Asn Ser Ile Val Lys Val Leu Glu Leu Ala Leu Lys
            260                 265                 270

Arg Gln Arg Pro Leu Leu Ile Val Ser Glu Asp Val Glu Ser Asp Ala
        275                 280                 285

Leu Ala Thr Leu Ile Leu Asn Lys Leu Arg Ala Gly Ile Lys Val Cys
    290                 295                 300

Ala Ile Lys Ala Pro Gly Phe Gly Glu Asn Arg Lys Ala Asn Leu Gln
305                 310                 315                 320

Asp Leu Ala Ala Leu Thr Gly Gly Glu Val Ile Thr Asp Glu Leu Gly
                325                 330                 335

Met Asn Leu Glu Lys Val Asp Leu Ser Met Leu Gly Thr Cys Lys Lys
            340                 345                 350

Val Thr Val Ser Lys Asp Asp Thr Val Ile Leu Asp Gly Ala Gly Asp
        355                 360                 365

Lys Lys Gly Ile Glu Glu Arg Cys Glu Gln Ile Arg Ser Ala Ile Glu
    370                 375                 380

Leu Ser Thr Ser Asp Tyr Asp Lys Glu Lys Leu Gln Glu Arg Leu Ala
385                 390                 395                 400

Lys Leu Ser Gly Gly Val Ala Val Leu Lys Ile Gly Gly Ala Ser Glu
                405                 410                 415

Ala Glu Val Gly Glu Lys Lys Asp Arg Val Thr Asp Ala Leu Asn Ala
            420                 425                 430

Thr Lys Ala Ala Val Glu Glu Gly Ile Leu Pro Gly Gly Gly Val Ala
        435                 440                 445

Leu Leu Tyr Ala Ala Arg Glu Leu Glu Lys Leu Pro Thr Ala Asn Phe
    450                 455                 460

Asp Gln Lys Ile Gly Val Gln Ile Ile Gln Asn Ala Leu Lys Thr Pro
465                 470                 475                 480

Val Tyr Thr Ile Ala Ser Asn Ala Gly Val Glu Gly Ala Val Ile Val
                485                 490                 495

Gly Lys Leu Leu Glu Gln Asp Asn Pro Asp Leu Gly Tyr Asp Ala Ala
            500                 505                 510

Lys Gly Glu Tyr Val Asp Met Val Lys Ala Gly Ile Ile Asp Pro Leu
        515                 520                 525

Lys Val Ile Arg Thr Ala Leu Val Asp Ala Ala Ser Val Ser Ser Leu
    530                 535                 540

Leu Thr Thr Thr Glu Ala Val Val Val Asp Leu Pro Lys Asp Glu Ser
545                 550                 555                 560

Glu Ser Gly Ala Ala Gly Ala Gly Met Gly Gly Met Gly Gly Met Asp
                565                 570                 575

Tyr
```

-continued

<210> SEQ ID NO 10
<211> LENGTH: 559
<212> TYPE: PRT
<213> ORGANISM: Saccharomyces sp
<220> FEATURE:
<221> NAME/KEY: MISC_FEATURE
<223> OTHER INFORMATION: TCP1 alpha subunit

<400> SEQUENCE: 10

```
Met Ser Gln Leu Phe Asn Asn Ser Arg Ser Asp Thr Leu Phe Leu Gly
1               5                   10                  15

Gly Glu Lys Ile Ser Gly Asp Asp Ile Arg Asn Gln Asn Val Leu Ala
            20                  25                  30

Thr Met Ala Val Ala Asn Val Val Lys Ser Ser Leu Gly Pro Val Gly
        35                  40                  45

Leu Asp Lys Met Leu Val Asp Asp Ile Gly Asp Phe Thr Val Thr Asn
    50                  55                  60

Asp Gly Ala Thr Ile Leu Ser Leu Leu Asp Val Gln His Pro Ala Gly
65                  70                  75                  80

Lys Ile Leu Val Glu Leu Ala Gln Gln Gln Asp Arg Glu Ile Gly Asp
                85                  90                  95

Gly Thr Thr Ser Val Val Ile Ile Ala Ser Glu Leu Leu Lys Arg Ala
            100                 105                 110

Asn Glu Leu Val Lys Asn Lys Ile His Pro Thr Thr Ile Ile Thr Gly
        115                 120                 125

Phe Arg Val Ala Leu Arg Glu Ala Ile Arg Phe Ile Asn Glu Val Leu
    130                 135                 140

Ser Thr Ser Val Asp Thr Leu Gly Lys Glu Thr Leu Ile Asn Ile Ala
145                 150                 155                 160

Lys Thr Ser Met Ser Ser Lys Ile Ile Gly Ala Asp Ser Asp Phe Phe
                165                 170                 175

Ser Asn Met Val Val Asp Ala Leu Leu Ala Val Lys Thr Gln Asn Ser
            180                 185                 190

Lys Gly Glu Ile Lys Tyr Pro Val Lys Ala Val Asn Val Leu Lys Ala
        195                 200                 205

His Gly Lys Ser Ala Thr Glu Ser Leu Leu Val Pro Gly Tyr Ala Leu
    210                 215                 220

Asn Cys Thr Val Ala Ser Gln Ala Met Pro Lys Arg Ile Ala Gly Gly
225                 230                 235                 240

Asn Val Lys Ile Ala Cys Leu Asp Leu Asn Leu Gln Lys Ala Arg Met
                245                 250                 255

Ala Met Gly Val Gln Ile Asn Ile Asp Asp Pro Glu Gln Leu Glu Gln
            260                 265                 270

Ile Arg Lys Arg Glu Ala Gly Ile Val Leu Glu Arg Val Lys Lys Ile
        275                 280                 285

Ile Asp Ala Gly Ala Gln Val Val Leu Thr Thr Lys Gly Ile Asp Asp
    290                 295                 300

Leu Cys Leu Lys Glu Phe Val Glu Ala Lys Ile Met Gly Val Arg Arg
305                 310                 315                 320

Cys Lys Lys Glu Asp Leu Arg Arg Ile Ala Arg Ala Thr Gly Ala Thr
                325                 330                 335

Leu Val Ser Ser Met Ser Asn Leu Glu Gly Glu Glu Thr Phe Glu Ser
            340                 345                 350

Ser Tyr Leu Gly Leu Cys Asp Glu Val Val Gln Ala Lys Phe Ser Asp
        355                 360                 365
```

-continued

```
Asp Glu Cys Ile Leu Ile Lys Gly Thr Ser Lys His Ser Ser Ser Ser
    370                 375                 380

Ile Ile Leu Arg Gly Ala Asn Asp Tyr Ser Leu Asp Glu Met Glu Arg
385                 390                 395                 400

Ser Leu His Asp Ser Leu Ser Val Val Lys Arg Thr Leu Glu Ser Gly
                405                 410                 415

Asn Val Val Pro Gly Gly Gly Cys Val Glu Ala Ala Leu Asn Ile Tyr
            420                 425                 430

Leu Asp Asn Phe Ala Thr Thr Val Gly Ser Arg Glu Gln Leu Ala Ile
        435                 440                 445

Ala Glu Phe Ala Ala Ala Leu Leu Ile Ile Pro Lys Thr Leu Ala Val
    450                 455                 460

Asn Ala Ala Lys Asp Ser Ser Glu Leu Val Ala Lys Leu Arg Ser Tyr
465                 470                 475                 480

His Ala Ala Ser Gln Met Ala Lys Pro Glu Asp Val Lys Arg Arg Ser
                485                 490                 495

Tyr Arg Asn Tyr Gly Leu Asp Leu Ile Arg Gly Lys Ile Val Asp Glu
            500                 505                 510

Ile His Ala Gly Val Leu Glu Pro Thr Ile Ser Lys Val Lys Ser Leu
        515                 520                 525

Lys Ser Ala Leu Glu Ala Cys Val Ala Ile Leu Arg Ile Asp Thr Met
    530                 535                 540

Ile Thr Val Asp Pro Glu Pro Pro Lys Glu Asp Pro His Asp His
545                 550                 555


<210> SEQ ID NO 11
<211> LENGTH: 485
<212> TYPE: PRT
<213> ORGANISM: Homo sapien
<220> FEATURE:
<221> NAME/KEY: MISC_FEATURE
<223> OTHER INFORMATION: Human mitochondrial HSP60

<400> SEQUENCE: 11

Met Pro Ser Lys Lys Met Pro Gly Lys Ser Asn His Gly Lys Asn Asn
1               5                   10                  15

Thr Phe Lys Leu Arg Ala Lys Phe Ser Phe Pro Ile Leu Ala Ala Asp
            20                  25                  30

Val Pro Ser Ala Phe Leu Tyr Gly Thr Ser His Ser Gly Gln Leu Ser
        35                  40                  45

Leu Pro Gly Ala Lys Arg Ser Tyr Gly Gln Leu Pro Pro Ser Leu Ala
    50                  55                  60

Leu Gln Asp Lys Tyr Lys Asn Thr Gly Ala Lys Leu Val Gln Asp Val
65                  70                  75                  80

Ala Asn Asn Thr Asn Glu Glu Ala Val Asp Gly Thr Thr Thr Val Thr
                85                  90                  95

Ala Leu Ala Arg Ser Ile Ala Lys Glu Gly Phe Glu Lys Ile Ser Lys
            100                 105                 110

Gly Ala Asn Pro Val Glu Ile Arg Arg Gly Val Met Leu Ala Val Asp
        115                 120                 125

Ala Ile Ile Ala Glu Pro Lys Lys Gln Ser Lys Pro Val Thr Thr Pro
    130                 135                 140

Glu Glu Ile Ala Arg Val Ala Thr Ile Ser Ala Asn Gly Asp Lys Glu
145                 150                 155                 160

Ile Gly Asn Ile Ile Ser Asp Ala Met Lys Lys Val Gly Ser Lys Gly
                165                 170                 175
```

-continued

```
Ile Ile Thr Val Asn Asn Gly Lys Ser Gln Lys Cys Glu Phe Gln Asp
            180                 185                 190

Ala Tyr Val Leu Leu Ser Glu Lys Lys Ile Ser Ser Val Gln Ser Ile
        195                 200                 205

Ala Pro Ala Leu Glu Ile Ala Asn Ala Tyr Ser Leu Val Ile Ile Ala
    210                 215                 220

Glu Asp Val Asn Gly Glu Ala Leu Ser Thr Leu Val Leu Asn Arg Leu
225                 230                 235                 240

Lys Val Gly Leu Gln Val Val Ala Val Lys Asp Pro Gly Phe Gly Asp
                245                 250                 255

Asn Arg Asn Asn Gln Leu Lys Asp Met Ala Ile Ala Thr Gly Gly Ala
            260                 265                 270

Val Phe Ala Glu Glu Gly Leu Thr Leu Asn Leu Glu Asp Val Gln Pro
        275                 280                 285

His Asp Leu Gly Lys Val Gly Glu Val Ile Val Thr Lys Asp Asp Ala
    290                 295                 300

Met Leu Leu Lys Gly Lys Asp Gly Val Ala Val Leu Lys Val Gly Gly
305                 310                 315                 320

Thr Ser Asp Ala Glu Val Asn Glu Lys Gln Asp Arg Val Thr Asp Ala
                325                 330                 335

Leu Asn Ala Thr Arg Ala Ala Val Glu Glu Gly Ile Val Leu Arg Gly
            340                 345                 350

Gly Arg Ala Leu Leu Arg Cys Ile Pro Ala Leu Asp Ser Leu Thr Pro
        355                 360                 365

Val Asn Glu Asp His Asn Ile Gly Ile Glu Ile Ile Lys Lys Thr Leu
    370                 375                 380

Lys Phe Pro Ala Met Thr Ile Ala Lys Asn Ala Gly Val Glu Val Ser
385                 390                 395                 400

Leu Ile Val Glu Lys Ile Met Gln Ser Ser Ser Glu Val Gly Tyr Asp
                405                 410                 415

Ala Met Gly Arg Asp Phe Val Asn Met Val Glu Lys Gly Ile Ile Asp
            420                 425                 430

Thr Thr Lys Phe Val Arg Thr Ala Leu Leu Asp Ala Ser Gly Val Ala
        435                 440                 445

Ser Leu Leu Thr Thr Ala Glu Val Leu Val Thr Glu Ile Pro Lys Glu
    450                 455                 460

Glu Lys Asp Pro Gly Met Gly Ala Met Asp Gly Met Gly Gly Gly Met
465                 470                 475                 480

Gly Gly Gly Met Phe
               485


<210> SEQ ID NO 12
<211> LENGTH: 573
<212> TYPE: PRT
<213> ORGANISM: Mus sp
<220> FEATURE:
<221> NAME/KEY: MISC_FEATURE
<223> OTHER INFORMATION: Mouse mitochondrial HSP60

<400> SEQUENCE: 12

Met Leu Arg Leu Pro Thr Val Leu Arg Gln Met Arg Pro Val Ser Arg
1               5                   10                  15

Ala Leu Ala Pro His Leu Thr Arg Ala Tyr Ala Lys Asp Val Lys Phe
            20                  25                  30

Gly Ala Asp Ala Arg Ala Leu Met Leu Gln Ala Val Asp Leu Leu Ala
```

-continued

```
        35                  40                  45

Asp Ala Val Ala Val Thr Met Gly Pro Lys Gly Arg Thr Val Ile Ile
    50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
            100                 105                 110

Thr Thr Thr Ser Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Asp Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Val Gln Ser
                245                 250                 255

Ile Val Pro Thr Leu Glu Ile Ala Asn Ala His Arg Lys Pro Leu Val
            260                 265                 270

Ile Ile Ala Glu Asp Val Asp Gly Glu Ala Leu Ser Thr Met Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Asn Leu Asn Leu Glu Asp
                325                 330                 335

Val Gln Ala His Asp Leu Gly Lys Val Gly Glu Val Ile Val Thr Lys
            340                 345                 350

Asp Asp Ala Met Leu Leu Lys Gly Lys Gly Asp Lys Ala His Ile Glu
        355                 360                 365

Lys Arg Ile Gln Glu Ile Thr Glu Gln Leu Asp Ile Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
        435                 440                 445

Pro Ala Leu Asp Ser Leu Lys Pro Ala Asn Glu Asp Gln Lys Ile Gly
    450                 455                 460
```

```
Ile Glu Ile Ile Lys Arg Ala Leu Lys Ile Pro Ala Met Thr Ile Ala
465                 470                 475                 480

Lys Asn Ala Gly Val Glu Gly Ser Leu Ile Val Glu Lys Ile Leu Gln
                485                 490                 495

Ser Ser Ser Glu Val Gly Tyr Asp Ala Arg Leu Gly Asp Phe Val Asn
            500                 505                 510

Met Val Glu Lys Gly Ile Ile Asp Pro Thr Lys Val Val Arg Thr Ala
        515                 520                 525

Leu Leu Asp Ala Ala Gly Val Ala Ser Leu Leu Thr Thr Ala Glu Ala
    530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Ser Met Leu
                565                 570


<210> SEQ ID NO 13
<211> LENGTH: 556
<212> TYPE: PRT
<213> ORGANISM: Homo sapien
<220> FEATURE:
<221> NAME/KEY: MISC_FEATURE
<223> OTHER INFORMATION: Human TCP1

<400> SEQUENCE: 13

Met Glu Gly Pro Leu Ser Val Phe Gly Asp Arg Ser Thr Gly Glu Thr
1               5                   10                  15

Ile Arg Ser Gln Asn Val Met Ala Ala Ala Ser Ile Ala Asn Ile Val
            20                  25                  30

Lys Ser Ser Leu Gly Pro Val Gly Leu Asp Lys Met Leu Val Asp Asp
        35                  40                  45

Ile Gly Asp Val Thr Ile Thr Asn Asp Gly Ala Thr Ile Leu Lys Leu
    50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Val Ile Ile
                85                  90                  95

Ala Ala Glu Leu Leu Lys Asn Ala Asp Glu Leu Val Lys Gln Lys Ile
            100                 105                 110

His Pro Thr Ser Val Ile Ser Gly Tyr Arg Leu Ala Cys Lys Glu Ala
        115                 120                 125

Val Arg Tyr Ile Asn Glu Asn Leu Ile Val Asn Thr Asp Glu Leu Gly
    130                 135                 140

Arg Asp Cys Leu Ile Asn Ala Ala Lys Thr Ser Met Ser Ser Lys Ile
145                 150                 155                 160

Ile Gly Ile Asn Gly Asp Phe Phe Ala Asn Met Val Val Asp Ala Val
                165                 170                 175

Leu Ala Ile Lys Tyr Thr Asp Ile Arg Gly Gln Pro Arg Tyr Pro Val
            180                 185                 190

Asn Ser Val Asn Ile Leu Lys Ala His Gly Arg Ser Gln Met Glu Ser
        195                 200                 205

Met Leu Ile Ser Gly Tyr Ala Leu Asn Cys Val Val Gly Ser Gln Gly
    210                 215                 220

Met Pro Lys Arg Ile Val Asn Ala Lys Ile Ala Cys Leu Asp Phe Ser
225                 230                 235                 240

Leu Gln Lys Thr Lys Met Lys Leu Gly Val Gln Val Val Ile Thr Asp
```

-continued

```
                245                 250                 255

Pro Glu Lys Leu Asp Gln Ile Arg Gln Arg Glu Ser Asp Ile Thr Lys
            260                 265                 270

Glu Arg Ile Gln Lys Ile Leu Ala Thr Gly Ala Asn Val Ile Leu Thr
        275                 280                 285

Thr Gly Gly Ile Asp Asp Met Cys Leu Lys Tyr Phe Val Glu Ala Gly
    290                 295                 300

Ala Met Ala Val Arg Arg Val Leu Lys Arg Asp Leu Lys Arg Ile Ala
305                 310                 315                 320

Lys Ala Ser Gly Ala Thr Ile Leu Ser Thr Leu Ala Asn Leu Glu Gly
                325                 330                 335

Glu Glu Thr Phe Glu Ala Ala Met Leu Gly Gln Ala Glu Glu Val Val
            340                 345                 350

Gln Glu Arg Ile Cys Asp Asp Glu Leu Ile Leu Ile Lys Asn Thr Lys
        355                 360                 365

Ala Arg Thr Ser Ala Ser Ile Ile Leu Arg Gly Ala Asn Asp Phe Met
    370                 375                 380

Cys Asp Glu Met Glu Arg Ser Leu His Asp Ala Leu Cys Val Val Lys
385                 390                 395                 400

Arg Val Leu Glu Ser Lys Ser Val Val Pro Gly Gly Gly Ala Val Glu
                405                 410                 415

Ala Ala Leu Ser Ile Tyr Leu Glu Asn Tyr Ala Thr Ser Met Gly Ser
            420                 425                 430

Arg Glu Gln Leu Ala Ile Ala Glu Phe Ala Arg Ser Leu Leu Val Ile
        435                 440                 445

Pro Asn Thr Leu Ala Val Asn Ala Ala Gln Asp Ser Thr Asp Leu Val
    450                 455                 460

Ala Lys Leu Arg Ala Phe His Asn Glu Ala Gln Val Asn Pro Glu Arg
465                 470                 475                 480

Lys Asn Leu Lys Trp Ile Gly Leu Asp Leu Ser Asn Gly Lys Pro Arg
                485                 490                 495

Asp Asn Lys Gln Ala Gly Val Phe Glu Pro Thr Ile Val Lys Val Lys
            500                 505                 510

Ser Leu Lys Phe Ala Thr Glu Ala Ala Ile Thr Ile Leu Arg Ile Asp
        515                 520                 525

Asp Leu Ile Lys Leu His Pro Glu Ser Lys Asp Asp Lys His Gly Ser
    530                 535                 540

Tyr Glu Asp Ala Val His Ser Gly Ala Leu Asn Asp
545                 550                 555


<210> SEQ ID NO 14
<211> LENGTH: 556
<212> TYPE: PRT
<213> ORGANISM: Mus sp
<220> FEATURE:
<221> NAME/KEY: MISC_FEATURE
<223> OTHER INFORMATION: Mouse TCP1

<400> SEQUENCE: 14

Met Glu Gly Pro Leu Ser Val Phe Gly Asp Arg Ser Thr Gly Glu Ala
1               5                   10                  15

Val Arg Ser Gln Asn Val Met Ala Ala Ala Ser Ile Ala Asn Ile Val
            20                  25                  30

Lys Ser Ser Phe Gly Pro Val Gly Leu Asp Lys Met Leu Val Asp Asp
        35                  40                  45
```

-continued

```
Ile Gly Asp Val Thr Ile Thr Asn Asp Gly Ala Thr Ile Leu Lys Leu
    50                  55                  60

Leu Glu Val Glu His Pro Ala Ala Lys Val Leu Cys Glu Leu Ala Asp
65                  70                  75                  80

Leu Gln Asp Lys Glu Val Gly Asp Gly Thr Thr Ser Val Val Ile Ile
                85                  90                  95

Ala Ala Glu Leu Leu Lys Asn Ala Asp Glu Leu Val Lys Gln Lys Ile
            100                 105                 110

His Pro Thr Ser Val Ile Ser Gly Tyr Arg Leu Ala Cys Lys Glu Ala
        115                 120                 125

Val Arg Tyr Ile Asn Glu Asn Leu Ile Ile Asn Thr Asp Glu Leu Gly
    130                 135                 140

Arg Asp Cys Leu Ile Asn Ala Ala Lys Thr Ser Met Ser Ser Lys Ile
145                 150                 155                 160

Ile Gly Ile Asn Gly Asp Tyr Phe Ala Asn Met Val Val Asp Ala Val
                165                 170                 175

Leu Ala Val Lys Tyr Thr Asp Ala Arg Gly Gln Pro Arg Tyr Pro Val
            180                 185                 190

Asn Ser Val Asn Ile Leu Lys Ala His Gly Arg Ser Gln Ile Glu Ser
        195                 200                 205

Met Leu Ile Asn Gly Tyr Ala Leu Asn Cys Val Val Gly Ser Gln Gly
    210                 215                 220

Met Pro Lys Arg Ile Val Asn Ala Lys Ile Ala Cys Leu Asp Phe Ser
225                 230                 235                 240

Leu Gln Lys Thr Lys Met Lys Leu Gly Val Gln Val Val Ile Thr Asp
                245                 250                 255

Pro Glu Lys Leu Asp Gln Ile Arg Gln Arg Glu Ser Asp Ile Thr Lys
            260                 265                 270

Glu Arg Ile Gln Lys Ile Leu Ala Thr Gly Ala Asn Val Ile Leu Thr
        275                 280                 285

Thr Gly Gly Ile Asp Asp Met Tyr Leu Lys Tyr Phe Val Glu Ala Gly
    290                 295                 300

Ala Met Ala Val Arg Arg Val Leu Lys Arg Asp Leu Lys His Val Ala
305                 310                 315                 320

Lys Ala Ser Gly Ala Ser Ile Leu Ser Thr Leu Ala Asn Leu Glu Gly
                325                 330                 335

Glu Glu Thr Phe Glu Val Thr Met Leu Gly Gln Ala Glu Glu Val Val
            340                 345                 350

Gln Glu Arg Ile Cys Asp Asp Glu Leu Ile Leu Ile Lys Asn Thr Lys
        355                 360                 365

Ala Arg Thr Ser Ala Ser Ile Ile Leu Arg Gly Ala Asn Asp Phe Met
    370                 375                 380

Cys Asp Glu Met Glu Arg Ser Leu His Asp Ala Leu Cys Val Val Lys
385                 390                 395                 400

Arg Val Leu Glu Leu Lys Ser Val Val Pro Gly Gly Gly Ala Val Glu
                405                 410                 415

Ala Ala Leu Ser Ile Tyr Leu Glu Asn Tyr Ala Thr Ser Met Gly Ser
            420                 425                 430

Arg Glu Gln Leu Ala Ile Ala Glu Phe Ala Arg Ser Leu Leu Val Ile
        435                 440                 445

Pro Asn Thr Leu Ala Val Asn Ala Ala Gln Asp Ser Thr Asp Leu Val
    450                 455                 460

Ala Lys Leu Arg Ala Phe His Asn Glu Ala Gln Val Asn Pro Glu Arg
```

-continued

```
465                 470                 475                 480

Lys Asn Leu Lys Trp Ile Gly Leu Asp Leu Val His Gly Lys Pro Arg
                485                 490                 495

Asp Asn Lys Gln Ala Gly Val Phe Glu Pro Thr Ile Val Lys Val Lys
            500                 505                 510

Ser Leu Lys Phe Ala Thr Glu Ala Ala Ile Thr Ile Leu Arg Ile Asp
        515                 520                 525

Asp Leu Ile Lys Leu His Pro Glu Ser Lys Asp Asp Lys His Gly Ser
    530                 535                 540

Tyr Glu Asn Ala Val His Ser Gly Ala Leu Asp Asp
545                 550                 555


<210> SEQ ID NO 15
<211> LENGTH: 606
<212> TYPE: PRT
<213> ORGANISM: Artificial
<220> FEATURE:
<223> OTHER INFORMATION: alignment consensus sequence

<400> SEQUENCE: 15

Glx Glx Glx Glx Glx Glx Glx Glx Glx Glx Glx Glx Glx Glx Glx Glx
1               5                   10                  15

Glx Glx Glx Glx Glx Glx Glx Glx Glx Glx Pro Ile Glx Ile Glx Glu
            20                  25                  30

Ala Glx Glx Arg Glx Phe Gly Glx Asp Ala Arg Glx Glx Asn Ile Glx
        35                  40                  45

Ala Ala Glx Ala Leu Ala Glu Ala Val Lys Ser Thr Leu Gly Pro Lys
    50                  55                  60

Gly Leu Asp Lys Met Leu Val Asp Ser Trp Gly Asp Ile Thr Ile Thr
65                  70                  75                  80

Asn Asp Gly Glx Thr Ile Leu Lys Glu Ile Glu Leu Glu His Pro Glx
                85                  90                  95

Glx Glx Glx Gly Ala Lys Leu Leu Glx Glu Val Ala Glx Glx Gln Asp
            100                 105                 110

Asp Glu Glx Gly Asp Gly Thr Thr Thr Ala Val Val Leu Ala Glx Ala
        115                 120                 125

Leu Leu Lys Glx Ala Glx Glu Leu Val Glx Glx Gly Ile His Pro Thr
    130                 135                 140

Glx Glx Ile Glx Gly Tyr Glx Leu Ala Val Glu Glx Ala Val Arg Glx
145                 150                 155                 160

Ile Glx Glx Glx Ala Glx Glx Glx Glx Glx Val Glx Glx Glx Glu Glx
                165                 170                 175

Ile Glx Gln Val Ala Glx Thr Ser Ala Glx Ser Lys Glx Glx Glx Gly
            180                 185                 190

Glx Glx Glx Ala Asp Ala Met Glx Glx Val Gly Val Glu Ala Val Ile
        195                 200                 205

Thr Val Glx Glu Glx Lys Glx Gly Glx Glx Glx Glx Glx Glx Val Glu
    210                 215                 220

Glx Val Lys Ile Asp Lys Gly Tyr Gly Glx Ser Glx Glx Asp Ser Glx
225                 230                 235                 240

Leu Ile Glx Gly Glx Glx Glx Glx Glx Val Glx Glu Glx Glx Gly Met
                245                 250                 255

Pro Lys Lys Ile Glx Glx Glx Glx Ala Lys Ile Glx Leu Leu Asp Glx
            260                 265                 270

Glx Leu Glx Glx Glx Lys Pro Glx Leu Glx Ile Glx Ile Glx Ile Glu
```

-continued

```
        275                 280                 285

Glx Glx Ala Leu Ser Glx Leu Val Leu Asn Arg Glu Arg Glx Ile Leu
    290                 295                 300

Lys Glu Val Ala Glx Lys Ile Glx Gly Glx Gly Ala Asn Val Val Glx
305                 310                 315                 320

Glx Lys Gly Ile Asp Asp Leu Glx Glx Glx Glx Glx Leu Ile Glx Glx
                325                 330                 335

Glx Glx Glx Glx Leu Ala Leu Arg Arg Val Lys Lys Glx Asp Leu Glx
            340                 345                 350

Lys Leu Ala Lys Ala Thr Gly Ala Lys Ile Val Thr Thr Ile Glx Glu
        355                 360                 365

Leu Glx Gly Glu Glx Glx Glx Glx Glx Glx Glx Glx Glx Glx Leu Gly
    370                 375                 380

Glx Ala Glx Glu Val Glx Glx Glx Lys Glx Glx Glx Asp Lys Leu Glx
385                 390                 395                 400

Glx Ile Glx Ala Glx Lys Ala Glx Gly Val Ala Ser Ile Leu Leu Arg
                405                 410                 415

Gly Ala Thr Glu Glx Glx Val Asp Glu Glx Glu Arg Ser Leu Glx Asp
            420                 425                 430

Ala Leu Glx Val Lys Ala Ala Leu Glu Glx Glu Gly Glx Val Val Gly
        435                 440                 445

Gly Gly Gly Ala Leu Glu Glx Leu Ala Glx Leu Leu Glx Glx Glx Tyr
    450                 455                 460

Ala Glx Thr Val Glx Gly Arg Glu Gln Leu Ala Ile Glx Glx Phe Ala
465                 470                 475                 480

Glx Ala Leu Glu Glx Ile Pro Glx Thr Leu Ala Glx Asn Ala Gly Leu
                485                 490                 495

Asp Glx Glx Asp Ile Val Glx Lys Leu Arg Ser Glx His Glx Glx Glx
            500                 505                 510

Glx Glx Glx Glx Glx Glx Glx Glx Glx Glx Glx Glx Glx Glx Glx Glx
        515                 520                 525

Gly Leu Asp Leu Glx Glx Glx Glx Glx Gly Glx Asp Met Val Glx Glx
    530                 535                 540

Gly Val Ile Asp Pro Glx Lys Val Lys Arg Glx Ala Leu Glx Glx Ala
545                 550                 555                 560

Thr Glu Ala Ala Glx Leu Ile Leu Arg Ile Asp Asp Val Val Glx Glx
                565                 570                 575

Glx Pro Glx Glx Glx Glx Asp Glx Glx Glx Ala Glx Glx Glx Glx Glx
            580                 585                 590

Glx Glx Glx Met Gly Glx Glx Glx Glx Glx Glx Glx Glx Glx
        595                 600                 605
```

<210> SEQ ID NO 16
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 16

```
Val Thr Ser Pro Asp Ser Thr Thr Gly Ala Met Ala
1               5                   10
```

<210> SEQ ID NO 17
<211> LENGTH: 12
<212> TYPE: PRT

-continued

<213> ORGANISM: Artificial
<220> FEATURE:
<223> OTHER INFORMATION: metal binding peptide - GaAs or InP

<400> SEQUENCE: 17

Ala Ala Ser Pro Thr Gln Ser Met Ser Gln Ala Pro
1 5 10

<210> SEQ ID NO 18
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 18

Ala Gln Asn Pro Ser Asp Asn Asn Thr His Thr His
1 5 10

<210> SEQ ID NO 19
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 19

Ala Ser Ser Ser Arg Ser His Phe Gly Gln Thr Asp
1 5 10

<210> SEQ ID NO 20
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 20

Trp Ala His Ala Pro Gln Leu Ala Ser Ser Ser Thr
1 5 10

<210> SEQ ID NO 21
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 21

Ala Arg Tyr Asp Leu Ser Ile Pro Ser Ser Glu Ser
1 5 10

<210> SEQ ID NO 22
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 22

Thr Pro Pro Arg Pro Ile Gln Tyr Asn His Thr Ser
1 5 10

<210> SEQ ID NO 23
<211> LENGTH: 12
<212> TYPE: PRT
<213> ORGANISM: Artificial

-continued

<220> FEATURE:
<223> OTHER INFORMATION: metal binding peptide - GaAs or InP

<400> SEQUENCE: 23

Ser Ser Leu Gln Leu Pro Glu Asn Ser Phe Pro His
1 5 10

<210> SEQ ID NO 24
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 24

Gly Thr Leu Ala Asn Gln Gln Ile Phe Leu Ser Ser
1 5 10

<210> SEQ ID NO 25
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 25

His Gly Asn Pro Leu Pro Met Thr Pro Phe Pro Gly
1 5 10

<210> SEQ ID NO 26
<211> LENGTH: 12
<212> TYPE: PRT
<213> ORGANISM: Artificial
<220> FEATURE:
<223> OTHER INFORMATION: metal binding peptide - GaAs or InP

<400> SEQUENCE: 26

Arg Leu Glu Leu Ala Ile Pro Leu Gln Gly Ser Gly
1 5 10

<210> SEQ ID NO 27
<211> LENGTH: 9
<212> TYPE: PRT
<213> ORGANISM: Artificial
<220> FEATURE:
<223> OTHER INFORMATION: metal binding peptide - ZnS

<400> SEQUENCE: 27

Cys Asn Asn Pro Met His Gln Asn Cys
1 5

<210> SEQ ID NO 28
<211> LENGTH: 12
<212> TYPE: PRT
<213> ORGANISM: Artificial
<220> FEATURE:
<223> OTHER INFORMATION: metal binding peptide - Ag

<400> SEQUENCE: 28

Ala Tyr Ser Ser Gly Ala Pro Pro Met Pro Pro Phe
1 5 10

<210> SEQ ID NO 29
<211> LENGTH: 12
<212> TYPE: PRT
<213> ORGANISM: Artificial
<220> FEATURE:

-continued

<223> OTHER INFORMATION: metal binding peptide - Ag

<400> SEQUENCE: 29

Asn Pro Ser Ser Leu Phe Arg Tyr Leu Pro Ser Asp
1 5 10

<210> SEQ ID NO 30
<211> LENGTH: 12
<212> TYPE: PRT
<213> ORGANISM: Artificial
<220> FEATURE:
<223> OTHER INFORMATION: metal binding peptide - Ag

<400> SEQUENCE: 30

Ser Leu Ala Thr Gln Pro Pro Arg Thr Pro Pro Val
1 5 10

<210> SEQ ID NO 31
<211> LENGTH: 14
<212> TYPE: PRT
<213> ORGANISM: Artificial
<220> FEATURE:
<223> OTHER INFORMATION: metal binding peptide - Au

<400> SEQUENCE: 31

Met His Gly Lys Thr Gln Ala Thr Ser Gly Thr Ile Gln Ser
1 5 10

<210> SEQ ID NO 32
<211> LENGTH: 14
<212> TYPE: PRT
<213> ORGANISM: Artificial
<220> FEATURE:
<223> OTHER INFORMATION: metal binding peptide - Au

<400> SEQUENCE: 32

Ala Leu Val Pro Thr Ala His Arg Leu Asp Gly Asn Met His
1 5 10

<210> SEQ ID NO 33
<211> LENGTH: 21
<212> TYPE: DNA
<213> ORGANISM: Artificial
<220> FEATURE:
<223> OTHER INFORMATION: PCR primer - gamma gene

<400> SEQUENCE: 33
atgaacttag agccttccta t 21

<210> SEQ ID NO 34
<211> LENGTH: 21
<212> TYPE: DNA
<213> ORGANISM: Artificial
<220> FEATURE:
<223> OTHER INFORMATION: PCR primer - P2 gamma gene

<400> SEQUENCE: 34
ttaactccat aagaaacttg t 21

<210> SEQ ID NO 35
<211> LENGTH: 40
<212> TYPE: DNA
<213> ORGANISM: Artificial
<220> FEATURE:
<223> OTHER INFORMATION: PCR primer - P1 primer

<400> SEQUENCE: 35

-continued gaaagaacat atggcctatt tattaagaga aggaacacag 40

<210> SEQ ID NO 36
<211> LENGTH: 43
<212> TYPE: DNA
<213> ORGANISM: Artificial
<220> FEATURE:
<223> OTHER INFORMATION: PCR primer - P2 primer

<400> SEQUENCE: 36
taaagtactc gagaaaacct aaataaaata atcatatctt aac 43

<210> SEQ ID NO 37
<211> LENGTH: 1607
<212> TYPE: DNA
<213> ORGANISM: Sulfolobus shibatae
<220> FEATURE:
<221> NAME/KEY: misc_feature
<223> OTHER INFORMATION: TF55 gamma subunit

<400> SEQUENCE: 37
atggcctatt tattaagaga aggaacacag agatctactg gaaacgaggt aatactaaac 60
aacatagctg tagccaaaat attactggaa atgctaaagt caagcctagg tcctaagggt 120
ttagacaaga tgttagttga ggggcaagac attacaataa ctaatgacgg tgcgacaata 180
gttaaaaaca tggaagtgca gcatcctact gcaaaattac tcattgaaac cgctaaaact 240
gttgataccg aggtaggaga tgggacaact tcagtagtcg ttcttgccgg gttactatta 300
gaaaaagctg aggatttgct gaatcagaag atccatccaa ctgtcataat agaaggttat 360
aggaaggctc taagttcatc attagaattg ttaaaaagta ttgcagataa gattagtcca 420
gaagatagga agatagttca cgatctagta tatactactc tatcgagtaa gttcttctca 480
acagagcata ctctagagaa gataataaat ctagttattg aagcttcatt ggcggtattg 540
gataaaagag atggaaccta tgatctggat attaagaata taaagattgt aaaagtcaat 600
ggtggggaat ttgatgatag tgagcttgta aatgggatcg ttgtagataa ggagcccacc 660
aatgagaata tgccgaaaag ggcggaaaac gttaaggtaa tgttagctga cttcccatta 720
aaacttgaaa aaacggaaat tagcatgaag ctgggaataa gtgaccccac tcagataaag 780
ggatacttgg atgaacaaac ggcatatgtt aagcaaatgg tggataagat aaaggctatg 840
ggcgttaaat tgtttattac acaaaaggac attgatgaag tcgcttcata tttaatggga 900
aaaagtggga taatagcgtt aaagaacgta aagaggagtg acatagagtt actgagtaga 960
gctactggtg cgaaaattgc aagtagcatg aaagacgcta atgagagtga tttaggggaa 1020
gctaaattag tggaggttag aaatttagga aagaacaaat acctcttcat tcaatctgat 1080
aaagctaaag cggtgactgt aatcataaag ggctcgaata acatggtaac tgatgaagca 1140
gaaaggagtt taaatgacgc ctttaactcc ataagaaact tgttactaga accctatatt 1200
gtggctggtg gtggtgctgt agaggaggag ttggctaaga ggttaaggga gaacgctgga 1260
aaagttcccg gaaaggagca attggcattt aatgcatttg cggatgcttt ggaggagtac 1320
gtttcaatac tatcagaaac tgctggcatg gatcccataa gtgcgttaac cgaaataaga 1380
cataaacatg caaacgggtt aaagaatgct gggattgaca tagttaaggc tagaatttac 1440
gataacatgc ttgagcttaa agtaatcgat tctctaaagg ttaaggaaca agttttaaag 1500
agcgccacag aagccgctac tgcgatttta aagatcgacg acatgatagc agcagctcct 1560
gcaaagcaac aacctcaacc acaacagcca aatccatact taggtta 1607

-continued

<210> SEQ ID NO 38
<211> LENGTH: 535
<212> TYPE: PRT
<213> ORGANISM: Sulfolobus shibatae
<220> FEATURE:
<221> NAME/KEY: MISC_FEATURE
<223> OTHER INFORMATION: TF55 gamma subunit

<400> SEQUENCE: 38

```
Met Ala Tyr Leu Leu Arg Glu Gly Thr Gln Arg Ser Thr Gly Asn Glu
1               5                   10                  15

Val Ile Leu Asn Asn Ile Ala Val Ala Lys Ile Leu Leu Glu Met Leu
            20                  25                  30

Lys Ser Ser Leu Gly Pro Lys Gly Leu Asp Lys Met Leu Val Glu Gly
        35                  40                  45

Gln Asp Ile Thr Ile Thr Asn Asp Gly Ala Thr Ile Val Lys Asn Met
    50                  55                  60

Glu Val Gln His Pro Thr Ala Lys Leu Leu Ile Glu Thr Ala Lys Thr
65                  70                  75                  80

Val Asp Thr Glu Val Gly Asp Gly Thr Thr Ser Val Val Val Leu Ala
                85                  90                  95

Gly Leu Leu Leu Glu Lys Ala Glu Asp Leu Leu Asn Gln Lys Ile His
            100                 105                 110

Pro Thr Val Ile Ile Glu Gly Tyr Arg Lys Ala Leu Ser Ser Ser Leu
        115                 120                 125

Glu Leu Leu Lys Ser Ile Ala Asp Lys Ile Ser Pro Glu Asp Arg Lys
    130                 135                 140

Ile Val His Asp Leu Val Tyr Thr Thr Leu Ser Ser Lys Phe Phe Ser
145                 150                 155                 160

Thr Glu His Thr Leu Glu Lys Ile Ile Asn Leu Val Ile Glu Ala Ser
                165                 170                 175

Leu Ala Val Leu Asp Lys Arg Asp Gly Thr Tyr Asp Leu Asp Ile Lys
            180                 185                 190

Asn Ile Lys Ile Val Lys Val Asn Gly Gly Glu Phe Asp Asp Ser Glu
        195                 200                 205

Leu Val Asn Gly Ile Val Val Asp Lys Glu Pro Thr Asn Glu Asn Met
    210                 215                 220

Pro Lys Arg Ala Glu Asn Val Lys Val Met Leu Ala Asp Phe Pro Leu
225                 230                 235                 240

Lys Leu Glu Lys Thr Glu Ile Ser Met Lys Leu Gly Ile Ser Asp Pro
                245                 250                 255

Thr Gln Ile Lys Gly Tyr Leu Asp Glu Gln Thr Ala Tyr Val Lys Gln
            260                 265                 270

Met Val Asp Lys Ile Lys Ala Met Gly Val Lys Leu Phe Ile Thr Gln
        275                 280                 285

Lys Asp Ile Asp Glu Val Ala Ser Tyr Leu Met Gly Lys Ser Gly Ile
    290                 295                 300

Ile Ala Leu Lys Asn Val Lys Arg Ser Asp Ile Glu Leu Leu Ser Arg
305                 310                 315                 320

Ala Thr Gly Ala Lys Ile Ala Ser Ser Met Lys Asp Ala Asn Glu Ser
                325                 330                 335

Asp Leu Gly Glu Ala Lys Leu Val Glu Val Arg Asn Leu Gly Lys Asn
            340                 345                 350

Lys Tyr Leu Phe Ile Gln Ser Asp Lys Ala Lys Ala Val Thr Val Ile
```

-continued

```
        355                 360                 365

Ile Lys Gly Ser Asn Asn Met Val Thr Asp Glu Ala Glu Arg Ser Leu
    370                 375                 380

Asn Asp Ala Phe Asn Ser Ile Arg Asn Leu Leu Leu Glu Pro Tyr Ile
385                 390                 395                 400

Val Ala Gly Gly Gly Ala Val Glu Glu Glu Leu Ala Lys Arg Leu Arg
                405                 410                 415

Glu Asn Ala Gly Lys Val Pro Gly Lys Glu Gln Leu Ala Phe Asn Ala
            420                 425                 430

Phe Ala Asp Ala Leu Glu Glu Tyr Val Ser Ile Leu Ser Glu Thr Ala
        435                 440                 445

Gly Met Asp Pro Ile Ser Ala Leu Thr Glu Ile Arg His Lys His Ala
    450                 455                 460

Asn Gly Leu Lys Asn Ala Gly Ile Asp Ile Val Lys Ala Arg Ile Tyr
465                 470                 475                 480

Asp Asn Met Leu Glu Leu Lys Val Ile Asp Ser Leu Lys Val Lys Glu
                485                 490                 495

Gln Val Leu Lys Ser Ala Thr Glu Ala Ala Thr Ala Ile Leu Lys Ile
            500                 505                 510

Asp Asp Met Ile Ala Ala Ala Pro Ala Lys Gln Gln Pro Gln Pro Gln
        515                 520                 525

Gln Pro Asn Pro Tyr Leu Gly
    530                 535


<210> SEQ ID NO 39
<211> LENGTH: 560
<212> TYPE: PRT
<213> ORGANISM: Sulfolobus shibatae
<220> FEATURE:
<221> NAME/KEY: MISC_FEATURE
<223> OTHER INFORMATION: TF55 alpha subunit

<400> SEQUENCE: 39

Met Ala Ser Pro Val Leu Leu Leu Lys Glu Gly Thr Ser Arg Thr Thr
1               5                   10                  15

Gly Arg Asp Ala Leu Arg Asn Asn Ile Leu Ala Ala Lys Thr Leu Ala
            20                  25                  30

Glu Met Leu Arg Ser Ser Leu Gly Pro Lys Gly Leu Asp Lys Met Leu
        35                  40                  45

Ile Asp Ser Phe Gly Asp Val Thr Ile Thr Asn Asp Gly Ala Thr Ile
    50                  55                  60

Val Lys Asp Met Glu Ile Gln His Pro Ala Ala Lys Leu Leu Val Glu
65                  70                  75                  80

Ala Ala Lys Ala Gln Asp Ala Glu Val Gly Asp Gly Thr Thr Ser Ala
                85                  90                  95

Val Val Leu Ala Gly Ala Leu Leu Glu Lys Ala Glu Ser Leu Leu Asp
            100                 105                 110

Gln Asn Ile His Pro Thr Ile Ile Ile Glu Gly Tyr Lys Lys Ala Tyr
        115                 120                 125

Thr Lys Ala Leu Glu Leu Leu Pro Gln Leu Gly Thr Arg Ile Asp Ile
    130                 135                 140

Arg Asp Leu Asn Ser Ser Val Ala Arg Asp Thr Leu Arg Lys Ile Ala
145                 150                 155                 160

Phe Thr Thr Leu Ala Ser Lys Phe Ile Ala Glu Gly Ala Glu Leu Asn
                165                 170                 175
```

-continued

```
Lys Ile Ile Asp Met Val Ile Asp Ala Ile Val Asn Val Ala Glu Pro
            180                 185                 190

Leu Pro Asn Gly Gly Tyr Asn Val Ser Leu Asp Leu Ile Lys Ile Asp
        195                 200                 205

Lys Lys Lys Gly Gly Ser Ile Glu Asp Ser Val Leu Val Lys Gly Leu
    210                 215                 220

Val Leu Asp Lys Glu Val Val His Pro Gly Met Pro Arg Arg Val Thr
225                 230                 235                 240

Lys Ala Lys Ile Ala Val Leu Asp Ala Ala Leu Glu Val Glu Lys Pro
                245                 250                 255

Glu Ile Ser Ala Lys Ile Ser Ile Thr Ser Pro Glu Gln Ile Lys Ala
            260                 265                 270

Phe Leu Asp Glu Glu Ser Lys Tyr Leu Lys Asp Met Val Asp Lys Leu
        275                 280                 285

Ala Ser Ile Gly Ala Asn Val Val Ile Cys Gln Lys Gly Ile Asp Asp
    290                 295                 300

Ile Ala Gln His Phe Leu Ala Lys Lys Gly Ile Leu Ala Val Arg Arg
305                 310                 315                 320

Val Lys Arg Ser Asp Ile Glu Lys Leu Glu Lys Ala Leu Gly Ala Arg
                325                 330                 335

Ile Ile Ser Ser Ile Lys Asp Ala Thr Pro Asp Asp Leu Gly Tyr Ala
            340                 345                 350

Glu Leu Val Glu Glu Arg Arg Val Gly Asn Asp Lys Met Val Phe Ile
        355                 360                 365

Glu Gly Ala Lys Asn Leu Lys Ala Val Asn Ile Leu Leu Arg Gly Ser
    370                 375                 380

Asn Asp Met Ala Leu Asp Glu Ala Glu Arg Ser Ile Asn Asp Ala Leu
385                 390                 395                 400

His Ala Leu Arg Asn Ile Leu Leu Glu Pro Val Ile Leu Pro Gly Gly
                405                 410                 415

Gly Ala Ile Glu Leu Glu Leu Ala Met Lys Leu Arg Glu Tyr Ala Arg
            420                 425                 430

Ser Val Gly Gly Lys Glu Gln Leu Ala Ile Glu Ala Phe Ala Asp Ala
        435                 440                 445

Leu Glu Glu Ile Pro Thr Ile Leu Ala Glu Thr Ala Gly Leu Glu Ala
    450                 455                 460

Ile Ser Ala Leu Met Asp Leu Arg Ala Arg His Ala Lys Gly Leu Thr
465                 470                 475                 480

Asn Thr Gly Val Asp Val Ile Gly Gly Lys Ile Val Asp Asp Val Tyr
                485                 490                 495

Ala Leu Asn Ile Ile Glu Pro Ile Arg Val Lys Ala Gln Val Leu Lys
            500                 505                 510

Ser Ala Thr Glu Ala Ala Thr Ala Ile Leu Lys Ile Asp Asp Leu Ile
        515                 520                 525

Ala Ala Ala Pro Leu Lys Ser Glu Lys Lys Gly Gly Glu Gly Ser Lys
    530                 535                 540

Glu Glu Ser Gly Gly Glu Gly Gly Ala Gly Thr Pro Ser Leu Gly Asp
545                 550                 555                 560
```

<210> SEQ ID NO 40
<211> LENGTH: 21
<212> TYPE: PRT
<213> ORGANISM: Artificial
<220> FEATURE:
<223> OTHER INFORMATION: metal binding peptide - Au

<400> SEQUENCE: 40

Ser Lys Thr Ser Leu Gly Gln Ser Gly Ala Ser Leu Gln Gly Ser Glu
1 5 10 15

Lys Leu Thr Asn Gly
20

<210> SEQ ID NO 41
<211> LENGTH: 21
<212> TYPE: PRT
<213> ORGANISM: Artificial
<220> FEATURE:
<223> OTHER INFORMATION: metal binding peptide - Au

<400> SEQUENCE: 41

Gln Ala Thr Ser Glu Lys Leu Val Arg Gly Met Glu Gly Ala Ser Leu
1 5 10 15

His Pro Ala Lys Thr
20

<210> SEQ ID NO 42
<211> LENGTH: 7
<212> TYPE: PRT
<213> ORGANISM: Artificial
<220> FEATURE:
<223> OTHER INFORMATION: metal binding peptide - Pt

<400> SEQUENCE: 42

Asp Arg Thr Ser Thr Trp Arg
1 5

<210> SEQ ID NO 43
<211> LENGTH: 7
<212> TYPE: PRT
<213> ORGANISM: Artificial
<220> FEATURE:
<223> OTHER INFORMATION: metal binding peptide - Pt

<400> SEQUENCE: 43

Gln Ser Val Thr Ser Thr Lys
1 5

<210> SEQ ID NO 44
<211> LENGTH: 7
<212> TYPE: PRT
<213> ORGANISM: Artificial
<220> FEATURE:
<223> OTHER INFORMATION: metal binding peptide - Pt

<400> SEQUENCE: 44

Ser Ser Ser His Leu Asn Lys
1 5

<210> SEQ ID NO 45
<211> LENGTH: 7
<212> TYPE: PRT
<213> ORGANISM: Artificial
<220> FEATURE:
<223> OTHER INFORMATION: metal binding peptide - Pd

<400> SEQUENCE: 45

Ser Val Thr Gln Asn Lys Tyr
1 5

<210> SEQ ID NO 46

-continued

```
<211> LENGTH: 7
<212> TYPE: PRT
<213> ORGANISM: Artificial
<220> FEATURE:
<223> OTHER INFORMATION: metal binding peptide - Pd

<400> SEQUENCE: 46

Ser Pro His Pro Gly Pro Tyr
1               5


<210> SEQ ID NO 47
<211> LENGTH: 7
<212> TYPE: PRT
<213> ORGANISM: Artificial
<220> FEATURE:
<223> OTHER INFORMATION: metal binding peptide - Pd

<400> SEQUENCE: 47

His Ala Pro Thr Pro Met Leu
1               5


<210> SEQ ID NO 48
<211> LENGTH: 12
<212> TYPE: PRT
<213> ORGANISM: Artificial
<220> FEATURE:
<223> OTHER INFORMATION: metal binding peptide - SiO2

<400> SEQUENCE: 48

Met Ser Pro His Pro His Pro Arg His His His Thr
1               5                   10


<210> SEQ ID NO 49
<211> LENGTH: 12
<212> TYPE: PRT
<213> ORGANISM: Artificial
<220> FEATURE:
<223> OTHER INFORMATION: metal binding peptide - SiO2

<400> SEQUENCE: 49

Arg Gly Arg Arg Arg Arg Leu Ser Cys Arg Leu Leu
1               5                   10


<210> SEQ ID NO 50
<211> LENGTH: 12
<212> TYPE: PRT
<213> ORGANISM: Artificial
<220> FEATURE:
<223> OTHER INFORMATION: metal binding peptide - SiO2

<400> SEQUENCE: 50

Lys Pro Ser His His His His His Thr Gly Ala Asn
1               5                   10


<210> SEQ ID NO 51
<211> LENGTH: 21
<212> TYPE: PRT
<213> ORGANISM: Artificial
<220> FEATURE:
<223> OTHER INFORMATION: metal binding peptide - zeolites

<400> SEQUENCE: 51

Val Lys Thr Gln Ala Thr Ser Arg Glu Glu Pro Pro Arg Leu Pro Ser
1               5                   10                  15

Lys His Arg Pro Gly
            20
```

-continued

<210> SEQ ID NO 52
<211> LENGTH: 14
<212> TYPE: PRT
<213> ORGANISM: Artificial
<220> FEATURE:
<223> OTHER INFORMATION: metal binding peptide - zeolites

<400> SEQUENCE: 52

Met Asp His Gly Lys Tyr Arg Gln Lys Gln Ala Thr Pro Gly
1               5                   10

<210> SEQ ID NO 53
<211> LENGTH: 20
<212> TYPE: PRT
<213> ORGANISM: Artificial
<220> FEATURE:
<223> OTHER INFORMATION: metal binding peptide - ZnO

<400> SEQUENCE: 53

Asn Thr Arg Met Thr Ala Arg Gln His Arg Ser Ala Asn His Lys Ser
1               5                   10                  15

Thr Gln Arg Ala
            20

<210> SEQ ID NO 54
<211> LENGTH: 9
<212> TYPE: PRT
<213> ORGANISM: Artificial
<220> FEATURE:
<223> OTHER INFORMATION: metal binding peptide ZnO

<400> SEQUENCE: 54

Tyr Asp Ser Arg Ser Met Arg Pro His
1               5

<210> SEQ ID NO 55
<211> LENGTH: 12
<212> TYPE: PRT
<213> ORGANISM: Artificial
<220> FEATURE:
<223> OTHER INFORMATION: metal binding peptide - CaCO3

<400> SEQUENCE: 55

His Thr Gln Asn Met Arg Met Tyr Glu Pro Trp Phe
1               5                   10

<210> SEQ ID NO 56
<211> LENGTH: 12
<212> TYPE: PRT
<213> ORGANISM: Artificial
<220> FEATURE:
<223> OTHER INFORMATION: metal binding peptide - CaCO3

<400> SEQUENCE: 56

Asp Val Phe Ser Ser Phe Asn Leu Lys His Met Arg
1               5                   10

<210> SEQ ID NO 57
<211> LENGTH: 8
<212> TYPE: PRT
<213> ORGANISM: Artificial
<220> FEATURE:
<223> OTHER INFORMATION: metal binding peptide - Cr2O3

<400> SEQUENCE: 57

Trp Arg Pro Lys Ala Ala Thr Asn

-continued 1 5

<210> SEQ ID NO 58
<211> LENGTH: 9
<212> TYPE: PRT
<213> ORGANISM: Artificial
<220> FEATURE:
<223> OTHER INFORMATION: metal binding peptide - Cr2O3

<400> SEQUENCE: 58

Arg Ile Arg His Arg Leu Val Gly Gln
1 5

<210> SEQ ID NO 59
<211> LENGTH: 9
<212> TYPE: PRT
<213> ORGANISM: Artificial
<220> FEATURE:
<223> OTHER INFORMATION: metal binding peptide - Fe2O3

<400> SEQUENCE: 59

Arg Arg Thr Val Lys His His Val Asn
1 5

<210> SEQ ID NO 60
<211> LENGTH: 11
<212> TYPE: PRT
<213> ORGANISM: Artificial
<220> FEATURE:
<223> OTHER INFORMATION: metal binding peptide - GaAs

<400> SEQUENCE: 60

Ala Gln Asn Pro Ser Asp Asn Asn Thr Thr His
1 5 10

<210> SEQ ID NO 61
<211> LENGTH: 12
<212> TYPE: PRT
<213> ORGANISM: Artificial
<220> FEATURE:
<223> OTHER INFORMATION: metal binding peptide - GaAs

<400> SEQUENCE: 61

Arg Leu Glu Leu Ala Ile Pro Leu Gln Gly Ser Gly
1 5 10

<210> SEQ ID NO 62
<211> LENGTH: 12
<212> TYPE: PRT
<213> ORGANISM: Artificial
<220> FEATURE:
<223> OTHER INFORMATION: metal binding peptide - GaAs

<400> SEQUENCE: 62

Thr Pro Pro Arg Pro Ile Gln Tyr Asn His Thr Ser
1 5 10

<210> SEQ ID NO 63
<211> LENGTH: 7
<212> TYPE: PRT
<213> ORGANISM: Artificial
<220> FEATURE:
<223> OTHER INFORMATION: metal binding peptide - ZnS

<400> SEQUENCE: 63

Asn Asn Pro Met His Gln Asn
1 5

<210> SEQ ID NO 64
<211> LENGTH: 6
<212> TYPE: PRT
<213> ORGANISM: Artificial
<220> FEATURE:
<223> OTHER INFORMATION: flexible peptide linker

<400> SEQUENCE: 64

Gly Gly Ser Gly Gly Thr
1               5

<210> SEQ ID NO 65
<211> LENGTH: 18
<212> TYPE: DNA
<213> ORGANISM: Artificial
<220> FEATURE:
<223> OTHER INFORMATION: flexible linker

<400> SEQUENCE: 65
ggtggttctg gtggtacc 18

<210> SEQ ID NO 66
<211> LENGTH: 1575
<212> TYPE: DNA
<213> ORGANISM: Sulfolobus shibatae
<220> FEATURE:
<221> NAME/KEY: misc_feature
<223> OTHER INFORMATION: chaperonin permutant 153

<400> SEQUENCE: 66
atggcaataa atgatactga cgtacttagg aaagtagcat taacatcctt aggcagtaag 60
gcagtagcag gcgcacgaga gtatttagct gaccttgtgg ttaaagcagt ggcacaagta 120
gcagaattaa gaggagataa gtggtatgtt gatctagata atgtacaaat agttaaaaaa 180
catggtggta gcattaatga tactcaatta gtatacggca tagtagttga taaggaagtt 240
gtacatccgg gcatgccaaa gaggattgaa aatgctaaga tagccctttt agacgcttca 300
ttagaagttg agaaacccga attggatgca gaaataagaa ttaacgatcc aacacagatg 360
cacaaattct tggaagaaga agaaaacata ttgaaagaaa aagtagataa gattgcagct 420
actggtgcta acgttgtaat agcgcagaaa ggtatcgatg aagttgcaca acactattta 480
gctaagaaag gtatattagc tgttaggaga gccaagaaga gtgatttaga gaaattagct 540
agagctaccg gaggtagagt catatcaaat attgatgaat taacttcaca agatctaggt 600
tatgccgcat tagtggaaga gagaaaagta ggtgaagaca agatcgtatt cgtagaaggt 660
gcaaagaatc caaaatcagt tagtatacta ataagaggag gattagagag agtagtagat 720
gagactgaaa gagctcttag ggacgcttta ggtacagtgg cagatgtaat aagggatggt 780
agagcagtag ctggtggtgg agctgttgag atagagatag ctaagagatt aagaaagtat 840
gccccacaag ttggtggtaa agagcaatta gcaattgaag catatgctaa tgcaatagag 900
ggtctcatta tgatattggc ggaaaacgca ggattagatc ctatagacaa attaatgcaa 960
ttaagaagtc ttcacgagaa tgagaccaat aaatggtatg gacttaattt atttactgga 1020
aatccagagg atatgtggaa attaggtgtt attgaaccgg cactagtgaa aatgaatgca 1080
attaaggctg caacagaagc agtaacatta gtgttaagaa tagatgatat tgtaggtggt 1140
tctggtggta ccatacctgt aataatttta aaagagggat caagtagaac atatggaaaa 1200
gaagctttaa gggctaatat tgctgcagtg aaagcaattg aagaggcatt aaaaagcacc 1260

```
tatggtccac gtggaatgga taagattctt gttgatagct taggagatat tacaataaca    1320

aatgatggag ccactattct tgataaaatg gatttacaac acccaacagg taagctttta    1380

gttcagatag ctaaaggaca agacgaggaa acagctgatg gcactaaaac tgctgtaatt    1440

cttgctggag aattagctaa aaaagcagaa gatcttttat ataaggagat tcacccaaca    1500

ataattgtaa gcggatataa gaaggcagaa gaaattgcat taaagaccat ccaagatata    1560

gcacaaccgg tcagc                                                     1575
```

<210> SEQ ID NO 67
<211> LENGTH: 525
<212> TYPE: PRT
<213> ORGANISM: Sulfolobus shibatae
<220> FEATURE:
<221> NAME/KEY: MISC_FEATURE
<223> OTHER INFORMATION: chaperonin permutant 153

<400> SEQUENCE: 67

```
Met Ala Ile Asn Asp Thr Asp Val Leu Arg Lys Val Ala Leu Thr Ser
  1               5                  10                  15

Leu Gly Ser Lys Ala Val Ala Gly Ala Arg Glu Tyr Leu Ala Asp Leu
             20                  25                  30

Val Val Lys Ala Val Ala Gln Val Ala Glu Leu Arg Gly Asp Lys Trp
         35                  40                  45

Tyr Val Asp Leu Asp Asn Val Gln Ile Val Lys Lys His Gly Gly Ser
     50                  55                  60

Ile Asn Asp Thr Gln Leu Val Tyr Gly Ile Val Val Asp Lys Glu Val
 65                  70                  75                  80

Val His Pro Gly Met Pro Lys Arg Ile Glu Asn Ala Lys Ile Ala Leu
                 85                  90                  95

Leu Asp Ala Ser Leu Glu Val Glu Lys Pro Glu Leu Asp Ala Glu Ile
            100                 105                 110

Arg Ile Asn Asp Pro Thr Gln Met His Lys Phe Leu Glu Glu Glu Glu
        115                 120                 125

Asn Ile Leu Lys Glu Lys Val Asp Lys Ile Ala Ala Thr Gly Ala Asn
    130                 135                 140

Val Val Ile Ala Gln Lys Gly Ile Asp Glu Val Ala Gln His Tyr Leu
145                 150                 155                 160

Ala Lys Lys Gly Ile Leu Ala Val Arg Arg Ala Lys Lys Ser Asp Leu
                165                 170                 175

Glu Lys Leu Ala Arg Ala Thr Gly Gly Arg Val Ile Ser Asn Ile Asp
            180                 185                 190

Glu Leu Thr Ser Gln Asp Leu Gly Tyr Ala Ala Leu Val Glu Glu Arg
        195                 200                 205

Lys Val Gly Glu Asp Lys Ile Val Phe Val Glu Gly Ala Lys Asn Pro
    210                 215                 220

Lys Ser Val Ser Ile Leu Ile Arg Gly Gly Leu Glu Arg Val Val Asp
225                 230                 235                 240

Glu Thr Glu Arg Ala Leu Arg Asp Ala Leu Gly Thr Val Ala Asp Val
                245                 250                 255

Ile Arg Asp Gly Arg Ala Val Ala Gly Gly Gly Ala Val Glu Ile Glu
            260                 265                 270

Ile Ala Lys Arg Leu Arg Lys Tyr Ala Pro Gln Val Gly Gly Lys Glu
        275                 280                 285

Gln Leu Ala Ile Glu Ala Tyr Ala Asn Ala Ile Glu Gly Leu Ile Met
    290                 295                 300
```

-continued

```
Ile Leu Ala Glu Asn Ala Gly Leu Asp Pro Ile Asp Lys Leu Met Gln
305                 310                 315                 320

Leu Arg Ser Leu His Glu Asn Glu Thr Asn Lys Trp Tyr Gly Leu Asn
                325                 330                 335

Leu Phe Thr Gly Asn Pro Glu Asp Met Trp Lys Leu Gly Val Ile Glu
            340                 345                 350

Pro Ala Leu Val Lys Met Asn Ala Ile Lys Ala Ala Thr Glu Ala Val
        355                 360                 365

Thr Leu Val Leu Arg Ile Asp Asp Ile Val Gly Gly Ser Gly Gly Thr
    370                 375                 380

Ile Pro Val Ile Ile Leu Lys Glu Gly Ser Ser Arg Thr Tyr Gly Lys
385                 390                 395                 400

Glu Ala Leu Arg Ala Asn Ile Ala Ala Val Lys Ala Ile Glu Glu Ala
                405                 410                 415

Leu Lys Ser Thr Tyr Gly Pro Arg Gly Met Asp Lys Ile Leu Val Asp
            420                 425                 430

Ser Leu Gly Asp Ile Thr Ile Thr Asn Asp Gly Ala Thr Ile Leu Asp
        435                 440                 445

Lys Met Asp Leu Gln His Pro Thr Gly Lys Leu Leu Val Gln Ile Ala
    450                 455                 460

Lys Gly Gln Asp Glu Glu Thr Ala Asp Gly Thr Lys Thr Ala Val Ile
465                 470                 475                 480

Leu Ala Gly Glu Leu Ala Lys Lys Ala Glu Asp Leu Leu Tyr Lys Glu
                485                 490                 495

Ile His Pro Thr Ile Ile Val Ser Gly Tyr Lys Lys Ala Glu Glu Ile
            500                 505                 510

Ala Leu Lys Thr Ile Gln Asp Ile Ala Gln Pro Val Ser
        515                 520                 525
```

<210> SEQ ID NO 68
<211> LENGTH: 1575
<212> TYPE: DNA
<213> ORGANISM: Sulfolobus shibatae
<220> FEATURE:
<221> NAME/KEY: misc_feature
<223> OTHER INFORMATION: chaperonin permutant 267

<400> SEQUENCE: 68

```
atggcagatc caacacagat gcacaaattc ttggaagaag aagaaaacat attgaaagaa      60

aaagtagata agattgcagc tactggtgct aacgttgtaa tagcgcagaa aggtatcgat     120

gaagttgcac aacactattt agctaagaaa ggtatattag ctgttaggag agccaagaag     180

agtgatttag agaaattagc tagagctacc ggaggtagag tcatatcaaa tattgatgaa     240

ttaacttcac aagatctagg ttatgccgca ttagtggaag agagaaaagt aggtgaagac     300

aagatcgtat tcgtagaagg tgcaaagaat ccaaaatcag ttagtatact aataagagga     360

ggattagaga gagtagtaga tgagactgaa agagctctta gggacgcttt aggtacagtg     420

gcagatgtaa taagggatgg tagagcagta gctggtggtg gagctgttga gatagagata     480

gctaagagat taagaaagta tgccccacaa gttggtggta aagagcaatt agcaattgaa     540

gcatatgcta atgcaataga gggtctcatt atgatattgg cggaaaacgc aggattagat     600

cctatagaca aattaatgca attaagaagt cttcacgaga atgagaccaa taaatggtat     660

ggacttaatt tatttactgg aaatccagag gatatgtgga aattaggtgt tattgaaccg     720

gcactagtga aaatgaatgc aattaaggct gcaacagaag cagtaacatt agtgttaaga     780
```

-continued

```
atagatgata ttgtaggtgg ttctggtggt accatacctg taataatttt aaaagaggga    840

tcaagtagaa catatggaaa agaagcttta agggctaata ttgctgcagt gaaagcaatt    900

gaagaggcat taaaaagcac ctatggtcca cgtggaatgg ataagattct tgttgatagc    960

ttaggagata ttacaataac aaatgatgga gccactattc ttgataaaat ggatttacaa   1020

cacccaacag gtaagctttt agttcagata gctaaaggac aagacgagga aacagctgat   1080

ggcactaaaa ctgctgtaat tcttgctgga gaattagcta aaaaagcaga agatctttta   1140

tataaggaga ttcacccaac aataattgta agcggatata agaaggcaga agaaattgca   1200

ttaaagacca tccaagatat agcacaaccg gtcagcataa atgatactga cgtacttagg   1260

aaagtagcat taacatcctt aggcagtaag gcagtagcag gcgcacgaga gtatttagct   1320

gaccttgtgg ttaaagcagt ggcacaagta gcagaattaa gaggagataa gtggtatgtt   1380

gatctagata atgtacaaat agttaaaaaa catggtggta gcattaatga tactcaatta   1440

gtatacggca tagtagttga taaggaagtt gtacatccgg gcatgccaaa gaggattgaa   1500

aatgctaaga tagccctttt agacgcttca ttagaagttg agaaacccga attggatgca   1560

gaaataagaa ttaac                                                    1575
```

<210> SEQ ID NO 69
<211> LENGTH: 525
<212> TYPE: PRT
<213> ORGANISM: Sulfolobus shibatae
<220> FEATURE:
<221> NAME/KEY: MISC_FEATURE
<223> OTHER INFORMATION: chaperonin permutant 267

<400> SEQUENCE: 69

```
Met Ala Asp Pro Thr Gln Met His Lys Phe Leu Glu Glu Glu Glu Asn
1               5                   10                  15

Ile Leu Lys Glu Lys Val Asp Lys Ile Ala Ala Thr Gly Ala Asn Val
            20                  25                  30

Val Ile Ala Gln Lys Gly Ile Asp Glu Val Ala Gln His Tyr Leu Ala
        35                  40                  45

Lys Lys Gly Ile Leu Ala Val Arg Arg Ala Lys Lys Ser Asp Leu Glu
    50                  55                  60

Lys Leu Ala Arg Ala Thr Gly Gly Arg Val Ile Ser Asn Ile Asp Glu
65                  70                  75                  80

Leu Thr Ser Gln Asp Leu Gly Tyr Ala Ala Leu Val Glu Glu Arg Lys
                85                  90                  95

Val Gly Glu Asp Lys Ile Val Phe Val Glu Gly Ala Lys Asn Pro Lys
            100                 105                 110

Ser Val Ser Ile Leu Ile Arg Gly Gly Leu Glu Arg Val Val Asp Glu
        115                 120                 125

Thr Glu Arg Ala Leu Arg Asp Ala Leu Gly Thr Val Ala Asp Val Ile
    130                 135                 140

Arg Asp Gly Arg Ala Val Ala Gly Gly Gly Ala Val Glu Ile Glu Ile
145                 150                 155                 160

Ala Lys Arg Leu Arg Lys Tyr Ala Pro Gln Val Gly Gly Lys Glu Gln
                165                 170                 175

Leu Ala Ile Glu Ala Tyr Ala Asn Ala Ile Glu Gly Leu Ile Met Ile
            180                 185                 190

Leu Ala Glu Asn Ala Gly Leu Asp Pro Ile Asp Lys Leu Met Gln Leu
        195                 200                 205
```

-continued

```
Arg Ser Leu His Glu Asn Glu Thr Asn Lys Trp Tyr Gly Leu Asn Leu
    210                 215                 220

Phe Thr Gly Asn Pro Glu Asp Met Trp Lys Leu Gly Val Ile Glu Pro
225                 230                 235                 240

Ala Leu Val Lys Met Asn Ala Ile Lys Ala Ala Thr Glu Ala Val Thr
                245                 250                 255

Leu Val Leu Arg Ile Asp Asp Ile Val Gly Gly Ser Gly Gly Thr Ile
            260                 265                 270

Pro Val Ile Ile Leu Lys Glu Gly Ser Ser Arg Thr Tyr Gly Lys Glu
        275                 280                 285

Ala Leu Arg Ala Asn Ile Ala Ala Val Lys Ala Ile Glu Glu Ala Leu
    290                 295                 300

Lys Ser Thr Tyr Gly Pro Arg Gly Met Asp Lys Ile Leu Val Asp Ser
305                 310                 315                 320

Leu Gly Asp Ile Thr Ile Thr Asn Asp Gly Ala Thr Ile Leu Asp Lys
                325                 330                 335

Met Asp Leu Gln His Pro Thr Gly Lys Leu Leu Val Gln Ile Ala Lys
            340                 345                 350

Gly Gln Asp Glu Glu Thr Ala Asp Gly Thr Lys Thr Ala Val Ile Leu
        355                 360                 365

Ala Gly Glu Leu Ala Lys Lys Ala Glu Asp Leu Leu Tyr Lys Glu Ile
    370                 375                 380

His Pro Thr Ile Ile Val Ser Gly Tyr Lys Lys Ala Glu Glu Ile Ala
385                 390                 395                 400

Leu Lys Thr Ile Gln Asp Ile Ala Gln Pro Val Ser Ile Asn Asp Thr
                405                 410                 415

Asp Val Leu Arg Lys Val Ala Leu Thr Ser Leu Gly Ser Lys Ala Val
            420                 425                 430

Ala Gly Ala Arg Glu Tyr Leu Ala Asp Leu Val Val Lys Ala Val Ala
        435                 440                 445

Gln Val Ala Glu Leu Arg Gly Asp Lys Trp Tyr Val Asp Leu Asp Asn
    450                 455                 460

Val Gln Ile Val Lys Lys His Gly Gly Ser Ile Asn Asp Thr Gln Leu
465                 470                 475                 480

Val Tyr Gly Ile Val Val Asp Lys Glu Val Val His Pro Gly Met Pro
                485                 490                 495

Lys Arg Ile Glu Asn Ala Lys Ile Ala Leu Leu Asp Ala Ser Leu Glu
            500                 505                 510

Val Glu Lys Pro Glu Leu Asp Ala Glu Ile Arg Ile Asn
        515                 520                 525
```

<210> SEQ ID NO 70
<211> LENGTH: 1575
<212> TYPE: DNA
<213> ORGANISM: Sulfolobus shibatae
<220> FEATURE:
<221> NAME/KEY: misc_feature
<223> OTHER INFORMATION: chaperonin permutant 316

<400> SEQUENCE: 70

```
atggcaatat tagctgttag gagagccaag aagagtgatt tagagaaatt agctagagct      60

accggaggta gagtcatatc aaatattgat gaattaactt cacaagatct aggttatgcc     120

gcattagtgg aagagagaaa agtaggtgaa gacaagatcg tattcgtaga aggtgcaaag     180

aatccaaaat cagttagtat actaataaga ggaggattag agagagtagt agatgagact     240
```

-continued

```
gaaagagctc ttagggacgc tttaggtaca gtggcagatg taataaggga tggtagagca    300

gtagctggtg gtggagctgt tgagatagag atagctaaga gattaagaaa gtatgcccca    360

caagttggtg gtaaagagca attagcaatt gaagcatatg ctaatgcaat agagggtctc    420

attatgatat tggcggaaaa cgcaggatta gatcctatag acaaattaat gcaattaaga    480

agtcttcacg agaatgagac caataaatgg tatggactta atttatttac tggaaatcca    540

gaggatatgt ggaaattagg tgttattgaa ccggcactag tgaaaatgaa tgcaattaag    600

gctgcaacag aagcagtaac attagtgtta agaatagatg atattgtagg tggttctggt    660

ggtaccatac ctgtaataat tttaaaagag ggatcaagta gaacatatgg aaaagaagct    720

ttaagggcta atattgctgc agtgaaagca attgaagagg cattaaaaag cacctatggt    780

ccacgtggaa tggataagat tcttgttgat agcttaggag atattacaat aacaaatgat    840

ggagccacta ttcttgataa aatggattta caacacccaa caggtaagct tttagttcag    900

atagctaaag gacaagacga ggaaacagct gatggcacta aaactgctgt aattcttgct    960

ggagaattag ctaaaaaagc agaagatctt ttatataagg agattcaccc aacaataatt   1020

gtaagcggat ataagaaggc agaagaaatt gcattaaaga ccatccaaga tatagcacaa   1080

ccggtcagca taaatgatac tgacgtactt aggaaagtag cattaacatc cttaggcagt   1140

aaggcagtag caggcgcacg agagtattta gctgaccttg tggttaaagc agtggcacaa   1200

gtagcagaat taagaggaga taagtggtat gttgatctag ataatgtaca aatagttaaa   1260

aaacatggtg gtagcattaa tgatactcaa ttagtatacg gcatagtagt tgataaggaa   1320

gttgtacatc cgggcatgcc aaagaggatt gaaaatgcta agatagccct tttagacgct   1380

tcattagaag ttgagaaacc cgaattggat gcagaaataa gaattaacga tccaacacag   1440

atgcacaaat tcttggaaga agaagaaaac atattgaaag aaaaagtaga taagattgca   1500

gctactggtg ctaacgttgt aatagcgcag aaaggtatcg atgaagttgc acaacactat   1560

ttagctaaga aaggt                                                     1575
```

```
<210> SEQ ID NO 71
<211> LENGTH: 525
<212> TYPE: PRT
<213> ORGANISM: Sulfolobus shibatae
<220> FEATURE:
<221> NAME/KEY: MISC_FEATURE
<223> OTHER INFORMATION: chaperonin permutant 316

<400> SEQUENCE: 71

Met Ala Ile Leu Ala Val Arg Arg Ala Lys Lys Ser Asp Leu Glu Lys
1               5                   10                  15

Leu Ala Arg Ala Thr Gly Gly Arg Val Ile Ser Asn Ile Asp Glu Leu
            20                  25                  30

Thr Ser Gln Asp Leu Gly Tyr Ala Ala Leu Val Glu Glu Arg Lys Val
        35                  40                  45

Gly Glu Asp Lys Ile Val Phe Val Glu Gly Ala Lys Asn Pro Lys Ser
    50                  55                  60

Val Ser Ile Leu Ile Arg Gly Gly Leu Glu Arg Val Val Asp Glu Thr
65                  70                  75                  80

Glu Arg Ala Leu Arg Asp Ala Leu Gly Thr Val Ala Asp Val Ile Arg
                85                  90                  95

Asp Gly Arg Ala Val Ala Gly Gly Gly Ala Val Glu Ile Glu Ile Ala
            100                 105                 110

Lys Arg Leu Arg Lys Tyr Ala Pro Gln Val Gly Gly Lys Glu Gln Leu
```

-continued

```
        115                 120                 125

Ala Ile Glu Ala Tyr Ala Asn Ala Ile Glu Gly Leu Ile Met Ile Leu
    130                 135                 140

Ala Glu Asn Ala Gly Leu Asp Pro Ile Asp Lys Leu Met Gln Leu Arg
145                 150                 155                 160

Ser Leu His Glu Asn Glu Thr Asn Lys Trp Tyr Gly Leu Asn Leu Phe
                165                 170                 175

Thr Gly Asn Pro Glu Asp Met Trp Lys Leu Gly Val Ile Glu Pro Ala
            180                 185                 190

Leu Val Lys Met Asn Ala Ile Lys Ala Ala Thr Glu Ala Val Thr Leu
        195                 200                 205

Val Leu Arg Ile Asp Asp Ile Val Gly Gly Ser Gly Gly Thr Ile Pro
    210                 215                 220

Val Ile Ile Leu Lys Glu Gly Ser Ser Arg Thr Tyr Gly Lys Glu Ala
225                 230                 235                 240

Leu Arg Ala Asn Ile Ala Ala Val Lys Ala Ile Glu Glu Ala Leu Lys
                245                 250                 255

Ser Thr Tyr Gly Pro Arg Gly Met Asp Lys Ile Leu Val Asp Ser Leu
            260                 265                 270

Gly Asp Ile Thr Ile Thr Asn Asp Gly Ala Thr Ile Leu Asp Lys Met
        275                 280                 285

Asp Leu Gln His Pro Thr Gly Lys Leu Leu Val Gln Ile Ala Lys Gly
    290                 295                 300

Gln Asp Glu Glu Thr Ala Asp Gly Thr Lys Thr Ala Val Ile Leu Ala
305                 310                 315                 320

Gly Glu Leu Ala Lys Lys Ala Glu Asp Leu Leu Tyr Lys Glu Ile His
                325                 330                 335

Pro Thr Ile Ile Val Ser Gly Tyr Lys Lys Ala Glu Glu Ile Ala Leu
            340                 345                 350

Lys Thr Ile Gln Asp Ile Ala Gln Pro Val Ser Ile Asn Asp Thr Asp
        355                 360                 365

Val Leu Arg Lys Val Ala Leu Thr Ser Leu Gly Ser Lys Ala Val Ala
    370                 375                 380

Gly Ala Arg Glu Tyr Leu Ala Asp Leu Val Val Lys Ala Val Ala Gln
385                 390                 395                 400

Val Ala Glu Leu Arg Gly Asp Lys Trp Tyr Val Asp Leu Asp Asn Val
                405                 410                 415

Gln Ile Val Lys Lys His Gly Gly Ser Ile Asn Asp Thr Gln Leu Val
            420                 425                 430

Tyr Gly Ile Val Val Asp Lys Glu Val Val His Pro Gly Met Pro Lys
        435                 440                 445

Arg Ile Glu Asn Ala Lys Ile Ala Leu Leu Asp Ala Ser Leu Glu Val
    450                 455                 460

Glu Lys Pro Glu Leu Asp Ala Glu Ile Arg Ile Asn Asp Pro Thr Gln
465                 470                 475                 480

Met His Lys Phe Leu Glu Glu Glu Glu Asn Ile Leu Lys Glu Lys Val
                485                 490                 495

Asp Lys Ile Ala Ala Thr Gly Ala Asn Val Val Ile Ala Gln Lys Gly
            500                 505                 510

Ile Asp Glu Val Ala Gln His Tyr Leu Ala Lys Lys Gly
        515                 520                 525
```

<210> SEQ ID NO 72

-continued

<211> LENGTH: 1575
<212> TYPE: DNA
<213> ORGANISM: Sulfolobus shibatae
<220> FEATURE:
<221> NAME/KEY: misc_feature
<223> OTHER INFORMATION: chaperonin permutant 480

<400> SEQUENCE: 72

```
atggcaaata aatggtatgg acttaattta tttactggaa atccagagga tatgtggaaa     60
ttaggtgtta ttgaaccggc actagtgaaa atgaatgcaa ttaaggctgc aacagaagca    120
gtaacattag tgttaagaat agatgatatt gtaggtggtt ctggtggtac catacctgta    180
ataattttaa aagagggatc aagtagaaca tatggaaaag aagctttaag ggctaatatt    240
gctgcagtga aagcaattga agaggcatta aaaagcacct atggtccacg tggaatggat    300
aagattcttg ttgatagctt aggagatatt acaataacaa atgatggagc cactattctt    360
gataaaatgg atttacaaca cccaacaggt aagcttttag ttcagatagc taaaggacaa    420
gacgaggaaa cagctgatgg cactaaaact gctgtaattc ttgctggaga attagctaaa    480
aaagcagaag atcttttata taaggagatt cacccaacaa taattgtaag cggatataag    540
aaggcagaag aaattgcatt aaagaccatc caagatatag cacaaccggt cagcataaat    600
gatactgacg tacttaggaa agtagcatta acatccttag gcagtaaggc agtagcaggc    660
gcacgagagt atttagctga ccttgtggtt aaagcagtgg cacaagtagc agaattaaga    720
ggagataagt ggtatgttga tctagataat gtacaaatag ttaaaaaaca tggtggtagc    780
attaatgata ctcaattagt atacggcata gtagttgata aggaagttgt acatccgggc    840
atgccaaaga ggattgaaaa tgctaagata gccctttttag acgcttcatt agaagttgag    900
aaacccgaat tggatgcaga aataagaatt aacgatccaa cacagatgca caaattcttg    960
gaagaagaag aaaacatatt gaaagaaaaa gtagataaga ttgcagctac tggtgctaac   1020
gttgtaatag cgcagaaagg tatcgatgaa gttgcacaac actatttagc taagaaaggt   1080
atattagctg ttaggagagc caagaagagt gatttagaga aattagctag agctaccgga   1140
ggtagagtca tatcaaatat tgatgaatta acttcacaag atctaggtta tgccgcatta   1200
gtggaagaga gaaaagtagg tgaagacaag atcgtattcg tagaaggtgc aaagaatcca   1260
aaatcagtta gtatactaat aagaggagga ttagagagag tagtagatga gactgaaaga   1320
gctcttaggg acgctttagg tacagtggca gatgtaataa gggatggtag agcagtagct   1380
ggtggtggag ctgttgagat agagatagct aagagattaa gaaagtatgc cccacaagtt   1440
ggtggtaaag agcaattagc aattgaagca tatgctaatg caatagaggg tctcattatg   1500
atattggcgg aaaacgcagg attagatcct atagacaaat taatgcaatt aagaagtctt   1560
cacgagaatg agacc                                                     1575
```

<210> SEQ ID NO 73
<211> LENGTH: 525
<212> TYPE: PRT
<213> ORGANISM: Sulfolobus shibatae
<220> FEATURE:
<221> NAME/KEY: MISC_FEATURE
<223> OTHER INFORMATION: chaperonin permutant 480

<400> SEQUENCE: 73

```
Met Ala Asn Lys Trp Tyr Gly Leu Asn Leu Phe Thr Gly Asn Pro Glu
1               5                   10                  15

Asp Met Trp Lys Leu Gly Val Ile Glu Pro Ala Leu Val Lys Met Asn
            20                  25                  30
```

-continued

```
Ala Ile Lys Ala Ala Thr Glu Ala Val Thr Leu Val Leu Arg Ile Asp
        35                  40                  45

Asp Ile Val Gly Gly Ser Gly Gly Thr Ile Pro Val Ile Ile Leu Lys
    50                  55                  60

Glu Gly Ser Ser Arg Thr Tyr Gly Lys Glu Ala Leu Arg Ala Asn Ile
65                  70                  75                  80

Ala Ala Val Lys Ala Ile Glu Glu Ala Leu Lys Ser Thr Tyr Gly Pro
                85                  90                  95

Arg Gly Met Asp Lys Ile Leu Val Asp Ser Leu Gly Asp Ile Thr Ile
            100                 105                 110

Thr Asn Asp Gly Ala Thr Ile Leu Asp Lys Met Asp Leu Gln His Pro
        115                 120                 125

Thr Gly Lys Leu Leu Val Gln Ile Ala Lys Gly Gln Asp Glu Glu Thr
    130                 135                 140

Ala Asp Gly Thr Lys Thr Ala Val Ile Leu Ala Gly Glu Leu Ala Lys
145                 150                 155                 160

Lys Ala Glu Asp Leu Leu Tyr Lys Glu Ile His Pro Thr Ile Ile Val
                165                 170                 175

Ser Gly Tyr Lys Lys Ala Glu Glu Ile Ala Leu Lys Thr Ile Gln Asp
            180                 185                 190

Ile Ala Gln Pro Val Ser Ile Asn Asp Thr Asp Val Leu Arg Lys Val
        195                 200                 205

Ala Leu Thr Ser Leu Gly Ser Lys Ala Val Ala Gly Ala Arg Glu Tyr
    210                 215                 220

Leu Ala Asp Leu Val Val Lys Ala Val Ala Gln Val Ala Glu Leu Arg
225                 230                 235                 240

Gly Asp Lys Trp Tyr Val Asp Leu Asp Asn Val Gln Ile Val Lys Lys
                245                 250                 255

His Gly Gly Ser Ile Asn Asp Thr Gln Leu Val Tyr Gly Ile Val Val
            260                 265                 270

Asp Lys Glu Val Val His Pro Gly Met Pro Lys Arg Ile Glu Asn Ala
        275                 280                 285

Lys Ile Ala Leu Leu Asp Ala Ser Leu Glu Val Glu Lys Pro Glu Leu
    290                 295                 300

Asp Ala Glu Ile Arg Ile Asn Asp Pro Thr Gln Met His Lys Phe Leu
305                 310                 315                 320

Glu Glu Glu Glu Asn Ile Leu Lys Glu Lys Val Asp Lys Ile Ala Ala
                325                 330                 335

Thr Gly Ala Asn Val Val Ile Ala Gln Lys Gly Ile Asp Glu Val Ala
            340                 345                 350

Gln His Tyr Leu Ala Lys Lys Gly Ile Leu Ala Val Arg Arg Ala Lys
        355                 360                 365

Lys Ser Asp Leu Glu Lys Leu Ala Arg Ala Thr Gly Gly Arg Val Ile
    370                 375                 380

Ser Asn Ile Asp Glu Leu Thr Ser Gln Asp Leu Gly Tyr Ala Ala Leu
385                 390                 395                 400

Val Glu Glu Arg Lys Val Gly Glu Asp Lys Ile Val Phe Val Glu Gly
                405                 410                 415

Ala Lys Asn Pro Lys Ser Val Ser Ile Leu Ile Arg Gly Gly Leu Glu
            420                 425                 430

Arg Val Val Asp Glu Thr Glu Arg Ala Leu Arg Asp Ala Leu Gly Thr
        435                 440                 445
```

-continued

```
Val Ala Asp Val Ile Arg Asp Gly Arg Ala Val Ala Gly Gly Gly Ala
    450                 455                 460

Val Glu Ile Glu Ile Ala Lys Arg Leu Arg Lys Tyr Ala Pro Gln Val
465                 470                 475                 480

Gly Gly Lys Glu Gln Leu Ala Ile Glu Ala Tyr Ala Asn Ala Ile Glu
                485                 490                 495

Gly Leu Ile Met Ile Leu Ala Glu Asn Ala Gly Leu Asp Pro Ile Asp
            500                 505                 510

Lys Leu Met Gln Leu Arg Ser Leu His Glu Asn Glu Thr
        515                 520                 525
```

<210> SEQ ID NO 74
<211> LENGTH: 1575
<212> TYPE: DNA
<213> ORGANISM: Sulfolobus shibatae
<220> FEATURE:
<221> NAME/KEY: misc_feature
<223> OTHER INFORMATION: chaperonin permutant 499

<400> SEQUENCE: 74

```
atggcattag gtgttattga accggcacta gtgaaaatga atgcaattaa ggctgcaaca      60

gaagcagtaa cattagtgtt aagaatagat gatattgtag gtggttctgg tggtaccata     120

cctgtaataa ttttaaaaga gggatcaagt agaacatatg gaaaagaagc tttaagggct     180

aatattgctg cagtgaaagc aattgaagag gcattaaaaa gcacctatgg tccacgtgga     240

atggataaga ttcttgttga tagcttagga gatattacaa taacaaatga tggagccact     300

attcttgata aaatggattt acaacaccca acaggtaagc ttttagttca gatagctaaa     360

ggacaagacg aggaaacagc tgatggcact aaaactgctg taattcttgc tggagaatta     420

gctaaaaaag cagaagatct tttatataag gagattcacc caacaataat tgtaagcgga     480

tataagaagg cagaagaaat tgcattaaag accatccaag atatagcaca accggtcagc     540

ataaatgata ctgacgtact taggaaagta gcattaacat ccttaggcag taaggcagta     600

gcaggcgcac gagagtattt agctgacctt gtggttaaag cagtggcaca agtagcagaa     660

ttaagaggag ataagtggta tgttgatcta gataatgtac aaatagttaa aaaacatggt     720

ggtagcatta atgatactca attagtatac ggcatagtag ttgataagga agttgtacat     780

ccgggcatgc caaagaggat tgaaaatgct aagatagccc ttttagacgc ttcattagaa     840

gttgagaaac ccgaattgga tgcagaaata agaattaacg atccaacaca gatgcacaaa     900

ttcttggaag aagaagaaaa catattgaaa gaaaaagtag ataagattgc agctactggt     960

gctaacgttg taatagcgca gaaaggtatc gatgaagttg cacaacacta tttagctaag    1020

aaaggtatat tagctgttag gagagccaag aagagtgatt tagagaaatt agctagagct    1080

accggaggta gagtcatatc aaatattgat gaattaactt cacaagatct aggttatgcc    1140

gcattagtgg aagagagaaa agtaggtgaa gacaagatcg tattcgtaga aggtgcaaag    1200

aatccaaaat cagttagtat actaataaga ggaggattag agagagtagt agatgagact    1260

gaaagagctc ttagggacgc tttaggtaca gtggcagatg taataaggga tggtagagca    1320

gtagctggtg gtggagctgt tgagatagag atagctaaga gattaagaaa gtatgcccca    1380

caagttggtg gtaaagagca attagcaatt gaagcatatg ctaatgcaat agagggtctc    1440

attatgatat tggcggaaaa cgcaggatta gatcctatag acaaattaat gcaattaaga    1500

agtcttcacg agaatgagac caataaatgg tatggactta atttatttac tggaaatcca    1560

gaggatatgt ggaaa                                                     1575
```

-continued

<210> SEQ ID NO 75
<211> LENGTH: 525
<212> TYPE: PRT
<213> ORGANISM: Sulfolobus shibatae
<220> FEATURE:
<221> NAME/KEY: MISC_FEATURE
<223> OTHER INFORMATION: chaperonin permutant 499

<400> SEQUENCE: 75

Met Ala Leu Gly Val Ile Glu Pro Ala Leu Val Lys Met Asn Ala Ile
1               5                   10                  15

Lys Ala Ala Thr Glu Ala Val Thr Leu Val Leu Arg Ile Asp Asp Ile
            20                  25                  30

Val Gly Gly Ser Gly Gly Thr Ile Pro Val Ile Ile Leu Lys Glu Gly
        35                  40                  45

Ser Ser Arg Thr Tyr Gly Lys Glu Ala Leu Arg Ala Asn Ile Ala Ala
    50                  55                  60

Val Lys Ala Ile Glu Glu Ala Leu Lys Ser Thr Tyr Gly Pro Arg Gly
65                  70                  75                  80

Met Asp Lys Ile Leu Val Asp Ser Leu Gly Asp Ile Thr Ile Thr Asn
                85                  90                  95

Asp Gly Ala Thr Ile Leu Asp Lys Met Asp Leu Gln His Pro Thr Gly
            100                 105                 110

Lys Leu Leu Val Gln Ile Ala Lys Gly Gln Asp Glu Glu Thr Ala Asp
        115                 120                 125

Gly Thr Lys Thr Ala Val Ile Leu Ala Gly Glu Leu Ala Lys Lys Ala
    130                 135                 140

Glu Asp Leu Leu Tyr Lys Glu Ile His Pro Thr Ile Ile Val Ser Gly
145                 150                 155                 160

Tyr Lys Lys Ala Glu Glu Ile Ala Leu Lys Thr Ile Gln Asp Ile Ala
                165                 170                 175

Gln Pro Val Ser Ile Asn Asp Thr Asp Val Leu Arg Lys Val Ala Leu
            180                 185                 190

Thr Ser Leu Gly Ser Lys Ala Val Ala Gly Ala Arg Glu Tyr Leu Ala
        195                 200                 205

Asp Leu Val Val Lys Ala Val Ala Gln Val Ala Glu Leu Arg Gly Asp
    210                 215                 220

Lys Trp Tyr Val Asp Leu Asp Asn Val Gln Ile Val Lys Lys His Gly
225                 230                 235                 240

Gly Ser Ile Asn Asp Thr Gln Leu Val Tyr Gly Ile Val Val Asp Lys
                245                 250                 255

Glu Val Val His Pro Gly Met Pro Lys Arg Ile Glu Asn Ala Lys Ile
            260                 265                 270

Ala Leu Leu Asp Ala Ser Leu Glu Val Glu Lys Pro Glu Leu Asp Ala
        275                 280                 285

Glu Ile Arg Ile Asn Asp Pro Thr Gln Met His Lys Phe Leu Glu Glu
    290                 295                 300

Glu Glu Asn Ile Leu Lys Glu Lys Val Asp Lys Ile Ala Ala Thr Gly
305                 310                 315                 320

Ala Asn Val Val Ile Ala Gln Lys Gly Ile Asp Glu Val Ala Gln His
                325                 330                 335

Tyr Leu Ala Lys Lys Gly Ile Leu Ala Val Arg Arg Ala Lys Lys Ser
            340                 345                 350

Asp Leu Glu Lys Leu Ala Arg Ala Thr Gly Gly Arg Val Ile Ser Asn

-continued

```
        355                 360                 365

Ile Asp Glu Leu Thr Ser Gln Asp Leu Gly Tyr Ala Ala Leu Val Glu
    370                 375                 380

Glu Arg Lys Val Gly Glu Asp Lys Ile Val Phe Val Glu Gly Ala Lys
385                 390                 395                 400

Asn Pro Lys Ser Val Ser Ile Leu Ile Arg Gly Gly Leu Glu Arg Val
                405                 410                 415

Val Asp Glu Thr Glu Arg Ala Leu Arg Asp Ala Leu Gly Thr Val Ala
            420                 425                 430

Asp Val Ile Arg Asp Gly Arg Ala Val Ala Gly Gly Gly Ala Val Glu
        435                 440                 445

Ile Glu Ile Ala Lys Arg Leu Arg Lys Tyr Ala Pro Gln Val Gly Gly
    450                 455                 460

Lys Glu Gln Leu Ala Ile Glu Ala Tyr Ala Asn Ala Ile Glu Gly Leu
465                 470                 475                 480

Ile Met Ile Leu Ala Glu Asn Ala Gly Leu Asp Pro Ile Asp Lys Leu
                485                 490                 495

Met Gln Leu Arg Ser Leu His Glu Asn Glu Thr Asn Lys Trp Tyr Gly
            500                 505                 510

Leu Asn Leu Phe Thr Gly Asn Pro Glu Asp Met Trp Lys
        515                 520                 525


<210> SEQ ID NO 76
<211> LENGTH: 2349
<212> TYPE: DNA
<213> ORGANISM: Sulfolobus shibatae
<220> FEATURE:
<221> NAME/KEY: misc_feature
<223> OTHER INFORMATION: chaperonin permutant 267-EYFP fusion

<400> SEQUENCE: 76

atggcagatc caacacagat gcacaaattc ttggaagaag aagaaaacat attgaaagaa      60

aaagtagata agattgcagc tactggtgct aacgttgtaa tagcgcagaa aggtatcgat     120

gaagttgcac aacactattt agctaagaaa ggtatattag ctgttaggag agccaagaag     180

agtgatttag agaaattagc tagagctacc ggaggtagag tcatatcaaa tattgatgaa     240

ttaacttcac aagatctagg ttatgccgca ttagtggaag agagaaaagt aggtgaagac     300

aagatcgtat tcgtagaagg tgcaaagaat ccaaaatcag ttagtatact aataagagga     360

ggattagaga gagtagtaga tgagactgaa agagctctta gggacgcttt aggtacagtg     420

gcagatgtaa taagggatgg tagagcagta gctggtggtg gagctgttga gatagagata     480

gctaagagat taagaaagta tgccccacaa gttggtggta aagagcaatt agcaattgaa     540

gcatatgcta atgcaataga gggtctcatt atgatattgg cggaaaacgc aggattagat     600

cctatagaca aattaatgca attaagaagt cttcacgaga atgagaccaa taaatggtat     660

ggacttaatt tatttactgg aaatccagag gatatgtgga aattaggtgt tattgaaccg     720

gcactagtga aaatgaatgc aattaaggct gcaacagaag cagtaacatt agtgttaaga     780

atagatgata ttgtaggtgg ttctggtggt accatacctg taataatttt aaaagaggga     840

tcaagtagaa catatggaaa agaagcttta agggctaata ttgctgcagt gaaagcaatt     900

gaagaggcat taaaaagcac ctatggtcca cgtggaatgg ataagattct tgttgatagc     960

ttaggagata ttacaataac aaatgatgga gccactattc ttgataaaat ggatttacaa    1020

cacccaacag gtaagctttt agttcagata gctaaaggac aagacgagga aacagctgat    1080
```

-continued

```
ggcactaaaa ctgctgtaat tcttgctgga gaattagcta aaaaagcaga agatctttta   1140

tataaggaga ttcacccaac aataattgta agcggatata agaaggcaga agaaattgca   1200

ttaaagacca tccaagatat agcacaaccg gtcagcataa atgatactga cgtacttagg   1260

aaagtagcat taacatcctt aggcagtaag gcagtagcag gcgcacgaga gtatttagct   1320

gaccttgtgg ttaaagcagt ggcacaagta gcagaattaa gaggagataa gtggtatgtt   1380

gatctagata atgtacaaat agttaaaaaa catggtggta gcattaatga tactcaatta   1440

gtatacggca tagtagttga taaggaagtt gtacatccgg gcatgccaaa gaggattgaa   1500

aatgctaaga tagccctttt agacgcttca ttagaagttg agaaacccga attggatgca   1560

gaaataagaa ttaacggcag cggcggatcc ggggtgagca agggcgagga gctgttcacc   1620

ggggtggtgc ccatcctggt cgagctggac ggcgacgtaa acggccacaa gttcagcgtg   1680

tccggcgagg gcgagggcga tgccacctac ggcaagctga ccctgaagtt catctgcacc   1740

accggcaagc tgcccgtgcc ctggcccacc ctcgtgacca ccttcggcta cggcctgcag   1800

tgcttcgccc gctaccccga ccacatgaag cagcacgact tcttcaagtc cgccatgccc   1860

gaaggctacg tccaggagcg caccatcttc ttcaaggacg acggcaacta caagacccgc   1920

gccgaggtga agttcgaggg cgacaccctg gtgaaccgca tcgagctgaa gggcatcgac   1980

ttcaaggagg acggcaacat cctggggcac aagctggagt acaacggcgg taccggatct   2040

ggaggtgagc tcaacagcca caacgtctat atcatggccg acaagcagaa gaacggcatc   2100

aaggtgaact tcaagatccg ccacaacatc gaggacggca gcgtgcagct cgccgaccac   2160

taccagcaga acacccccat cggcgacggc cccgtgctgc tgcccgacaa ccactacctg   2220

agctaccagt ccgccctgag caaagacccc aacgagaagc gcgatcacat ggtcctgctg   2280

gagttcgtga ccgccgccgg gatcactctc ggcatggacg agctgtacaa gcaccaccat   2340

caccatcac                                                           2349
```

<210> SEQ ID NO 77
<211> LENGTH: 783
<212> TYPE: PRT
<213> ORGANISM: Sulfolobus shibatae
<220> FEATURE:
<221> NAME/KEY: MISC_FEATURE
<223> OTHER INFORMATION: chaperonin permutant 267-EYFP fusion

<400> SEQUENCE: 77

```
Met Ala Asp Pro Thr Gln Met His Lys Phe Leu Glu Glu Glu Glu Asn
1               5                   10                  15

Ile Leu Lys Glu Lys Val Asp Lys Ile Ala Ala Thr Gly Ala Asn Val
            20                  25                  30

Val Ile Ala Gln Lys Gly Ile Asp Glu Val Ala Gln His Tyr Leu Ala
        35                  40                  45

Lys Lys Gly Ile Leu Ala Val Arg Arg Ala Lys Lys Ser Asp Leu Glu
    50                  55                  60

Lys Leu Ala Arg Ala Thr Gly Gly Arg Val Ile Ser Asn Ile Asp Glu
65                  70                  75                  80

Leu Thr Ser Gln Asp Leu Gly Tyr Ala Ala Leu Val Glu Glu Arg Lys
                85                  90                  95

Val Gly Glu Asp Lys Ile Val Phe Val Glu Gly Ala Lys Asn Pro Lys
            100                 105                 110

Ser Val Ser Ile Leu Ile Arg Gly Gly Leu Glu Arg Val Val Asp Glu
        115                 120                 125
```

-continued

```
Thr Glu Arg Ala Leu Arg Asp Ala Leu Gly Thr Val Ala Asp Val Ile
    130                 135                 140

Arg Asp Gly Arg Ala Val Ala Gly Gly Gly Ala Val Glu Ile Glu Ile
145                 150                 155                 160

Ala Lys Arg Leu Arg Lys Tyr Ala Pro Gln Val Gly Gly Lys Glu Gln
                165                 170                 175

Leu Ala Ile Glu Ala Tyr Ala Asn Ala Ile Glu Gly Leu Ile Met Ile
            180                 185                 190

Leu Ala Glu Asn Ala Gly Leu Asp Pro Ile Asp Lys Leu Met Gln Leu
        195                 200                 205

Arg Ser Leu His Glu Asn Glu Thr Asn Lys Trp Tyr Gly Leu Asn Leu
    210                 215                 220

Phe Thr Gly Asn Pro Glu Asp Met Trp Lys Leu Gly Val Ile Glu Pro
225                 230                 235                 240

Ala Leu Val Lys Met Asn Ala Ile Lys Ala Ala Thr Glu Ala Val Thr
                245                 250                 255

Leu Val Leu Arg Ile Asp Asp Ile Val Gly Gly Ser Gly Gly Thr Ile
            260                 265                 270

Pro Val Ile Ile Leu Lys Glu Gly Ser Ser Arg Thr Tyr Gly Lys Glu
        275                 280                 285

Ala Leu Arg Ala Asn Ile Ala Ala Val Lys Ala Ile Glu Glu Ala Leu
    290                 295                 300

Lys Ser Thr Tyr Gly Pro Arg Gly Met Asp Lys Ile Leu Val Asp Ser
305                 310                 315                 320

Leu Gly Asp Ile Thr Ile Thr Asn Asp Gly Ala Thr Ile Leu Asp Lys
                325                 330                 335

Met Asp Leu Gln His Pro Thr Gly Lys Leu Leu Val Gln Ile Ala Lys
            340                 345                 350

Gly Gln Asp Glu Glu Thr Ala Asp Gly Thr Lys Thr Ala Val Ile Leu
        355                 360                 365

Ala Gly Glu Leu Ala Lys Lys Ala Glu Asp Leu Leu Tyr Lys Glu Ile
    370                 375                 380

His Pro Thr Ile Ile Val Ser Gly Tyr Lys Lys Ala Glu Glu Ile Ala
385                 390                 395                 400

Leu Lys Thr Ile Gln Asp Ile Ala Gln Pro Val Ser Ile Asn Asp Thr
                405                 410                 415

Asp Val Leu Arg Lys Val Ala Leu Thr Ser Leu Gly Ser Lys Ala Val
            420                 425                 430

Ala Gly Ala Arg Glu Tyr Leu Ala Asp Leu Val Val Lys Ala Val Ala
        435                 440                 445

Gln Val Ala Glu Leu Arg Gly Asp Lys Trp Tyr Val Asp Leu Asp Asn
    450                 455                 460

Val Gln Ile Val Lys Lys His Gly Gly Ser Ile Asn Asp Thr Gln Leu
465                 470                 475                 480

Val Tyr Gly Ile Val Val Asp Lys Glu Val Val His Pro Gly Met Pro
                485                 490                 495

Lys Arg Ile Glu Asn Ala Lys Ile Ala Leu Leu Asp Ala Ser Leu Glu
            500                 505                 510

Val Glu Lys Pro Glu Leu Asp Ala Glu Ile Arg Ile Asn Gly Ser Gly
        515                 520                 525

Gly Ser Gly Val Ser Lys Gly Glu Glu Leu Phe Thr Gly Val Val Pro
    530                 535                 540

Ile Leu Val Glu Leu Asp Gly Asp Val Asn Gly His Lys Phe Ser Val
```

-continued

```
545                 550                 555                 560

Ser Gly Glu Gly Glu Gly Asp Ala Thr Tyr Gly Lys Leu Thr Leu Lys
                565                 570                 575

Phe Ile Cys Thr Thr Gly Lys Leu Pro Val Pro Trp Pro Thr Leu Val
            580                 585                 590

Thr Thr Phe Gly Tyr Gly Leu Gln Cys Phe Ala Arg Tyr Pro Asp His
        595                 600                 605

Met Lys Gln His Asp Phe Phe Lys Ser Ala Met Pro Glu Gly Tyr Val
    610                 615                 620

Gln Glu Arg Thr Ile Phe Phe Lys Asp Asp Gly Asn Tyr Lys Thr Arg
625                 630                 635                 640

Ala Glu Val Lys Phe Glu Gly Asp Thr Leu Val Asn Arg Ile Glu Leu
                645                 650                 655

Lys Gly Ile Asp Phe Lys Glu Asp Gly Asn Ile Leu Gly His Lys Leu
            660                 665                 670

Glu Tyr Asn Gly Gly Thr Gly Ser Gly Gly Glu Leu Asn Ser His Asn
        675                 680                 685

Val Tyr Ile Met Ala Asp Lys Gln Lys Asn Gly Ile Lys Val Asn Phe
    690                 695                 700

Lys Ile Arg His Asn Ile Glu Asp Gly Ser Val Gln Leu Ala Asp His
705                 710                 715                 720

Tyr Gln Gln Asn Thr Pro Ile Gly Asp Gly Pro Val Leu Leu Pro Asp
                725                 730                 735

Asn His Tyr Leu Ser Tyr Gln Ser Ala Leu Ser Lys Asp Pro Asn Glu
            740                 745                 750

Lys Arg Asp His Met Val Leu Leu Glu Phe Val Thr Ala Ala Gly Ile
        755                 760                 765

Thr Leu Gly Met Asp Glu Leu Tyr Lys His His His His His His
    770                 775                 780
```

<210> SEQ ID NO 78
<211> LENGTH: 2355
<212> TYPE: DNA
<213> ORGANISM: Sulfolobus shibatae
<220> FEATURE:
<221> NAME/KEY: misc_feature
<223> OTHER INFORMATION: chaperonin permutant 480-EYFP fusion

<400> SEQUENCE: 78

```
atggcaaata aatggtatgg acttaattta tttactggaa atccagagga tatgtggaaa      60

ttaggtgtta ttgaaccggc actagtgaaa atgaatgcaa ttaaggctgc aacagaagca     120

gtaacattag tgttaagaat agatgatatt gtaggtggtt ctggtggtac catacctgta     180

ataattttaa aagagggatc aagtagaaca tatggaaaag aagctttaag ggctaatatt     240

gctgcagtga aagcaattga agaggcatta aaaagcacct atggtccacg tggaatggat     300

aagattcttg ttgatagctt aggagatatt acaataacaa atgatggagc cactattctt     360

gataaaatgg atttacaaca cccaacaggt aagcttttag ttcagatagc taaaggacaa     420

gacgaggaaa cagctgatgg cactaaaact gctgtaattc ttgctggaga attagctaaa     480

aaagcagaag atcttttata taaggagatt cacccaacaa taattgtaag cggatataag     540

aaggcagaag aaattgcatt aaagaccatc caagatatag cacaaccggt cagcataaat     600

gatactgacg tacttaggaa agtagcatta acatccttag gcagtaaggc agtagcaggc     660

gcacgagagt atttagctga ccttgtggtt aaagcagtgg cacaagtagc agaattaaga     720
```

-continued

```
ggagataagt ggtatgttga tctagataat gtacaaatag ttaaaaaaca tggtggtagc    780

attaatgata ctcaattagt atacggcata gtagttgata aggaagttgt acatccgggc    840

atgccaaaga ggattgaaaa tgctaagata gccctttttag acgcttcatt agaagttgag   900

aaacccgaat tggatgcaga aataagaatt aacgatccaa cacagatgca caaattcttg    960

gaagaagaag aaaacatatt gaaagaaaaa gtagataaga ttgcagctac tggtgctaac   1020

gttgtaatag cgcagaaagg tatcgatgaa gttgcacaac actatttagc taagaaaggt   1080

atattagctg ttaggagagc caagaagagt gatttagaga aattagctag agctaccgga   1140

ggtagagtca tatcaaatat tgatgaatta acttcacaag atctaggtta tgccgcatta   1200

gtggaagaga gaaaagtagg tgaagacaag atcgtattcg tagaaggtgc aaagaatcca   1260

aaatcagtta gtatactaat aagaggagga ttagagagag tagtagatga gactgaaaga   1320

gctcttaggg acgctttagg tacagtggca gatgtaataa gggatggtag agcagtagct   1380

ggtggtggag ctgttgagat agagatagct aagagattaa gaaagtatgc cccacaagtt   1440

ggtggtaaag agcaattagc aattgaagca tatgctaatg caatagaggg tctcattatg   1500

atattggcgg aaaacgcagg attagatcct atagacaaat taatgcaatt aagaagtctt   1560

cacgagaatg agaccggctc tggcggatcc ggatccgggg tgagcaaggg cgaggagctg   1620

ttcaccgggg tggtgcccat cctggtcgag ctggacggcg acgtaaacgg ccacaagttc   1680

agcgtgtccg gcgagggcga gggcgatgcc acctacggca agctgaccct gaagttcatc   1740

tgcaccaccg gcaagctgcc cgtgccctgg cccaccctcg tgaccacctt cggctacggc   1800

ctgcagtgct tcgcccgcta ccccgaccac atgaagcagc acgacttctt caagtccgcc   1860

atgcccgaag gctacgtcca ggagcgcacc atcttcttca aggacgacgg caactacaag   1920

acccgcgccg aggtgaagtt cgagggcgac accctggtga accgcatcga gctgaagggc   1980

atcgacttca aggaggacgg caacatcctg gggcacaagc tggagtacaa cggcggtacc   2040

ggatctggag gtgagctcaa cagccacaac gtctatatca tggccgacaa gcagaagaac   2100

ggcatcaagg tgaacttcaa gatccgccac aacatcgagg acggcagcgt gcagctcgcc   2160

gaccactacc agcagaacac ccccatcggc gacggccccg tgctgctgcc cgacaaccac   2220

tacctgagct accagtccgc cctgagcaaa gaccccaacg agaagcgcga tcacatggtc   2280

ctgctggagt tcgtgaccgc cgccgggatc actctcggca tggacgagct gtacaagcac   2340

caccatcacc atcac                                                     2355
```

<210> SEQ ID NO 79
<211> LENGTH: 785
<212> TYPE: PRT
<213> ORGANISM: Sulfolobus shibatae
<220> FEATURE:
<221> NAME/KEY: MISC_FEATURE
<223> OTHER INFORMATION: chaperonin permutant 480-EYFP fusion

<400> SEQUENCE: 79

```
Met Ala Asn Lys Trp Tyr Gly Leu Asn Leu Phe Thr Gly Asn Pro Glu
1               5                   10                  15

Asp Met Trp Lys Leu Gly Val Ile Glu Pro Ala Leu Val Lys Met Asn
            20                  25                  30

Ala Ile Lys Ala Ala Thr Glu Ala Val Thr Leu Val Leu Arg Ile Asp
        35                  40                  45

Asp Ile Val Gly Gly Ser Gly Gly Thr Ile Pro Val Ile Ile Leu Lys
    50                  55                  60
```

-continued

```
Glu Gly Ser Ser Arg Thr Tyr Gly Lys Glu Ala Leu Arg Ala Asn Ile
65                  70                  75                  80

Ala Ala Val Lys Ala Ile Glu Glu Ala Leu Lys Ser Thr Tyr Gly Pro
                85                  90                  95

Arg Gly Met Asp Lys Ile Leu Val Asp Ser Leu Gly Asp Ile Thr Ile
            100                 105                 110

Thr Asn Asp Gly Ala Thr Ile Leu Asp Lys Met Asp Leu Gln His Pro
        115                 120                 125

Thr Gly Lys Leu Leu Val Gln Ile Ala Lys Gly Gln Asp Glu Glu Thr
    130                 135                 140

Ala Asp Gly Thr Lys Thr Ala Val Ile Leu Ala Gly Glu Leu Ala Lys
145                 150                 155                 160

Lys Ala Glu Asp Leu Leu Tyr Lys Glu Ile His Pro Thr Ile Ile Val
                165                 170                 175

Ser Gly Tyr Lys Lys Ala Glu Glu Ile Ala Leu Lys Thr Ile Gln Asp
            180                 185                 190

Ile Ala Gln Pro Val Ser Ile Asn Asp Thr Asp Val Leu Arg Lys Val
        195                 200                 205

Ala Leu Thr Ser Leu Gly Ser Lys Ala Val Ala Gly Ala Arg Glu Tyr
    210                 215                 220

Leu Ala Asp Leu Val Val Lys Ala Val Ala Gln Val Ala Glu Leu Arg
225                 230                 235                 240

Gly Asp Lys Trp Tyr Val Asp Leu Asp Asn Val Gln Ile Val Lys Lys
                245                 250                 255

His Gly Gly Ser Ile Asn Asp Thr Gln Leu Val Tyr Gly Ile Val Val
            260                 265                 270

Asp Lys Glu Val Val His Pro Gly Met Pro Lys Arg Ile Glu Asn Ala
        275                 280                 285

Lys Ile Ala Leu Leu Asp Ala Ser Leu Glu Val Glu Lys Pro Glu Leu
    290                 295                 300

Asp Ala Glu Ile Arg Ile Asn Asp Pro Thr Gln Met His Lys Phe Leu
305                 310                 315                 320

Glu Glu Glu Glu Asn Ile Leu Lys Glu Lys Val Asp Lys Ile Ala Ala
                325                 330                 335

Thr Gly Ala Asn Val Val Ile Ala Gln Lys Gly Ile Asp Glu Val Ala
            340                 345                 350

Gln His Tyr Leu Ala Lys Lys Gly Ile Leu Ala Val Arg Arg Ala Lys
        355                 360                 365

Lys Ser Asp Leu Glu Lys Leu Ala Arg Ala Thr Gly Gly Arg Val Ile
    370                 375                 380

Ser Asn Ile Asp Glu Leu Thr Ser Gln Asp Leu Gly Tyr Ala Ala Leu
385                 390                 395                 400

Val Glu Glu Arg Lys Val Gly Glu Asp Lys Ile Val Phe Val Glu Gly
                405                 410                 415

Ala Lys Asn Pro Lys Ser Val Ser Ile Leu Ile Arg Gly Gly Leu Glu
            420                 425                 430

Arg Val Val Asp Glu Thr Glu Arg Ala Leu Arg Asp Ala Leu Gly Thr
        435                 440                 445

Val Ala Asp Val Ile Arg Asp Gly Arg Ala Val Ala Gly Gly Gly Ala
    450                 455                 460

Val Glu Ile Glu Ile Ala Lys Arg Leu Arg Lys Tyr Ala Pro Gln Val
465                 470                 475                 480

Gly Gly Lys Glu Gln Leu Ala Ile Glu Ala Tyr Ala Asn Ala Ile Glu
```

-continued

```
                485                 490                 495

Gly Leu Ile Met Ile Leu Ala Glu Asn Ala Gly Leu Asp Pro Ile Asp
            500                 505                 510

Lys Leu Met Gln Leu Arg Ser Leu His Glu Asn Glu Thr Gly Ser Gly
        515                 520                 525

Gly Ser Gly Ser Gly Val Ser Lys Gly Glu Glu Leu Phe Thr Gly Val
    530                 535                 540

Val Pro Ile Leu Val Glu Leu Asp Gly Asp Val Asn Gly His Lys Phe
545                 550                 555                 560

Ser Val Ser Gly Glu Gly Glu Gly Asp Ala Thr Tyr Gly Lys Leu Thr
                565                 570                 575

Leu Lys Phe Ile Cys Thr Thr Gly Lys Leu Pro Val Pro Trp Pro Thr
            580                 585                 590

Leu Val Thr Thr Phe Gly Tyr Gly Leu Gln Cys Phe Ala Arg Tyr Pro
        595                 600                 605

Asp His Met Lys Gln His Asp Phe Phe Lys Ser Ala Met Pro Glu Gly
    610                 615                 620

Tyr Val Gln Glu Arg Thr Ile Phe Phe Lys Asp Asp Gly Asn Tyr Lys
625                 630                 635                 640

Thr Arg Ala Glu Val Lys Phe Glu Gly Asp Thr Leu Val Asn Arg Ile
                645                 650                 655

Glu Leu Lys Gly Ile Asp Phe Lys Glu Asp Gly Asn Ile Leu Gly His
            660                 665                 670

Lys Leu Glu Tyr Asn Gly Gly Thr Gly Ser Gly Gly Glu Leu Asn Ser
        675                 680                 685

His Asn Val Tyr Ile Met Ala Asp Lys Gln Lys Asn Gly Ile Lys Val
    690                 695                 700

Asn Phe Lys Ile Arg His Asn Ile Glu Asp Gly Ser Val Gln Leu Ala
705                 710                 715                 720

Asp His Tyr Gln Gln Asn Thr Pro Ile Gly Asp Gly Pro Val Leu Leu
                725                 730                 735

Pro Asp Asn His Tyr Leu Ser Tyr Gln Ser Ala Leu Ser Lys Asp Pro
            740                 745                 750

Asn Glu Lys Arg Asp His Met Val Leu Leu Glu Phe Val Thr Ala Ala
        755                 760                 765

Gly Ile Thr Leu Gly Met Asp Glu Leu Tyr Lys His His His His His
    770                 775                 780

His
785
```

<210> SEQ ID NO 80
<211> LENGTH: 1680
<212> TYPE: DNA
<213> ORGANISM: Sulfolobus shibatae
<220> FEATURE:
<221> NAME/KEY: misc_feature
<223> OTHER INFORMATION: TF55 alpha subunit

<400> SEQUENCE: 80

```
atggcgagcc cggtcttgtt attgaaagag ggaacgagta gaactactgg tagagatgcg     60

ttaaggaata atatacttgc tgcaaagaca ctagccgaaa tgttaaggag tagtttaggt    120

cctaaaggtc ttgataaaat gttaattgat agtttcggtg acgtaaccat aactaatgat    180

ggtgctacaa tagtaaagga tatggagata cagcatccag cagcaaagct attagtagaa    240

gcagctaaag cacaagatgc tgaagtaggt gatggtacta caagcgctgt agtattagct    300
```

-continued

```
ggtgctctat tggagaaagc tgaaagttta ttggatcaaa atatacatcc aacaataatt    360
attgaggggt ataagaaggc atataccaag gccttggagt tacttccaca gttaggaact    420
aggatcgata taagggattt gaattcttca gttgctaggg atactctaag aaaaatagca    480
tttactacac tagcaagtaa gtttattgca gaaggtgctg aattaaataa aataattgac    540
atggtaatag acgcaatagt taatgttgca gaacctctac ctaatggtgg gtacaatgtg    600
agtttagact taataaagat agataagaag aaaggtggaa gtatagagga tagcgtctta    660
gttaaaggac tagtattaga taaggaggtt gtgcaccctg gaatgcctag aagagtcact    720
aaagccaaga tagctgtttt ggatgcagca ttagaggtag aaaagcctga aatctcagct    780
aagataagta taacatcacc agagcaaatc aaggctttct tagatgagga atccaaatat    840
cttaaggaca tggttgataa actagcgtca ataggcgcta acgttgtaat atgccagaaa    900
ggtattgatg atatcgcaca gcacttctta gctaagaaag gtatattggc tgtaagaagg    960
gttaagagga gcgatataga gaaattagag aaggcattag gcgcgagaat aataagcagt   1020
attaaagacg ctactcccga tgatttagga tacgccgaat tagttgagga aaggagagtt   1080
ggaaatgaca aaatggtatt tatagaaggt gctaagaatc tgaaggccgt gaatatcttg   1140
ttaagaggtt caaatgatat ggcattagat gaggctgaga ggagtataaa tgatgcattg   1200
catgctctga ggaacatatt attagagcca gtaatattgc caggtggtgg cgctatcgag   1260
ttagaattag cgatgaaatt aagagagtat gctagaagtg taggaggtaa ggagcaatta   1320
gctatagaag catttgcaga tgcattagag gagataccta tgattttagc tgaaactgca   1380
gggctggagg ctatatctgc actaatggac ttaagagcta gacacgctaa gggattaacc   1440
aatactggtg tagatgtaat aggtgggaag atcgtagacg atgtatatgc cttaaacatc   1500
attgagccta taagagtaaa ggctcaagtg ttaaagagcg caacagaggc ggctacagca   1560
atattaaaga ttgatgacct aatagctgca gctccattaa agagcgagaa gaaaggtgga   1620
gaaggaagta aagaagaaag tggtggagaa ggaggagctg gtactccatc tttaggagac   1680
```

<210> SEQ ID NO 81
<211> LENGTH: 1272
<212> TYPE: DNA
<213> ORGANISM: Sulfolobus shibatae
<220> FEATURE:
<221> NAME/KEY: misc_feature
<223> OTHER INFORMATION: chaperonin dwarf deletion permutant 267

<400> SEQUENCE: 81

```
atggtattcg tagaaggtgc aaagaatcca aaatcagtta gtatactaat aagaggagga     60
ttagagagag tagtagatga gactgaaaga gctcttaggg acgctttagg tacagtggca    120
gatgtaataa gggatggtag agcagtagct ggtggtggag ctgttgagat agagatagct    180
aagagattaa gaaagtatgc cccacaagtt ggtggtaaag agcaattagc aattgaagca    240
tatgctaatg caatagaagg acttatcatg atattggcgg aaaacgcagg attagatcct    300
atagacaaat taatgcaatt aagaagtctt cacgagaatg agaccaataa atggtatgga    360
cttaatttat ttactggaaa tccagaggat atgtggaaat taggtgttat tgaaccggca    420
ctagtgaaaa tgaatgcaat taaggctgca acagaagcag taacattagt gttaagaata    480
gatgatattg taggtggttc tggtggtacc atacctgtaa taattttaaa agagggatca    540
agtagaacat atggaaaaga agctttaagg gctaatattg ctgcagtgaa agcaattgaa    600
gaggcattaa aaagcaccta tggtccacgt ggaatggata agatgcttgt tgatagctta    660
```

```
ggagatatta caataacaaa tgatggagcc actattcttg ataaaatgga tttacaacac    720

ccaacaggta agcttttagt tcagatagct aaaggacaag acgaggaaac agctgatggc    780

actaaaactg ctgtaattct tgctggagaa ttagctaaaa aagcagaaga tcttttatat    840

aaggagattc acccaacaat aattgtaagc ggatataaga aggcagaaga aattgcatta    900

aagaccatcc aagatatagc acaaccggtc agcataaatg atactgacgt acttaggaaa    960

gtagcattaa catccttagg cagtaaggca gtagcaggcg cacgagagta tttagctgac   1020

cttgtggtta aagcagtggc acaagtagca gaattaagag gagataagtg gtatgttgat   1080

ctagataatg tacaaatagt taaaaaacat ggtggtagca ttaatgatac tcaattagta   1140

tacggcatag tagttgataa ggaagttgta catccgggca tgccaaagag gattgaaaat   1200

gctaagatag ccctttttaga cgcttcatta gaagttgaga aacccgaatt ggatgcagaa   1260

ataagaatta ac                                                       1272
```

```
<210> SEQ ID NO 82
<211> LENGTH: 424
<212> TYPE: PRT
<213> ORGANISM: Sulfolobus shibatae
<220> FEATURE:
<221> NAME/KEY: MISC_FEATURE
<223> OTHER INFORMATION: chaperonin dwarf deletion permutant 267

<400> SEQUENCE: 82

Met Val Phe Val Glu Gly Ala Lys Asn Pro Lys Ser Val Ser Ile Leu
1               5                   10                  15

Ile Arg Gly Gly Leu Glu Arg Val Val Asp Glu Thr Glu Arg Ala Leu
            20                  25                  30

Arg Asp Ala Leu Gly Thr Val Ala Asp Val Ile Arg Asp Gly Arg Ala
        35                  40                  45

Val Ala Gly Gly Gly Ala Val Glu Ile Glu Ile Ala Lys Arg Leu Arg
    50                  55                  60

Lys Tyr Ala Pro Gln Val Gly Gly Lys Glu Gln Leu Ala Ile Glu Ala
65                  70                  75                  80

Tyr Ala Asn Ala Ile Glu Gly Leu Ile Met Ile Leu Ala Glu Asn Ala
                85                  90                  95

Gly Leu Asp Pro Ile Asp Lys Leu Met Gln Leu Arg Ser Leu His Glu
            100                 105                 110

Asn Glu Thr Asn Lys Trp Tyr Gly Leu Asn Leu Phe Thr Gly Asn Pro
        115                 120                 125

Glu Asp Met Trp Lys Leu Gly Val Ile Glu Pro Ala Leu Val Lys Met
    130                 135                 140

Asn Ala Ile Lys Ala Ala Thr Glu Ala Val Thr Leu Val Leu Arg Ile
145                 150                 155                 160

Asp Asp Ile Val Gly Gly Ser Gly Gly Thr Ile Pro Val Ile Ile Leu
                165                 170                 175

Lys Glu Gly Ser Ser Arg Thr Tyr Gly Lys Glu Ala Leu Arg Ala Asn
            180                 185                 190

Ile Ala Ala Val Lys Ala Ile Glu Glu Ala Leu Lys Ser Thr Tyr Gly
        195                 200                 205

Pro Arg Gly Met Asp Lys Met Leu Val Asp Ser Leu Gly Asp Ile Thr
    210                 215                 220

Ile Thr Asn Asp Gly Ala Thr Ile Leu Asp Lys Met Asp Leu Gln His
225                 230                 235                 240
```

-continued

```
Pro Thr Gly Lys Leu Leu Val Gln Ile Ala Lys Gly Gln Asp Glu Glu
                245                 250                 255

Thr Ala Asp Gly Thr Lys Thr Ala Val Ile Leu Ala Gly Glu Leu Ala
            260                 265                 270

Lys Lys Ala Glu Asp Leu Leu Tyr Lys Glu Ile His Pro Thr Ile Ile
        275                 280                 285

Val Ser Gly Tyr Lys Lys Ala Glu Glu Ile Ala Leu Lys Thr Ile Gln
    290                 295                 300

Asp Ile Ala Gln Pro Val Ser Ile Asn Asp Thr Asp Val Leu Arg Lys
305                 310                 315                 320

Val Ala Leu Thr Ser Leu Gly Ser Lys Ala Val Ala Gly Ala Arg Glu
                325                 330                 335

Tyr Leu Ala Asp Leu Val Val Lys Ala Val Ala Gln Val Ala Glu Leu
            340                 345                 350

Arg Gly Asp Lys Trp Tyr Val Asp Leu Asp Asn Val Gln Ile Val Lys
        355                 360                 365

Lys His Gly Gly Ser Ile Asn Asp Thr Gln Leu Val Tyr Gly Ile Val
    370                 375                 380

Val Asp Lys Glu Val Val His Pro Gly Met Pro Lys Arg Ile Glu Asn
385                 390                 395                 400

Ala Lys Ile Ala Leu Leu Asp Ala Ser Leu Glu Val Glu Lys Pro Glu
                405                 410                 415

Leu Asp Ala Glu Ile Arg Ile Asn
            420


<210> SEQ ID NO 83
<211> LENGTH: 6
<212> TYPE: PRT
<213> ORGANISM: Artificial
<220> FEATURE:
<223> OTHER INFORMATION: peptide linker 267 EYFP

<400> SEQUENCE: 83

Gly Ser Gly Gly Ser Gly
1               5


<210> SEQ ID NO 84
<211> LENGTH: 8
<212> TYPE: PRT
<213> ORGANISM: Artificial
<220> FEATURE:
<223> OTHER INFORMATION: peptide linker 267 EYFP

<400> SEQUENCE: 84

Gly Ser Gly Gly Ser Gly Ser Gly
1               5


<210> SEQ ID NO 85
<211> LENGTH: 1656
<212> TYPE: DNA
<213> ORGANISM: Sulfolobus shibatae
<220> FEATURE:
<221> NAME/KEY: misc_feature
<223> OTHER INFORMATION: TF55 beta subunit (HENET)

<400> SEQUENCE: 85

atggcaacag ctacagttgc aactacaccc gaaggtatac ctgtaataat tttaaaagag      60

ggatcaagta gaacatatgg aaaagaagct ttaagggcta atattgctgc agtgaaagca     120

attgaagagg cattaaaaag cacctatggt ccacgtggaa tggataagat gttcgttgat     180
```

-continued

```
agcttaggag atattacaat aacaaatgat ggagccacta ttcttgataa aatggattta    240

caacacccaa caggtaagct tttagttcag atagctaaag gacaagacga ggaaacagct    300

gatggcacta aaactgctgt aattcttgct ggagaattag ctaaaaaagc agaagatctt    360

ttatataagg agattcaccc aacaataatt gtaagcggat ataagaaggc agaagaaatt    420

gcattaaaga ccatccaaga tatagcacaa ccggtcagca taaatgatac tgacgtactt    480

aggaaagtag cattaacatc cttaggcagt aaggcagtag caggcgcacg agagtattta    540

gctgaccttg tggttaaagc agtggcacaa gtagcagaat taagaggaga taagtggtat    600

gttgatctag ataatgtaca aatagttaaa aaacatggtg gtagcattaa tgatactcaa    660

ttagtatacg gcatagtagt tgataaggaa gttgtacatc cgggcatgcc aaagaggatt    720

gaaaatgcta agatagccct tttagacgct tcattagaag ttgagaaacc cgaattggat    780

gcagaaataa gaattaacga tccaacacag atgcacaaat tcttggaaga agaagaaaac    840

atattgaaag aaaaagtaga taagattgca gctactggtg ctaacgttgt aatatgccag    900

aaaggtatcg atgaagttgc acaacactat ttagctaaga aaggtatatt agctgttagg    960

agagccaaga agagtgattt agagaaatta gctagagcta ccggaggtag agtcatatca   1020

aatattgatg aattaacttc acaagatcta ggttatgccg cattagtgga agagagaaaa   1080

gtaggagagg ataagatggt attcgtagaa ggtgcaaaga atccaaaatc agttagtata   1140

ctaataagag gaggattaga gagagtagta gatgagactg aaagagctct tagggacgct   1200

ttaggtacag tggcagatgt aataagggat ggtagagcag tagctggtgg tggagctgtt   1260

gagatagaga tagctaagag attaagaaag tatgccccac aagttggtgg taaagagcaa   1320

ttagcaattg aagcatatgc taatgcaata gaaggactta tcatgatatt ggcggaaaac   1380

gcaggattag atcctataga caaattaatg caattaagaa gtcttcacga gaatgagacc   1440

aataaatggt atggacttaa tttatttact ggaaatccag aggatatgtg gaaattaggt   1500

gttattgaac cggcactagt gaaaatgaat gcaattaagg ctgcaacaga agcagtaaca   1560

ttagtgttaa gaatagatga tattgtagca gctggaaaga agggtggaag tgagccaggc   1620

ggtaagaaag agaaagaaga aaagtcctct gaagac                              1656
```

<210> SEQ ID NO 86
<211> LENGTH: 1656
<212> TYPE: DNA
<213> ORGANISM: Sulfolobus shibatae
<220> FEATURE:
<221> NAME/KEY: misc_feature
<223> OTHER INFORMATION: TF55 beta subunit (HDNET)

<400> SEQUENCE: 86

```
atggcaacag ctacagttgc aactacaccc gaaggtatac ctgtaataat tttaaaagag     60

ggatcaagta gaacatatgg aaaagaagct ttaagggcta atattgctgc agtgaaagca    120

attgaagagg cattaaaaag cacctatggt ccacgtggaa tggataagat gttcgttgat    180

agcttaggag atattacaat aacaaatgat ggagccacta ttcttgataa aatggattta    240

caacacccaa caggtaagct tttagttcag atagctaaag gacaagacga ggaaacagct    300

gatggcacta aaactgctgt aattcttgct ggagaattag ctaaaaaagc agaagatctt    360

ttatataagg agattcaccc aacaataatt gtaagcggat ataagaaggc agaagaaatt    420

gcattaaaga ccatccaaga tatagcacaa ccggtcagca taaatgatac tgacgtactt    480

aggaaagtag cattaacatc cttaggcagt aaggcagtag caggcgcacg agagtattta    540
```

-continued

```
gctgaccttg tggttaaagc agtggcacaa gtagcagaat taagaggaga taagtggtat    600

gttgatctag ataatgtaca aatagttaaa aaacatggtg gtagcattaa tgatactcaa    660

ttagtatacg gcatagtagt tgataaggaa gttgtacatc cgggcatgcc aaagaggatt    720

gaaaatgcta agatagccct tttagacgct tcattagaag ttgagaaacc cgaattggat    780

gcagaaataa gaattaacga tccaacacag atgcacaaat tcttggaaga agaagaaaac    840

atattgaaag aaaaagtaga taagattgca gctactggtg ctaacgttgt aatatgccag    900

aaaggtatcg atgaagttgc acaacactat ttagctaaga aaggtatatt agctgttagg    960

agagccaaga agagtgattt agagaaatta gctagagcta ccggaggtag agtcatatca   1020

aatattgatg aattaacttc acaagatcta ggttatgccg cattagtgga agagagaaaa   1080

gtaggagagg ataagatggt attcgtagaa ggtgcaaaga atccaaaatc agttagtata   1140

ctaataagag gaggattaga gagagtagta gatgagactg aaagagctct tagggacgct   1200

ttaggtacag tggcagatgt aataagggat ggtagagcag tagctggtgg tggagctgtt   1260

gagatagaga tagctaagag attaagaaag tatgccccac aagttggtgg taaagagcaa   1320

ttagcaattg aagcatatgc taatgcaata gaaggactta tcatgatatt ggcggaaaac   1380

gcaggattag atcctataga caaattaatg caattaagaa gtcttcacga caatgagacc   1440

aataaatggt atggacttaa tttatttact ggaaatccag aggatatgtg gaaattaggt   1500

gttattgaac cggcactagt gaaaatgaat gcaattaagg ctgcaacaga agcagtaaca   1560

ttagtgttaa gaatagatga tattgtagca gctggaaaga agggtggaag tgagccaggc   1620

ggtaagaaag agaaagaaga aaagtcctct gaagac                             1656
```

<210> SEQ ID NO 87
<211> LENGTH: 28
<212> TYPE: PRT
<213> ORGANISM: Artificial Sequence
<220> FEATURE:
<223> OTHER INFORMATION: metal binding peptide - Au

<400> SEQUENCE: 87

```
Pro Gly Met Lys Ala Ser Lys Ser Met Arg Asn Gln Ala Thr Pro Gly
1               5                   10                  15

Met Pro Ser Ser Leu Asp Leu Thr Trp Gln Ala Thr
            20                  25
```

<210> SEQ ID NO 88
<211> LENGTH: 28
<212> TYPE: PRT
<213> ORGANISM: Artificial Sequence
<220> FEATURE:
<223> OTHER INFORMATION: metal binding peptide - Au

<400> SEQUENCE: 88

```
Pro Gly Met Lys Met Arg Leu Ser Gly Ala Lys Glu Ala Thr Pro Gly
1               5                   10                  15

Met Ser Thr Thr Val Ala Gly Leu Leu Gln Ala Thr
            20                  25
```

<210> SEQ ID NO 89
<211> LENGTH: 28
<212> TYPE: PRT
<213> ORGANISM: Artificial Sequence
<220> FEATURE:
<223> OTHER INFORMATION: metal binding peptide - Au

<400> SEQUENCE: 89

-continued

```
Pro Gly Met Ile His Val Gln Lys Thr Ala Val Gln Ala Thr Pro Gly
1               5                   10                  15

Met Val Asn Leu Thr Ser Pro Val Lys Gln Ala Thr
            20                  25


<210> SEQ ID NO 90
<211> LENGTH: 14
<212> TYPE: PRT
<213> ORGANISM: Artificial Sequence
<220> FEATURE:
<223> OTHER INFORMATION: metal binding peptide - Au

<400> SEQUENCE: 90

Ala Leu Asp Ser Pro Ala Gly Cys Leu Ser Phe Ser Met His
1               5                   10


<210> SEQ ID NO 91
<211> LENGTH: 246
<212> TYPE: PRT
<213> ORGANISM: Artificial Sequence
<220> FEATURE:
<223> OTHER INFORMATION: EYFP  Yellow Fluroescent Protein

<400> SEQUENCE: 91

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Gly Gly Thr Gly Ser Gly Gly Glu Leu Asn Ser His Asn Val Tyr Ile
145                 150                 155                 160

Met Ala Asp Lys Gln Lys Asn Gly Ile Lys Val Asn Phe Lys Ile Arg
                165                 170                 175

His Asn Ile Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Tyr Gln Ser Ala Leu Ser Lys Asp Pro Asn Glu Lys Arg Asp
    210                 215                 220

His Met Val Leu Leu Glu Phe Val Thr Ala Ala Gly Ile Thr Leu Gly
225                 230                 235                 240

Met Asp Glu Leu Tyr Lys
                245
```